(12) United States Patent
Curtin et al.

(10) Patent No.: US 9,758,511 B2
(45) Date of Patent: Sep. 12, 2017

(54) NAMPT INHIBITORS

(71) Applicant: AbbVie Inc., North Chicago, IL (US)

(72) Inventors: Michael L. Curtin, Pleasant Prairie, WI (US); Kenton Longenecker, Grayslake, IL (US); Todd M. Hansen, Grayslake, IL (US); Richard F. Clark, Gurnee, IL (US); Bryan Sorensen, Antioch, IL (US); Howard R. Heyman, Deerfield, IL (US); Zhiqin Ji, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 15/048,574

(22) Filed: Feb. 19, 2016

(65) Prior Publication Data
US 2016/0168134 A1  Jun. 16, 2016

Related U.S. Application Data

(63) Continuation of application No. 13/891,363, filed on May 10, 2013, now Pat. No. 9,296,723.

(60) Provisional application No. 61/779,702, filed on Mar. 13, 2013, provisional application No. 61/719,008, filed on Oct. 26, 2012, provisional application No. 61/645,685, filed on May 11, 2012.

(51) Int. Cl.
| | | |
|---|---|---|
| C07D 401/14 | (2006.01) | |
| C07D 405/14 | (2006.01) | |
| C07D 409/14 | (2006.01) | |
| C07D 417/14 | (2006.01) | |
| A61K 45/06 | (2006.01) | |

(52) U.S. Cl.
CPC ............ *C07D 405/14* (2013.01); *A61K 45/06* (2013.01); *C07D 401/14* (2013.01); *C07D 409/14* (2013.01); *C07D 417/14* (2013.01)

(58) Field of Classification Search
CPC .. C07D 401/14; C07D 405/14; C07D 409/14; C07D 417/14

USPC .......... 546/194, 284.7, 187, 269.7; 544/364, 544/238
See application file for complete search history.

(56) References Cited

U.S. PATENT DOCUMENTS

2006/0241109 A1   10/2006   Little et al.

FOREIGN PATENT DOCUMENTS

| WO | 0185714 A1 | 11/2001 |
|---|---|---|
| WO | 2004011441 A1 | 2/2004 |
| WO | 2008085317 A1 | 7/2008 |
| WO | 2009105348 A1 | 8/2009 |
| WO | 2011130740 A2 | 10/2011 |
| WO | 2012031196 A1 | 3/2012 |

OTHER PUBLICATIONS

STN data base Registry No. 1350260-49-9/RN; enetered STN: Dec. 7, 2011.*
Tafesse et al. Synthesis and evaluation of pyridazinylpiperazines as vanilloid receptor 1 antagonists. Bioorganic & Medicinal Chemistry Letters 14 (2004), pp. 5513-5519.*
Garten A., et al., "Nampt: Linking NAD Biology, Metabolism and Cancer," Trends in Endocrinology and Metabolism, 2009, vol. 20 (3), pp. 130-138.
International Search Report and Written Opinion for Application No. PCT/US2013/040479, mailed on Jul. 1, 2013, 14 pages.
Mane U.R., et al., "Pyrido[1,2-a]pyrimidin-4-ones as Antiplasmodial Falcipain-2 Inhibitors," Bioorganic & Medicinal chemistry, 2012, vol. 20 (21), pp. 6296-6304.
Swanson D.M., et al., "Identification and Biological Evaluation of 4-(3-Trifluoromethylpyridin-2-YI)Piperazine-1-Carboxylic Acid (5-Trifluoromethylpyridin-2-YI)Amide, A High Affinity Trpv1 (Vr1) Vanilloid Receptor Antagonist," Journal of Medicinal Chemistry , 2005, vol. 48, pp. 1857-1872.

\* cited by examiner

*Primary Examiner* — Jennifer M Kim
(74) *Attorney, Agent, or Firm* — Glen Gesicki

(57) ABSTRACT

Disclosed are compounds which inhibit the activity of NAMPT, compositions containing the compounds and methods of treating diseases during which NAMPT is expressed.

7 Claims, No Drawings

NAMPT INHIBITORS

This application is a continuation of U.S. application Ser. No. 13/891,363, filed May 10, 2013, which claims priority to U.S. Provisional Application Ser. No. 61/645,685, filed May 11, 2012, U.S. Provisional Application Ser. No. 61/719,008, filed Oct. 26, 2012, and U.S. Provisional Application Ser. No. 61/779,702, filed May 13, 2013 which are incorporated by reference in their entirety.

FIELD OF THE INVENTION

This invention pertains to compounds which inhibit the activity of NAMPT, compositions containing the compounds, and methods of treating diseases during which NAMPT is expressed.

BACKGROUND OF THE INVENTION

NAD+ (nicotinamide adenine dinucleotide) is a coenzyme that plays a critical role in many physiologically essential processes (Ziegkel, M. *Eur. J. Biochem.* 267, 1550-1564, 2000). NAD is necessary for several signaling pathways including among others poly ADP-ribosylation in DNA repair, mono-ADP-ribosylation in both the immune system and G-protein-coupled signaling, and NAD is also required by sirtuins for their deacetylase activity (Garten, A. et al *Trends in Endocrinology and Metabolism,* 20, 130-138, 2008).

NAMPT (also known as pre-B-cell-colony-enhancing factor (PBEF) and visfatin) is an enzyme that catalyzes the phosphoribosylation of nicotinamide and is the rate-limiting enzyme in one of two pathways that salvage NAD.

tumor growth in xenograft models (Olese, U. H. et al. *Mol Cancer Ther.* 9, 1609-1617, 2010).

NAMPT inhibitors also have potential as therapeutic agents in inflammatory and metabolic disorders (Galli, M. et al *Cancer Res.* 70, 8-11, 2010). For example, NAMPT is the predominant enzyme in T and B lymphocytes. Selective inhibition of NAMPT leads to NAD+ depletion in lymphocytes blocking the expansion that accompanies autoimmune disease progression whereas cell types expressing the other NAD+ generating pathways might be spared. A small molecule NAMPT inhibitor (FK866) has been shown to selectively block proliferation and induce apoptosis of activated T cells and was efficacious in animal models of arthritis (collagen-induced arthritis) (Busso, N. et al. *Plos One* 3, e2267, 2008). FK866 ameliorated the manifestations of experimental autoimmune encephalomyelitis (EAE), a model of T-cell mediated autoimmune disorders. (Bruzzone, S et al. *Plos One* 4, e7897, 2009). NaMPT activity increases NF-kB transcriptional activity in human vascular endothelial cell, resulting in MMP-2 and MMP-9 activation, suggesting a role for NAMPT inhibitors in the prevention of inflammatory mediated complications of obesity and type 2 diabetes (Adya, R. et. Al. *Diabetes Care,* 31, 758-760, 2008).

SUMMARY OF THE INVENTION

One embodiment of this invention, therefore, pertains to compounds or pharmaceutically acceptable salts thereof, which are useful as inhibitors of NAMPT, the compounds having Formula (IA)

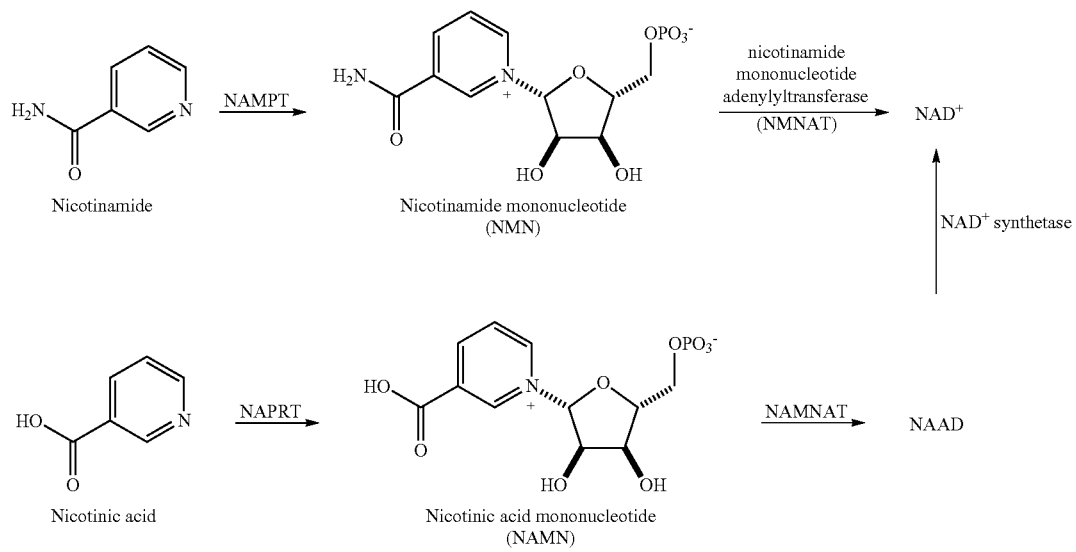

Increasing evidence suggests that NAMPT inhibitors have potential as anticancer agents. Cancer cells have a higher basal turnover of NAD and also display higher energy requirements compared with normal cells. Additionally, increased NAMPT expression has been reported in colorectal cancer (Van Beijnum, J. R. et al *Int. J. Cancer* 101, 118-127, 2002) and NAMPT is involved in angiogenesis (Kim, S. R. et al. Biochem. *Biophys. Res. Commun.* 357, 150-156, 2007). Small-molecule inhibitors of NAMPT have been shown to cause depletion of intracellular NAD+ levels and ultimately induce tumor cell death (Hansen, C M et al. *Anticancer Res.* 20, 42111-4220, 2000) as well as inhibit

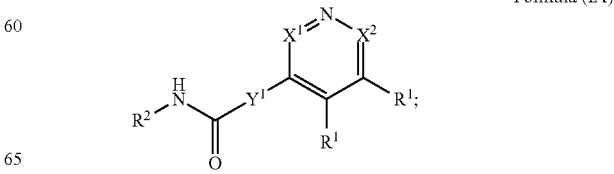

Formula (IA)

wherein
X¹ is N and X² is CR¹; or
X¹ is CR¹ and X² is N; or
X¹ is CR¹ and X² is CR¹;
Y¹ is

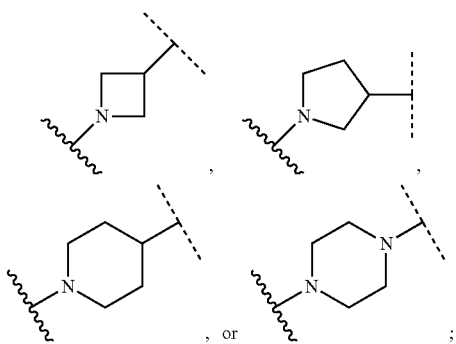

, or                ;

wherein ∼ indicates the point of attachment to the carbonyl and ∖ indicates the point of attachment to the nitrogen containing heteroaryl;

R¹, at each occurrence, is independently selected from the group consisting of hydrogen, alkyl, alkenyl, alkynyl, haloalkyl, hydoxyalkyl, alkoxy, OH, $NH_2$, CN, $NO_2$, F, Cl, Br and I;

R² is independently selected from the group consisting of $C_4$-$C_6$-alkyl, $C_4$-$C_6$-alkenyl, $C_4$-$C_6$-alkynyl, aryl, 3-12 membered heterocyclyl, cycloalkyl, and cycloalkenyl; wherein each R² $C_4$-$C_6$-alkyl, $C_4$-$C_6$-alkenyl, and $C_4$-$C_6$-alkynyl is substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(N)NH_2$, $C(N)NHR^3$, $C(N)N(R^3)_2$, $CNOH$, $CNOCH_3$, OH, (O), CN, $N_3$, $NO_2$, F, Cl, Br and I; wherein each R² aryl, 3-12 membered heterocyclyl, cycloalkyl, and cycloalkenyl is optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, $CNOH$, $CNOCH_3$, OH, CN, $N_3$, $NO_2$, F, Cl, Br and I;

R³, at each occurrence, is independently selected from the group consisting of alkyl, alkenyl, alkynyl, aryl, cycloalkyl, cycloalkenyl, and heterocyclyl; wherein each R³ alkyl, alkenyl, and alkynyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, $CNOH$, $CNOCH_3$, OH, (O), CN, $N_3$, $NO_2$, F, Cl, Br and I; wherein each R³ aryl, cycloalkyl, cycloalkenyl, and heterocyclyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, $CNOH$, $CNOCH_3$, OH, CN, $N_3$, $NO_2$, F, Cl, Br and I;

R⁴, at each occurrence, is independently selected from the group consisting of alkyl, alkenyl, alkynyl, aryl, heterocyclyl, cycloalkyl, and cycloalkenyl; wherein each R⁴ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, $CNOH$, $CNOCH_3$, OH, (O), CN, $N_3$, $NO_2$, F, Cl, Br and I;

R⁵, at each occurrence, is independently selected from the group consisting of alkyl, alkenyl, alkynyl, aryl, heterocyclyl, cycloalkyl, and cycloalkenyl; wherein each R⁵ alkyl, alkenyl, and alkynyl is optionally substituted with one or more substituents independently selected from the group consisting of $R^8$, $OR^8$, $SR^8$, $S(O)R^8$, $SO_2R^8$, $NHR^8$, $N(R^8)_2$, $C(O)R^8$, $C(O)NH_2$, $C(O)NHR^8$, $C(O)N(R^8)_2$, $NHC(O)R^8$, $NR^8C(O)R^8$, $NHSO_2R^8$, $NHC(O)OR^8$, $SO_2NH_2$, $SO_2NHR^8$, $SO_2N(R^8)_2$, $NHC(O)NH_2$, $NHC(O)NHR^8$, OH, (O), C(O)OH, $N_3$, CN, $NH_2$, F, Cl, Br and I;

R⁶, at each occurrence, is independently selected from the group consisting of alkyl, alkenyl, alkynyl, aryl, heterocyclyl, cycloalkyl, and cycloalkenyl; wherein each R⁶ alkyl, alkenyl, and alkynyl is optionally substituted with one or more substituents independently selected from the group consisting of $R^9$, $OR^9$, $SR^9$, $S(O)R^9$, $SO_2R^9$, $NHR^9$, $N(R^9)_2$, $C(O)R^9$, $C(O)NH_2$, $C(O)NHR^9$, $C(O)N(R^9)_2$, $NHC(O)R^9$, $NR^9C(O)R^9$, $NHSO_2R^9$, $NHC(O)OR^9$, $SO_2NH_2$, $SO_2NHR^9$, $SO_2N(R^9)_2$, $NHC(O)NH_2$, $NHC(O)NHR^9$, OH, (O), C(O)OH, $N_3$, CN, $NH_2$, $CF_3$, $CF_2CF_3$, F, Cl, Br and I;

R⁷, at each occurrence, is independently selected from the group consisting of alkyl, alkenyl, alkynyl, aryl, heterocyclyl, cycloalkyl, and cycloalkenyl;

R⁸, at each occurrence, is independently selected from the group consisting of alkyl, alkenyl, alkynyl, aryl, heterocyclyl, cycloalkyl, and cycloalkenyl;

R⁹, at each occurrence, is independently selected from the group consisting of alkyl, alkenyl, alkynyl, aryl, heterocyclyl, cycloalkyl, and cycloalkenyl;

wherein the cyclic moieties represented by $R^4$, $R^5$, $R^6$, $R^7$, $R^8$, and $R^9$ are independently optionally substituted with one or more substituents independently selected from the group consisting of $R^{10}$, $OR^{10}$, $SR^{10}$, $S(O)R^{10}$, $C(O)C(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, NHC(O)NH$_2$, NHC(O)NHR$^{10}$, NHC(O)N(R$^{10}$)$_2$, NR$^{10}$C(O)NHR$^{10}$, NR$^{10}$C(O)N(R$^{10}$)$_2$, C(O)NH$_2$, C(O)NHR$^{10}$, C(O)N(R$^{10}$)$_2$, C(O)NHOH, C(O)NHOR$^{10}$, C(O)NHSO$_2$R$^{10}$, C(O)NR$^{10}$SO$_2$R$^{10}$, SO$_2$NH$_2$, SO$_2$NHR$^{10}$, SO$_2$N(R$^{10}$)$_2$, C(O)H, C(O)OH, C(N)NH$_2$, C(N)NHR$^{10}$, C(N)N(R$^{10}$)$_2$, CNOH, CNOCH$_3$, OH, CN, N$_3$, NO$_2$, F, Cl, Br and I;

R$^{10}$, at each occurrence, is independently selected from the group consisting of alkyl, alkenyl, alkynyl, aryl, heterocyclyl, cycloalkyl, and cycloalkenyl; wherein each R$^{10}$ alkyl, alkenyl, and alkynyl is optionally substituted with one or more substituents independently selected from the group consisting of R$^{11}$, OR$^{11}$, SR$^{11}$, S(O)R$^{11}$, SO$_2$R$^{11}$, C(O)R$^{11}$, CO(O)R$^{11}$, OC(O)R$^{11}$, OC(O)OR$^{11}$, NH$_2$, NHR$^{11}$, N(R$^{11}$)$_2$, NHC(O)R$^{11}$, NR$^{11}$C(O)R$^{11}$, NHS(O)$_2$R$^{11}$, NR$^{11}$S(O)$_2$R$^{11}$, NHC(O)OR$^{11}$, NR$^{11}$C(O)OR$^{11}$, NHC(O)NH$_2$, NHC(O)NHR$^{11}$, NHC(O)N(R$^{11}$)$_2$, NR$^{11}$C(O)NHR$^{11}$, NR$^{11}$C(O)N(R$^{11}$)$_2$, C(O)NH$_2$, C(O)NHR$^{11}$, C(O)N(R$^{11}$)$_2$, C(O)NHOH, C(O)NHOR$^{11}$, C(O)NHSO$_2$R$^{11}$, C(O)NR$^{11}$SO$_2$R$^{11}$, SO$_2$NH$_2$, SO$_2$NHR$^{11}$, SO$_2$N(R$^{11}$)$_2$, C(O)H, C(O)OH, C(N)NH$_2$, C(N)NHR$^{11}$, C(N)N(R$^{11}$)$_2$, CNOH, CNOCH$_3$, OH, (O), CN, N$_3$, NO$_2$, F, Cl, Br and I; wherein each R$^{10}$ aryl, heterocyclyl, cycloalkyl, and cycloalkenyl is optionally substituted with one or more substituents independently selected from the group consisting of R$^{12}$, OR$^{12}$, SR$^{12}$, S(O)R$^{12}$, SO$_2$R$^{12}$, C(O)R$^{12}$, CO(O)R$^{12}$, OC(O)R$^{12}$, OC(O)OR$^{12}$, NH$_2$, NHR$^{12}$, N(R$^{12}$)$_2$, NHC(O)R$^{12}$, NR$^{12}$C(O)R$^{12}$, NHS(O)$_2$R$^{12}$, NR$^{12}$S(O)$_2$R$^{12}$, NHC(O)OR$^{12}$, NR$^{12}$C(O)OR$^{12}$, NHC(O)NH$_2$, NHC(O)NHR$^{12}$, NHC(O)N(R$^{12}$)$_2$, NR$^{12}$C(O)NHR$^{12}$, NR$^{12}$C(O)N(R$^{12}$)$_2$, C(O)NH$_2$, C(O)NHR$^{12}$, C(O)N(R$^{12}$)$_2$, C(O)NHOH, C(O)NHOR$^{12}$, C(O)NHSO$_2$R$^{12}$, C(O)NR$^{12}$SO$_2$R$^{12}$, SO$_2$NH$_2$, SO$_2$NHR$^{12}$, SO$_2$N(R$^{12}$)$_2$, C(O)H, C(O)OH, C(N)NH$_2$, C(N)NHR$^{12}$, C(N)N(R$^{12}$)$_2$, CNOH, CNOCH$_3$, OH, CN, N$_3$, NO$_2$, F, Cl, Br and I;

R$^{11}$, at each occurrence, is independently selected from the group consisting of alkyl, alkenyl, alkynyl, aryl, heterocyclyl, cycloalkyl, and cycloalkenyl; wherein each R$^{11}$ alkyl, alkenyl, and alkynyl is optionally substituted with alkyl or alkoxy; wherein each R$^{11}$ aryl, heterocyclyl, cycloalkyl, and cycloalkenyl is optionally substituted with alkyl or alkoxy; and R$^{12}$, at each occurrence, is independently selected alkyl.

In one embodiment of Formula (IA), X$^1$ is CR$^1$ and X$^2$ is CR$^1$. In another embodiment of Formula (IA), R$^1$, at each occurrence, is hydrogen. In another embodiment of Formula (IA), X$^1$ is CR$^1$ and X$^2$ is CR$^1$, and R$^1$, at each occurrence, is hydrogen. In another embodiment of Formula (IA), Y$^1$ is

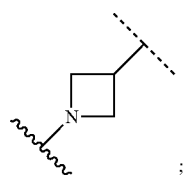

wherein ⁓ indicates the point of attachment to the carbonyl and ⁀ indicates the point of attachment to the nitrogen containing heteroaryl. In another embodiment of Formula (IA), Y$^1$ is

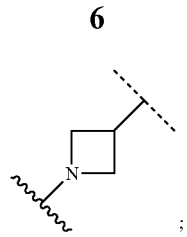

wherein ⁓ indicates the point of attachment to the carbonyl and ⁀ indicates the point of attachment to the nitrogen containing heteroaryl; and R$^2$ is phenyl; wherein each R$^2$ phenyl is substituted with one OR$^4$. In another embodiment of Formula (IA), Y$^1$ is

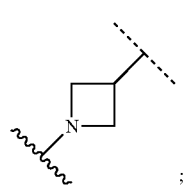

wherein ⁓ indicates the point of attachment to the carbonyl and ⁀ indicates the point of attachment to the nitrogen containing heteroaryl; and R$^2$ is phenyl; wherein each R$^2$ phenyl is substituted with one R$^4$. In another embodiment of Formula (IA), Y$^1$ is

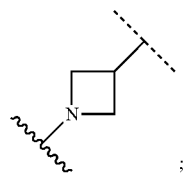

wherein ⁓ indicates the point of attachment to the carbonyl and ⁀ indicates the point of attachment to the nitrogen containing heteroaryl; R$^2$ is phenyl; wherein each R$^2$ phenyl is substituted with one OR$^4$, and, R$^4$, at each occurrence, is heterocyclyl. In another embodiment of Formula (IA), Y$^1$ is

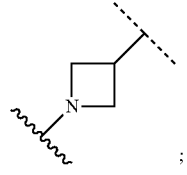

wherein ⁓ indicates the point of attachment to the carbonyl and ⁀ indicates the point of attachment to the nitrogen containing heteroaryl; R$^2$ is phenyl; wherein each R$^2$ phenyl is substituted with one R$^4$, and, R$^4$, at each occurrence, is heterocyclyl.

Still another embodiment pertains to compounds, which are

N-[4-({1-[(2S)-2-methylbutanoyl]azetidin-3-yl}oxy)phenyl]-3-(pyridin-3-yl)azetidine-1-carboxamide;

3-(pyridin-3-yl)-N-(4-{[1-(tetrahydro-2H-pyran-4-ylacetyl)piperidin-4-yl]oxy}phenyl)azetidine-1-carboxamide;

3-(5-fluoropyridin-3-yl)-N-(4-{[1-(tetrahydro-2H-pyran-4-ylacetyl)piperidin-4-yl]oxy}phenyl)azetidine-1-carboxamide;

N-[4-({1-[(2S)-2-methylbutanoyl]piperidin-4-yl}oxy)phenyl]-3-(pyridin-3-yl)azetidine-1-carboxamide;
3-(pyridin-3-yl)-N-[4-({1-[(2R)-tetrahydrofuran-2-ylcarbonyl]piperidin-4-yl}oxy)phenyl]azetidine-1-carboxamide;
3-(pyridin-3-yl)-N-(4-{[1-(3,3,3-trifluoropropanoyl)piperidin-4-yl]oxy}phenyl)azetidine-1-carboxamide;
N-(4-{[1-(2-hydroxy-2-methylpropanoyl)piperidin-4-yl]oxy}phenyl)-3-(pyridin-3-yl)azetidine-1-carboxamide;
3-(6-methylpyridin-3-yl)-N-(4-{[1-(tetrahydro-2H-pyran-4-ylacetyl)piperidin-4-yl]oxy}phenyl)azetidine-1-carboxamide;
N-(4-{1-[(2S)-2-methylbutanoyl]-1,2,3,6-tetrahydropyridin-4-yl}phenyl)-3-(pyridin-3-yl)azetidine-1-carboxamide;
3-(pyridin-3-yl)-N-(4-{1-[(2R)-tetrahydrofuran-2-ylcarbonyl]-1,2,3,6-tetrahydropyridin-4-yl}phenyl)azetidine-1-carboxamide;
3-(pyridin-3-yl)-N-(4-{1-[(2S)-tetrahydrofuran-2-ylcarbonyl]-1,2,3,6-tetrahydropyridin-4-yl}phenyl)azetidine-1-carboxamide;
N-{4-[1-(2-hydroxy-2-methylpropanoyl)-1,2,3,6-tetrahydropyridin-4-yl]phenyl}-3-(pyridin-3-yl)azetidine-1-carboxamide;
methyl 4-({[3-(pyridin-3-yl)azetidin-1-yl]carbonyl}amino)benzoate;
N-(4-cyanophenyl)-3-(pyridin-3-yl)azetidine-1-carboxamide;
tert-butyl 4-[4-({[3-(pyridin-3-yl)azetidin-1-yl]carbonyl}amino)butyl]piperidine-1-carboxylate;
N-{4-[1-(2,2-dimethylbutanoyl)-1,2,3,6-tetrahydropyridin-4-yl]phenyl}-3-(pyridin-3-yl)azetidine-1-carboxamide;
N-{4-[1-(3,3-dimethylbutanoyl)-1,2,3,6-tetrahydropyridin-4-yl]phenyl}-3-(pyridin-3-yl)azetidine-1-carboxamide;
3-(pyridin-3-yl)-N-{4-[1-(3,3,3-trifluoropropanoyl)-1,2,3,6-tetrahydropyridin-4-yl]phenyl}azetidine-1-carboxamide;
3-(pyridin-3-yl)-N-{4-[1-(4,4,4-trifluorobutanoyl)-1,2,3,6-tetrahydropyridin-4-yl]phenyl}azetidine-1-carboxamide;
N-{4-[1-(methoxyacetyl)-1,2,3,6-tetrahydropyridin-4-yl]phenyl}-3-(pyridin-3-yl)azetidine-1-carboxamide;
N-(4-{1-[(methylsulfanyl)acetyl]-1,2,3,6-tetrahydropyridin-4-yl}phenyl)-3-(pyridin-3-yl)azetidine-1-carboxamide;
N-(4-{1-(ethoxyacetyl)-1,2,3,6-tetrahydropyridin-4-yl}phenyl)-3-(pyridin-3-yl)azetidine-1-carboxamide;
N-(4-{1-[(2-methoxyethoxy)acetyl]-1,2,3,6-tetrahydropyridin-4-yl}phenyl)-3-(pyridin-3-yl)azetidine-1-carboxamide;
N-(4-{1-[3-(methylsulfanyl)propanoyl]-1,2,3,6-tetrahydropyridin-4-yl}phenyl)-3-(pyridin-3-yl)azetidine-1-carboxamide;
N-{4-[1-(cyclopropylcarbonyl)-1,2,3,6-tetrahydropyridin-4-yl]phenyl}-3-(pyridin-3-yl)azetidine-1-carboxamide;
N-{4-[1-(cyclopropylacetyl)-1,2,3,6-tetrahydropyridin-4-yl]phenyl}-3-(pyridin-3-yl)azetidine-1-carboxamide;
N-{4-[1-(2-methylpropanoyl)-1,2,3,6-tetrahydropyridin-4-yl]phenyl}-3-(pyridin-3-yl)azetidine-1-carboxamide;
3-(pyridin-3-yl)-N-[4-({1-[(2R)-tetrahydrofuran-2-ylcarbonyl]azetidin-3-yl}oxy)phenyl]azetidine-1-carboxamide;
3-(pyridin-3-yl)-N-[4-({1-[(2S)-tetrahydrofuran-2-ylcarbonyl]azetidin-3-yl}oxy)phenyl]azetidine-1-carboxamide;
N-(4-{[1-(2-hydroxy-2-methylpropanoyl)azetidin-3-yl]oxy}phenyl)-3-(pyridin-3-yl)azetidine-1-carboxamide;
3-(pyridin-3-yl)-N-[4-({1-[(2S)-tetrahydrofuran-2-ylcarbonyl]piperidin-4-yl}oxy)phenyl]azetidine-1-carboxamide;
3-(pyridin-3-yl)-N-(4-{[1-(thiophen-2-ylcarbonyl)piperidin-4-yl]oxy}phenyl)azetidine-1-carboxamide;
3-(pyridin-3-yl)-N-(4-{[1-(thiophen-3-ylcarbonyl)piperidin-4-yl]oxy}phenyl)azetidine-1-carboxamide;
N-[4-({1-[(1-acetylpiperidin-4-yl)carbonyl]piperidin-4-yl}oxy)phenyl]-3-(pyridin-3-yl)azetidine-1-carboxamide;
N-[4-({1-[(2-methylcyclopropyl)carbonyl]piperidin-4-yl}oxy)phenyl]-3-(pyridin-3-yl)azetidine-1-carboxamide;
N-[4-({1-[(1-methyl-1H-pyrrol-2-yl)carbonyl]piperidin-4-yl}oxy)phenyl]-3-(pyridin-3-yl)azetidine-1-carboxamide;
N-[4-({1-[3-(morpholin-4-yl)propanoyl]piperidin-4-yl}oxy)phenyl]-3-(pyridin-3-yl)azetidine-1-carboxamide;
N-[4-({1-[3-(4-methylpiperazin-1-yl)propanoyl]piperidin-4-yl}oxy)phenyl]-3-(pyridin-3-yl)azetidine-1-carboxamide;
3-(pyridin-3-yl)-N-[4-({1-[3-(pyrrolidin-1-yl)propanoyl]piperidin-4-yl}oxy)phenyl]azetidine-1-carboxamide;
N-(4-{[1-(cyclopropylacetyl)piperidin-4-yl]oxy}phenyl)-3-(pyridin-3-yl)azetidine-1-carboxamide;
N-(4-{[1-(3-methylpentanoyl)piperidin-4-yl]oxy}phenyl)-3-(pyridin-3-yl)azetidine-1-carboxamide;
N-(4-{[1-(4-methylpentanoyl)piperidin-4-yl]oxy}phenyl)-3-(pyridin-3-yl)azetidine-1-carboxamide;
N-{4-[(1-butanoylpiperidin-4-yl)oxy]phenyl}-3-(pyridin-3-yl)azetidine-1-carboxamide;
N-(4-{[1-(2,2-dimethylpropanoyl)piperidin-4-yl]oxy}phenyl)-3-(pyridin-3-yl)azetidine-1-carboxamide;
N-(4-{[1-(3,3-dimethylbutanoyl)piperidin-4-yl]oxy}phenyl)-3-(pyridin-3-yl)azetidine-1-carboxamide;
N-(4-{[1-(ethoxyacetyl)piperidin-4-yl]oxy}phenyl)-3-(pyridin-3-yl)azetidine-1-carboxamide;
N-(4-{[1-(cyclopropylcarbonyl)piperidin-4-yl]oxy}phenyl)-3-(pyridin-3-yl)azetidine-1-carboxamide;
N-(4-{[1-(methoxyacetyl)piperidin-4-yl]oxy}phenyl)-3-(pyridin-3-yl)azetidine-1-carboxamide;
3-(pyridin-3-yl)-N-{4-[(tetrahydrofuran-3-ylmethyl)carbamoyl]phenyl}azetidine-1-carboxamide;
3-(pyridin-3-yl)-N-{4-[1-(tetrahydro-2H-pyran-4-ylacetyl)piperidin-4-yl]phenyl}azetidine-1-carboxamide;
N-{4-[1-(2-hydroxy-2-methylpropanoyl)piperidin-4-yl]phenyl}-3-(pyridin-3-yl)azetidine-1-carboxamide;
3-(pyridin-3-yl)-N-(4-{1-[(2S)-tetrahydrofuran-2-ylcarbonyl]piperidin-4-yl}phenyl)azetidine-1-carboxamide;
3-(pyridin-3-yl)-N-{4-[1-(tetrahydrofuran-3-ylcarbonyl)piperidin-4-yl]phenyl}azetidine-1-carboxamide;
3-(pyridin-3-yl)-N-(4-{1-[(2R)-tetrahydrofuran-2-ylcarbonyl]piperidin-4-yl}phenyl)azetidine-1-carboxamide;
N-{4-[1-(cyclopropylacetyl)piperidin-4-yl]phenyl}-3-(pyridin-3-yl)azetidine-1-carboxamide;
N-{4-[1-(2-methylpropanoyl)piperidin-4-yl]phenyl}-3-(pyridin-3-yl)azetidine-1-carboxamide;
N-[4-(1-benzoylpiperidin-4-yl)phenyl]-3-(pyridin-3-yl)azetidine-1-carboxamide;
3-(pyridin-3-yl)-N-{4-[1-(3,3,3-trifluoropropanoyl)piperidin-4-yl]phenyl}azetidine-1-carboxamide;
tert-butyl 3-[4-({[3-(pyridin-3-yl)azetidin-1-yl]carbonyl}amino)phenyl]pyrrolidine-1-carboxylate;
tert-butyl (3R)-3-[4-({[3-(pyridin-3-yl)azetidin-1-yl]carbonyl}amino)phenoxy]pyrrolidine-1-carboxylate;
tert-butyl (3S)-3-[4-({[3-(pyridin-3-yl)azetidin-1-yl]carbonyl}amino)phenoxy]pyrrolidine-1-carboxylate;
tert-butyl 3-[4-({[3-(pyridin-3-yl)azetidin-1-yl]carbonyl}amino)phenyl]azetidine-1-carboxylate;
tert-butyl 3-[4-({[3-(pyridin-3-yl)azetidin-1-yl]carbonyl}amino)phenoxy]azetidine-1-carboxylate;
3-(pyridin-3-yl)-N-{4-[1-(tetrahydro-2H-pyran-4-ylacetyl)pyrrolidin-3-yl]phenyl}azetidine-1-carboxamide;

N-{4-[1-(2-methylpropanoyl)pyrrolidin-3-yl]phenyl}-3-(pyridin-3-yl)azetidine-1-carboxamide;
3-(pyridin-3-yl)-N-(4-{1-[(2S)-tetrahydrofuran-2-ylcarbonyl]pyrrolidin-3-yl}phenyl)azetidine-1-carboxamide;
3-(pyridin-3-yl)-N-(4-{1-[(2R)-tetrahydrofuran-2-ylcarbonyl]pyrrolidin-3-yl}phenyl)azetidine-1-carboxamide;
3-(pyridin-3-yl)-N-{4-[1-(tetrahydrofuran-3-ylcarbonyl)pyrrolidin-3-yl]phenyl}azetidine-1-carboxamide;
N-{4-[1-(cyclopropylacetyl)pyrrolidin-3-yl]phenyl}-3-(pyridin-3-yl)azetidine-1-carboxamide;
N-{4-[1-(2-hydroxy-2-methylpropanoyl)pyrrolidin-3-yl]phenyl}-3-(pyridin-3-yl)azetidine-1-carboxamide;
N-[4-(1-benzoylpyrrolidin-3-yl)phenyl]-3-(pyridin-3-yl)azetidine-1-carboxamide;
3-(pyridin-3-yl)-N-{4-[1-(3,3,3-trifluoropropanoyl)pyrrolidin-3-yl]phenyl}azetidine-1-carboxamide;
N-{4-[1-(cyclopropylcarbonyl)pyrrolidin-3-yl]phenyl}-3-(pyridin-3-yl)azetidine-1-carboxamide;
N-(4-{1-[(2S)-2-methylbutanoyl]pyrrolidin-3-yl}phenyl)-3-(pyridin-3-yl)azetidine-1-carboxamide;
N-[4-(1-butanoylpyrrolidin-3-yl)phenyl]-3-(pyridin-3-yl)azetidine-1-carboxamide;
3-(pyridin-3-yl)-N-(4-{[(3R)-1-(tetrahydro-2H-pyran-4-ylacetyl)pyrrolidin-3-yl]oxy}phenyl)azetidine-1-carboxamide;
N-(4-{[(3R)-1-(2-methylpropanoyl)pyrrolidin-3-yl]oxy}phenyl)-3-(pyridin-3-yl)azetidine-1-carboxamide;
3-(pyridin-3-yl)-N-[4-({(3R)-1-[(2S)-tetrahydrofuran-2-ylcarbonyl]pyrrolidin-3-yl}oxy)phenyl]azetidine-1-carboxamide;
3-(pyridin-3-yl)-N-[4-({(3R)-1-[(2R)-tetrahydrofuran-2-ylcarbonyl]pyrrolidin-3-yl}oxy)phenyl]azetidine-1-carboxamide;
3-(pyridin-3-yl)-N-(4-{[(3R)-1-(tetrahydrofuran-3-ylcarbonyl)pyrrolidin-3-yl]oxy}phenyl)azetidine-1-carboxamide;
N-(4-{[(3R)-1-(cyclopropylacetyl)pyrrolidin-3-yl]oxy}phenyl)-3-(pyridin-3-yl)azetidine-1-carboxamide;
N-(4-{[(3R)-1-(2-hydroxy-2-methylpropanoyl)pyrrolidin-3-yl]oxy}phenyl)-3-(pyridin-3-yl)azetidine-1-carboxamide;
N-(4-{[(3R)-1-benzoylpyrrolidin-3-yl]oxy}phenyl)-3-(pyridin-3-yl)azetidine-1-carboxamide;
3-(pyridin-3-yl)-N-(4-{[(3R)-1-(3,3,3-trifluoropropanoyl)pyrrolidin-3-yl]oxy}phenyl)azetidine-1-carboxamide;
N-(4-{[(3R)-1-(cyclopropylcarbonyl)pyrrolidin-3-yl]oxy}phenyl)-3-(pyridin-3-yl)azetidine-1-carboxamide;
N-[4-({(3R)-1-[(2S)-2-methylbutanoyl]pyrrolidin-3-yl}oxy)phenyl]-3-(pyridin-3-yl)azetidine-1-carboxamide;
N-(4-{[(3R)-1-butanoylpyrrolidin-3-yl]oxy}phenyl)-3-(pyridin-3-yl)azetidine-1-carboxamide;
3-(pyridin-3-yl)-N-(4-{[(3S)-1-(tetrahydro-2H-pyran-4-ylacetyl)pyrrolidin-3-yl]oxy}phenyl)azetidine-1-carboxamide;
N-(4-{[(3S)-1-(2-methylpropanoyl)pyrrolidin-3-yl]oxy}phenyl)-3-(pyridin-3-yl)azetidine-1-carboxamide;
3-(pyridin-3-yl)-N-[4-({(3S)-1-[(2S)-tetrahydrofuran-2-ylcarbonyl]pyrrolidin-3-yl}oxy)phenyl]azetidine-1-carboxamide;
3-(pyridin-3-yl)-N-[4-({(3S)-1-[(2R)-tetrahydrofuran-2-ylcarbonyl]pyrrolidin-3-yl}oxy)phenyl]azetidine-1-carboxamide;
3-(pyridin-3-yl)-N-(4-{[(3S)-1-(tetrahydrofuran-3-ylcarbonyl)pyrrolidin-3-yl]oxy}phenyl)azetidine-1-carboxamide;
N-(4-{[(3S)-1-(cyclopropylacetyl)pyrrolidin-3-yl]oxy}phenyl)-3-(pyridin-3-yl)azetidine-1-carboxamide;
N-(4-{[(3S)-1-(2-hydroxy-2-methylpropanoyl)pyrrolidin-3-yl]oxy}phenyl)-3-(pyridin-3-yl)azetidine-1-carboxamide;
N-(4-{[(3S)-1-benzoylpyrrolidin-3-yl]oxy}phenyl)-3-(pyridin-3-yl)azetidine-1-carboxamide;
3-(pyridin-3-yl)-N-(4-{[(3S)-1-(3,3,3-trifluoropropanoyl)pyrrolidin-3-yl]oxy}phenyl)azetidine-1-carboxamide;
N-(4-{[(3S)-1-(cyclopropylcarbonyl)pyrrolidin-3-yl]oxy}phenyl)-3-(pyridin-3-yl)azetidine-1-carboxamide;
N-[4-({(3S)-1-[(2S)-2-methylbutanoyl]pyrrolidin-3-yl}oxy)phenyl]-3-(pyridin-3-yl)azetidine-1-carboxamide;
N-(4-{[(3S)-1-butanoylpyrrolidin-3-yl]oxy}phenyl)-3-(pyridin-3-yl)azetidine-1-carboxamide;
3-(pyridin-3-yl)-N-{4-[1-(tetrahydro-2H-pyran-4-ylacetyl)azetidin-3-yl]phenyl}azetidine-1-carboxamide;
N-{4-[1-(2-methylpropanoyl)azetidin-3-yl]phenyl}-3-(pyridin-3-yl)azetidine-1-carboxamide;
3-(pyridin-3-yl)-N-(4-{1-[(2S)-tetrahydrofuran-2-ylcarbonyl]azetidin-3-yl}phenyl)azetidine-1-carboxamide;
3-(pyridin-3-yl)-N-(4-{1-[(2R)-tetrahydrofuran-2-ylcarbonyl]azetidin-3-yl}phenyl)azetidine-1-carboxamide;
3-(pyridin-3-yl)-N-{4-[1-(tetrahydrofuran-3-ylcarbonyl)azetidin-3-yl]phenyl}azetidine-1-carboxamide;
N-{4-[1-(cyclopropylacetyl)azetidin-3-yl]phenyl}-3-(pyridin-3-yl)azetidine-1-carboxamide;
N-{4-[1-(2-hydroxy-2-methylpropanoyl)azetidin-3-yl]phenyl}-3-(pyridin-3-yl)azetidine-1-carboxamide;
N-[4-(1-benzoylazetidin-3-yl)phenyl]-3-(pyridin-3-yl)azetidine-1-carboxamide;
3-(pyridin-3-yl)-N-{4-[1-(3,3,3-trifluoropropanoyl)azetidin-3-yl]phenyl}azetidine-1-carboxamide;
N-{4-[1-(cyclopropylcarbonyl)azetidin-3-yl]phenyl}-3-(pyridin-3-yl)azetidine-1-carboxamide;
N-(4-{1-[(2S)-2-methylbutanoyl]azetidin-3-yl}phenyl)-3-(pyridin-3-yl)azetidine-1-carboxamide;
N-[4-(1-butanoylazetidin-3-yl)phenyl]-3-(pyridin-3-yl)azetidine-1-carboxamide;
tert-butyl 4-[4-({[3-(2-chloropyridin-3-yl)azetidin-1-yl]carbonyl}amino)phenyl]piperidine-1-carboxylate;
tert-butyl 4-[4-({[3-(4-chloropyridin-3-yl)azetidin-1-yl]carbonyl}amino)phenyl]piperidine-1-carboxylate;
N-(4-{[1-(cyclopropylacetyl)azetidin-3-yl]oxy}phenyl)-3-(pyridin-3-yl)azetidine-1-carboxamide;
N-(4-{[1-(furan-2-ylcarbonyl)azetidin-3-yl]oxy}phenyl)-3-(pyridin-3-yl)azetidine-1-carboxamide;
tert-butyl 4-[4-({[3-(2-fluoropyridin-3-yl)azetidin-1-yl]carbonyl}amino)phenyl]piperidine-1-carboxylate;
N-{4-[(1-pentanoylazetidin-3-yl)oxy]phenyl}-3-(pyridin-3-yl)azetidine-1-carboxamide;
N-[4-({1-[(2-methoxyethoxy)acetyl]azetidin-3-yl}oxy)phenyl]-3-(pyridin-3-yl)azetidine-1-carboxamide;
N-(4-{[1-(ethoxyacetyl)azetidin-3-yl]oxy}phenyl)-3-(pyridin-3-yl)azetidine-1-carboxamide;
N-(4-{[1-(methoxyacetyl)azetidin-3-yl]oxy}phenyl)-3-(pyridin-3-yl)azetidine-1-carboxamide;
N-(4-{[1-(3-methylpentanoyl)azetidin-3-yl]oxy}phenyl)-3-(pyridin-3-yl)azetidine-1-carboxamide;
N-[4-({1-[(1 S,4R)-bicyclo[2.2.1]hept-2-ylacetyl]azetidin-3-yl}oxy)phenyl]-3-(pyridin-3-yl)azetidine-1-carboxamide;
N-(4-{[1-(2,3-dimethylbutanoyl)azetidin-3-yl]oxy}phenyl)-3-(pyridin-3-yl)azetidine-1-carboxamide;
N-(4-{[1-(4-methylpentanoyl)azetidin-3-yl]oxy}phenyl)-3-(pyridin-3-yl)azetidine-1-carboxamide;

N-[4-({1-[(2-methylcyclopropyl)carbonyl]azetidin-3-yl}oxy)phenyl]-3-(pyridin-3-yl)azetidine-1-carboxamide;
3-(pyridin-3-yl)-N-(4-{[1-(4,4,4-trifluorobutanoyl)azetidin-3-yl]oxy}phenyl)azetidine-1-carboxamide;
N-(4-{[1-(2-methylpropanoyl)azetidin-3-yl]oxy}phenyl)-3-(pyridin-3-yl)azetidine-1-carboxamide;
N-(4-{[1-(2,2-dimethylpropanoyl)azetidin-3-yl]oxy}phenyl)-3-(pyridin-3-yl)azetidine-1-carboxamide;
N-{4-[(1-butanoylazetidin-3-yl)oxy]phenyl}-3-(pyridin-3-yl)azetidine-1-carboxamide;
N-{4-[(1-propanoylazetidin-3-yl)oxy]phenyl}-3-(pyridin-3-yl)azetidine-1-carboxamide;
N-(4-{[1-(2,2-dimethylbutanoyl)azetidin-3-yl]oxy}phenyl)-3-(pyridin-3-yl)azetidine-1-carboxamide;
N-(4-{[1-(3-methylbutanoyl)azetidin-3-yl]oxy}phenyl)-3-(pyridin-3-yl)azetidine-1-carboxamide;
N-(4-{[1-(3,3-dimethylbutanoyl)azetidin-3-yl]oxy}phenyl)-3-(pyridin-3-yl)azetidine-1-carboxamide;
3-(pyridin-3-yl)-N-(4-{[1-(3,3,3-trifluoropropanoyl)azetidin-3-yl]oxy}phenyl)azetidine-1-carboxamide;
N-[4-({1-[(1-methylcyclopropyl)carbonyl]azetidin-3-yl}oxy)phenyl]-3-(pyridin-3-yl)azetidine-1-carboxamide;
N-(4-{[1-(2-methylpentanoyl)azetidin-3-yl]oxy}phenyl)-3-(pyridin-3-yl)azetidine-1-carboxamide;
N-{4-[(1-acetylazetidin-3-yl)oxy]phenyl}-3-(pyridin-3-yl)azetidine-1-carboxamide;
N-(4-{[1-(cyclohexylacetyl)azetidin-3-yl]oxy}phenyl)-3-(pyridin-3-yl)azetidine-1-carboxamide;
N-(4-{[1-(cyclohexylcarbonyl)azetidin-3-yl]oxy}phenyl)-3-(pyridin-3-yl)azetidine-1-carboxamide;
N-(4-{[1-(cyclopropylcarbonyl)azetidin-3-yl]oxy}phenyl)-3-(pyridin-3-yl)azetidine-1-carboxamide;
3-(pyridin-3-yl)-N-(4-{[1-(thiophen-2-ylcarbonyl)azetidin-3-yl]oxy}phenyl)azetidine-1-carboxamide;
N-(4-{[1-(cyclopentylcarbonyl)azetidin-3-yl]oxy}phenyl)-3-(pyridin-3-yl)azetidine-1-carboxamide;
N-(4-{[1-(morpholin-4-ylacetyl)azetidin-3-yl]oxy}phenyl)-3-(pyridin-3-yl)azetidine-1-carboxamide;
3-(pyridin-3-yl)-N-(4-{[1-(1,3-thiazol-5-ylcarbonyl)azetidin-3-yl]oxy}phenyl)azetidine-1-carboxamide;
N-[4-({1-[(3,5-dimethyl-1,2-oxazol-4-yl)carbonyl]azetidin-3-yl}oxy)phenyl]-3-(pyridin-3-yl)azetidine-1-carboxamide;
3-(pyridin-3-yl)-N-(4-{[1-(thiophen-3-ylcarbonyl)azetidin-3-yl]oxy}phenyl)azetidine-1-carboxamide;
3-(pyridin-3-yl)-N-(4-{[1-(1,3-thiazol-4-ylcarbonyl)azetidin-3-yl]oxy}phenyl)azetidine-1-carboxamide;
N-(4-{[1-(1,2-oxazol-5-ylcarbonyl)azetidin-3-yl]oxy}phenyl)-3-(pyridin-3-yl)azetidine-1-carboxamide;
N-[4-({1-[(4-methylpiperazin-1-yl)acetyl]azetidin-3-yl}oxy)phenyl]-3-(pyridin-3-yl)azetidine-1-carboxamide;
N-(4-{[1-(N,N-dimethyl-beta-alanyl)azetidin-3-yl]oxy}phenyl)-3-(pyridin-3-yl)azetidine-1-carboxamide;
N-(4-{[1-(furan-3-ylcarbonyl)azetidin-3-yl]oxy}phenyl)-3-(pyridin-3-yl)azetidine-1-carboxamide;
N-[4-({1-[(1-methylcyclohexyl)carbonyl]azetidin-3-yl}oxy)phenyl]-3-(pyridin-3-yl)azetidine-1-carboxamide;
N-(4-{[1-(cyclopentylacetyl)azetidin-3-yl]oxy}phenyl)-3-(pyridin-3-yl)azetidine-1-carboxamide;
3-(pyridin-3-yl)-N-(4-{[1-(1,3-thiazol-2-ylcarbonyl)azetidin-3-yl]oxy}phenyl)azetidine-1-carboxamide;
3-(pyridin-3-yl)-N-(4-{[1-(pyrrolidin-1-ylacetyl)azetidin-3-yl]oxy}phenyl)azetidine-1-carboxamide;
3-(2-fluoropyridin-3-yl)-N-{4-[1-(2-hydroxy-2-methylpropanoyl)piperidin-4-yl]phenyl}azetidine-1-carboxamide;
N-{4-[1-(2-methylpropyl)-1H-pyrazol-4-yl]phenyl}-3-(pyridin-3-yl)azetidine-1-carboxamide;
N-[4-(1-propyl-1H-pyrazol-4-yl)phenyl]-3-(pyridin-3-yl)azetidine-1-carboxamide;
3-(pyridin-3-yl)-N-(4-{1-[(3S)-tetrahydrofuran-3-ylcarbonyl]piperidin-4-yl}phenyl)azetidine-1-carboxamide;
3-(4-chloropyridin-3-yl)-N-(4-{1-[(3S)-tetrahydrofuran-3-ylcarbonyl]piperidin-4-yl}phenyl)azetidine-1-carboxamide;
3-(2-chloropyridin-3-yl)-N-{4-[1-(2-hydroxy-2-methylpropanoyl)piperidin-4-yl]phenyl}azetidine-1-carboxamide;
4-(pyridin-3-yl)-N-(4-{[1-(tetrahydro-2H-pyran-4-ylacetyl)piperidin-4-yl]oxy}phenyl)piperazine-1-carboxamide;
N-[4-(1-pentanoylpiperidin-4-yl)phenyl]-3-(pyridin-3-yl)azetidine-1-carboxamide;
N-(4-{1-[(2-methylcyclopropyl)carbonyl]piperidin-4-yl}phenyl)-3-(pyridin-3-yl)azetidine-1-carboxamide;
N-(4-{1-[(1S,4R)-bicyclo[2.2.1]hept-2-ylacetyl]piperidin-4-yl}phenyl)-3-(pyridin-3-yl)azetidine-1-carboxamide;
N-{4-[1-(4-methylpentanoyl)piperidin-4-yl]phenyl}-3-(pyridin-3-yl)azetidine-1-carboxamide;
N-{4-[1-(3-methylpentanoyl)piperidin-4-yl]phenyl}-3-(pyridin-3-yl)azetidine-1-carboxamide;
N-{4-[1-(3-ethoxypropanoyl)piperidin-4-yl]phenyl}-3-(pyridin-3-yl)azetidine-1-carboxamide;
N-{4-[1-(2,2-dimethylbutanoyl)piperidin-4-yl]phenyl}-3-(pyridin-3-yl)azetidine-1-carboxamide;
N-{4-[1-(3,3-dimethylbutanoyl)piperidin-4-yl]phenyl}-3-(pyridin-3-yl)azetidine-1-carboxamide;
N-{4-[1-(2,2-dimethylpropanoyl)piperidin-4-yl]phenyl}-3-(pyridin-3-yl)azetidine-1-carboxamide;
N-[4-(1-butanoylpiperidin-4-yl)phenyl]-3-(pyridin-3-yl)azetidine-1-carboxamide;
N-{4-[1-(ethoxyacetyl)piperidin-4-yl]phenyl}-3-(pyridin-3-yl)azetidine-1-carboxamide;
N-{4-[1-(3-methylbutanoyl)piperidin-4-yl]phenyl}-3-(pyridin-3-yl)azetidine-1-carboxamide;
N-{4-[1-(N-acetyl-L-leucyl)piperidin-4-yl]phenyl}-3-(pyridin-3-yl)azetidine-1-carboxamide;
N-(4-{1-[(2-methoxyethoxy)acetyl]piperidin-4-yl}phenyl)-3-(pyridin-3-yl)azetidine-1-carboxamide;
N-{4-[1-(cyclohexylcarbonyl)piperidin-4-yl]phenyl}-3-(pyridin-3-yl)azetidine-1-carboxamide;
N-{4-[1-(cyclohexylacetyl)piperidin-4-yl]phenyl}-3-(pyridin-3-yl)azetidine-1-carboxamide;
3-(pyridin-3-yl)-N-{4-[1-(4,4,4-trifluorobutanoyl)piperidin-4-yl]phenyl}azetidine-1-carboxamide;
N-{4-[1-(cyclopentylcarbonyl)piperidin-4-yl]phenyl}-3-(pyridin-3-yl)azetidine-1-carboxamide;
N-(4-{1-[(1-methylcyclohexyl)carbonyl]piperidin-4-yl}phenyl)-3-(pyridin-3-yl)azetidine-1-carboxamide;
N-{4-[1-(furan-3-ylcarbonyl)piperidin-4-yl]phenyl}-3-(pyridin-3-yl)azetidine-1-carboxamide;
N-[4-(1-acetylpiperidin-4-yl)phenyl]-3-(pyridin-3-yl)azetidine-1-carboxamide;
N-{4-[1-(methoxyacetyl)piperidin-4-yl]phenyl}-3-(pyridin-3-yl)azetidine-1-carboxamide;
3-(pyridin-3-yl)-N-{4-[1-(thiophen-3-ylcarbonyl)piperidin-4-yl]phenyl}azetidine-1-carboxamide;
N-(4-{1-[(3-methylthiophen-2-yl)carbonyl]piperidin-4-yl}phenyl)-3-(pyridin-3-yl)azetidine-1-carboxamide;
N-{4-[1-(morpholin-4-ylacetyl)piperidin-4-yl]phenyl}-3-(pyridin-3-yl)azetidine-1-carboxamide;
3-(pyridin-3-yl)-N-{4-[1-(thiophen-2-ylcarbonyl)piperidin-4-yl]phenyl}azetidine-1-carboxamide;

N-(4-{1-[(5-methylthiophen-2-yl)carbonyl]piperidin-4-yl}phenyl)-3-(pyridin-3-yl)azetidine-1-carboxamide;
N-{4-[1-(furan-2-ylcarbonyl)piperidin-4-yl]phenyl}-3-(pyridin-3-yl)azetidine-1-carboxamide;
N-(4-{1-[(1-methyl-1H-pyrrol-2-yl)carbonyl]piperidin-4-yl}phenyl)-3-(pyridin-3-yl)azetidine-1-carboxamide;
N-[4-(1-propanoylpiperidin-4-yl)phenyl]-3-(pyridin-3-yl)azetidine-1-carboxamide;
N-(4-{1-[(1-methylcyclopropyl)carbonyl]piperidin-4-yl}phenyl)-3-(pyridin-3-yl)azetidine-1-carboxamide;
3-(pyridin-3-yl)-N-{4-[1-(pyrrolidin-1-ylacetyl)piperidin-4-yl]phenyl}azetidine-1-carboxamide;
3-(pyridin-3-yl)-N-{4-[1-(1,3-thiazol-2-ylcarbonyl)piperidin-4-yl]phenyl}azetidine-1-carboxamide;
N-{4-[1-(cyclopentylacetyl)piperidin-4-yl]phenyl}-3-(pyridin-3-yl)azetidine-1-carboxamide;
N-{4-[1-(2,3-dimethylbutanoyl)piperidin-4-yl]phenyl}-3-(pyridin-3-yl)azetidine-1-carboxamide;
N-[4-(1-pentanoylazetidin-3-yl)phenyl]-3-(pyridin-3-yl)azetidine-1-carboxamide;
N-(4-{1-[(2-methylcyclopropyl)carbonyl]azetidin-3-yl}phenyl)-3-(pyridin-3-yl)azetidine-1-carboxamide;
N-(4-{1-[(1S,4R)-bicyclo[2.2.1]hept-2-ylacetyl]azetidin-3-yl}phenyl)-3-(pyridin-3-yl)azetidine-1-carboxamide;
N-{4-[1-(4-methylpentanoyl)azetidin-3-yl]phenyl}-3-(pyridin-3-yl)azetidine-1-carboxamide;
N-{4-[1-(3-methylpentanoyl)azetidin-3-yl]phenyl}-3-(pyridin-3-yl)azetidine-1-carboxamide;
N-{4-[1-(3-ethoxypropanoyl)azetidin-3-yl]phenyl}-3-(pyridin-3-yl)azetidine-1-carboxamide;
N-{4-[1-(2,2-dimethylbutanoyl)azetidin-3-yl]phenyl}-3-(pyridin-3-yl)azetidine-1-carboxamide;
N-{4-[1-(3,3-dimethylbutanoyl)azetidin-3-yl]phenyl}-3-(pyridin-3-yl)azetidine-1-carboxamide;
N-{4-[1-(2,2-dimethylpropanoyl)azetidin-3-yl]phenyl}-3-(pyridin-3-yl)azetidine-1-carboxamide;
N-{4-[1-(ethoxyacetyl)azetidin-3-yl]phenyl}-3-(pyridin-3-yl)azetidine-1-carboxamide;
N-{4-[1-(3-methylbutanoyl)azetidin-3-yl]phenyl}-3-(pyridin-3-yl)azetidine-1-carboxamide;
N-{4-[1-(N-acetyl-L-leucyl)azetidin-3-yl]phenyl}-3-(pyridin-3-yl)azetidine-1-carboxamide;
N-(4-{1-[(2-methoxyethoxy)acetyl]azetidin-3-yl}phenyl)-3-(pyridin-3-yl)azetidine-1-carboxamide;
N-{4-[1-(cyclohexylcarbonyl)azetidin-3-yl]phenyl}-3-(pyridin-3-yl)azetidine-1-carboxamide;
N-{4-[1-(cyclohexylacetyl)azetidin-3-yl]phenyl}-3-(pyridin-3-yl)azetidine-1-carboxamide;
3-(pyridin-3-yl)-N-{4-[1-(4,4,4-trifluorobutanoyl)azetidin-3-yl]phenyl}azetidine-1-carboxamide;
N-{4-[1-(cyclopentylcarbonyl)azetidin-3-yl]phenyl}-3-(pyridin-3-yl)azetidine-1-carboxamide;
N-(4-{1-[(1-methylcyclohexyl)carbonyl]azetidin-3-yl}phenyl)-3-(pyridin-3-yl)azetidine-1-carboxamide;
N-{4-[1-(furan-3-ylcarbonyl)azetidin-3-yl]phenyl}-3-(pyridin-3-yl)azetidine-1-carboxamide;
N-[4-(1-acetylazetidin-3-yl)phenyl]-3-(pyridin-3-yl)azetidine-1-carboxamide;
N-{4-[1-(methoxyacetyl)azetidin-3-yl]phenyl}-3-(pyridin-3-yl)azetidine-1-carboxamide;
3-(pyridin-3-yl)-N-{4-[1-(thiophen-3-ylcarbonyl)azetidin-3-yl]phenyl}azetidine-1-carboxamide;
N-(4-{1-[(3-methylthiophen-2-yl)carbonyl]azetidin-3-yl}phenyl)-3-(pyridin-3-yl)azetidine-1-carboxamide;
N-{4-[1-(morpholin-4-ylacetyl) azetidin-3-yl]phenyl}-3-(pyridin-3-yl)azetidine-1-carboxamide;
3-(pyridin-3-yl)-N-{4-[1-(thiophen-2-ylcarbonyl)azetidin-3-yl]phenyl}azetidine-1-carboxamide;
N-(4-{1-[(5-methylthiophen-2-yl)carbonyl]azetidin-3-yl}phenyl)-3-(pyridin-3-yl)azetidine-1-carboxamide;
N-{4-[1-(furan-2-ylcarbonyl)azetidin-3-yl]phenyl}-3-(pyridin-3-yl)azetidine-1-carboxamide;
N-(4-{1-[(1-methyl-1H-pyrrol-2-yl)carbonyl]azetidin-3-yl}phenyl)-3-(pyridin-3-yl)azetidine-1-carboxamide;
N-[4-(1-propanoylazetidin-3-yl)phenyl]-3-(pyridin-3-yl)azetidine-1-carboxamide;
N-(4-{1-[(1-methylcyclopropyl)carbonyl]azetidin-3-yl}phenyl)-3-(pyridin-3-yl)azetidine-1-carboxamide;
3-(pyridin-3-yl)-N-{4-[1-(1,3-thiazol-2-ylcarbonyl)azetidin-3-yl]phenyl}azetidine-1-carboxamide;
N-{4-[1-(cyclopentylacetyl)azetidin-3-yl]phenyl}-3-(pyridin-3-yl)azetidine-1-carboxamide;
N-{4-[1-(2,3-dimethylbutanoyl)azetidin-3-yl]phenyl}-3-(pyridin-3-yl)azetidine-1-carboxamide;
N-{4-[1-(cyclopentylmethyl)piperidin-4-yl]phenyl}-3-(pyridin-3-yl)azetidine-1-carboxamide;
N-{4-[1-(cyclohexylmethyl)piperidin-4-yl]phenyl}-3-(pyridin-3-yl)azetidine-1-carboxamide;
N-{4-[1-(3,3-dimethylbutyl)piperidin-4-yl]phenyl}-3-(pyridin-3-yl)azetidine-1-carboxamide;
N-{4-[1-(2-methylpentyl)piperidin-4-yl]phenyl}-3-(pyridin-3-yl)azetidine-1-carboxamide;
N-{4-[1-(2-methylpropyl)piperidin-4-yl]phenyl}-3-(pyridin-3-yl)azetidine-1-carboxamide;
N-{4-[1-(3-methylbutyl)piperidin-4-yl]phenyl}-3-(pyridin-3-yl)azetidine-1-carboxamide;
N-{4-[1-(2-ethylbutyl)piperidin-4-yl]phenyl}-3-(pyridin-3-yl)azetidine-1-carboxamide;
N-{4-[1-(2,2-dimethylpropyl)piperidin-4-yl]phenyl}-3-(pyridin-3-yl)azetidine-1-carboxamide;
N-{4-[1-(2-methylbutyl)piperidin-4-yl]phenyl}-3-(pyridin-3-yl)azetidine-1-carboxamide;
N-[4-(1-butylpiperidin-4-yl)phenyl]-3-(pyridin-3-yl)azetidine-1-carboxamide;
N-[4-(1-propylpiperidin-4-yl)phenyl]-3-(pyridin-3-yl)azetidine-1-carboxamide;
N-{4-[1-(2-cyclopropylethyl)piperidin-4-yl]phenyl}-3-(pyridin-3-yl)azetidine-1-carboxamide;
3-(pyridin-3-yl)-N-{4-[1-(tetrahydrofuran-3-ylmethyl)piperidin-4-yl]phenyl}azetidine-1-carboxamide;
N-{4-[1-(2,2-dimethylbutyl)piperidin-4-yl]phenyl}-3-(pyridin-3-yl)azetidine-1-carboxamide;
N-{4-[1-(cyclopentylmethyl)azetidin-3-yl]phenyl}-3-(pyridin-3-yl)azetidine-1-carboxamide;
N-{4-[1-(cyclohexylmethyl)azetidin-3-yl]phenyl}-3-(pyridin-3-yl)azetidine-1-carboxamide;
N-{4-[1-(3,3-dimethylbutyl)azetidin-3-yl]phenyl}-3-(pyridin-3-yl)azetidine-1-carboxamide;
N-{4-[1-(cyclopropylmethyl)azetidin-3-yl]phenyl}-3-(pyridin-3-yl)azetidine-1-carboxamide;
N-{4-[1-(2-methylpentyl)azetidin-3-yl]phenyl}-3-(pyridin-3-yl)azetidine-1-carboxamide;
3-(pyridin-3-yl)-N-{4-[1-(tetrahydrofuran-2-ylmethyl)azetidin-3-yl]phenyl}azetidine-1-carboxamide;
N-{4-[1-(2-methylpropyl)azetidin-3-yl]phenyl}-3-(pyridin-3-yl)azetidine-1-carboxamide;
N-{4-[1-(3-methylbutyl)azetidin-3-yl]phenyl}-3-(pyridin-3-yl)azetidine-1-carboxamide;
N-{4-[1-(2-ethylbutyl)azetidin-3-yl]phenyl}-3-(pyridin-3-yl)azetidine-1-carboxamide;
N-{4-[1-(2,2-dimethylpropyl)azetidin-3-yl]phenyl}-3-(pyridin-3-yl)azetidine-1-carboxamide;

N-{4-[1-(2-methylbutyl)azetidin-3-yl]phenyl}-3-(pyridin-3-yl)azetidine-1-carboxamide;
3-(pyridin-3-yl)-N-{4-[1-(tetrahydrofuran-3-ylmethyl)azetidin-3-yl]phenyl}azetidine-1-carboxamide;
N-{4-[1-(2,2-dimethylbutyl)azetidin-3-yl]phenyl}-3-(pyridin-3-yl)azetidine-1-carboxamide;
N-[4-(1-pentanoylpyrrolidin-3-yl)phenyl]-3-(pyridin-3-yl)azetidine-1-carboxamide;
N-{4-[1-(3-methylpentanoyl)pyrrolidin-3-yl]phenyl}-3-(pyridin-3-yl)azetidine-1-carboxamide;
N-(4-{1-[(1S,4R)-bicyclo[2.2.1]hept-2-ylacetyl]pyrrolidin-3-yl}phenyl)-3-(pyridin-3-yl)azetidine-1-carboxamide;
N-{4-[1-(cyclopentylacetyl)pyrrolidin-3-yl]phenyl}-3-(pyridin-3-yl)azetidine-1-carboxamide;
N-(4-{1-[(2-methylcyclopropyl)carbonyl]pyrrolidin-3-yl}phenyl)-3-(pyridin-3-yl)azetidine-1-carboxamide;
N-{4-[1-(morpholin-4-ylacetyl)pyrrolidin-3-yl]phenyl}-3-(pyridin-3-yl)azetidine-1-carboxamide;
N-{4-[1-(furan-3-ylcarbonyl)pyrrolidin-3-yl]phenyl}-3-(pyridin-3-yl)azetidine-1-carboxamide;
3-(pyridin-3-yl)-N-{4-[1-(pyrrolidin-1-ylacetyl)pyrrolidin-3-yl]phenyl}azetidine-1-carboxamide;
N-{4-[1-(N,N-dimethyl-beta-alanyl)pyrrolidin-3-yl]phenyl}-3-(pyridin-3-yl)azetidine-1-carboxamide;
3-(pyridin-3-yl)-N-{4-[1-(1,3-thiazol-2-ylcarbonyl)pyrrolidin-3-yl]phenyl}azetidine-1-carboxamide;
3-(pyridin-3-yl)-N-{4-[1-(thiophen-3-ylcarbonyl)pyrrolidin-3-yl]phenyl}azetidine-1-carboxamide;
N-(4-{1-[(1-methylcyclopropyl)carbonyl]pyrrolidin-3-yl}phenyl)-3-(pyridin-3-yl)azetidine-1-carboxamide;
N-(4-{1-[(3-methylthiophen-2-yl)carbonyl]pyrrolidin-3-yl}phenyl)-3-(pyridin-3-yl)azetidine-1-carboxamide;
3-(pyridin-3-yl)-N-{4-[1-(4,4,4-trifluorobutanoyl)pyrrolidin-3-yl]phenyl}azetidine-1-carboxamide;
N-(4-{1-[(4-methylpiperazin-1-yl)acetyl]pyrrolidin-3-yl}phenyl)-3-(pyridin-3-yl)azetidine-1-carboxamide;
N-{4-[1-(5-oxo-L-prolyl)pyrrolidin-3-yl]phenyl}-3-(pyridin-3-yl)azetidine-1-carboxamide;
N-{4-[1-(3-ethoxypropanoyl)pyrrolidin-3-yl]phenyl}-3-(pyridin-3-yl)azetidine-1-carboxamide;
N-{4-[1-(4-methylpentanoyl)pyrrolidin-3-yl]phenyl}-3-(pyridin-3-yl)azetidine-1-carboxamide;
N-(4-{1-[(1-methylcyclohexyl)carbonyl]pyrrolidin-3-yl}phenyl)-3-(pyridin-3-yl)azetidine-1-carboxamide;
N-[4-(1-acetylpyrrolidin-3-yl)phenyl]-3-(pyridin-3-yl)azetidine-1-carboxamide;
N-{4-[1-(cyclohexylacetyl)pyrrolidin-3-yl]phenyl}-3-(pyridin-3-yl)azetidine-1-carboxamide;
N-[4-(1-propanoylpyrrolidin-3-yl)phenyl]-3-(pyridin-3-yl)azetidine-1-carboxamide;
N-(4-{1-[(2-methoxyethoxy)acetyl]pyrrolidin-3-yl}phenyl)-3-(pyridin-3-yl)azetidine-1-carboxamide;
N-(4-{1-[3-(morpholin-4-yl)propanoyl]pyrrolidin-3-yl}phenyl)-3-(pyridin-3-yl)azetidine-1-carboxamide;
N-{4-[1-(2,2-dimethylpropanoyl)pyrrolidin-3-yl]phenyl}-3-(pyridin-3-yl)azetidine-1-carboxamide;
N-(4-{1-[(5-methylthiophen-2-yl)carbonyl]pyrrolidin-3-yl}phenyl)-3-(pyridin-3-yl)azetidine-1-carboxamide;
3-(pyridin-3-yl)-N-{4-[1-(thiophen-2-ylcarbonyl)pyrrolidin-3-yl]phenyl}azetidine-1-carboxamide;
N-(4-{1-[(1-methyl-1H-pyrrol-2-yl)carbonyl]pyrrolidin-3-yl}phenyl)-3-(pyridin-3-yl)azetidine-1-carboxamide;
N-{4-[1-(furan-2-ylcarbonyl)pyrrolidin-3-yl]phenyl}-3-(pyridin-3-yl)azetidine-1-carboxamide;
N-(4-{1-[3-(piperidin-1-yl)propanoyl]pyrrolidin-3-yl}phenyl)-3-(pyridin-3-yl)azetidine-1-carboxamide;
N-{4-[1-(ethoxyacetyl)pyrrolidin-3-yl]phenyl}-3-(pyridin-3-yl)azetidine-1-carboxamide;
N-{4-[1-(3,3-dimethylbutanoyl)pyrrolidin-3-yl]phenyl}-3-(pyridin-3-yl)azetidine-1-carboxamide;
N-{4-[1-(2,2-dimethylbutanoyl)pyrrolidin-3-yl]phenyl}-3-(pyridin-3-yl)azetidine-1-carboxamide;
N-{4-[1-(2-oxopropanoyl)pyrrolidin-3-yl]phenyl}-3-(pyridin-3-yl)azetidine-1-carboxamide;
N-{4-[1-(methoxyacetyl)pyrrolidin-3-yl]phenyl}-3-(pyridin-3-yl)azetidine-1-carboxamide;
N-{4-[1-(cyclohexylcarbonyl)pyrrolidin-3-yl]phenyl}-3-(pyridin-3-yl)azetidine-1-carboxamide;
N-{4-[1-(3-methylbutanoyl)pyrrolidin-3-yl]phenyl}-3-(pyridin-3-yl)azetidine-1-carboxamide;
N-{4-[1-(cyclopentylcarbonyl)pyrrolidin-3-yl]phenyl}-3-(pyridin-3-yl)azetidine-1-carboxamide;
N-{4-[1-(2,3-dimethylbutanoyl)pyrrolidin-3-yl]phenyl}-3-(pyridin-3-yl)azetidine-1-carboxamide;
N-(4-{[(3R)-1-pentanoylpyrrolidin-3-yl]oxy}phenyl)-3-(pyridin-3-yl)azetidine-1-carboxamide;
N-(4-{[(3R)-1-(3-methylpentanoyl)pyrrolidin-3-yl]oxy}phenyl)-3-(pyridin-3-yl)azetidine-1-carboxamide;
N-(4-{[1-(bicyclo[2.2.1]hept-2-ylacetyl)pyrrolidin-3-yl]oxy}phenyl)-3-(pyridin-3-yl)azetidine-1-carboxamide;
N-(4-{[(3R)-1-(cyclopentylacetyl)pyrrolidin-3-yl]oxy}phenyl)-3-(pyridin-3-yl)azetidine-1-carboxamide;
N-[4-({(3R)-1-[(2-methylcyclopropyl)carbonyl]pyrrolidin-3-yl}oxy)phenyl]-3-(pyridin-3-yl)azetidine-1-carboxamide;
N-(4-{[(3R)-1-(morpholin-4-ylacetyl)pyrrolidin-3-yl]oxy}phenyl)-3-(pyridin-3-yl)azetidine-1-carboxamide;
N-(4-{[(3R)-1-(furan-3-ylcarbonyl)pyrrolidin-3-yl]oxy}phenyl)-3-(pyridin-3-yl)azetidine-1-carboxamide;
3-(pyridin-3-yl)-N-(4-{[(3R)-1-(pyrrolidin-1-ylacetyl)pyrrolidin-3-yl]oxy}phenyl)azetidine-1-carboxamide;
N-(4-{[(3R)-1-(5-oxo-D-prolyl)pyrrolidin-3-yl]oxy}phenyl)-3-(pyridin-3-yl)azetidine-1-carboxamide;
N-(4-{[(3R)-1-(N,N-dimethyl-beta-alanyl)pyrrolidin-3-yl]oxy}phenyl)-3-(pyridin-3-yl)azetidine-1-carboxamide;
3-(pyridin-3-yl)-N-(4-{[(3R)-1-(1,3-thiazol-2-ylcarbonyl)pyrrolidin-3-yl]oxy}phenyl)azetidine-1-carboxamide;
3-(pyridin-3-yl)-N-(4-{[(3R)-1-(thiophen-3-ylcarbonyl)pyrrolidin-3-yl]oxy}phenyl)azetidine-1-carboxamide;
N-[4-({(3R)-1-[(1-methylcyclopropyl)carbonyl]pyrrolidin-3-yl}oxy)phenyl]-3-(pyridin-3-yl)azetidine-1-carboxamide;
N-[4-({(3R)-1-[(3-methylthiophen-2-yl)carbonyl]pyrrolidin-3-yl}oxy)phenyl]-3-(pyridin-3-yl)azetidine-1-carboxamide;
3-(pyridin-3-yl)-N-(4-{[(3R)-1-(4,4,4-trifluorobutanoyl)pyrrolidin-3-yl]oxy}phenyl)azetidine-1-carboxamide;
N-[4-({(3R)-1-[(4-methylpiperazin-1-yl)acetyl]pyrrolidin-3-yl}oxy)phenyl]-3-(pyridin-3-yl)azetidine-1-carboxamide;
N-(4-{[(3R)-1-(5-oxo-L-prolyl)pyrrolidin-3-yl]oxy}phenyl)-3-(pyridin-3-yl)azetidine-1-carboxamide;
N-(4-{[(3R)-1-(3-ethoxypropanoyl)pyrrolidin-3-yl]oxy}phenyl)-3-(pyridin-3-yl)azetidine-1-carboxamide;
N-(4-{[(3R)-1-(4-methylpentanoyl)pyrrolidin-3-yl]oxy}phenyl)-3-(pyridin-3-yl)azetidine-1-carboxamide;
N-[4-({(3R)-1-[(1-methylcyclohexyl)carbonyl]pyrrolidin-3-yl}oxy)phenyl]-3-(pyridin-3-yl)azetidine-1-carboxamide;
N-(4-{[(3R)-1-(cyclohexylacetyl)pyrrolidin-3-yl]oxy}phenyl)-3-(pyridin-3-yl)azetidine-1-carboxamide;
N-(4-{[(3R)-1-(N-acetyl-L-leucyl)pyrrolidin-3-yl]oxy}phenyl)-3-(pyridin-3-yl)azetidine-1-carboxamide;

N-(4-{[(3R)-1-propanoylpyrrolidin-3-yl]oxy}phenyl)-3-(pyridin-3-yl)azetidine-1-carboxamide;
N-[4-({(3R)-1-[(2-methoxyethoxy)acetyl]pyrrolidin-3-yl}oxy)phenyl]-3-(pyridin-3-yl)azetidine-1-carboxamide;
N-[4-({(3R)-1-[3-(morpholin-4-yl)propanoyl]pyrrolidin-3-yl}oxy)phenyl]-3-(pyridin-3-yl)azetidine-1-carboxamide;
N-(4-{[(3R)-1-(2,2-dimethylpropanoyl)pyrrolidin-3-yl]oxy}phenyl)-3-(pyridin-3-yl)azetidine-1-carboxamide;
N-[4-({(3R)-1-[(5-methylthiophen-2-yl)carbonyl]pyrrolidin-3-yl}oxy)phenyl]-3-(pyridin-3-yl)azetidine-1-carboxamide;
3-(pyridin-3-yl)-N-(4-{[(3R)-1-(thiophen-2-ylcarbonyl)pyrrolidin-3-yl]oxy}phenyl)azetidine-1-carboxamide;
N-[4-({(3R)-1-[(1-methyl-1H-pyrrol-2-yl)carbonyl]pyrrolidin-3-yl}oxy)phenyl]-3-(pyridin-3-yl)azetidine-1-carboxamide;
N-(4-{[(3R)-1-(furan-2-ylcarbonyl)pyrrolidin-3-yl]oxy}phenyl)-3-(pyridin-3-yl)azetidine-1-carboxamide;
N-[4-({(3R)-1-[3-(piperidin-1-yl)propanoyl]pyrrolidin-3-yl}oxy)phenyl]-3-(pyridin-3-yl)azetidine-1-carboxamide;
N-(4-{[(3R)-1-(ethoxyacetyl)pyrrolidin-3-yl]oxy}phenyl)-3-(pyridin-3-yl)azetidine-1-carboxamide;
N-(4-{[(3R)-1-(3,3-dimethylbutanoyl)pyrrolidin-3-yl]oxy}phenyl)-3-(pyridin-3-yl)azetidine-1-carboxamide;
N-(4-{[(3R)-1-(2,2-dimethylbutanoyl)pyrrolidin-3-yl]oxy}phenyl)-3-(pyridin-3-yl)azetidine-1-carboxamide;
N-(4-{[(3R)-1-(methoxyacetyl)pyrrolidin-3-yl]oxy}phenyl)-3-(pyridin-3-yl)azetidine-1-carboxamide;
N-(4-{[(3R)-1-(cyclohexylcarbonyl)pyrrolidin-3-yl]oxy}phenyl)-3-(pyridin-3-yl)azetidine-1-carboxamide;
N-(4-{[(3R)-1-(3-methylbutanoyl)pyrrolidin-3-yl]oxy}phenyl)-3-(pyridin-3-yl)azetidine-1-carboxamide;
N-(4-{[(3R)-1-(cyclopentylcarbonyl)pyrrolidin-3-yl]oxy}phenyl)-3-(pyridin-3-yl)azetidine-1-carboxamide;
N-(4-{[(3R)-1-(2,3-dimethylbutanoyl)pyrrolidin-3-yl]oxy}phenyl)-3-(pyridin-3-yl)azetidine-1-carboxamide;
N-[4-(1-benzoylpiperidin-4-yl)phenyl]-3-(pyridazin-3-yl)azetidine-1-carboxamide;
N-{4-[1-(2-fluorobenzoyl)piperidin-4-yl]phenyl}-3-(pyridazin-3-yl)azetidine-1-carboxamide;
N-{4-[1-(2-methylbenzoyl)piperidin-4-yl]phenyl}-3-(pyridazin-3-yl)azetidine-1-carboxamide;
N-{4-[1-(2,2-dimethylpropanoyl)piperidin-4-yl]phenyl}-3-(pyridazin-3-yl)azetidine-1-carboxamide;
N-{4-[1-(cyclopropylcarbonyl)piperidin-4-yl]phenyl}-3-(pyridazin-3-yl)azetidine-1-carboxamide;
N-[4-(1-acetylpiperidin-4-yl)phenyl]-3-(pyridazin-3-yl)azetidine-1-carboxamide;
N-{4-[1-(3,3-dimethylbutanoyl)piperidin-4-yl]phenyl}-3-(pyridazin-3-yl)azetidine-1-carboxamide;
N-{4-[1-(cyclobutylcarbonyl)piperidin-4-yl]phenyl}-3-(pyridazin-3-yl)azetidine-1-carboxamide;
3-(pyridazin-3-yl)-N-{4-[1-(4,4,4-trifluorobutanoyl)piperidin-4-yl]phenyl}azetidine-1-carboxamide;
3-(pyridazin-3-yl)-N-{4-[1-(3,3,3-trifluoropropanoyl)piperidin-4-yl]phenyl}azetidine-1-carboxamide;
N-(4-{1-[(1-methylcyclopropyl)carbonyl]piperidin-4-yl}phenyl)-3-(pyridazin-3-yl)azetidine-1-carboxamide;
N-{4-[1-(cyclopropylacetyl)piperidin-4-yl]phenyl}-3-(pyridazin-3-yl)azetidine-1-carboxamide;
N-{4-[(1-benzoylpiperidin-4-yl)methyl]phenyl}-3-(pyridazin-3-yl)azetidine-1-carboxamide;
N-(4-{[1-(2-fluorobenzoyl)piperidin-4-yl]methyl}phenyl)-3-(pyridazin-3-yl)azetidine-1-carboxamide;
N-(4-{[1-(2,2-dimethylpropanoyl)piperidin-4-yl]methyl}phenyl)-3-(pyridazin-3-yl)azetidine-1-carboxamide;
N-(4-{[1-(3,3-dimethylbutanoyl)piperidin-4-yl]methyl}phenyl)-3-(pyridazin-3-yl)azetidine-1-carboxamide;
N-(4-{[1-(2-ethylbutanoyl)piperidin-4-yl]methyl}phenyl)-3-(pyridazin-3-yl)azetidine-1-carboxamide;
3-(pyridazin-3-yl)-N-(4-{[1-(4,4,4-trifluorobutanoyl)piperidin-4-yl]methyl}phenyl)azetidine-1-carboxamide;
N-(4-{[1-(2-methylpropanoyl)piperidin-4-yl]methyl}phenyl)-3-(pyridazin-3-yl)azetidine-1-carboxamide;
N-{4-[(1-acetylpiperidin-4-yl)methyl]phenyl}-3-(pyridazin-3-yl)azetidine-1-carboxamide;
N-[4-({1-[(2S)-2-methylbutanoyl]piperidin-4-yl}methyl)phenyl]-3-(pyridazin-3-yl)azetidine-1-carboxamide;
N-[4-({1-[(1-methylcyclopropyl)carbonyl]piperidin-4-yl}methyl)phenyl]-3-(pyridazin-3-yl)azetidine-1-carboxamide; and pharmaceutically acceptable salts thereof.

Another embodiment pertains to a composition for treating inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, atherosclerosis, restenosis, diabetes, glomerulonephritis, cancer, particularly wherein the cancer is selected from breast, prostate, lung, colon, cervix, ovary, skin, CNS, bladder, pancreas, leukemia, lymphoma or Hodgkin's disease, cachexia, inflammation associated with infection and certain viral infections, including Acquired Immune Deficiency Syndrome (AIDS), adult respiratory distress syndrome, and ataxia telengiectasia, said composition comprising an excipient and a therapeutically effective amount of a compound of Formula (IA), or pharmaceutically acceptable salts thereof.

Another embodiment pertains to a method of treating inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, atherosclerosis, restenosis, diabetes, glomerulonephritis, cancer, particularly wherein the cancer is selected from breast, prostate, lung, colon, cervix, ovary, skin, CNS, bladder, pancreas, leukemia, lymphoma or Hodgkin's disease, cachexia, inflammation associated with infection and certain viral infections, including Acquired Immune Deficiency Syndrome (AIDS), adult respiratory distress syndrome, and ataxia telengiectasia in a patient, said method comprising administering to the patient a therapeutically effective amount of a compound of Formula (IA), or pharmaceutically acceptable salts thereof.

Another embodiment pertains to a method of treating inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, atherosclerosis, restenosis, diabetes, glomerulonephritis, cancer, particularly wherein the cancer is selected from breast, prostate, lung, colon, cervix, ovary, skin, CNS, bladder, pancreas, leukemia, lymphoma or Hodgkin's disease, cachexia, inflammation associated with infection and certain viral infections, including Acquired Immune Deficiency Syndrome (AIDS), adult respiratory distress syndrome, and ataxia telengiectasia or spleen cancer in a patient, said method comprising administering to the patient therapeutically effective amount of the compound of Formula (IA), or pharmaceutically acceptable salts thereof; and a therapeutically effective amount of one additional therapeutic agent or more than one additional therapeutic agent.

DETAILED DESCRIPTION OF THE INVENTION

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

Abbreviations And Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

As used in the specification and the appended claims, unless specified to the contrary, the following terms have the meaning indicated:

The term "alkyl" (alone or in combination with another term(s)) means a straight- or branched-chain saturated hydrocarbyl substituent typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. Examples of such substituents include methyl, ethyl, n-propyl, isopropyl, n-butyl, isobutyl, sec-butyl, tert-butyl, pentyl, iso-amyl, and hexyl and the like.

The term "alkenyl" (alone or in combination with another term(s)) means a straight- or branched-chain hydrocarbyl substituent containing one or more double bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl and the like.

The term "alkynyl" (alone or in combination with another term(s)) means a straight- or branched-chain hydrocarbyl substituent containing one or more triple bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethynyl, 2-propynyl, 3-propynyl, 2-butynyl, and 3-butynyl and the like.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains from 3 to 8 ring atoms, more typically from 3 to 6 ring atoms, and even more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl may alternatively be polycyclic (i.e., may contain more than one ring). Examples of polycyclic carbocyclyls include bridged, fused, and spirocyclic carbocyclyls. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, two or more rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl, and decalinyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 8 carbon ring atoms and more typically from 3 to 6 ring atoms. Examples of single-ring cycloalkyls include cyclopropyl, cyclobutyl, cyclopentyl, and cyclohexyl. A cycloalkyl may alternatively be polycyclic or contain more than one ring. Examples of polycyclic cycloalkyls include bridged, fused, and spirocyclic carbocyclyls.

The term "aryl" (alone or in combination with another term(s)) means an aromatic carbocyclyl containing from 6 to 14 carbon ring atoms. An aryl may be monocyclic or polycyclic (i.e., may contain more than one ring). In the case of polycyclic aromatic rings, only one ring the polycyclic system is required to be unsaturated while the remaining ring(s) may be saturated, partially saturated or unsaturated. Examples of aryls include phenyl, naphthalenyl, indenyl, indanyl, and tetrahydronapthyl.

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_8$-cycloalkyl means a saturated hydrocarbyl ring containing from 3 to 8 carbon ring atoms.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —$NH_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical. If a substituent is described as being optionally substituted with one or more non-hydrogen radicals, that substituent may be either (1) not substituted; or (2) substituted by up to the maximum number of substitutable positions on the substituent. Thus, for example, if a substituent is described as a heteroaryl optionally substituted with one or more non-hydrogen radicals, then any heteroaryl with 3 substitutable positions would be optionally substituted by one, two or three non-hydrogen radicals. To illustrate, tetrazolyl (which has only one substitutable position) would be optionally substituted with up to one non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

The term "carbonyl" (alone or in combination with another term(s)) means —C(O)—.

The term "aminocarbonyl" (alone or in combination with another term(s)) means —C(O)—$NH_2$.

The term "oxo" (alone or in combination with another term(s)) means (=O).

The term "oxy" (alone or in combination with another term(s)) means an ether substituent, and may be depicted as —O—.

The term "alkylhydroxy" (alone or in combination with another term(s)) means -alkyl-OH.

The term "alkylamino" (alone or in combination with another term(s)) means -alkyl-$NH_2$.

The term "alkyloxy" (alone or in combination with another term(s)) means an alkylether substituent, i.e., —O-alkyl. Examples of such a substituent include methoxy (—O—$CH_3$), ethoxy, n-propoxy, isopropoxy, n-butoxy, isobutoxy, sec-butoxy, and tert-butoxy.

The term "alkylcarbonyl" (alone or in combination with another term(s)) means —C(O)-alkyl.

The term "aminoalkylcarbonyl" (alone or in combination with another term(s)) means —C(O)-alkyl-$NH_2$.

The term "alkyloxycarbonyl" (alone or in combination with another term(s)) means —C(O)—O-alkyl.

The term "carbocyclylcarbonyl" (alone or in combination with another term(s)) means —C(O)-carbocyclyl.

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl.

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl.

The term "carbocyclylalkyloxycarbonyl" (alone or in combination with another term(s)) means —C(O)—O-alkyl-carbocyclyl.

The term "thio" or "thia" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-thio-alkyl" means alkyl-S-alkyl (alkyl-sulfanyl-alkyl).

The term "thiol" or "sulfhydryl" (alone or in combination with another term(s)) means a sulfhydryl substituent, and may be depicted as —SH.

The term "(thiocarbonyl)" (alone or in combination with another term(s)) means a carbonyl wherein the oxygen atom has been replaced with a sulfur. Such a substituent may be depicted as —C(S)—.

The term "sulfonyl" (alone or in combination with another term(s)) means —S(O)$_2$—.

The term "aminosulfonyl" (alone or in combination with another term(s)) means —S(O)$_2$—NH$_2$.

The term "sulfinyl" or "sulfoxido" (alone or in combination with another term(s)) means —S(O)—.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocyclyl may be a single-ring (monocyclic) or polycyclic ring structure.

A heterocyclyl may be a single ring, which typically contains from 3 to 7 ring atoms, more typically from 3 to 6 ring atoms, and even more typically 5 to 6 ring atoms. Examples of single-ring heterocyclyls include 1,2,3,6-tetrahydropyridine, thiomorpholinyl, tetrahydropyranyl, furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, pyrrolidin-2-only, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, and diazepinyl.

A heterocyclyl may alternatively be polycyclic (i.e., may contain more than one ring). Examples of polycyclic heterocyclyls include bridged, fused, and spirocyclic heterocyclyls. In a spirocyclic heterocyclyl, one atom is common to two different rings. In a bridged heterocyclyl, the rings share at least two common non-adjacent atoms. In a fused-ring heterocyclyl, two or more rings may be fused together, such that two rings share one common bond. Examples of fused-ring heterocyclyls include hexahydro-furo[3,4-c]pyrrole, hexahydro-furo[3,4-b]pyrrole, octahydro-pyrrolo[3,4-b]pyridine, octahydro-pyrrolo[3,4-c]pyridine, (3aR,6aR)-5-methyl-octahydro-pyrrolo[3,4-b]pyrrole, (3aR,6aR)-octahydro-pyrrolo[3,4-b]pyrrole, 6-methyl-2,6-diaza-bicyclo[3.2.0]heptane, (3aS,6aR)-2-methyl-octahydro-pyrrolo[3,4-c]pyrrole, decahydro-[1,5]naphthyridine, 2,3-dihydrobenzofuranyl, 2,3,4,9-tetrahydro-1H-pyrido[3,4-b]indolyl, thieno[3,2-c]pyridinyl, furo[3,2-c]pyridinyl, phthalazin-1(2H)-onyl, isoquinolinyl, isoquinolin-1(2H)-onyl, 5,6,7,8-tetrahydrophthalazin-1(2H)-onyl, fluorophthalazin-1(2H)-onyl, (Z)-3H-benzo[d][1,2]diazepin-4(5H)-onyl, (trifluoromethyl)phthalazin-1(2H)-onyl, pyrrolo[1,2-d][1,2,4]triazin-1 (2H)-onyl, 1,2,3,4-tetrahydroisoquinolinyl, 2,3-dihydrobenzo[b][1,4]dioxinyl, 5,6,7,8-tetrahydrophthalazin-1(2H)-onyl, 5,6,7,8-tetrahydro-[1,2,4]triazolo[4,3-a]pyrazinyl, 5,6,7,8-tetrahydroimidazo[1,5-a]pyrazinyl, thieno[3,2-c]pyridinyl, furo[3,2-c]pyridinyl, indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as benzimidazolyl, benzo[d][1,3]dioxolyl, indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl). Examples of spirocyclic heterocyclyls include 1,4-dioxa-8-azaspiro[4.5]decanyl.

The term "3-12 membered heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 12 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A 3-12 membered heterocyclyl may be a single-ring (monocyclic) or polycyclic ring structure.

The term "heterocycloalkyl" (alone or in combination with another term(s)) means a saturated heterocyclyl.

The term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, benzisoxazolyl, benzoxazolyl, and purinyl; and 6/6-membered fused rings such as benzopyranyl, quinolinyl, isoquinolinyl, cinnolinyl, quinazolinyl, and benzoxazinyl.

A prefix attached to a multi-component substituent only applies to the first component. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "modulate" refers to the ability of a compound to increase or decrease the function, or activity, of a kinase. "Modulation", as used herein in its various forms, is intended to encompass antagonism, agonism, partial antagonism and/or partial agonism of the activity associated with kinase. Kinase inhibitors are compounds that, e.g., bind to, partially or totally block stimulation, decrease, prevent, delay activation, inactivate, desensitize, or down regulate signal transduction. Kinase activators are compounds that, e.g., bind to, stimulate, increase, open, activate, facilitate, enhance activation, sensitize or up regulate signal transduction.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

Isotope Enriched or Labeled Compounds

Compounds of the invention can exist in isotope-labeled or isotope-enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^2H$, $^3H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

In another embodiment, the isotope-labeled compounds contain deuterium ($^2H$), tritium ($^3H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., *Drugs Fut*, 21(11), 1116 (1996); Brickner, S J et al., *J Med Chem*, 39(3), 673 (1996); Mallesham, B et al., *Org Lett*, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. *Labelled Comp. Radiopharmaceut.*, 36(10): 927-932 (1995); Kushner et al., *Can. J. Physiol. Pharmacol.*, 77, 79-88 (1999).

In addition, non-radio active isotope containing drugs, such as deuterated drugs called "heavy drugs," can be used for the treatment of diseases and conditions related to NAMPT activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

Compounds

Suitable groups for $X^1$, $X^2$, $Y^1$, $R^1$, and $R^2$ in compounds of Formula (I) are independently selected. The described embodiments of the present invention may be combined. Such combination is contemplated and within the scope of the present invention. For example, it is contemplated that embodiments for any of $X^1$, $X^2$, $Y^1$, $R^1$, and $R^2$ can be combined with embodiments defined for any other of $X^1$, $X^2$, $Y^1$, $R^1$, and $R^2$.

Embodiments of Formula (I)

One embodiment of this invention, therefore, pertains to compounds or pharmaceutically acceptable salts thereof, which are useful as inhibitors of NAMPT, the compounds having Formula (I)

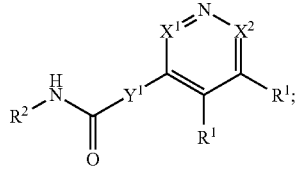

Formula (I)

wherein
$X^1$ is N and $X^2$ is $CR^1$; or
$X^1$ is $CR^1$ and $X^2$ is N; or
$X^1$ is $CR^1$ and $X^2$ is $CR^1$;
$Y^1$ is

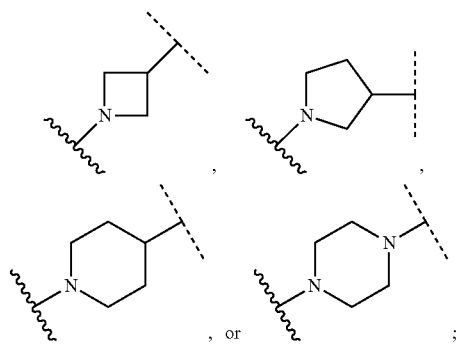

, or ;

wherein ⌇ indicates the point of attachment to the carbonyl and ∖ indicates the point of attachment to the nitrogen containing heteroaryl;

$R^1$, at each occurrence, is independently selected from the group consisting of hydrogen, alkyl, alkenyl, alkynyl, haloalkyl, hydoxyalkyl, alkoxy, OH, $NH_2$, CN, $NO_2$, F, Cl, Br and I;

$R^2$ is independently selected from the group consisting of $C_4$-$C_6$-alkyl, $C_4$-$C_6$-alkenyl, $C_4$-$C_6$-alkynyl, aryl, 3-12 membered heterocyclyl, cycloalkyl, and cycloalkenyl; wherein each $R^2$ $C_4$-$C_6$-alkyl, $C_4$-$C_6$-alkenyl, and $C_4$-$C_6$-alkynyl is substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(N)NH_2$, $C(N)NHR^3$, $C(N)N(R^3)_2$, CNOH, $CNOCH_3$, OH, (O), CN, $N_3$, $NO_2$, F, Cl, Br and I; wherein each $R^2$ aryl, 3-12 membered heterocyclyl, cycloalkyl, and cycloalkenyl is optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I;

$R^3$, at each occurrence, is independently selected from the group consisting of alkyl, alkenyl, alkynyl, aryl, cycloalkyl, cycloalkenyl, and heterocyclyl; wherein each $R^3$ alkyl, alkenyl, and alkynyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, (O), CN, $N_3$, $NO_2$, F, Cl, Br and I; wherein each $R^3$ aryl, cycloalkyl, cycloalkenyl, and heterocyclyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, CNOH, $CNOCH_3$, OH, CN, $N_3$, $NO_2$, F, Cl, Br and I;

$R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, (O), CN, $N_3$, $NO_2$, F, Cl, Br and I;

$R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one or more substituents independently selected from the group consisting of $R^8$, $OR^8$, $SR^8$, $S(O)R^8$, $SO_2R^8$, $NHR^8$, $N(R^8)_2$, $C(O)R^8$, $C(O)NH_2$, $C(O)NHR^8$, $C(O)N(R^8)_2$, $NHC(O)R^8$, $NR^8C(O)R^8$, $NHSO_2R^8$, $NHC(O)OR^8$, $SO_2NH_2$, $SO_2NHR^8$, $SO_2N(R^8)_2$, $NHC(O)NH_2$, $NHC(O)NHR^8$, OH, (O), C(O)OH, $N_3$, CN, $NH_2$, F, Cl, Br and I;

$R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one or more substituents independently selected from the group consisting of $R^9$, $OR^9$, $SR^9$, $S(O)R^9$, $SO_2R^9$, $NHR^9$, $N(R^9)_2$, $C(O)R^9$, $C(O)NH_2$, $C(O)NHR^9$, $C(O)N(R^9)_2$, $NHC(O)R^9$, $NR^9C(O)R^9$, $NHSO_2R^9$, $NHC(O)OR^9$, $SO_2NH_2$, $SO_2NHR^9$, $SO_2N(R^9)_2$, $NHC(O)NH_2$, $NHC(O)NHR^9$, OH, (O), C(O)OH, $N_3$, CN, $NH_2$, $CF_3$, $CF_2CF_3$, F, Cl, Br and I;

$R^7$, at each occurrence, is independently selected from the group consisting of alkyl, alkenyl, alkynyl, aryl, heterocyclyl, cycloalkyl, and cycloalkenyl;

$R^8$, at each occurrence, is independently selected from the group consisting of alkyl, alkenyl, alkynyl, aryl, heterocyclyl, cycloalkyl, and cycloalkenyl;

$R^9$, at each occurrence, is independently selected from the group consisting of alkyl, alkenyl, alkynyl, aryl, heterocyclyl, cycloalkyl, and cycloalkenyl;

wherein the cyclic moieties represented by $R^4$, $R^5$, $R^6$, $R^7$, $R^8$, and $R^9$ are independently optionally substituted with one or more substituents independently selected from the group consisting of $R^{10}$, $OR^{10}$, $SR^{10}$, $S(O)R^{10}$, $C(O)C(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, C(O)NHOH, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, C(O)H, C(O)OH, $C(N)NH_2$, $C(N)NHR^{10}$, $C(N)N(R^{10})_2$, CNOH, $CNOCH_3$, OH, CN, $N_3$, $NO_2$, F, Cl, Br and I;

$R^{10}$, at each occurrence, is independently selected from the group consisting of alkyl, alkenyl, alkynyl, aryl, heterocyclyl, cycloalkyl, and cycloalkenyl; wherein each $R^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, C(O)NHOH, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, C(O)H, C(O)OH, $C(N)NH_2$, $C(N)NHR^{11}$, $C(N)N(R^{11})_2$, CNOH, $CNOCH_3$, OH, (O), CN, $N_3$, $NO_2$, F, Cl, Br and I; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, C(O)NHOH, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, C(O)H, C(O)OH, $C(N)NH_2$, $C(N)NHR^{12}$, $C(N)N(R^{12})_2$, CNOH, $CNOCH_3$, OH, CN, $N_3$, $NO_2$, F, Cl, Br and I;

$R^{11}$, at each occurrence, is independently selected from the group consisting of alkyl, alkenyl, alkynyl, aryl, heterocyclyl, cycloalkyl, and cycloalkenyl; wherein each $R^{11}$ alkyl, alkenyl, and alkynyl is optionally substituted with alkyl or alkoxy; wherein each $R^{11}$ aryl, heterocyclyl, cycloalkyl, and cycloalkenyl is optionally substituted with alkyl or alkoxy; and $R^{12}$, at each occurrence, is independently selected alkyl.

In one embodiment of Formula (I), $X^1$ is N and $X^2$ is $CR^1$. In another embodiment of Formula (I), $X^1$ is $CR^1$ and $X^2$ is N. In another embodiment of Formula (I), $X^1$ is $CR^1$ and $X^2$ is $CR^1$. In another embodiment of Formula (I), $X^1$ is $CR^1$ and $X^2$ is $CR^1$, and $R^1$, at each occurrence, is independently selected from the group consisting of hydrogen, alkyl, alkenyl, alkynyl, haloalkyl, hydoxyalkyl, alkoxy, OH, $NH_2$, CN, $NO_2$, F, Cl, Br and I. In another embodiment of Formula (I), $X^1$ is $CR^1$ and $X^2$ is $CR^1$, and $R^1$, at each occurrence, is independently selected from the group consisting of hydrogen, alkyl, F, Cl, Br and I. In another embodiment of Formula (I), $X^1$ is $CR^1$ and $X^2$ is $CR^1$, and $R^1$, at each occurrence, is hydrogen.

In one embodiment of Formula (I), $R^1$, at each occurrence, is independently selected from the group consisting of hydrogen, alkyl, alkenyl, alkynyl, haloalkyl, hydoxyalkyl, alkoxy, OH, $NH_2$, CN, $NO_2$, F, Cl, Br and I. In another embodiment of Formula (I), $R^1$, at each occurrence, is independently selected from the group consisting of hydrogen, alkyl, F, Cl, Br and I. In another embodiment of Formula (I), $R^1$, at each occurrence, is independently selected from the group consisting of hydrogen, alkyl, F, and Cl. In another embodiment of Formula (I), $R^1$, at each occurrence, is hydrogen.

In one embodiment of Formula (I), $Y^1$ is

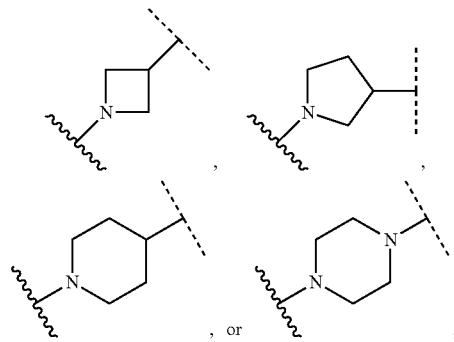

wherein ⌇ indicates the point of attachment to the carbonyl and ⟍ indicates the point of attachment to the nitrogen containing heteroaryl. In another embodiment of Formula (I), $Y^1$ is

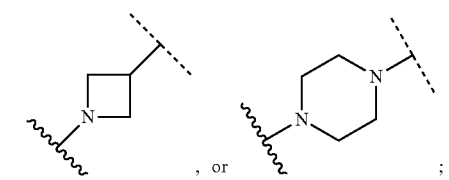

wherein ⌇ indicates the point of attachment to the carbonyl and ⟍ indicates the point of attachment to the nitrogen containing heteroaryl. In another embodiment of Formula (I), $Y^1$ is

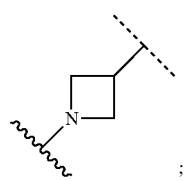

wherein ⤳ indicates the point of attachment to the carbonyl and ⇘ indicates the point of attachment to the nitrogen containing heteroaryl.

In one embodiment of Formula (I), $R^2$ is independently selected from the group consisting of $C_4$-$C_6$-alkyl, $C_4$-$C_6$-alkenyl, $C_4$-$C_6$-alkynyl, aryl, 3-12 membered heterocyclyl, cycloalkyl, and cycloalkenyl; wherein each $R^2$ $C_4$-$C_6$-alkyl, $C_4$-$C_6$-alkenyl, and $C_4$-$C_6$-alkynyl is substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(N)NH_2$, $C(N)NHR^3$, $C(N)N(R^3)_2$, CNOH, CNOCH_3, OH, (O), CN, $N_3$, $NO_2$, F, Cl, Br and I; wherein each $R^2$ aryl, 3-12 membered heterocyclyl, cycloalkyl, and cycloalkenyl is optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, CNOCH_3, OH, (O), CN, $N_3$, $NO_2$, F, Cl, Br and I. In another embodiment of Formula (I), $R^2$ is independently selected from the group consisting of $C_4$-$C_6$-alkyl, and aryl; wherein each $R^2$ $C_4$-$C_6$-alkyl is substituted with one or more substituents independently selected from the group consisting of $R^3$, F, Cl, Br and I; wherein each $R^2$ aryl is optionally substituted with one or more substituents independently selected from the group consisting of $R^4$, $OR^4$, $CO(O)R^4$, $C(O)NHR^4$, CN, F, Cl, Br and I. In another embodiment of Formula (I), $R^2$ is independently selected from the group consisting of $C_4$-$C_6$-alkyl, and aryl; wherein each $R^2$ $C_4$-$C_6$-alkyl is substituted with one or more $R^3$; wherein each $R^2$ aryl is optionally substituted with one or more substituents independently selected from the group consisting of $R^4$, $OR^4$, $CO(O)R^4$, $C(O)NHR^4$, and CN. In another embodiment of Formula (I), $R^2$ is $C_4$-$C_6$-alkyl; wherein each $R^2$ $C_4$-$C_6$-alkyl is substituted with one or more $R^3$. In another embodiment of Formula (I), $R^2$ is aryl; wherein each $R^2$ aryl is substituted with one or more substituents independently selected from the group consisting of $R^4$, $OR^4$, $CO(O)R^4$, $C(O)NHR^4$, and CN. In another embodiment of Formula (I), $R^2$ is aryl; wherein each $R^2$ aryl is substituted with one $C(O)NHR^4$. In another embodiment of Formula (I), $R^2$ is phenyl; wherein each $R^2$ phenyl is substituted with one $C(O)NHR^4$. In another embodiment of Formula (I), $R^2$ is phenyl; wherein each $R^2$ phenyl is substituted with one $OR^4$. In another embodiment of Formula (I), $R^2$ is phenyl; wherein each $R^2$ phenyl is substituted with one $R^4$.

In one embodiment of Formula (I), $R^3$, at each occurrence, is independently selected from the group consisting of alkyl, alkenyl, alkynyl, aryl, cycloalkyl, cycloalkenyl, and heterocyclyl; wherein each $R^3$ alkyl, alkenyl, and alkynyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, CNOCH_3, OH, (O), CN, $N_3$, $NO_2$, F, Cl, Br and I; wherein each $R^3$ aryl, cycloalkyl, cycloalkenyl, and heterocyclyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, CNOH, CNOCH_3, OH, CN, $N_3$, $NO_2$, F, Cl, Br and I. In another embodiment of Formula (I), $R^3$, at each occurrence, is independently heterocyclyl; wherein each $R^3$ heterocyclyl is optionally substituted with one or more substituents independently selected from the group consisting of $CO(O)R^6$, F, Cl, Br and I. In another embodiment of Formula (I), $R^3$, at each occurrence, is independently heterocyclyl; wherein each $R^3$ heterocyclyl is optionally substituted with one or more $CO(O)R^6$.

In one embodiment of Formula (I), $R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one or more substituents independently selected from the group consisting of $R^9$, $OR^9$, $SR^9$, $S(O)R^9$, $SO_2R^9$, $NHR^9$, $N(R^9)_2$, $C(O)R^9$, $C(O)NH_2$, $C(O)NHR^9$, $C(O)N(R^9)_2$, $NHC(O)R^9$, $NR^9C(O)R^9$, $NHSO_2R^9$, $NHC(O)OR^9$, $SO_2NH_2$, $SO_2NHR^9$, $SO_2N(R^9)_2$, $NHC(O)NH_2$, $NHC(O)NHR^9$, OH, (O), $C(O)OH$, $N_3$, CN, $NH_2$, $CF_3$, $CF_2CF_3$, F, Cl, Br and I. In another embodiment of Formula (I), $R^6$, at each occurrence, is alkyl.

In one embodiment of Formula (I), $R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, CNOCH_3, OH, (O), CN, $N_3$, $NO_2$, F, Cl, Br and I; wherein the cyclic moiety represented by $R^4$ is independently optionally substituted with one or more substituents independently selected from the group consisting of $R^{10}$, $OR^{10}$, $SR^{10}$, $S(O)R^{10}$, $C(O)C(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)$ OR$^{10}$, NHC(O)NH$_2$, NHC(O)NHR$^{10}$, NHC(O)N(R$^{10}$)$_2$, NR$^{10}$C(O)NHR$^{10}$, NR$^{10}$C(O)N(R$^{10}$)$_2$, C(O)NH$_2$, C(O)NHR$^{10}$, C(O)N(R$^{10}$)$_2$, C(O)NHOH, C(O)NHOR$^{10}$, C(O)NHSO$_2$R$^{10}$, C(O)NR$^{10}$SO$_2$R$^{10}$, SO$_2$NH$_2$, SO$_2$NHR$^{10}$, SO$_2$N(R$^{10}$)$_2$, C(O)H, C(O)OH, C(N)NH$_2$, C(N)NHR$^{10}$, C(N)N(R$^{10}$)$_2$, CNOH, CNOCH$_3$, OH, CN, N$_3$, NO$_2$, F, Cl, Br and I. In another embodiment of Formula (I), R$^4$, at each occurrence, is independently selected from the group consisting of alkyl and heterocyclyl; wherein each R$^4$ alkyl is optionally substituted with one or more substituents independently selected from the group consisting of R$^7$, F, Cl, Br and I; wherein the cyclic moiety represented by R$^4$ is independently optionally substituted with one or more substituents independently selected from the group consisting of R$^{10}$, C(O)C(O)R$^{10}$, C(O)R$^{10}$, CO(O)R$^{10}$, F, Cl, Br and I. In another embodiment of Formula (I), R$^4$, at each occurrence, is heterocyclyl. In another embodiment of Formula (I), R$^4$, at each occurrence, is heterocyclyl; wherein the cyclic moiety represented by R$^4$ is independently optionally substituted with one or more substituents independently selected from the group consisting of R$^{10}$, C(O)C(O)R$^{10}$, C(O)R$^{10}$, CO(O)R$^{10}$, F, Cl, Br and I.

In one embodiment of Formula (I), R$^7$, at each occurrence, is independently selected from the group consisting of alkyl, alkenyl, alkynyl, aryl, heterocyclyl, cycloalkyl, and cycloalkenyl. In another embodiment of Formula (I), R$^7$, at each occurrence, is independently heterocyclyl.

In one embodiment of Formula (I), R$^{10}$, at each occurrence, is independently selected from the group consisting of alkyl, alkenyl, alkynyl, aryl, heterocyclyl, cycloalkyl, and cycloalkenyl; wherein each R$^{10}$ alkyl, alkenyl, and alkynyl is optionally substituted with one or more substituents independently selected from the group consisting of R$^{11}$, OR$^{11}$, SR$^{11}$, S(O)R$^{11}$, SO$_2$R$^{11}$, C(O)R$^{11}$, CO(O)R$^{11}$, OC(O)R$^{11}$, OC(O)OR$^{11}$, NH$_2$, NHR$^{11}$, N(R$^{11}$)$_2$, NHC(O)R$^{11}$, NR$^{11}$C(O)R$^{11}$, NHS(O)$_2$R$^{11}$, NR$^{11}$S(O)$_2$R$^{11}$, NHC(O)OR$^{11}$, NR$^{11}$C(O)OR$^{11}$, NHC(O)NH$_2$, NHC(O)NHR$^{11}$, NHC(O)N(R$^{11}$)$_2$, NR$^{11}$C(O)NHR$^{11}$, NR$^{11}$C(O)N(R$^{11}$)$_2$, C(O)NH$_2$, C(O)NHR$^{11}$, C(O)N(R$^{11}$)$_2$, C(O)NHOH, C(O)NHOR$^{11}$, C(O)NHSO$_2$R$^{11}$, C(O)NR$^{11}$SO$_2$R$^{11}$, SO$_2$NH$_2$, SO$_2$NHR$^{11}$, SO$_2$N(R$^{11}$)$_2$, C(O)H, C(O)OH, C(N)NH$_2$, C(N)NHR$^{11}$, C(N)N(R$^{11}$)$_2$, CNOH, CNOCH$_3$, OH, (O), CN, N$_3$, NO$_2$, F, Cl, Br and I; wherein each R$^{10}$ aryl, heterocyclyl, cycloalkyl, and cycloalkenyl is optionally substituted with one or more substituents independently selected from the group consisting of R$^{12}$, OR$^{12}$, SR$^{12}$, S(O)R$^{12}$, SO$_2$R$^{12}$, C(O)R$^{12}$, CO(O)R$^{12}$, OC(O)R$^{12}$, OC(O)OR$^{12}$, NH$_2$, NHR$^{12}$, N(R$^{12}$)$_2$, NHC(O)R$^{12}$, NR$^{12}$C(O)R$^{12}$, NHS(O)$_2$R$^{12}$, NR$^{12}$S(O)$_2$R$^{12}$, NHC(O)OR$^{12}$, NR$^{12}$C(O)OR$^{12}$, NHC(O)NH$_2$, NHC(O)NHR$^{12}$, NHC(O)N(R$^{12}$)$_2$, NR$^{12}$C(O)NHR$^{12}$, NR$^{12}$C(O)N(R$^{12}$)$_2$, C(O)NH$_2$, C(O)NHR$^{12}$, C(O)N(R$^{12}$)$_2$, C(O)NHOH, C(O)NHOR$^{12}$, C(O)NHSO$_2$R$^{12}$, C(O)NR$^{12}$SO$_2$R$^{12}$, SO$_2$NH$_2$, SO$_2$NHR$^{12}$, SO$_2$N(R$^{12}$)$_2$, C(O)H, C(O)OH, C(N)NH$_2$, C(N)NHR$^{12}$, C(N)N(R$^{12}$)$_2$, CNOH, CNOCH$_3$, OH, CN, N$_3$, NO$_2$, F, Cl, Br and I; R$^{11}$, at each occurrence, is independently selected from the group consisting of alkyl, alkenyl, alkynyl, aryl, heterocyclyl, cycloalkyl, and cycloalkenyl; wherein each R$^{11}$ alkyl, alkenyl, and alkynyl is optionally substituted with alkyl or alkoxy; wherein each R$^{11}$ aryl, heterocyclyl, cycloalkyl, and cycloalkenyl is optionally substituted with alkyl or alkoxy; and R$^{12}$, at each occurrence, is independently selected alkyl. In another embodiment of Formula (I), R$^{10}$, at each occurrence, is independently selected from the group consisting of alkyl, aryl, heterocyclyl, and cycloalkyl; wherein each R$^{10}$ alkyl is optionally substituted with one or more substituents independently selected from the group consisting of R$^{11}$, OR$^{11}$, SR$^{11}$, N(R$^{11}$)$_2$, NHC(O)R$^{11}$, OH, F, Cl, Br and I; wherein each R$^{10}$ heterocyclyl, and cycloalkyl is optionally substituted with one or more substituents independently selected from the group consisting of R$^{12}$, C(O)R$^{12}$, F, Cl, Br and I; R$^{11}$, at each occurrence, is independently selected from the group consisting of alkyl, heterocyclyl, and cycloalkyl; wherein each R$^{11}$ alkyl is optionally substituted with alkoxy; wherein each R$^{11}$ heterocyclyl and cycloalkyl is optionally substituted with alkyl; and R$^{12}$, at each occurrence, is independently selected alkyl. In another embodiment of Formula (I), R$^{10}$, at each occurrence, is independently selected from the group consisting of alkyl, aryl, heterocyclyl, and cycloalkyl; wherein each R$^{10}$ alkyl is optionally substituted with one or more substituents independently selected from the group consisting of R$^{11}$, OR$^{11}$, SR$^{11}$, N(R$^{11}$)$_2$, NHC(O)R$^{11}$, OH, and F; wherein each R$^{10}$ heterocyclyl, and cycloalkyl is optionally substituted with one or more substituents independently selected from the group consisting of R$^{12}$, and C(O)R$^{12}$; R$^{11}$, at each occurrence, is independently selected from the group consisting of alkyl, heterocyclyl, and cycloalkyl; wherein each R$^{11}$ alkyl is optionally substituted with alkoxy; wherein each R$^{11}$ heterocyclyl and cycloalkyl is optionally substituted with alkyl; and R$^{12}$, at each occurrence, is independently selected alkyl.

One embodiment of this invention pertains to compounds or pharmaceutically acceptable salts thereof, which are useful as inhibitors of NAMPT, the compounds having Formula (I)

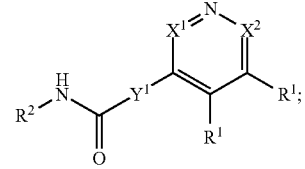

Formula (I)

wherein
X$^1$ is CR$^1$ and X$^2$ is CR$^1$;
Y$^1$ is

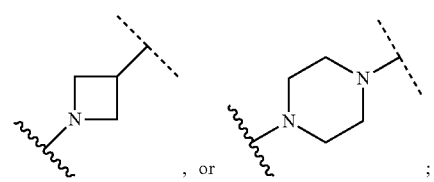

, or        ;

wherein ⌇ indicates the point of attachment to the carbonyl and ⌇ indicates the point of attachment to the nitrogen containing heteroaryl;

R$^1$, at each occurrence, is independently selected from the group consisting of hydrogen, alkyl, F, and Cl;

R$^2$ is independently selected from the group consisting of C$_4$-C$_6$-alkyl, and aryl; wherein each R$^2$ C$_4$-C$_6$-alkyl is substituted with one or more R$^3$; wherein each R$^2$ aryl is optionally substituted with one or more substituents independently selected from the group consisting of R$^4$, OR$^4$, CO(O)R$^4$, C(O)NHR$^4$, and CN;

R$^3$, at each occurrence, is heterocyclyl; wherein each R$^3$ heterocyclyl is optionally substituted with one or more CO(O)R$^6$;

R⁴, at each occurrence, is independently selected from the group consisting of alkyl, and heterocyclyl; wherein each R⁴ alkyl is optionally substituted with one or more R⁷;

R⁶, at each occurrence, is independently alkyl;

R⁷, at each occurrence, is independently heterocyclyl;

wherein the cyclic moieties represented by R⁴ are independently optionally substituted with one or more substituents independently selected from the group consisting of R¹⁰, C(O)C(O)R¹⁰, C(O)R¹⁰, and CO(O)R¹⁰;

R¹⁰, at each occurrence, is independently selected from the group consisting of alkyl, aryl, heterocyclyl, and cycloalkyl; wherein each R¹⁰ alkyl is optionally substituted with one or more substituents independently selected from the group consisting of R¹¹, OR¹¹, SR¹¹, N(R¹¹)₂, NHC(O)R¹¹, OH, and F; wherein each R¹⁰ heterocyclyl, and cycloalkyl is optionally substituted with one or more substituents independently selected from the group consisting of R¹², and C(O)R¹²;

R¹¹, at each occurrence, is independently selected from the group consisting of alkyl, heterocyclyl, and cycloalkyl; wherein each R¹¹ alkyl is optionally substituted with alkoxy; wherein each R¹¹ heterocyclyl is optionally substituted with alkyl; and R¹², at each occurrence, is independently selected alkyl.

Still another embodiment pertains to compounds having Formula (I), which includes Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, and pharmaceutically acceptable salts thereof.

Embodiments of Formula (II)

In another aspect, the present invention provides compounds of Formula (II)

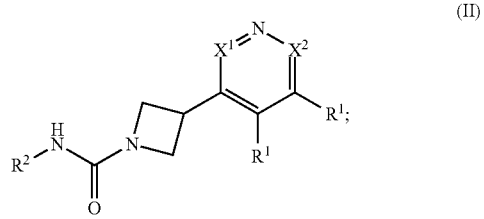

(II)

and pharmaceutically acceptable salts thereof; wherein $X^1$, $X^2$, $R^1$ and $R^2$ are as described herein for Formula (I).

One embodiment of this invention pertains to compounds of Formula (II) or pharmaceutically acceptable salts thereof; wherein $X^1$ is N and $X^2$ is $CR^1$; or
$X^1$ is $CR^1$ and $X^2$ is N; or
$X^1$ is $CR^1$ and $X^2$ is $CR^1$;

$R^1$, at each occurrence, is independently selected from the group consisting of hydrogen, alkyl, alkenyl, alkynyl, haloalkyl, hydoxyalkyl, alkoxy, OH, $NH_2$, CN, $NO_2$, F, Cl, Br and I;

$R^2$ is independently selected from the group consisting of $C_4$-$C_6$-alkyl, $C_4$-$C_6$-alkenyl, $C_4$-$C_6$-alkynyl, aryl, 3-12 membered heterocyclyl, cycloalkyl, and cycloalkenyl; wherein each $R^2$ $C_4$-$C_6$-alkyl, $C_4$-$C_6$-alkenyl, and $C_4$-$C_6$-alkynyl is substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(N)NH_2$, $C(N)NHR^3$, $C(N)N(R^3)_2$, CNOH, $CNOCH_3$, OH, (O), CN, $N_3$, $NO_2$, F, Cl, Br and I; wherein each $R^2$ aryl, 3-12 membered heterocyclyl, cycloalkyl, and cycloalkenyl is optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I;

$R^3$, at each occurrence, is independently selected from the group consisting of alkyl, alkenyl, alkynyl, aryl, cycloalkyl, cycloalkenyl, and heterocyclyl; wherein each $R^3$ alkyl, alkenyl, and alkynyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, (O), CN, $N_3$, $NO_2$, F, Cl, Br and I; wherein each $R^3$ aryl, cycloalkyl, cycloalkenyl, and heterocyclyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, CNOH, $CNOCH_3$, OH, CN, $N_3$, $NO_2$, F, Cl, Br and I;

$R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, $CNOH$, $CNOCH_3$, OH, (O), CN, $N_3$, $NO_2$, F, Cl, Br and I;

$R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one or more substituents independently selected from the group consisting of $R^8$, $OR^8$, $SR^8$, $S(O)R^8$, $SO_2R^8$, $NHR^8$, $N(R^8)_2$, $C(O)R^8$, $C(O)NH_2$, $C(O)NHR^8$, $C(O)N(R^8)_2$, $NHC(O)R^8$, $NR^8C(O)R^8$, $NHSO_2R^8$, $NHC(O)OR^8$, $SO_2NH_2$, $SO_2NHR^8$, $SO_2N(R^8)_2$, $NHC(O)NH_2$, $NHC(O)NHR^8$, OH, (O), $C(O)OH$, $N_3$, CN, $NH_2$, F, Cl, Br and I;

$R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one or more substituents independently selected from the group consisting of $R^9$, $OR^9$, $SR^9$, $S(O)R^9$, $SO_2R^9$, $NHR^9$, $N(R^9)_2$, $C(O)R^9$, $C(O)NH_2$, $C(O)NHR^9$, $C(O)N(R^9)_2$, $NHC(O)R^9$, $NR^9C(O)R^9$, $NHSO_2R^9$, $NHC(O)OR^9$, $SO_2NH_2$, $SO_2NHR^9$, $SO_2N(R^9)_2$, $NHC(O)NH_2$, $NHC(O)NHR^9$, OH, (O), $C(O)OH$, $N_3$, CN, $NH_2$, $CF_3$, $CF_2CF_3$, F, Cl, Br and I;

$R^7$, at each occurrence, is independently selected from the group consisting of alkyl, alkenyl, alkynyl, aryl, heterocyclyl, cycloalkyl, and cycloalkenyl;

$R^8$, at each occurrence, is independently selected from the group consisting of alkyl, alkenyl, alkynyl, aryl, heterocyclyl, cycloalkyl, and cycloalkenyl;

$R^9$, at each occurrence, is independently selected from the group consisting of alkyl, alkenyl, alkynyl, aryl, heterocyclyl, cycloalkyl, and cycloalkenyl; wherein the cyclic moieties represented by $R^4$, $R^5$, $R^6$, $R^7$, $R^8$, and $R^9$ are independently optionally substituted with one or more substituents independently selected from the group consisting of $R^{10}$, $OR^{10}$, $SR^{10}$, $S(O)R^{10}$, $C(O)C(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, $CNOH$, $CNOCH_3$, OH, CN, $N_3$, $NO_2$, F, Cl, Br and I;

$R^{10}$, at each occurrence, is independently selected from the group consisting of alkyl, alkenyl, alkynyl, aryl, heterocyclyl, cycloalkyl, and cycloalkenyl; wherein each $R^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $C(N)NH_2$, $C(N)NHR^{11}$, $C(N)N(R^{11})_2$, $CNOH$, $CNOCH_3$, OH, (O), CN, $N_3$, $NO_2$, F, Cl, Br and I; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, $CNOH$, $CNOCH_3$, OH, CN, $N_3$, $NO_2$, F, Cl, Br and I;

$R^{11}$, at each occurrence, is independently selected from the group consisting of alkyl, alkenyl, alkynyl, aryl, heterocyclyl, cycloalkyl, and cycloalkenyl; wherein each $R^{11}$ alkyl, alkenyl, and alkynyl is optionally substituted with alkyl or alkoxy; wherein each $R^{11}$ aryl, heterocyclyl, cycloalkyl, and cycloalkenyl is optionally substituted with alkyl or alkoxy; and $R^{12}$, at each occurrence, is independently selected alkyl.

In one embodiment of Formula (II), $X^1$ is N and $X^2$ is $CR^1$. In another embodiment of Formula (II), $X^1$ is $CR^1$ and $X^2$ is N. In another embodiment of Formula (II), $X^1$ is $CR^1$ and $X^2$ is $CR^1$. In another embodiment of Formula (II), $X^1$ is $CR^1$ and $X^2$ is $CR^1$, and $R^1$, at each occurrence, is independently selected from the group consisting of hydrogen, alkyl, alkenyl, alkynyl, haloalkyl, hydoxyalkyl, alkoxy, OH, $NH_2$, CN, $NO_2$, F, Cl, Br and I. In another embodiment of Formula (II), $X^1$ is $CR^1$ and $X^2$ is $CR^1$, and $R^1$, at each occurrence, is independently selected from the group consisting of hydrogen, alkyl, F, Cl, Br and I. In another embodiment of Formula (II), $X^1$ is $CR^1$ and $X^2$ is $CR^1$, and $R^1$, at each occurrence, is hydrogen.

In one embodiment of Formula (II), $R^1$, at each occurrence, is independently selected from the group consisting of hydrogen, alkyl, alkenyl, alkynyl, haloalkyl, hydoxyalkyl, alkoxy, OH, $NH_2$, CN, $NO_2$, F, Cl, Br and I. In another embodiment of Formula (II), $R^1$, at each occurrence, is independently selected from the group consisting of hydrogen, alkyl, F, Cl, Br and I. In another embodiment of Formula (II), $R^1$, at each occurrence, is independently selected from the group consisting of hydrogen, alkyl, F, and Cl. In another embodiment of Formula (II), $R^1$, at each occurrence, is hydrogen.

In one embodiment of Formula (II), $R^2$ is independently selected from the group consisting of $C_4$-$C_6$-alkyl, $C_4$-$C_6$-alkenyl, $C_4$-$C_6$-alkynyl, aryl, 3-12 membered heterocyclyl, cycloalkyl, and cycloalkenyl; wherein each $R^2$ $C_4$-$C_6$-alkyl, $C_4$-$C_6$-alkenyl, and $C_4$-$C_6$-alkynyl is substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(N)NH_2$, $C(N)NHR^3$, $C(N)N(R^3)_2$, $CNOH$, $CNOCH_3$, OH, (O), CN, $N_3$, $NO_2$, F, Cl, Br and I; wherein each $R^2$ aryl, 3-12 membered heterocyclyl, cycloalkyl, and cycloalkenyl is optionally substituted with one or more substituents independently selected from the group consisting of $R^4$, $OR^4$, $SR^4$, $S(O)R^4$, $SO_2R^4$, $C(O)R^4$, CO(O)R$^4$, OC(O)R$^4$, OC(O)OR$^4$, NH$_2$, NHR$^4$, N(R$^4$)$_2$, NHC(O)R$^4$, NR$^4$C(O)R$^4$, NHS(O)$_2$R$^4$, NR$^4$S(O)$_2$R$^4$, NHC(O)OR$^4$, NR$^4$C(O)OR$^4$, NHC(O)NH$_2$, NHC(O)NHR$^4$, NHC(O)N(R$^4$)$_2$, NR$^4$C(O)NHR$^4$, NR$^4$C(O)N(R$^4$)$_2$, C(O)NH$_2$, C(O)NHR$^4$, C(O)N(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, C(O)H, C(O)OH, C(N)NH$_2$, C(N)NHR$^4$, C(N)N(R$^4$)$_2$, CNOH, CNOCH$_3$, OH, CN, N$_3$, NO$_2$, F, Cl, Br and I. In another embodiment of Formula (II), R$^2$ is independently selected from the group consisting of C$_4$-C$_6$-alkyl, and aryl; wherein each R$^2$ C$_4$-C$_6$-alkyl is substituted with one or more substituents independently selected from the group consisting of R$^3$, F, Cl, Br and I; wherein each R$^2$ aryl is optionally substituted with one or more substituents independently selected from the group consisting of R$^4$, OR$^4$, CO(O)R$^4$, C(O)NHR$^4$, CN, F, Cl, Br and I. In another embodiment of Formula (II), R$^2$ is independently selected from the group consisting of C$_4$-C$_6$-alkyl, and aryl; wherein each R$^2$ C$_4$-C$_6$-alkyl is substituted with one or more R$^3$; wherein each R$^2$ aryl is optionally substituted with one or more substituents independently selected from the group consisting of R$^4$, OR$^4$, CO(O)R$^4$, C(O)NHR$^4$, and CN. In another embodiment of Formula (II), R$^2$ is C$_4$-C$_6$-alkyl; wherein each R$^2$ C$_4$-C$_6$-alkyl is substituted with one or more R$^3$. In another embodiment of Formula (II), R$^2$ is aryl; wherein each R$^2$ aryl is substituted with one or more substituents independently selected from the group consisting of R$^4$, OR$^4$, CO(O)R$^4$, C(O)NHR$^4$, and CN. In another embodiment of Formula (II), R$^2$ is aryl; wherein each R$^2$ aryl is substituted with one C(O)NHR$^4$. In another embodiment of Formula (II), R$^2$ is phenyl; wherein each R$^2$ phenyl is substituted with one C(O)NHR$^4$. In another embodiment of Formula (II), R$^2$ is phenyl; wherein each R$^2$ phenyl is substituted with one OR$^4$. In another embodiment of Formula (II), R$^2$ is phenyl; wherein each R$^2$ phenyl is substituted with one R$^4$.

In one embodiment of Formula (II), R$^3$, at each occurrence, is independently selected from the group consisting of alkyl, alkenyl, alkynyl, aryl, cycloalkyl, cycloalkenyl, and heterocyclyl; wherein each R$^3$ alkyl, alkenyl, and alkynyl is optionally substituted with one or more substituents independently selected from the group consisting of R$^5$, OR$^5$, SR$^5$, S(O)R$^5$, SO$_2$R$^5$, C(O)R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, NHS(O)$_2$R$^5$, NR$^5$S(O)$_2$R$^5$, NHC(O)OR$^5$, NR$^5$C(O)OR$^5$, NHC(O)NH$_2$, NHC(O)NHR$^5$, NHC(O)N(R$^5$)$_2$, NR$^5$C(O)NHR$^5$, NR$^5$C(O)N(R$^5$)$_2$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, C(O)H, C(O)OH, C(N)NH$_2$, C(N)NHR$^5$, C(N)N(R$^5$)$_2$, CNOH, CNOCH$_3$, OH, (O), CN, N$_3$, NO$_2$, F, Cl, Br and I; wherein each R$^3$ aryl, cycloalkyl, cycloalkenyl, and heterocyclyl is optionally substituted with one or more substituents independently selected from the group consisting of R$^6$, OR$^6$, SR$^6$, S(O)R$^6$, SO$_2$R$^6$, C(O)R$^6$, CO(O)R$^6$, OC(O)R$^6$, OC(O)OR$^6$, NH$_2$, NHR$^6$, N(R$^6$)$_2$, NHC(O)R$^6$, NR$^6$C(O)R$^6$, NHS(O)$_2$R$^6$, NR$^6$S(O)$_2$R$^6$, NHC(O)OR$^6$, NR$^6$C(O)OR$^6$, NHC(O)NH$_2$, NHC(O)NHR$^6$, NHC(O)N(R$^6$)$_2$, NR$^6$C(O)NHR$^6$, NR$^6$C(O)N(R$^6$)$_2$, C(O)NH$_2$, C(O)NHR$^6$, C(O)N(R$^6$)$_2$, C(O)NHOH, C(O)NHOR$^6$, C(O)NHSO$_2$R$^6$, C(O)NR$^6$SO$_2$R$^6$, SO$_2$NH$_2$, SO$_2$NHR$^6$, SO$_2$N(R$^6$)$_2$, C(O)H, C(O)OH, C(N)NH$_2$, C(N)NHR$^6$, C(N)N(R$^6$)$_2$, CNOH, CNOCH$_3$, OH, CN, N$_3$, NO$_2$, F, Cl, Br and I. In another embodiment of Formula (II), R$^3$, at each occurrence, is independently heterocyclyl; wherein each R$^3$ heterocyclyl is optionally substituted with one or more substituents independently selected from the group consisting of CO(O)R$^6$, F, Cl, Br and I. In another embodiment of Formula (II), R$^3$, at each occurrence, is independently heterocyclyl; wherein each R$^3$ heterocyclyl is optionally substituted with one or more CO(O)R$^6$.

In one embodiment of Formula (II), R$^6$, at each occurrence, is independently selected from the group consisting of alkyl, alkenyl, alkynyl, aryl, heterocyclyl, cycloalkyl, and cycloalkenyl; wherein each R$^6$ alkyl, alkenyl, and alkynyl is optionally substituted with one or more substituents independently selected from the group consisting of R$^9$, OR$^9$, SR$^9$, S(O)R$^9$, SO$_2$R$^9$, NHR$^9$, N(R$^9$)$_2$, C(O)R$^9$, C(O)NH$_2$, C(O)NHR$^9$, C(O)N(R$^9$)$_2$, NHC(O)R$^9$, NR$^9$C(O)R$^9$, NHSO$_2$R$^9$, NHC(O)OR$^9$, SO$_2$NH$_2$, SO$_2$NHR$^9$, SO$_2$N(R$^9$)$_2$, NHC(O)NH$_2$, NHC(O)NHR$^9$, OH, (O), C(O)OH, N$_3$, CN, NH$_2$, CF$_3$, CF$_2$CF$_3$, F, Cl, Br and I. In another embodiment of Formula (II), R$^6$, at each occurrence, is alkyl.

In one embodiment of Formula (II), R$^4$, at each occurrence, is independently selected from the group consisting of alkyl, alkenyl, alkynyl, aryl, heterocyclyl, cycloalkyl, and cycloalkenyl; wherein each R$^4$ alkyl, alkenyl, and alkynyl is optionally substituted with one or more substituents independently selected from the group consisting of R$^7$, OR$^7$, SR$^7$, S(O)R$^7$, SO$_2$R$^7$, C(O)R$^7$, CO(O)R$^7$, OC(O)R$^7$, OC(O)OR$^7$, NH$_2$, NHR$^7$, N(R$^7$)$_2$, NHC(O)R$^7$, NR$^7$C(O)R, NHS(O)$_2$R$^7$, NR$^7$S(O)$_2$R$^7$, NHC(O)OR$^7$, NR$^7$C(O)OR$^7$, NHC(O)NH$_2$, NHC(O)NHR$^7$, NHC(O)N(R$^7$)$_2$, NR$^7$C(O)NHR$^7$, NR$^7$C(O)N(R$^7$)$_2$, C(O)NH$_2$, C(O)NHR$^7$, C(O)N(R$^7$)$_2$, C(O)NHOH, C(O)NHOR$^7$, C(O)NHSO$_2$R$^7$, C(O)NR$^7$SO$_2$R$^7$, SO$_2$NH$_2$, SO$_2$NHR$^7$, SO$_2$N(R$^7$)$_2$, C(O)H, C(O)OH, C(N)NH$_2$, C(N)NHR$^7$, C(N)N(R$^7$)$_2$, CNOH, CNOCH$_3$, OH, (O), CN, N$_3$, NO$_2$, F, Cl, Br and I; wherein the cyclic moiety represented by R$^4$ is independently optionally substituted with one or more substituents independently selected from the group consisting of R$^{10}$, OR$^{10}$, SR$^{10}$, S(O)R$^{10}$, C(O)C(O)R$^{10}$, SO$_2$R$^{10}$, C(O)R$^{10}$, CO(O)R$^{10}$, OC(O)R$^{10}$, OC(O)OR$^{10}$, NH$_2$, NHR$^{10}$, N(R$^{10}$)$_2$, NHC(O)R$^{10}$, NR$^{10}$C(O)R$^{10}$, NHS(O)$_2$R$^{10}$, NR$^{10}$S(O)$_2$R$^{10}$, NHC(O)OR$^{10}$, NR$^{10}$C(O)OR$^{10}$, NHC(O)NH$_2$, NHC(O)NHR$^{10}$, NHC(O)N(R$^{10}$)$_2$, NR$^{10}$C(O)NHR$^{10}$, NR$^{10}$C(O)N(R$^{10}$)$_2$, C(O)NH$_2$, C(O)NHR$^{10}$, C(O)N(R$^{10}$)$_2$, C(O)NHOH, C(O)NHOR$^{10}$, C(O)NHSO$_2$R$^{10}$, C(O)NR$^{10}$SO$_2$R$^{10}$, SO$_2$NH$_2$, SO$_2$NHR$^{10}$, SO$_2$N(R$^{10}$)$_2$, C(O)H, C(O)OH, C(N)NH$_2$, C(N)NHR$^{10}$, C(N)N(R$^{10}$)$_2$, CNOH, CNOCH$_3$, OH, CN, N$_3$, NO$_2$, F, Cl, Br and I. In another embodiment of Formula (II), R$^4$, at each occurrence, is independently selected from the group consisting of alkyl and heterocyclyl; wherein each R$^4$ alkyl is optionally substituted with one or more substituents independently selected from the group consisting of R$^7$, F, Cl, Br and I; wherein the cyclic moiety represented by R$^4$ is independently optionally substituted with one or more substituents independently selected from the group consisting of R$^{10}$, C(O)C(O)R$^{10}$, C(O)R$^{10}$, CO(O)R$^{10}$, F, Cl, Br and I. In another embodiment of Formula (II), R$^4$, at each occurrence, is heterocyclyl. In another embodiment of Formula (II), R$^4$, at each occurrence, is heterocyclyl; wherein the cyclic moiety represented by R$^4$ is independently optionally substituted with one or more substituents independently selected from the group consisting of R$^{10}$, C(O)C(O)R$^{10}$, C(O)R$^{10}$, CO(O)R$^{10}$, F, Cl, Br and I.

In one embodiment of Formula (II), R$^7$, at each occurrence, is independently selected from the group consisting of alkyl, alkenyl, alkynyl, aryl, heterocyclyl, cycloalkyl, and cycloalkenyl. In another embodiment of Formula (II), R$^7$, at each occurrence, is independently heterocyclyl.

In one embodiment of Formula (II), R$^{10}$, at each occurrence, is independently selected from the group consisting of alkyl, alkenyl, alkynyl, aryl, heterocyclyl, cycloalkyl, and cycloalkenyl; wherein each R$^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $C(N)NH_2$, $C(N)NHR^{11}$, $C(N)N(R^{11})_2$, $CNOH$, $CNOCH_3$, $OH$, $(O)$, $CN$, $N_3$, $NO_2$, F, Cl, Br and I; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, $CNOH$, $CNOCH_3$, $OH$, $CN$, $N_3$, $NO_2$, F, Cl, Br and I; $R^{11}$, at each occurrence, is independently selected from the group consisting of alkyl, alkenyl, alkynyl, aryl, heterocyclyl, cycloalkyl, and cycloalkenyl; wherein each $R^{11}$ alkyl, alkenyl, and alkynyl is optionally substituted with alkyl or alkoxy; wherein each $R^{11}$ aryl, heterocyclyl, cycloalkyl, and cycloalkenyl is optionally substituted with alkyl or alkoxy; and $R^{12}$, at each occurrence, is independently selected alkyl. In another embodiment of Formula (II), $R^{10}$, at each occurrence, is independently selected from the group consisting of alkyl, aryl, heterocyclyl, and cycloalkyl; wherein each $R^{10}$ alkyl is optionally substituted with one or more substituents independently selected from the group consisting of $R^{11}$, $OR^{11}$, $SR^{11}$, $N(R^{11})_2$, $NHC(O)R^{11}$, OH, F, Cl, Br and I; wherein each $R^{10}$ heterocyclyl, and cycloalkyl is optionally substituted with one or more substituents independently selected from the group consisting of $R^{12}$, $C(O)R^{12}$, F, Cl, Br and I; $R^{11}$, at each occurrence, is independently selected from the group consisting of alkyl, heterocyclyl, and cycloalkyl; wherein each $R^{11}$ alkyl is optionally substituted with alkoxy; wherein each $R^{11}$ heterocyclyl and cycloalkyl is optionally substituted with alkyl; and $R^{12}$, at each occurrence, is independently selected alkyl. In another embodiment of Formula (II), $R^{10}$, at each occurrence, is independently selected from the group consisting of alkyl, aryl, heterocyclyl, and cycloalkyl; wherein each $R^{10}$ alkyl is optionally substituted with one or more substituents independently selected from the group consisting of $R^{11}$, $OR^{11}$, $SR^{11}$, $N(R^{11})_2$, $NHC(O)R^{11}$, OH, and F; wherein each $R^{10}$ heterocyclyl, and cycloalkyl is optionally substituted with one or more substituents independently selected from the group consisting of $R^{12}$, and $C(O)R^{12}$; $R^{11}$, at each occurrence, is independently selected from the group consisting of alkyl, heterocyclyl, and cycloalkyl; wherein each $R^{11}$ alkyl is optionally substituted with alkoxy; wherein each $R^{11}$ heterocyclyl and cycloalkyl is optionally substituted with alkyl; and $R^{12}$, at each occurrence, is independently selected alkyl.

One embodiment of this invention pertains to compounds or pharmaceutically acceptable salts thereof, which are useful as inhibitors of NAMPT, the compounds having Formula (II)

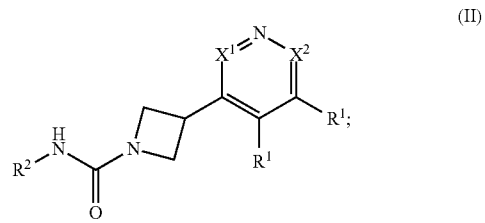

(II)

wherein
$X^1$ is $CR^1$ and $X^2$ is $CR^1$;
$R^1$, at each occurrence, is independently selected from the group consisting of hydrogen, alkyl, F, and Cl;
$R^2$ is independently selected from the group consisting of $C_4$-$C_6$-alkyl, and aryl; wherein each $R^2$ $C_4$-$C_6$-alkyl is substituted with one or more $R^3$; wherein each $R^2$ aryl is optionally substituted with one or more substituents independently selected from the group consisting of $R^4$, $OR^4$, $CO(O)R^4$, $C(O)NHR^4$, and CN;
$R^3$, at each occurrence, is heterocyclyl; wherein each $R^3$ heterocyclyl is optionally substituted with one or more $CO(O)R^6$;
$R^4$, at each occurrence, is independently selected from the group consisting of alkyl, and heterocyclyl; wherein each $R^4$ alkyl is optionally substituted with one or more $R^7$;
$R^6$, at each occurrence, is independently alkyl;
$R^7$, at each occurrence, is independently heterocyclyl;
wherein the cyclic moieties represented by $R^4$ are independently optionally substituted with one or more substituents independently selected from the group consisting of $R^{10}$, $C(O)C(O)R^{10}$, $C(O)R^{10}$, and $CO(O)R^{10}$;
$R^{10}$, at each occurrence, is independently selected from the group consisting of alkyl, aryl, heterocyclyl, and cycloalkyl; wherein each $R^{10}$ alkyl is optionally substituted with one or more substituents independently selected from the group consisting of $R^{11}$, $OR^{11}$, $SR^{11}$, $N(R^{11})_2$, $NHC(O)R^{11}$, OH, and F; wherein each $R^{10}$ heterocyclyl, and cycloalkyl is optionally substituted with one or more substituents independently selected from the group consisting of $R^{12}$, and $C(O)R^{12}$;
$R^{11}$, at each occurrence, is independently selected from the group consisting of alkyl, heterocyclyl, and cycloalkyl; wherein each $R^{11}$ alkyl is optionally substituted with alkoxy; wherein each $R^{11}$ heterocyclyl is optionally substituted with alkyl; and
$R^{12}$, at each occurrence, is independently selected alkyl.

Still another embodiment pertains to compounds having Formula (II), which includes Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, and pharmaceutically acceptable salts thereof.

Embodiments of Formula (III)

In another aspect, the present invention provides compounds of Formula (III)

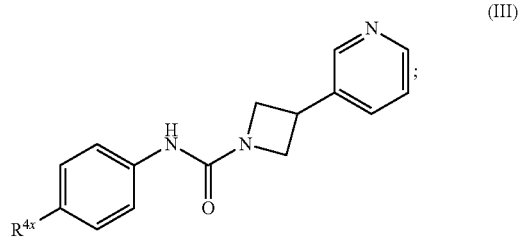

and pharmaceutically acceptable salts thereof: wherein $R^{4x}$ is as described herein for substituents on $R^2$ when $R^2$ is aryl in Formula (I).

One embodiment of this invention pertains to compounds of Formula (III) or pharmaceutically acceptable salts thereof;
wherein
$R^{4x}$ is independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I;

$R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, (O), CN, $N_3$, $NO_2$, F, Cl, Br and I;

$R^7$, at each occurrence, is independently selected from the group consisting of alkyl, alkenyl, alkynyl, aryl, heterocyclyl, cycloalkyl, and cycloalkenyl;
wherein the cyclic moieties represented by $R^4$ and $R^7$ are independently optionally substituted with one or more substituents independently selected from the group consisting of $R^{10}$, $OR^{10}$, $SR^{10}$, $S(O)R^{10}$, $C(O)C(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I;

$R^{10}$, at each occurrence, is independently selected from the group consisting of alkyl, alkenyl, alkynyl, aryl, heterocyclyl, cycloalkyl, and cycloalkenyl; wherein each $R^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $C(N)NH_2$, $C(N)NHR^{11}$, $C(N)N(R^{11})_2$, CNOH, $CNOCH_3$, OH, (O), CN, $N_3$, $NO_2$, F, Cl, Br and I; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^2S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^2$, $C(O)N(R^{12})_2$, $C(O)NHOH$, $C(O)NHOR^{12}$, $C(O)NHSO_2R^{12}$, $C(O)NR^2SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, CNOH, $CNOCH_3$, OH, CN, $N_3$, $NO_2$, F, Cl, Br and I;

$R^{11}$, at each occurrence, is independently selected from the group consisting of alkyl, alkenyl, alkynyl, aryl, heterocyclyl, cycloalkyl, and cycloalkenyl; wherein each $R^{11}$ alkyl, alkenyl, and alkynyl is optionally substituted with alkyl or alkoxy; wherein each $R^{11}$ aryl, heterocyclyl, cycloalkyl, and cycloalkenyl is optionally substituted with alkyl or alkoxy; and $R^{12}$, at each occurrence, is independently selected alkyl.

In one embodiment of Formula (III), $R^{4x}$ is independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I. In another embodiment of Formula (III), $R^{4x}$ is independently selected from the group consisting of $R^4$, $OR^4$, $CO(O)R^4$, $C(O)NHR^4$, CN, F, Cl, Br and I. In another embodiment of Formula (III), $R^{4x}$ is independently selected from the group consisting of $R^4$, $OR^4$, $CO(O)R^4$, $C(O)NHR^4$, and CN. In another embodiment of Formula (III), $R^{4x}$ is $C(O)NHR^4$. In another embodiment of Formula (III), $R^{4x}$ is $OR^4$. In another embodiment of Formula (III), $R^{4x}$ is $R^4$.

In one embodiment of Formula (III), $R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, SR$^7$, S(O)R$^7$, SO$_2$R$^7$, C(O)R$^7$, CO(O)R$^7$, OC(O)R$^7$, OC(O)OR$^7$, NH$_2$, NHR$^7$, N(R$^7$)$_2$, NHC(O)R$^7$, NR$^7$C(O)R$^7$, NHS(O)$_2$R$^7$, NR$^7$S(O)$_2$R$^7$, NHC(O)OR$^7$, NR$^7$C(O)OR$^7$, NHC(O)NH$_2$, NHC(O)NHR$^7$, NHC(O)N(R$^7$)$_2$, NR$^7$C(O)NHR$^7$, NR$^7$C(O)N(R$^7$)$_2$, C(O)NH$_2$, C(O)NHR$^7$, C(O)N(R$^7$)$_2$, C(O)NHOH, C(O)NHOR$^7$, C(O)NHSO$_2$R$^7$, C(O)NR$^7$SO$_2$R$^7$, SO$_2$NH$_2$, SO$_2$NHR$^7$, SO$_2$N(R$^7$)$_2$, C(O)H, C(O)OH, C(N)NH$_2$, C(N)NHR$^7$, C(N)N(R$^7$)$_2$, CNOH, CNOCH$_3$, OH, (O), CN, N$_3$, NO$_2$, F, Cl, Br and I; wherein the cyclic moiety represented by R$^4$ is independently optionally substituted with one or more substituents independently selected from the group consisting of R$^{10}$, OR$^{10}$, SR$^{10}$, S(O)R$^{10}$, C(O)C(O)R$^{10}$, SO$_2$R$^{10}$, C(O)R$^{10}$, CO(O)R$^{10}$, OC(O)R$^{10}$, OC(O)OR$^{10}$, NH$_2$, NHR$^{10}$, N(R$^{10}$)$_2$, NHC(O)R$^{10}$, NR$^{10}$C(O)R$^{10}$, NHS(O)$_2$R$^{10}$, NR$^{10}$S(O)$_2$R$^{10}$, NHC(O)OR$^{10}$, NR$^{10}$C(O)OR$^{10}$, NHC(O)NH$_2$, NHC(O)NHR$^{10}$, NHC(O)N(R$^{10}$)$_2$, NR$^{10}$C(O)NHR$^{10}$, NR$^{10}$C(O)N(R$^{10}$)$_2$, C(O)NH$_2$, C(O)NHR$^{10}$, C(O)N(R$^{10}$)$_2$, C(O)NHOH, C(O)NHOR$^{10}$, C(O)NHSO$_2$R$^{10}$, C(O)NR$^{10}$SO$_2$R$^{10}$, SO$_2$NH$_2$, SO$_2$NHR$^{10}$, SO$_2$N(R$^{10}$)$_2$, C(O)H, C(O)OH, C(N)NH$_2$, C(N)NHR$^{10}$, C(N)N(R$^{10}$)$_2$, CNOH, CNOCH$_3$, OH, CN, N$_3$, NO$_2$, F, Cl, Br and I. In another embodiment of Formula (III), R$^4$, at each occurrence, is independently selected from the group consisting of alkyl and heterocyclyl; wherein each R$^4$ alkyl is optionally substituted with one or more substituents independently selected from the group consisting of R$^7$, F, Cl, Br and I; wherein the cyclic moiety represented by R$^4$ is independently optionally substituted with one or more substituents independently selected from the group consisting of R$^{10}$, C(O)C(O)R$^{10}$, C(O)R$^{10}$, CO(O)R$^{10}$, F, Cl, Br and I. In another embodiment of Formula (III), R$^4$, at each occurrence, is heterocyclyl. In another embodiment of Formula (III), R$^4$, at each occurrence, is heterocyclyl; wherein the cyclic moiety represented by R$^4$ is independently optionally substituted with one or more substituents independently selected from the group consisting of R$^{10}$, C(O)C(O)R$^{10}$, C(O)R$^{10}$, CO(O)R$^{10}$, F, Cl, Br and I.

In one embodiment of Formula (III), R$^7$, at each occurrence, is independently selected from the group consisting of alkyl, alkenyl, alkynyl, aryl, heterocyclyl, cycloalkyl, and cycloalkenyl. In another embodiment of Formula (III), R$^7$, at each occurrence, is independently heterocyclyl.

In one embodiment of Formula (III), R$^{10}$, at each occurrence, is independently selected from the group consisting of alkyl, alkenyl, alkynyl, aryl, heterocyclyl, cycloalkyl, and cycloalkenyl; wherein each R$^{10}$ alkyl, alkenyl, and alkynyl is optionally substituted with one or more substituents independently selected from the group consisting of R$^{11}$, OR$^{11}$, SR$^{11}$, S(O)R$^{11}$, SO$_2$R$^{11}$, C(O)R$^{11}$, CO(O)R$^{11}$, OC(O)R$^{11}$, OC(O)OR$^{11}$, NH$_2$, NHR$^{11}$, N(R$^{11}$)$_2$, NHC(O)R$^{11}$, NR$^{11}$C(O)R$^{11}$, NHS(O)$_2$R$^{11}$, NR$^{11}$S(O)$_2$R$^{11}$, NHC(O)OR$^{11}$, NR$^{11}$C(O)OR$^{11}$, NHC(O)NH$_2$, NHC(O)NHR$^{11}$, NHC(O)N(R$^{11}$)$_2$, NR$^{11}$C(O)NHR$^{11}$, NR$^{11}$C(O)N(R$^{11}$)$_2$, C(O)NH$_2$, C(O)NHR$^{11}$, C(O)N(R$^{11}$)$_2$, C(O)NHOH, C(O)NHOR$^{11}$, C(O)NHSO$_2$R$^{11}$, C(O)NR$^{11}$SO$_2$R$^{11}$, SO$_2$NH$_2$, SO$_2$NHR$^{11}$, SO$_2$N(R$^{11}$)$_2$, C(O)H, C(O)OH, C(N)NH$_2$, C(N)NHR$^{11}$, C(N)N(R$^{11}$)$_2$, CNOH, CNOCH$_3$, OH, (O), CN, N$_3$, NO$_2$, F, Cl, Br and I; wherein each R$^{10}$ aryl, heterocyclyl, cycloalkyl, and cycloalkenyl is optionally substituted with one or more substituents independently selected from the group consisting of R$^{12}$, OR$^{12}$, SR$^{12}$, S(O)R$^{12}$, SO$_2$R$^{12}$, C(O)R$^{12}$, CO(O)R$^{12}$, OC(O)R$^{12}$, OC(O)OR$^{12}$, NH$_2$, NHR$^{12}$, N(R$^{12}$)$_2$, NHC(O)R$^{12}$, NR$^{12}$C(O)R$^{12}$, NHS(O)$_2$R$^{12}$, NR$^{12}$S(O)$_2$R$^{12}$, NHC(O)OR$^{12}$, NR$^{12}$C(O)OR$^{12}$, NHC(O)NH$_2$, NHC(O)NHR$^{12}$, NHC(O)N(R$^{12}$)$_2$, NR$^{12}$C(O)NHR$^{12}$, NR$^{12}$C(O)N(R$^{12}$)$_2$, C(O)NH$_2$, C(O)NHR$^{12}$, C(O)N(R$^{12}$)$_2$, C(O)NHOH, C(O)NHOR$^{12}$, C(O)NHSO$_2$R$^{12}$, C(O)NR$^{12}$SO$_2$R$^{12}$, SO$_2$NH$_2$, SO$_2$NHR$^{12}$, SO$_2$N(R$^{12}$)$_2$, C(O)H, C(O)OH, C(N)NH$_2$, C(N)NHR$^{12}$, C(N)N(R$^{12}$)$_2$, CNOH, CNOCH$_3$, OH, CN, N$_3$, NO$_2$, F, Cl, Br and I; R$^{11}$, at each occurrence, is independently selected from the group consisting of alkyl, alkenyl, alkynyl, aryl, heterocyclyl, cycloalkyl, and cycloalkenyl; wherein each R$^{11}$ alkyl, alkenyl, and alkynyl is optionally substituted with alkyl or alkoxy; wherein each R$^{11}$ aryl, heterocyclyl, cycloalkyl, and cycloalkenyl is optionally substituted with alkyl or alkoxy; and R$^{12}$, at each occurrence, is independently selected alkyl. In another embodiment of Formula (III), R$^{10}$, at each occurrence, is independently selected from the group consisting of alkyl, aryl, heterocyclyl, and cycloalkyl; wherein each R$^{10}$ alkyl is optionally substituted with one or more substituents independently selected from the group consisting of R$^{11}$, OR$^{11}$, SR$^{11}$, N(R$^{11}$)$_2$, NHC(O)R$^{11}$, OH, F, Cl, Br and I; wherein each R$^{10}$ heterocyclyl, and cycloalkyl is optionally substituted with one or more substituents independently selected from the group consisting of R$^{12}$, C(O)R$^{12}$, F, Cl, Br and I; R$^{11}$, at each occurrence, is independently selected from the group consisting of alkyl, heterocyclyl, and cycloalkyl; wherein each R$^{11}$ alkyl is optionally substituted with alkoxy; wherein each R$^{11}$ heterocyclyl and cycloalkyl is optionally substituted with alkyl; and R$^{12}$, at each occurrence, is independently selected alkyl. In another embodiment of Formula (III), R$^{10}$, at each occurrence, is independently selected from the group consisting of alkyl, aryl, heterocyclyl, and cycloalkyl; wherein each R$^{10}$ alkyl is optionally substituted with one or more substituents independently selected from the group consisting of R$^{11}$, OR$^{11}$, SR$^{11}$, N(R$^{11}$)$_2$, NHC(O)R$^{11}$, OH, and F; wherein each R$^{10}$ heterocyclyl, and cycloalkyl is optionally substituted with one or more substituents independently selected from the group consisting of R$^{12}$, and C(O)R$^{12}$; R$^{11}$, at each occurrence, is independently selected from the group consisting of alkyl, heterocyclyl, and cycloalkyl; wherein each R$^{11}$ alkyl is optionally substituted with alkoxy; wherein each R$^{11}$ heterocyclyl and cycloalkyl is optionally substituted with alkyl; and R$^{12}$, at each occurrence, is independently selected alkyl.

One embodiment of this invention pertains to compounds or pharmaceutically acceptable salts thereof, which are useful as inhibitors of NAMPT, the compounds having Formula (III)

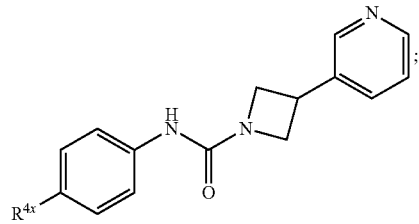

Formula (III)

wherein
R$^{4x}$ is independently selected from the group consisting of R$^4$, OR$^4$, CO(O)R$^4$, C(O)NHR$^4$, and CN;
R$^4$, at each occurrence, is independently selected from the group consisting of alkyl, and heterocyclyl; wherein each R$^4$ alkyl is optionally substituted with one or more R$^7$;
R$^7$, at each occurrence, is independently heterocyclyl;
wherein the cyclic moiety represented by R$^4$ is independently optionally substituted with one or more substituents independently selected from the group consisting of $R^{10}$, $C(O)C(O)R^{10}$, $C(O)R^{10}$, and $CO(O)R^{10}$;

$R^{10}$, at each occurrence, is independently selected from the group consisting of alkyl, aryl, heterocyclyl, and cycloalkyl; wherein each $R^{10}$ alkyl is optionally substituted with one or more substituents independently selected from the group consisting of $R^{11}$, $OR^{11}$, $SR^{11}$, $N(R^{11})_2$, $NHC(O)R^{11}$, OH, and F; wherein each $R^{10}$ heterocyclyl, and cycloalkyl is optionally substituted with one or more substituents independently selected from the group consisting of $R^{12}$, and $C(O)R^{12}$;

$R^{11}$, at each occurrence, is independently selected from the group consisting of alkyl, heterocyclyl, and cycloalkyl; wherein each $R^{11}$ alkyl is optionally substituted with alkoxy; wherein each $R^{11}$ heterocyclyl is optionally substituted with alkyl; and $R^{12}$, at each occurrence, is independently selected alkyl.

Still another embodiment pertains to compounds having Formula (III), which includes Examples 1, 2, 4, 5, 6, 7, 9, 10, 11, 12, 13, 14, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 114, 115, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 157, 158, 159, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, and pharmaceutically acceptable salts thereof.

Embodiments of Formula (IA)

One embodiment of this invention, therefore, pertains to compounds or pharmaceutically acceptable salts thereof, which are useful as inhibitors of NAMPT, the compounds having Formula (IA)

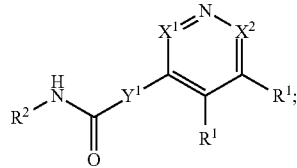

Formula (IA)

wherein
$X^1$ is N and $X^2$ is $CR^1$; or
$X^1$ is $CR^1$ and $X^2$ is N; or
$X^1$ is $CR^1$ and $X^2$ is $CR^1$;

$Y^1$ is

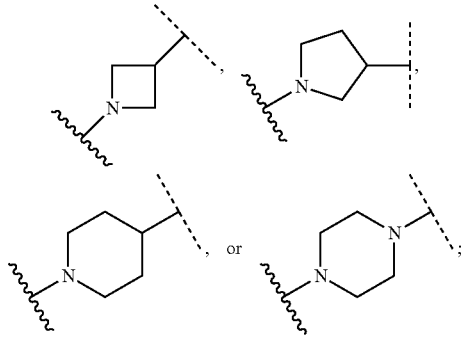

wherein ⤳ indicates the point of attachment to the carbonyl and ⤵ indicates the point of attachment to the nitrogen containing heteroaryl;

$R^1$, at each occurrence, is independently selected from the group consisting of hydrogen, alkyl, alkenyl, alkynyl, haloalkyl, hydoxyalkyl, alkoxy, OH, $NH_2$, CN, $NO_2$, F, Cl, Br and I;

$R^2$ is independently selected from the group consisting of $C_4$-$C_6$-alkyl, $C_4$-$C_6$-alkenyl, $C_4$-$C_6$-alkynyl, aryl, 3-12 membered heterocyclyl, cycloalkyl, and cycloalkenyl; wherein each $R^2$ $C_4$-$C_6$-alkyl, $C_4$-$C_6$-alkenyl, and $C_4$-$C_6$-alkynyl is substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(N)NH_2$, $C(N)NHR^3$, $C(N)N(R^3)_2$, CNOH, $CNOCH_3$, OH, (O), CN, $N_3$, $NO_2$, F, Cl, Br and I; wherein each $R^2$ aryl, 3-12 membered heterocyclyl, cycloalkyl, and cycloalkenyl is optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I;

$R^3$, at each occurrence, is independently selected from the group consisting of alkyl, alkenyl, alkynyl, aryl, cycloalkyl, cycloalkenyl, and heterocyclyl; wherein each $R^3$ alkyl, alkenyl, and alkynyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, (O), CN, $N_3$, $NO_2$, F, Cl, Br and I; wherein each $R^3$ aryl, cycloalkyl, cycloalkenyl, and heterocyclyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, CNOH, $CNOCH_3$, OH, CN, $N_3$, $NO_2$, F, Cl, Br and I;

$R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, (O), CN, $N_3$, $NO_2$, F, Cl, Br and I;

$R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one or more substituents independently selected from the group consisting of $R^8$, $OR^8$, $SR^8$, $S(O)R^8$, $SO_2R^8$, $NHR^8$, $N(R^8)_2$, $C(O)R^8$, $C(O)NH_2$, $C(O)NHR^8$, $C(O)N(R^8)_2$, $NHC(O)R^8$, $NR^8C(O)R^8$, $NHSO_2R^8$, $NHC(O)OR^8$, $SO_2NH_2$, $SO_2NHR^8$, $SO_2N(R^8)_2$, $NHC(O)NH_2$, $NHC(O)NHR^8$, OH, (O), $C(O)OH$, $N_3$, CN, $NH_2$, F, Cl, Br and I;

$R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted from the group consisting of $R^9$, $OR^9$, $SR^9$, $S(O)R^9$, $SO_2R^9$, $NHR^9$, $N(R^9)_2$, $C(O)R^9$, $C(O)NH_2$, $C(O)NHR^9$, $C(O)N(R^9)_2$, $NHC(O)R^9$, $NR^9C(O)R^9$, $NHSO_2R^9$, $NHC(O)OR^9$, $SO_2NH_2$, $SO_2NHR^9$, $SO_2N(R^9)_2$, $NHC(O)NH_2$, $NHC(O)NHR^9$, OH, (O), $C(O)OH$, $N_3$, CN, $NH_2$, $CF_3$, $CF_2CF_3$, F, Cl, Br and I;

$R^7$, at each occurrence, is independently selected from the group consisting of alkyl, alkenyl, alkynyl, aryl, heterocyclyl, cycloalkyl, and cycloalkenyl;

$R^8$, at each occurrence, is independently selected from the group consisting of alkyl, alkenyl, alkynyl, aryl, heterocyclyl, cycloalkyl, and cycloalkenyl;

$R^9$, at each occurrence, is independently selected from the group consisting of alkyl, alkenyl, alkynyl, aryl, heterocyclyl, cycloalkyl, and cycloalkenyl;

wherein the cyclic moieties represented by $R^4$, $R^5$, $R^6$, $R^7$, $R^8$, and $R^9$ are independently optionally substituted with one or more substituents independently selected from the group consisting of $R^{10}$, $OR^{10}$, $SR^{10}$, $S(O)R^{10}$, $C(O)C(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I;

$R^{10}$, at each occurrence, is independently selected from the group consisting of alkyl, alkenyl, alkynyl, aryl, heterocyclyl, cycloalkyl, and cycloalkenyl; wherein each $R^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $C(N)NH_2$, $C(N)NHR^{11}$, $C(N)N(R^{11})_2$, CNOH, $CNOCH_3$, OH, (O), CN, $N_3$, $NO_2$, F, Cl, Br and I; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, CNOH, $CNOCH_3$, OH, CN, $N_3$, $NO_2$, F, Cl, Br and I;

$R^{11}$, at each occurrence, is independently selected from the group consisting of alkyl, alkenyl, alkynyl, aryl, heterocyclyl, cycloalkyl, and cycloalkenyl; wherein each $R^{11}$ alkyl, alkenyl, and alkynyl is optionally substituted with alkyl or alkoxy; wherein each $R^{11}$ aryl, heterocyclyl, cycloalkyl, and cycloalkenyl is optionally substituted with alkyl or alkoxy; and $R^{12}$, at each occurrence, is independently selected alkyl.

In one embodiment of Formula (IA), $X^1$ is N and $X^2$ is $CR^1$. In another embodiment of Formula (IA), $X^1$ is $CR^1$ and $X^2$ is N. In another embodiment of Formula (IA), $X^1$ is $CR^1$ and $X^2$ is $CR^1$. In another embodiment of Formula (IA), $X^1$ is $CR^1$ and $X^2$ is $CR^1$, and $R^1$, at each occurrence, is independently selected from the group consisting of hydrogen, alkyl, alkenyl, alkynyl, haloalkyl, hydoxyalkyl, alkoxy, OH, $NH_2$, CN, $NO_2$, F, Cl, Br and I. In another embodiment of Formula (IA), $X^1$ is $CR^1$ and $X^2$ is $CR^1$, and $R^1$, at each occurrence, is independently selected from the group consisting of hydrogen, alkyl, F, Cl, Br and I. In another embodiment of Formula (IA), $X^1$ is $CR^1$ and $X^2$ is $CR^1$, and $R^1$, at each occurrence, is hydrogen.

In one embodiment of Formula (IA), $R^1$, at each occurrence, is independently selected from the group consisting of hydrogen, alkyl, alkenyl, alkynyl, haloalkyl, hydoxyalkyl, alkoxy, OH, $NH_2$, CN, $NO_2$, F, Cl, Br and I. In another embodiment of Formula (IA), $R^1$, at each occurrence, is independently selected from the group consisting of hydrogen, alkyl, F, Cl, Br and I. In another embodiment of Formula (IA), $R^1$, at each occurrence, is independently selected from the group consisting of hydrogen, alkyl, F, and Cl. In another embodiment of Formula (IA), $R^1$, at each occurrence, is hydrogen.

In one embodiment of Formula (IA), Y$^1$ is

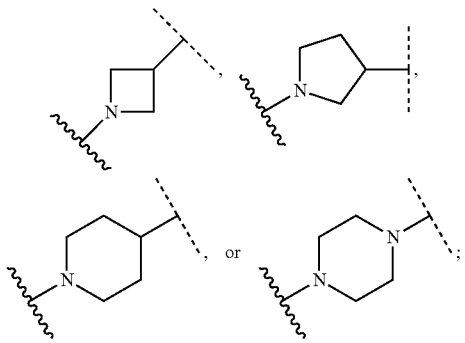

wherein ⁓ indicates the point of attachment to the carbonyl and ⦵ indicates the point of attachment to the nitrogen containing heteroaryl. In another embodiment of Formula (IA), Y$^1$ is

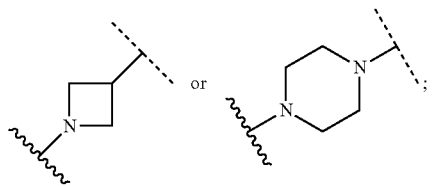

wherein ⁓ indicates the point of attachment to the carbonyl and ⦵ indicates the point of attachment to the nitrogen containing heteroaryl. In another embodiment of Formula (IA), Y$^1$ is

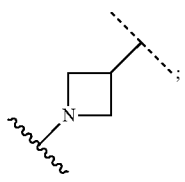

wherein ⁓ indicates the point of attachment to the carbonyl and ⦵ indicates the point of attachment to the nitrogen containing heteroaryl.

In one embodiment of Formula (IA), R$^2$ is independently selected from the group consisting of C$_4$-C$_6$-alkyl, C$_4$-C$_6$-alkenyl, C$_4$-C$_6$-alkynyl, aryl, 3-12 membered heterocyclyl, cycloalkyl, and cycloalkenyl; wherein each R$^2$ C$_4$-C$_6$-alkyl, C$_4$-C$_6$-alkenyl, and C$_4$-C$_6$-alkynyl is substituted with one or more substituents independently selected from the group consisting of R$^3$, OR$^3$, SR$^3$, S(O)R$^3$, SO$_2$R$^3$, C(O)R$^3$, CO(O)R$^3$, OC(O)R$^3$, OC(O)OR$^3$, NH$_2$, NHR$^3$, N(R$^3$)$_2$, NHC(O)R$^3$, NR$^3$C(O)R$^3$, NHS(O)$_2$R$^3$, NR$^3$S(O)$_2$R$^3$, NHC(O)OR$^3$, NR$^3$C(O)OR$^3$, NHC(O)NH$_2$, NHC(O)NHR$^3$, NHC(O)N(R$^3$)$_2$, NR$^3$C(O)NHR$^3$, NR$^3$C(O)N(R$^3$)$_2$, C(O)NH$_2$, C(O)NHR$^3$, C(O)N(R$^3$)$_2$, C(O)NHOH, C(O)NHOR$^3$, C(O)NHSO$_2$R$^3$, C(O)NR$^3$SO$_2$R$^3$, SO$_2$NH$_2$, SO$_2$NHR$^3$, SO$_2$N(R$^3$)$_2$, C(O)H, C(O)OH, C(N)NH$_2$, C(N)NHR$^3$, C(N)N(R$^3$)$_2$, CNOH, CNOCH$_3$, OH, (O), CN, N$_3$, NO$_2$, F, Cl, Br and I; wherein each R$^2$ aryl, 3-12 membered heterocyclyl, cycloalkyl, and cycloalkenyl is optionally substituted with one or more substituents independently selected from the group consisting of R$^4$, OR$^4$, SR$^4$, S(O)R$^4$, SO$_2$R$^4$, C(O)R$^4$, CO(O)R$^4$, OC(O)R$^4$, OC(O)OR$^4$, NH$_2$, NHR$^4$, N(R$^4$)$_2$, NHC(O)R$^4$, NR$^4$C(O)R$^4$, NHS(O)$_2$R$^4$, NR$^4$S(O)$_2$R$^4$, NHC(O)OR$^4$, NR$^4$C(O)OR$^4$, NHC(O)NH$_2$, NHC(O)NHR$^4$, NHC(O)N(R$^4$)$_2$, NR$^4$C(O)NHR$^4$, NR$^4$C(O)N(R$^4$)$_2$, C(O)NH$_2$, C(O)NHR$^4$, C(O)N(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, C(O)H, C(O)OH, C(N)NH$_2$, C(N)NHR$^4$, C(N)N(R$^4$)$_2$, CNOH, CNOCH$_3$, OH, CN, N$_3$, NO$_2$, F, Cl, Br and I. In another embodiment of Formula (IA), R$^2$ is independently selected from the group consisting of C$_4$-C$_6$-alkyl, and aryl; wherein each R$^2$ C$_4$-C$_6$-alkyl is substituted with one or more substituents independently selected from the group consisting of R$^3$, F, Cl, Br and I; wherein each R$^2$ aryl is optionally substituted with one or more substituents independently selected from the group consisting of R$^4$, OR$^4$, CO(O)R$^4$, C(O)NHR$^4$, CN, F, Cl, Br and I. In another embodiment of Formula (IA), R$^2$ is independently selected from the group consisting of C$_4$-C$_6$-alkyl, and aryl; wherein each R$^2$ C$_4$-C$_6$-alkyl is substituted with one or more R$^3$; wherein each R$^2$ aryl is optionally substituted with one or more substituents independently selected from the group consisting of R$^4$, OR$^4$, CO(O)R$^4$, C(O)NHR$^4$, and CN. In another embodiment of Formula (IA), R$^2$ is C$_4$-C$_6$-alkyl; wherein each R$^2$ C$_4$-C$_6$-alkyl is substituted with one or more R$^3$. In another embodiment of Formula (IA), R$^2$ is aryl; wherein each R$^2$ aryl is substituted with one or more substituents independently selected from the group consisting of R$^4$, OR$^4$, CO(O)R$^4$, C(O)NHR$^4$, and CN. In another embodiment of Formula (IA), R$^2$ is aryl; wherein each R$^2$ aryl is substituted with one C(O)NHR$^4$. In another embodiment of Formula (IA), R$^2$ is phenyl; wherein each R$^2$ phenyl is substituted with one C(O)NHR$^4$. In another embodiment of Formula (IA), R$^2$ is phenyl; wherein each R$^2$ phenyl is substituted with one OR$^4$. In another embodiment of Formula (IA), R$^2$ is phenyl; wherein each R$^2$ phenyl is substituted with one R$^4$.

In one embodiment of Formula (IA), R$^3$, at each occurrence, is independently selected from the group consisting of alkyl, alkenyl, alkynyl, aryl, cycloalkyl, cycloalkenyl, and heterocyclyl; wherein each R$^3$ alkyl, alkenyl, and alkynyl is optionally substituted with one or more substituents independently selected from the group consisting of R$^5$, OR$^5$, SR$^5$, S(O)R$^5$, SO$_2$R$^5$, C(O)R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, NHS(O)$_2$R$^5$, NR$^5$S(O)$_2$R$^5$, NHC(O)OR$^5$, NR$^5$C(O)OR$^5$, NHC(O)NH$_2$, NHC(O)NHR$^5$, NHC(O)N(R$^5$)$_2$, NR$^5$C(O)NHR$^5$, NR$^5$C(O)N(R$^5$)$_2$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, C(O)H, C(O)OH, C(N)NH$_2$, C(N)NHR$^5$, C(N)N(R$^5$)$_2$, CNOH, CNOCH$_3$, OH, (O), CN, N$_3$, NO$_2$, F, Cl, Br and I; wherein each R$^3$ aryl, cycloalkyl, cycloalkenyl, and heterocyclyl is optionally substituted with one or more substituents independently selected from the group consisting of R$^6$, OR$^6$, SR$^6$, S(O)R$^6$, SO$_2$R$^6$, C(O)R$^6$, CO(O)R$^6$, OC(O)R$^6$, OC(O)OR$^6$, NH$_2$, NHR$^6$, N(R$^6$)$_2$, NHC(O)R$^6$, NR$^6$C(O)R$^6$, NHS(O)$_2$R$^6$, NR$^6$S(O)$_2$R$^6$, NHC(O)OR$^6$, NR$^6$C(O)OR$^6$, NHC(O)NH$_2$, NHC(O)NHR$^6$, NHC(O)N(R$^6$)$_2$, NR$^6$C(O)NHR$^6$, NR$^6$C(O)N(R$^6$)$_2$, C(O)NH$_2$, C(O)NHR$^6$, C(O)N(R$^6$)$_2$, C(O)NHOH, C(O)NHOR$^6$, C(O)NHSO$_2$R$^6$, C(O)NR$^6$SO$_2$R$^6$, SO$_2$NH$_2$, SO$_2$NHR$^6$, SO$_2$N(R$^6$)$_2$, C(O)H, C(O)OH, C(N)NH$_2$, C(N)NHR$^6$, C(N)N(R$^6$)$_2$, CNOH, CNOCH$_3$, OH, CN, N$_3$, NO$_2$, F, Cl, Br and I. In another embodiment of Formula (IA), R$^3$, at each occurrence, is independently heterocyclyl; wherein each R$^3$ heterocyclyl is optionally substituted with one or more substituents independently selected from the group consisting of $CO(O)R^6$, F, Cl, Br and I. In another embodiment of Formula (IA), $R^3$, at each occurrence, is independently heterocyclyl; wherein each $R^3$ heterocyclyl is optionally substituted with one or more $CO(O)R^6$.

In one embodiment of Formula (IA), $R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one or more substituents independently selected from the group consisting of $R^9$, $OR^9$, $SR^9$, $S(O)R^9$, $SO_2R^9$, $NHR^9$, $N(R^9)_2$, $C(O)R^9$, $C(O)NH_2$, $C(O)NHR^9$, $C(O)N(R^9)_2$, $NHC(O)R^9$, $NR^9C(O)R^9$, $NHSO_2R^9$, $NHC(O)OR^9$, $SO_2NH_2$, $SO_2NHR^9$, $SO_2N(R^9)_2$, $NHC(O)NH_2$, $NHC(O)NHR^9$, OH, (O), $C(O)OH$, $N_3$, CN, $NH_2$, $CF_3$, $CF_2CF_3$, F, Cl, Br and I. In another embodiment of Formula (IA), $R^6$, at each occurrence, is alkyl.

In one embodiment of Formula (IA), $R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, (O), CN, $N_3$, $NO_2$, F, Cl, Br and I; wherein the cyclic moiety represented by $R^4$ is independently optionally substituted with one or more substituents independently selected from the group consisting of $R^{10}$, $OR^{10}$, $SR^{10}$, $S(O)R^{10}$, $C(O)C(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I. In another embodiment of Formula (IA), $R^4$, at each occurrence, is independently selected from the group consisting of alkyl and heterocyclyl; wherein each $R^4$ alkyl is optionally substituted with one or more substituents independently selected from the group consisting of $R^7$, F, Cl, Br and I; wherein the cyclic moiety represented by $R^4$ is independently optionally substituted with one or more substituents independently selected from the group consisting of $R^{10}$, $C(O)C(O)R^{10}$, $C(O)R^{10}$, $CO(O)R^{10}$, F, Cl, Br and I. In another embodiment of Formula (IA), $R^4$, at each occurrence, is heterocyclyl. In another embodiment of Formula (IA), $R^4$, at each occurrence, is heterocyclyl; wherein the cyclic moiety represented by $R^4$ is independently optionally substituted with one or more substituents independently selected from the group consisting of $R^{10}$, $C(O)C(O)R^{10}$, $C(O)R^{10}$, $CO(O)R^{10}$, F, Cl, Br and I.

In one embodiment of Formula (IA), $R^7$, at each occurrence, is independently selected from the group consisting of alkyl, alkenyl, alkynyl, aryl, heterocyclyl, cycloalkyl, and cycloalkenyl. In another embodiment of Formula (IA), $R^7$, at each occurrence, is independently heterocyclyl. In another embodiment of Formula (IA), $R^7$, at each occurrence, is heterocyclyl; wherein the cyclic moiety represented by R is independently optionally substituted with one or more substituents independently selected from the group consisting of $R^{10}$, $C(O)C(O)R^{10}$, $C(O)R^{10}$, $CO(O)R^{10}$, F, Cl, Br and I.

In one embodiment of Formula (IA), $R^{10}$, at each occurrence, is independently selected from the group consisting of alkyl, alkenyl, alkynyl, aryl, heterocyclyl, cycloalkyl, and cycloalkenyl; wherein each $R^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $C(N)NH_2$, $C(N)NHR^{11}$, $C(N)N(R^{11})_2$, CNOH, $CNOCH_3$, OH, (O), CN, $N_3$, $NO_2$, F, Cl, Br and I; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, CNOH, $CNOCH_3$, OH, CN, $N_3$, $NO_2$, F, Cl, Br and I; $R^{11}$, at each occurrence, is independently selected from the group consisting of alkyl, alkenyl, alkynyl, aryl, heterocyclyl, cycloalkyl, and cycloalkenyl; wherein each $R^{11}$ alkyl, alkenyl, and alkynyl is optionally substituted with alkyl or alkoxy; wherein each $R^{11}$ aryl, heterocyclyl, cycloalkyl, and cycloalkenyl is optionally substituted with alkyl or alkoxy; and $R^{12}$, at each occurrence, is independently selected alkyl. In another embodiment of Formula (IA), $R^{10}$, at each occurrence, is independently selected from the group consisting of alkyl, aryl, heterocyclyl, and cycloalkyl; wherein each $R^{10}$ alkyl is optionally substituted with one or more substituents independently selected from the group consisting of $R^{11}$, $OR^{11}$, $SR^{11}$, $N(R^{11})_2$, $NHC(O)R^{11}$, OH, F, Cl, Br and I; wherein each $R^{10}$ aryl, heterocyclyl, and cycloalkyl is optionally substituted with one or more substituents independently selected from the group consisting of $R^{12}$, $C(O)R^{12}$, F, Cl, Br and I; $R^{11}$, at each occurrence, is independently selected from the group consisting of alkyl, heterocyclyl, and cycloalkyl; wherein each $R^{11}$ alkyl is optionally substituted with alkoxy; wherein each $R^{11}$ heterocyclyl and cycloalkyl is optionally substituted with alkyl; and $R^{12}$, at each occurrence, is independently selected alkyl. In another embodiment of Formula (IA), $R^{10}$, at each occurrence, is independently selected from the group consisting of alkyl, aryl, heterocyclyl, and cycloalkyl; wherein each $R^{10}$ alkyl is optionally substituted with one or more substituents independently selected from the group consisting of $R^{11}$, $OR^{11}$, $SR^{11}$, $N(R^{11})_2$, $NHC(O)R^{11}$, OH, and F; wherein each $R^{10}$ aryl, heterocyclyl, and cycloalkyl is optionally substituted with one or more substituents independently selected from the group consisting of $R^{12}$, $C(O)R^{12}$, and F; $R^{11}$, at each occurrence, is independently selected from the group consisting of alkyl, heterocyclyl, and cycloalkyl; wherein each $R^{11}$ alkyl is optionally substituted with alkoxy; wherein each $R^{11}$ heterocyclyl and cycloalkyl is optionally substituted with alkyl; and $R^{12}$, at each occurrence, is independently selected alkyl.

One embodiment of this invention pertains to compounds or pharmaceutically acceptable salts thereof, which are useful as inhibitors of NAMPT, the compounds having Formula (IA)

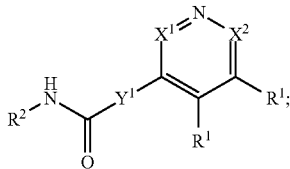

Formula (IA)

wherein
$X^1$ is $CR^1$ and $X^2$ is $CR^1$;
Y is

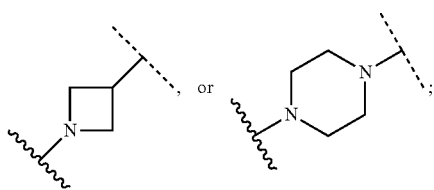

wherein ⁓ indicates the point of attachment to the carbonyl and ⟍ indicates the point of attachment to the nitrogen containing heteroaryl;

$R^1$, at each occurrence, is independently selected from the group consisting of hydrogen, alkyl, F, and Cl;

$R^2$ is independently selected from the group consisting of $C_4$-$C_6$-alkyl, and aryl; wherein each $R^2$ $C_4$-$C_6$-alkyl is substituted with one or more $R^3$; wherein each $R^2$ aryl is optionally substituted with one or more substituents independently selected from the group consisting of $R^4$, $OR^4$, $CO(O)R^4$, $C(O)NHR^4$, and CN;

$R^3$, at each occurrence, is heterocyclyl; wherein each $R^3$ heterocyclyl is optionally substituted with one or more $CO(O)R^6$;

$R^4$, at each occurrence, is independently selected from the group consisting of alkyl, and heterocyclyl; wherein each $R^4$ alkyl is optionally substituted with one or more $R^7$;

$R^6$, at each occurrence, is independently alkyl;

$R^7$, at each occurrence, is independently heterocyclyl;

wherein the cyclic moieties represented by $R^4$ and $R^7$ are independently optionally substituted with one or more substituents independently selected from the group consisting of $R^{10}$, $C(O)C(O)R^{10}$, $C(O)R^{10}$, and $CO(O)R^{10}$;

$R^{10}$, at each occurrence, is independently selected from the group consisting of alkyl, aryl, heterocyclyl, and cycloalkyl; wherein each $R^{10}$ alkyl is optionally substituted with one or more substituents independently selected from the group consisting of $R^{11}$, $OR^{11}$, $SR^{11}$, $N(R^{11})_2$, NHC(O)$R^{11}$, OH, and F; wherein each $R^{10}$ aryl, heterocyclyl, and cycloalkyl is optionally substituted with one or more substituents independently selected from the group consisting of $R^{12}$, $C(O)R^{12}$, and F;

$R^{11}$, at each occurrence, is independently selected from the group consisting of alkyl, heterocyclyl, and cycloalkyl; wherein each $R^{11}$ alkyl is optionally substituted with alkoxy; wherein each $R^{11}$ heterocyclyl is optionally substituted with alkyl; and $R^{12}$, at each occurrence, is independently selected alkyl.

Still another embodiment pertains to compounds having Formula (IA), which include N-[4-({1-[(2S)-2-methylbutanoyl]azetidin-3-yl}oxy)phenyl]-3-(pyridin-3-yl)azetidine-1-carboxamide;

3-(pyridin-3-yl)-N-(4-{[1-(tetrahydro-2H-pyran-4-ylacetyl)piperidin-4-yl]oxy}phenyl)azetidine-1-carboxamide;

3-(5-fluoropyridin-3-yl)-N-(4-{[1-(tetrahydro-2H-pyran-4-ylacetyl)piperidin-4-yl]oxy}phenyl)azetidine-1-carboxamide;

N-[4-({1-[(2S)-2-methylbutanoyl]piperidin-4-yl}oxy)phenyl]-3-(pyridin-3-yl)azetidine-1-carboxamide;

3-(pyridin-3-yl)-N-[4-({1-[(2R)-tetrahydrofuran-2-ylcarbonyl]piperidin-4-yl}oxy)phenyl]azetidine-1-carboxamide;

3-(pyridin-3-yl)-N-(4-{[1-(3,3,3-trifluoropropanoyl)piperidin-4-yl]oxy}phenyl)azetidine-1-carboxamide;

N-(4-{[1-(2-hydroxy-2-methylpropanoyl)piperidin-4-yl]oxy}phenyl)-3-(pyridin-3-yl)azetidine-1-carboxamide;

3-(6-methylpyridin-3-yl)-N-(4-{[1-(tetrahydro-2H-pyran-4-ylacetyl)piperidin-4-yl]oxy}phenyl)azetidine-1-carboxamide;

N-(4-{1-[(2S)-2-methylbutanoyl]-1,2,3,6-tetrahydropyridin-4-yl}phenyl)-3-(pyridin-3-yl)azetidine-1-carboxamide;

3-(pyridin-3-yl)-N-(4-{1-[(2R)-tetrahydrofuran-2-ylcarbonyl]-1,2,3,6-tetrahydropyridin-4-yl}phenyl)azetidine-1-carboxamide;

3-(pyridin-3-yl)-N-(4-{1-[(2S)-tetrahydrofuran-2-ylcarbonyl]-1,2,3,6-tetrahydropyridin-4-yl}phenyl)azetidine-1-carboxamide;

N-{4-[1-(2-hydroxy-2-methylpropanoyl)-1,2,3,6-tetrahydropyridin-4-yl]phenyl}-3-(pyridin-3-yl)azetidine-1-carboxamide;

methyl 4-({[3-(pyridin-3-yl)azetidin-1-yl]carbonyl}amino)benzoate;

N-(4-cyanophenyl)-3-(pyridin-3-yl)azetidine-1-carboxamide;

tert-butyl 4-[4-({[3-(pyridin-3-yl)azetidin-1-yl]carbonyl}amino)butyl]piperidine-1-carboxylate;

N-{4-[1-(2,2-dimethylbutanoyl)-1,2,3,6-tetrahydropyridin-4-yl]phenyl}-3-(pyridin-3-yl)azetidine-1-carboxamide;

N-{4-[1-(3,3-dimethylbutanoyl)-1,2,3,6-tetrahydropyridin-4-yl]phenyl}-3-(pyridin-3-yl)azetidine-1-carboxamide;

3-(pyridin-3-yl)-N-{4-[1-(3,3,3-trifluoropropanoyl)-1,2,3,6-tetrahydropyridin-4-yl]phenyl}azetidine-1-carboxamide;

3-(pyridin-3-yl)-N-{4-[1-(4,4,4-trifluorobutanoyl)-1,2,3,6-tetrahydropyridin-4-yl]phenyl}azetidine-1-carboxamide;

N-{4-[1-(methoxyacetyl)-1,2,3,6-tetrahydropyridin-4-yl]phenyl}-3-(pyridin-3-yl)azetidine-1-carboxamide;

N-(4-{1-[(methylsulfanyl)acetyl]-1,2,3,6-tetrahydropyridin-4-yl}phenyl)-3-(pyridin-3-yl)azetidine-1-carboxamide;

N-{4-[1-(ethoxyacetyl)-1,2,3,6-tetrahydropyridin-4-yl]phenyl}-3-(pyridin-3-yl)azetidine-1-carboxamide;

N-(4-{1-[(2-methoxyethoxy)acetyl]-1,2,3,6-tetrahydropyridin-4-yl}phenyl)-3-(pyridin-3-yl)azetidine-1-carboxamide;

N-(4-{1-[3-(methylsulfanyl)propanoyl]-1,2,3,6-tetrahydropyridin-4-yl}phenyl)-3-(pyridin-3-yl)azetidine-1-carboxamide;

N-{4-[1-(cyclopropylcarbonyl)-1,2,3,6-tetrahydropyridin-4-yl]phenyl}-3-(pyridin-3-yl)azetidine-1-carboxamide;

N-{4-[1-(cyclopropylacetyl)-1,2,3,6-tetrahydropyridin-4-yl]phenyl}-3-(pyridin-3-yl)azetidine-1-carboxamide;

N-{4-[1-(2-methylpropanoyl)-1,2,3,6-tetrahydropyridin-4-yl]phenyl}-3-(pyridin-3-yl)azetidine-1-carboxamide;

3-(pyridin-3-yl)-N-[4-({1-[(2R)-tetrahydrofuran-2-ylcarbonyl]azetidin-3-yl}oxy)phenyl]azetidine-1-carboxamide;

3-(pyridin-3-yl)-N-[4-({1-[(2S)-tetrahydrofuran-2-ylcarbonyl]azetidin-3-yl}oxy)phenyl]azetidine-1-carboxamide;
N-(4-{[1-(2-hydroxy-2-methylpropanoyl)azetidin-3-yl]oxy}phenyl)-3-(pyridin-3-yl)azetidine-1-carboxamide;
3-(pyridin-3-yl)-N-[4-({1-[(2S)-tetrahydrofuran-2-ylcarbonyl]piperidin-4-yl}oxy)phenyl]azetidine-1-carboxamide;
3-(pyridin-3-yl)-N-(4-{[1-(thiophen-2-ylcarbonyl)piperidin-4-yl]oxy}phenyl)azetidine-1-carboxamide;
3-(pyridin-3-yl)-N-(4-{[1-(thiophen-3-ylcarbonyl)piperidin-4-yl]oxy}phenyl)azetidine-1-carboxamide;
N-[4-({1-[(1-acetylpiperidin-4-yl)carbonyl]piperidin-4-yl}oxy)phenyl]-3-(pyridin-3-yl)azetidine-1-carboxamide;
N-[4-({1-[(2-methylcyclopropyl)carbonyl]piperidin-4-yl}oxy)phenyl]-3-(pyridin-3-yl)azetidine-1-carboxamide;
N-[4-({1-[(1-methyl-1H-pyrrol-2-yl)carbonyl]piperidin-4-yl}oxy)phenyl]-3-(pyridin-3-yl)azetidine-1-carboxamide;
N-[4-({1-[3-(morpholin-4-yl)propanoyl]piperidin-4-yl}oxy)phenyl]-3-(pyridin-3-yl)azetidine-1-carboxamide;
N-[4-({1-[3-(4-methylpiperazin-1-yl)propanoyl]piperidin-4-yl}oxy)phenyl]-3-(pyridin-3-yl)azetidine-1-carboxamide;
3-(pyridin-3-yl)-N-[4-({1-[3-(pyrrolidin-1-yl)propanoyl]piperidin-4-yl}oxy)phenyl]azetidine-1-carboxamide;
N-(4-{[1-(cyclopropylacetyl)piperidin-4-yl]oxy}phenyl)-3-(pyridin-3-yl)azetidine-1-carboxamide;
N-(4-{[1-(3-methylpentanoyl)piperidin-4-yl]oxy}phenyl)-3-(pyridin-3-yl)azetidine-1-carboxamide;
N-(4-{[1-(4-methylpentanoyl)piperidin-4-yl]oxy}phenyl)-3-(pyridin-3-yl)azetidine-1-carboxamide;
N-{4-[(1-butanoylpiperidin-4-yl)oxy]phenyl}-3-(pyridin-3-yl)azetidine-1-carboxamide;
N-(4-{[1-(2,2-dimethylpropanoyl)piperidin-4-yl]oxy}phenyl)-3-(pyridin-3-yl)azetidine-1-carboxamide;
N-(4-{[1-(3,3-dimethylbutanoyl)piperidin-4-yl]oxy}phenyl)-3-(pyridin-3-yl)azetidine-1-carboxamide;
N-(4-{[1-(ethoxyacetyl)piperidin-4-yl]oxy}phenyl)-3-(pyridin-3-yl)azetidine-1-carboxamide;
N-(4-{[1-(cyclopropylcarbonyl)piperidin-4-yl]oxy}phenyl)-3-(pyridin-3-yl)azetidine-1-carboxamide;
N-(4-{[1-(methoxyacetyl)piperidin-4-yl]oxy}phenyl)-3-(pyridin-3-yl)azetidine-1-carboxamide;
3-(pyridin-3-yl)-N-{4-[(tetrahydrofuran-3-ylmethyl)carbamoyl]phenyl}azetidine-1-carboxamide;
3-(pyridin-3-yl)-N-{4-[1-(tetrahydro-2H-pyran-4-ylacetyl)piperidin-4-yl]phenyl}azetidine-1-carboxamide;
N-{4-[1-(2-hydroxy-2-methylpropanoyl)piperidin-4-yl]phenyl}-3-(pyridin-3-yl)azetidine-1-carboxamide;
3-(pyridin-3-yl)-N-(4-{1-[(2S)-tetrahydrofuran-2-ylcarbonyl]piperidin-4-yl}phenyl)azetidine-1-carboxamide;
3-(pyridin-3-yl)-N-{4-[1-(tetrahydrofuran-3-ylcarbonyl)piperidin-4-yl]phenyl}azetidine-1-carboxamide;
3-(pyridin-3-yl)-N-(4-{1-[(2R)-tetrahydrofuran-2-ylcarbonyl]piperidin-4-yl}phenyl)azetidine-1-carboxamide;
N-{4-[1-(cyclopropylacetyl)piperidin-4-yl]phenyl}-3-(pyridin-3-yl)azetidine-1-carboxamide;
N-{4-[1-(2-methylpropanoyl)piperidin-4-yl]phenyl}-3-(pyridin-3-yl)azetidine-1-carboxamide;
N-[4-(1-benzoylpiperidin-4-yl)phenyl]-3-(pyridin-3-yl)azetidine-1-carboxamide;
3-(pyridin-3-yl)-N-{4-[1-(3,3,3-trifluoropropanoyl)piperidin-4-yl]phenyl}azetidine-1-carboxamide;
tert-butyl 3-[4-({[3-(pyridin-3-yl)azetidin-1-yl]carbonyl}amino)phenyl]pyrrolidine-1-carboxylate;
tert-butyl (3R)-3-[4-({[3-(pyridin-3-yl)azetidin-1-yl]carbonyl}amino)phenoxy]pyrrolidine-1-carboxylate;
tert-butyl (3S)-3-[4-({[3-(pyridin-3-yl)azetidin-1-yl]carbonyl}amino)phenoxy]pyrrolidine-1-carboxylate;
tert-butyl 3-[4-({[3-(pyridin-3-yl)azetidin-1-yl]carbonyl}amino)phenyl]azetidine-1-carboxylate;
tert-butyl 3-[4-({[3-(pyridin-3-yl)azetidin-1-yl]carbonyl}amino)phenoxy]azetidine-1-carboxylate;
3-(pyridin-3-yl)-N-{4-[1-(tetrahydro-2H-pyran-4-ylacetyl)pyrrolidin-3-yl]phenyl}azetidine-1-carboxamide;
N-{4-[1-(2-methylpropanoyl)pyrrolidin-3-yl]phenyl}-3-(pyridin-3-yl)azetidine-1-carboxamide;
3-(pyridin-3-yl)-N-(4-{1-[(2S)-tetrahydrofuran-2-ylcarbonyl]pyrrolidin-3-yl}phenyl)azetidine-1-carboxamide;
3-(pyridin-3-yl)-N-(4-{1-[(2R)-tetrahydrofuran-2-ylcarbonyl]pyrrolidin-3-yl}phenyl)azetidine-1-carboxamide;
3-(pyridin-3-yl)-N-{4-[1-(tetrahydrofuran-3-ylcarbonyl)pyrrolidin-3-yl]phenyl}azetidine-1-carboxamide;
N-{4-[1-(cyclopropylacetyl)pyrrolidin-3-yl]phenyl}-3-(pyridin-3-yl)azetidine-1-carboxamide;
N-{4-[1-(2-hydroxy-2-methylpropanoyl)pyrrolidin-3-yl]phenyl}-3-(pyridin-3-yl)azetidine-1-carboxamide;
N-[4-(1-benzoylpyrrolidin-3-yl)phenyl]-3-(pyridin-3-yl)azetidine-1-carboxamide;
3-(pyridin-3-yl)-N-{4-[1-(3,3,3-trifluoropropanoyl)pyrrolidin-3-yl]phenyl}azetidine-1-carboxamide;
N-{4-[1-(cyclopropylcarbonyl)pyrrolidin-3-yl]phenyl}-3-(pyridin-3-yl)azetidine-1-carboxamide;
N-(4-{1-[(2S)-2-methylbutanoyl]pyrrolidin-3-yl}phenyl)-3-(pyridin-3-yl)azetidine-1-carboxamide;
N-[4-(1-butanoylpyrrolidin-3-yl)phenyl]-3-(pyridin-3-yl)azetidine-1-carboxamide;
3-(pyridin-3-yl)-N-(4-{[(3R)-1-(tetrahydro-2H-pyran-4-ylacetyl)pyrrolidin-3-yl]oxy}phenyl)azetidine-1-carboxamide;
N-(4-{[(3R)-1-(2-methylpropanoyl)pyrrolidin-3-yl]oxy}phenyl)-3-(pyridin-3-yl)azetidine-1-carboxamide;
3-(pyridin-3-yl)-N-[4-({(3R)-1-[(2S)-tetrahydrofuran-2-ylcarbonyl]pyrrolidin-3-yl}oxy)phenyl]azetidine-1-carboxamide;
3-(pyridin-3-yl)-N-[4-({(3R)-1-[(2R)-tetrahydrofuran-2-ylcarbonyl]pyrrolidin-3-yl}oxy)phenyl]azetidine-1-carboxamide;
3-(pyridin-3-yl)-N-(4-{[(3R)-1-(tetrahydrofuran-3-ylcarbonyl)pyrrolidin-3-yl]oxy}phenyl)azetidine-1-carboxamide;
N-(4-{[(3R)-1-(cyclopropylacetyl)pyrrolidin-3-yl]oxy}phenyl)-3-(pyridin-3-yl)azetidine-1-carboxamide;
N-(4-{[(3R)-1-(2-hydroxy-2-methylpropanoyl)pyrrolidin-3-yl]oxy}phenyl)-3-(pyridin-3-yl)azetidine-1-carboxamide;
N-(4-{[(3R)-1-benzoylpyrrolidin-3-yl]oxy}phenyl)-3-(pyridin-3-yl)azetidine-1-carboxamide;
3-(pyridin-3-yl)-N-(4-{[(3R)-1-(3,3,3-trifluoropropanoyl)pyrrolidin-3-yl]oxy}phenyl)azetidine-1-carboxamide;
N-(4-{[(3R)-1-(cyclopropylcarbonyl)pyrrolidin-3-yl]oxy}phenyl)-3-(pyridin-3-yl)azetidine-1-carboxamide;
N-[4-({(3R)-1-[(2S)-2-methylbutanoyl]pyrrolidin-3-yl}oxy)phenyl]-3-(pyridin-3-yl)azetidine-1-carboxamide;
N-(4-{[(3R)-1-butanoylpyrrolidin-3-yl]oxy}phenyl)-3-(pyridin-3-yl)azetidine-1-carboxamide;
3-(pyridin-3-yl)-N-(4-{[(3S)-1-(tetrahydro-2H-pyran-4-ylacetyl)pyrrolidin-3-yl]oxy}phenyl)azetidine-1-carboxamide;
N-(4-{[(3S)-1-(2-methylpropanoyl)pyrrolidin-3-yl]oxy}phenyl)-3-(pyridin-3-yl)azetidine-1-carboxamide;

3-(pyridin-3-yl)-N-[4-({(3S)-1-[(2S)-tetrahydrofuran-2-yl-carbonyl]pyrrolidin-3-yl}oxy)phenyl]azetidine-1-carboxamide;

3-(pyridin-3-yl)-N-[4-({(3S)-1-[(2R)-tetrahydrofuran-2-yl-carbonyl]pyrrolidin-3-yl}oxy)phenyl]azetidine-1-carboxamide;

3-(pyridin-3-yl)-N-(4-{[(3S)-1-(tetrahydrofuran-3-ylcarbonyl)pyrrolidin-3-yl]oxy}phenyl)azetidine-1-carboxamide;

N-(4-{[(3S)-1-(cyclopropylacetyl)pyrrolidin-3-yl]oxy}phenyl)-3-(pyridin-3-yl)azetidine-1-carboxamide;

N-(4-{[(3S)-1-(2-hydroxy-2-methylpropanoyl)pyrrolidin-3-yl]oxy}phenyl)-3-(pyridin-3-yl)azetidine-1-carboxamide;

N-(4-{[(3S)-1-benzoylpyrrolidin-3-yl]oxy}phenyl)-3-(pyridin-3-yl)azetidine-1-carboxamide;

3-(pyridin-3-yl)-N-(4-{[(3S)-1-(3,3,3-trifluoropropanoyl)pyrrolidin-3-yl]oxy}phenyl)azetidine-1-carboxamide;

N-(4-{[(3S)-1-(cyclopropylcarbonyl)pyrrolidin-3-yl]oxy}phenyl)-3-(pyridin-3-yl)azetidine-1-carboxamide;

N-[4-({(3S)-1-[(2S)-2-methylbutanoyl]pyrrolidin-3-yl}oxy)phenyl]-3-(pyridin-3-yl)azetidine-1-carboxamide;

N-(4-{[(3S)-1-butanoylpyrrolidin-3-yl]oxy}phenyl)-3-(pyridin-3-yl)azetidine-1-carboxamide;

3-(pyridin-3-yl)-N-{4-[1-(tetrahydro-2H-pyran-4-ylacetyl)azetidin-3-yl]phenyl}azetidine-1-carboxamide;

N-{4-[1-(2-methylpropanoyl)azetidin-3-yl]phenyl}-3-(pyridin-3-yl)azetidine-1-carboxamide;

3-(pyridin-3-yl)-N-(4-{1-[(2S)-tetrahydrofuran-2-ylcarbonyl]azetidin-3-yl}phenyl)azetidine-1-carboxamide;

3-(pyridin-3-yl)-N-(4-{1-[(2R)-tetrahydrofuran-2-ylcarbonyl]azetidin-3-yl}phenyl)azetidine-1-carboxamide;

3-(pyridin-3-yl)-N-{4-[1-(tetrahydrofuran-3-ylcarbonyl)azetidin-3-yl]phenyl}azetidine-1-carboxamide;

N-{4-[1-(cyclopropylacetyl)azetidin-3-yl]phenyl}-3-(pyridin-3-yl)azetidine-1-carboxamide;

N-{4-[1-(2-hydroxy-2-methylpropanoyl)azetidin-3-yl]phenyl}-3-(pyridin-3-yl)azetidine-1-carboxamide;

N-[4-(1-benzoylazetidin-3-yl)phenyl]-3-(pyridin-3-yl)azetidine-1-carboxamide;

3-(pyridin-3-yl)-N-{4-[1-(3,3,3-trifluoropropanoyl)azetidin-3-yl]phenyl}azetidine-1-carboxamide;

N-{4-[1-(cyclopropylcarbonyl)azetidin-3-yl]phenyl}-3-(pyridin-3-yl)azetidine-1-carboxamide;

N-(4-{1-[(2S)-2-methylbutanoyl]azetidin-3-yl}phenyl)-3-(pyridin-3-yl)azetidine-1-carboxamide;

N-[4-(1-butanoylazetidin-3-yl)phenyl]-3-(pyridin-3-yl)azetidine-1-carboxamide;

tert-butyl 4-[4-({[3-(2-chloropyridin-3-yl)azetidin-1-yl]carbonyl}amino)phenyl]piperidine-1-carboxylate;

tert-butyl 4-[4-({[3-(4-chloropyridin-3-yl)azetidin-1-yl]carbonyl}amino)phenyl]piperidine-1-carboxylate;

N-(4-{[1-(cyclopropylacetyl)azetidin-3-yl]oxy}phenyl)-3-(pyridin-3-yl)azetidine-1-carboxamide;

N-(4-{[1-(furan-2-ylcarbonyl)azetidin-3-yl]oxy}phenyl)-3-(pyridin-3-yl)azetidine-1-carboxamide;

tert-butyl 4-[4-({[3-(2-fluoropyridin-3-yl)azetidin-1-yl]carbonyl}amino)phenyl]piperidine-1-carboxylate;

N-{4-[(1-pentanoylazetidin-3-yl)oxy]phenyl}-3-(pyridin-3-yl)azetidine-1-carboxamide;

N-[4-({1-[(2-methoxyethoxy)acetyl]azetidin-3-yl}oxy)phenyl]-3-(pyridin-3-yl)azetidine-1-carboxamide;

N-(4-{[1-(ethoxyacetyl)azetidin-3-yl]oxy}phenyl)-3-(pyridin-3-yl)azetidine-1-carboxamide;

N-(4-{[1-(methoxyacetyl)azetidin-3-yl]oxy}phenyl)-3-(pyridin-3-yl)azetidine-1-carboxamide;

N-(4-{[1-(3-methylpentanoyl)azetidin-3-yl]oxy}phenyl)-3-(pyridin-3-yl)azetidine-1-carboxamide;

N-[4-({1-[(1 S,4R)-bicyclo[2.2.1]hept-2-ylacetyl]azetidin-3-yl}oxy)phenyl]-3-(pyridin-3-yl)azetidine-1-carboxamide;

N-(4-{[1-(2,3-dimethylbutanoyl)azetidin-3-yl]oxy}phenyl)-3-(pyridin-3-yl)azetidine-1-carboxamide;

N-(4-{[1-(4-methylpentanoyl)azetidin-3-yl]oxy}phenyl)-3-(pyridin-3-yl)azetidine-1-carboxamide;

N-[4-({1-[(2-methylcyclopropyl)carbonyl]azetidin-3-yl}oxy)phenyl]-3-(pyridin-3-yl)azetidine-1-carboxamide;

3-(pyridin-3-yl)-N-(4-{[1-(4,4,4-trifluorobutanoyl)azetidin-3-yl]oxy}phenyl)azetidine-1-carboxamide;

N-(4-{[1-(2-methylpropanoyl)azetidin-3-yl]oxy}phenyl)-3-(pyridin-3-yl)azetidine-1-carboxamide;

N-(4-{[1-(2,2-dimethylpropanoyl)azetidin-3-yl]oxy}phenyl)-3-(pyridin-3-yl)azetidine-1-carboxamide;

N-{4-[(1-butanoylazetidin-3-yl)oxy]phenyl}-3-(pyridin-3-yl)azetidine-1-carboxamide;

N-{4-[(1-propanoylazetidin-3-yl)oxy]phenyl}-3-(pyridin-3-yl)azetidine-1-carboxamide;

N-(4-{[1-(2,2-dimethylbutanoyl)azetidin-3-yl]oxy}phenyl)-3-(pyridin-3-yl)azetidine-1-carboxamide;

N-(4-{[1-(3-methylbutanoyl)azetidin-3-yl]oxy}phenyl)-3-(pyridin-3-yl)azetidine-1-carboxamide;

N-(4-{[1-(3,3-dimethylbutanoyl)azetidin-3-yl]oxy}phenyl)-3-(pyridin-3-yl)azetidine-1-carboxamide;

3-(pyridin-3-yl)-N-(4-{[1-(3,3,3-trifluoropropanoyl)azetidin-3-yl]oxy}phenyl)azetidine-1-carboxamide;

N-[4-({1-[(1-methylcyclopropyl)carbonyl]azetidin-3-yl}oxy)phenyl]-3-(pyridin-3-yl)azetidine-1-carboxamide;

N-(4-{[1-(2-methylpentanoyl)azetidin-3-yl]oxy}phenyl)-3-(pyridin-3-yl)azetidine-1-carboxamide;

N-{4-[(1-acetylazetidin-3-yl)oxy]phenyl}-3-(pyridin-3-yl)azetidine-1-carboxamide;

N-(4-{[1-(cyclohexylacetyl)azetidin-3-yl]oxy}phenyl)-3-(pyridin-3-yl)azetidine-1-carboxamide;

N-(4-{[1-(cyclohexylcarbonyl)azetidin-3-yl]oxy}phenyl)-3-(pyridin-3-yl)azetidine-1-carboxamide;

N-(4-{[1-(cyclopropylcarbonyl)azetidin-3-yl]oxy}phenyl)-3-(pyridin-3-yl)azetidine-1-carboxamide;

3-(pyridin-3-yl)-N-(4-{[1-(thiophen-2-ylcarbonyl)azetidin-3-yl]oxy}phenyl)azetidine-1-carboxamide;

N-(4-{[1-(cyclopentylcarbonyl)azetidin-3-yl]oxy}phenyl)-3-(pyridin-3-yl)azetidine-1-carboxamide;

N-(4-{[1-(morpholin-4-ylacetyl)azetidin-3-yl]oxy}phenyl)-3-(pyridin-3-yl)azetidine-1-carboxamide;

3-(pyridin-3-yl)-N-(4-{[1-(1,3-thiazol-5-ylcarbonyl)azetidin-3-yl]oxy}phenyl)azetidine-1-carboxamide;

N-[4-({1-[(3,5-dimethyl-1,2-oxazol-4-yl)carbonyl]azetidin-3-yl}oxy)phenyl]-3-(pyridin-3-yl)azetidine-1-carboxamide;

3-(pyridin-3-yl)-N-(4-{[1-(thiophen-3-ylcarbonyl)azetidin-3-yl]oxy}phenyl)azetidine-1-carboxamide;

3-(pyridin-3-yl)-N-(4-{[1-(1,3-thiazol-4-ylcarbonyl)azetidin-3-yl]oxy}phenyl)azetidine-1-carboxamide;

N-(4-{[1-(1,2-oxazol-5-ylcarbonyl)azetidin-3-yl]oxy}phenyl)-3-(pyridin-3-yl)azetidine-1-carboxamide;

N-[4-({1-[(4-methylpiperazin-1-yl)acetyl]azetidin-3-yl}oxy)phenyl]-3-(pyridin-3-yl)azetidine-1-carboxamide;

N-(4-{[1-(N,N-dimethyl-beta-alanyl)azetidin-3-yl]oxy}phenyl)-3-(pyridin-3-yl)azetidine-1-carboxamide;

N-(4-{[1-(furan-3-ylcarbonyl)azetidin-3-yl]oxy}phenyl)-3-(pyridin-3-yl)azetidine-1-carboxamide;

N-[4-({1-[(1-methylcyclohexyl)carbonyl]azetidin-3-yl}oxy)phenyl]-3-(pyridin-3-yl)azetidine-1-carboxamide;
N-(4-{[1-(cyclopentylacetyl)azetidin-3-yl]oxy}phenyl)-3-(pyridin-3-yl)azetidine-1-carboxamide;
3-(pyridin-3-yl)-N-(4-{[1-(1,3-thiazol-2-ylcarbonyl)azetidin-3-yl]oxy}phenyl)azetidine-1-carboxamide;
3-(pyridin-3-yl)-N-(4-{[1-(pyrrolidin-1-ylacetyl)azetidin-3-yl]oxy}phenyl)azetidine-1-carboxamide;
3-(2-fluoropyridin-3-yl)-N-{4-[1-(2-hydroxy-2-methylpropanoyl)piperidin-4-yl]phenyl}azetidine-1-carboxamide;
N-{4-[1-(2-methylpropyl)-1H-pyrazol-4-yl]phenyl}-3-(pyridin-3-yl)azetidine-1-carboxamide;
N-[4-(1-propyl-1H-pyrazol-4-yl)phenyl]-3-(pyridin-3-yl)azetidine-1-carboxamide;
3-(pyridin-3-yl)-N-(4-{1-[(3S)-tetrahydrofuran-3-ylcarbonyl]piperidin-4-yl}phenyl)azetidine-1-carboxamide;
3-(4-chloropyridin-3-yl)-N-(4-{1-[(3S)-tetrahydrofuran-3-ylcarbonyl]piperidin-4-yl}phenyl)azetidine-1-carboxamide;
3-(2-chloropyridin-3-yl)-N-{4-[1-(2-hydroxy-2-methylpropanoyl)piperidin-4-yl]phenyl}azetidine-1-carboxamide;
4-(pyridin-3-yl)-N-(4-{[1-(tetrahydro-2H-pyran-4-ylacetyl)piperidin-4-yl]oxy}phenyl)piperazine-1-carboxamide;
N-[4-(1-pentanoylpiperidin-4-yl)phenyl]-3-(pyridin-3-yl)azetidine-1-carboxamide;
N-(4-{1-[(2-methylcyclopropyl)carbonyl]piperidin-4-yl}phenyl)-3-(pyridin-3-yl)azetidine-1-carboxamide;
N-(4-{1-[(1S,4R)-bicyclo[2.2.1]hept-2-ylacetyl]piperidin-4-yl}phenyl)-3-(pyridin-3-yl)azetidine-1-carboxamide;
N-{4-[1-(4-methylpentanoyl)piperidin-4-yl]phenyl}-3-(pyridin-3-yl)azetidine-1-carboxamide;
N-{4-[1-(3-methylpentanoyl)piperidin-4-yl]phenyl}-3-(pyridin-3-yl)azetidine-1-carboxamide;
N-{4-[1-(3-ethoxypropanoyl)piperidin-4-yl]phenyl}-3-(pyridin-3-yl)azetidine-1-carboxamide;
N-{4-[1-(2,2-dimethylbutanoyl)piperidin-4-yl]phenyl}-3-(pyridin-3-yl)azetidine-1-carboxamide;
N-{4-[1-(3,3-dimethylbutanoyl)piperidin-4-yl]phenyl}-3-(pyridin-3-yl)azetidine-1-carboxamide;
N-{4-[1-(2,2-dimethylpropanoyl)piperidin-4-yl]phenyl}-3-(pyridin-3-yl)azetidine-1-carboxamide;
N-[4-(1-butanoylpiperidin-4-yl)phenyl]-3-(pyridin-3-yl)azetidine-1-carboxamide;
N-{4-[1-(ethoxyacetyl)piperidin-4-yl]phenyl}-3-(pyridin-3-yl)azetidine-1-carboxamide;
N-{4-[1-(3-methylbutanoyl)piperidin-4-yl]phenyl}-3-(pyridin-3-yl)azetidine-1-carboxamide;
N-{4-[1-(N-acetyl-L-leucyl)piperidin-4-yl]phenyl}-3-(pyridin-3-yl)azetidine-1-carboxamide;
N-(4-{1-[(2-methoxyethoxy)acetyl]piperidin-4-yl}phenyl)-3-(pyridin-3-yl)azetidine-1-carboxamide;
N-{4-[1-(cyclohexylcarbonyl)piperidin-4-yl]phenyl}-3-(pyridin-3-yl)azetidine-1-carboxamide;
N-{4-[1-(cyclohexylacetyl)piperidin-4-yl]phenyl}-3-(pyridin-3-yl)azetidine-1-carboxamide;
3-(pyridin-3-yl)-N-{4-[1-(4,4,4-trifluorobutanoyl)piperidin-4-yl]phenyl}azetidine-1-carboxamide;
N-{4-[1-(cyclopentylcarbonyl)piperidin-4-yl]phenyl}-3-(pyridin-3-yl)azetidine-1-carboxamide;
N-(4-{1-[(1-methylcyclohexyl)carbonyl]piperidin-4-yl}phenyl)-3-(pyridin-3-yl)azetidine-1-carboxamide;
N-{4-[1-(furan-3-ylcarbonyl)piperidin-4-yl]phenyl}-3-(pyridin-3-yl)azetidine-1-carboxamide;
N-[4-(1-acetylpiperidin-4-yl)phenyl]-3-(pyridin-3-yl)azetidine-1-carboxamide;
N-{4-[1-(methoxyacetyl)piperidin-4-yl]phenyl}-3-(pyridin-3-yl)azetidine-1-carboxamide;
3-(pyridin-3-yl)-N-{4-[1-(thiophen-3-ylcarbonyl)piperidin-4-yl]phenyl}azetidine-1-carboxamide;
N-(4-{1-[(3-methylthiophen-2-yl)carbonyl]piperidin-4-yl}phenyl)-3-(pyridin-3-yl)azetidine-1-carboxamide;
N-{4-[1-(morpholin-4-ylacetyl)piperidin-4-yl]phenyl}-3-(pyridin-3-yl)azetidine-1-carboxamide;
3-(pyridin-3-yl)-N-{4-[1-(thiophen-2-ylcarbonyl)piperidin-4-yl]phenyl}azetidine-1-carboxamide;
N-(4-{1-[(5-methylthiophen-2-yl)carbonyl]piperidin-4-yl}phenyl)-3-(pyridin-3-yl)azetidine-1-carboxamide;
N-{4-[1-(furan-2-ylcarbonyl)piperidin-4-yl]phenyl}-3-(pyridin-3-yl)azetidine-1-carboxamide;
N-(4-{1-[(1-methyl-1H-pyrrol-2-yl)carbonyl]piperidin-4-yl}phenyl)-3-(pyridin-3-yl)azetidine-1-carboxamide;
N-[4-(1-propanoylpiperidin-4-yl)phenyl]-3-(pyridin-3-yl)azetidine-1-carboxamide;
N-(4-{1-[(1-methylcyclopropyl)carbonyl]piperidin-4-yl}phenyl)-3-(pyridin-3-yl)azetidine-1-carboxamide;
3-(pyridin-3-yl)-N-{4-[1-(pyrrolidin-1-ylacetyl)piperidin-4-yl]phenyl}azetidine-1-carboxamide;
3-(pyridin-3-yl)-N-{4-[1-(1,3-thiazol-2-ylcarbonyl)piperidin-4-yl]phenyl}azetidine-1-carboxamide;
N-{4-[1-(cyclopentylacetyl)piperidin-4-yl]phenyl}-3-(pyridin-3-yl)azetidine-1-carboxamide;
N-{4-[1-(2,3-dimethylbutanoyl)piperidin-4-yl]phenyl}-3-(pyridin-3-yl)azetidine-1-carboxamide;
N-[4-(1-pentanoylazetidin-3-yl)phenyl]-3-(pyridin-3-yl)azetidine-1-carboxamide;
N-(4-{1-[(2-methylcyclopropyl)carbonyl]azetidin-3-yl}phenyl)-3-(pyridin-3-yl)azetidine-1-carboxamide;
N-(4-{1-[(1 S,4R)-bicyclo[2.2.1]hept-2-ylacetyl]azetidin-3-yl}phenyl)-3-(pyridin-3-yl)azetidine-1-carboxamide;
N-{4-[1-(4-methylpentanoyl)azetidin-3-yl]phenyl}-3-(pyridin-3-yl)azetidine-1-carboxamide;
N-{4-[1-(3-methylpentanoyl)azetidin-3-yl]phenyl}-3-(pyridin-3-yl)azetidine-1-carboxamide;
N-{4-[1-(3-ethoxypropanoyl)azetidin-3-yl]phenyl}-3-(pyridin-3-yl)azetidine-1-carboxamide;
N-{4-[1-(2,2-dimethylbutanoyl)azetidin-3-yl]phenyl}-3-(pyridin-3-yl)azetidine-1-carboxamide;
N-{4-[1-(3,3-dimethylbutanoyl)azetidin-3-yl]phenyl}-3-(pyridin-3-yl)azetidine-1-carboxamide;
N-{4-[1-(2,2-dimethylpropanoyl)azetidin-3-yl]phenyl}-3-(pyridin-3-yl)azetidine-1-carboxamide;
N-{4-[1-(ethoxyacetyl)azetidin-3-yl]phenyl}-3-(pyridin-3-yl)azetidine-1-carboxamide;
N-{4-[1-(3-methylbutanoyl)azetidin-3-yl]phenyl}-3-(pyridin-3-yl)azetidine-1-carboxamide;
N-{4-[1-(N-acetyl-L-leucyl)azetidin-3-yl]phenyl}-3-(pyridin-3-yl)azetidine-1-carboxamide;
N-(4-{1-[(2-methoxyethoxy)acetyl]azetidin-3-yl}phenyl)-3-(pyridin-3-yl)azetidine-1-carboxamide;
N-{4-[1-(cyclohexylcarbonyl)azetidin-3-yl]phenyl}-3-(pyridin-3-yl)azetidine-1-carboxamide;
N-{4-[1-(cyclohexylacetyl)azetidin-3-yl]phenyl}-3-(pyridin-3-yl)azetidine-1-carboxamide;
3-(pyridin-3-yl)-N-{4-[1-(4,4,4-trifluorobutanoyl)azetidin-3-yl]phenyl}azetidine-1-carboxamide;
N-{4-[1-(cyclopentylcarbonyl)azetidin-3-yl]phenyl}-3-(pyridin-3-yl)azetidine-1-carboxamide;
N-(4-{1-[(1-methylcyclohexyl)carbonyl]azetidin-3-yl}phenyl)-3-(pyridin-3-yl)azetidine-1-carboxamide;
N-{4-[1-(furan-3-ylcarbonyl)azetidin-3-yl]phenyl}-3-(pyridin-3-yl)azetidine-1-carboxamide;

N-[4-(1-acetylazetidin-3-yl)phenyl]-3-(pyridin-3-yl)azetidine-1-carboxamide;
N-{4-[1-(methoxyacetyl)azetidin-3-yl]phenyl}-3-(pyridin-3-yl)azetidine-1-carboxamide;
3-(pyridin-3-yl)-N-{4-[1-(thiophen-3-ylcarbonyl)azetidin-3-yl]phenyl}azetidine-1-carboxamide;
N-(4-{1-[(3-methylthiophen-2-yl)carbonyl]azetidin-3-yl}phenyl)-3-(pyridin-3-yl)azetidine-1-carboxamide;
N-{4-[1-(morpholin-4-ylacetyl)azetidin-3-yl]phenyl}-3-(pyridin-3-yl)azetidine-1-carboxamide;
3-(pyridin-3-yl)-N-{4-[1-(thiophen-2-ylcarbonyl)azetidin-3-yl]phenyl}azetidine-1-carboxamide;
N-(4-{1-[(5-methylthiophen-2-yl)carbonyl]azetidin-3-yl}phenyl)-3-(pyridin-3-yl)azetidine-1-carboxamide;
N-{4-[1-(furan-2-ylcarbonyl)azetidin-3-yl]phenyl}-3-(pyridin-3-yl)azetidine-1-carboxamide;
N-(4-{1-[(1-methyl-1H-pyrrol-2-yl)carbonyl]azetidin-3-yl}phenyl)-3-(pyridin-3-yl)azetidine-1-carboxamide;
N-[4-(1-propanoylazetidin-3-yl)phenyl]-3-(pyridin-3-yl)azetidine-1-carboxamide;
N-(4-{1-[(1-methylcyclopropyl)carbonyl]azetidin-3-yl}phenyl)-3-(pyridin-3-yl)azetidine-1-carboxamide;
3-(pyridin-3-yl)-N-{4-[1-(1,3-thiazol-2-ylcarbonyl)azetidin-3-yl]phenyl}azetidine-1-carboxamide;
N-{4-[1-(cyclopentylacetyl)azetidin-3-yl]phenyl}-3-(pyridin-3-yl)azetidine-1-carboxamide;
N-{4-[1-(2,3-dimethylbutanoyl)azetidin-3-yl]phenyl}-3-(pyridin-3-yl)azetidine-1-carboxamide;
N-{4-[1-(cyclopentylmethyl)piperidin-4-yl]phenyl}-3-(pyridin-3-yl)azetidine-1-carboxamide;
N-{4-[1-(cyclohexylmethyl)piperidin-4-yl]phenyl}-3-(pyridin-3-yl)azetidine-1-carboxamide;
N-{4-[1-(3,3-dimethylbutyl)piperidin-4-yl]phenyl}-3-(pyridin-3-yl)azetidine-1-carboxamide;
N-{4-[1-(2-methylpentyl)piperidin-4-yl]phenyl}-3-(pyridin-3-yl)azetidine-1-carboxamide;
N-{4-[1-(2-methylpropyl)piperidin-4-yl]phenyl}-3-(pyridin-3-yl)azetidine-1-carboxamide;
N-{4-[1-(3-methylbutyl)piperidin-4-yl]phenyl}-3-(pyridin-3-yl)azetidine-1-carboxamide;
N-{4-[1-(2-ethylbutyl)piperidin-4-yl]phenyl}-3-(pyridin-3-yl)azetidine-1-carboxamide;
N-{4-[1-(2,2-dimethylpropyl)piperidin-4-yl]phenyl}-3-(pyridin-3-yl)azetidine-1-carboxamide;
N-{4-[1-(2-methylbutyl)piperidin-4-yl]phenyl}-3-(pyridin-3-yl)azetidine-1-carboxamide;
N-[4-(1-butylpiperidin-4-yl)phenyl]-3-(pyridin-3-yl)azetidine-1-carboxamide;
N-[4-(1-propylpiperidin-4-yl)phenyl]-3-(pyridin-3-yl)azetidine-1-carboxamide;
N-{4-[1-(2-cyclopropylethyl)piperidin-4-yl]phenyl}-3-(pyridin-3-yl)azetidine-1-carboxamide;
3-(pyridin-3-yl)-N-{4-[1-(tetrahydrofuran-3-ylmethyl)piperidin-4-yl]phenyl}azetidine-1-carboxamide;
N-{4-[1-(2,2-dimethylbutyl)piperidin-4-yl]phenyl}-3-(pyridin-3-yl)azetidine-1-carboxamide;
N-{4-[1-(cyclopentylmethyl)azetidin-3-yl]phenyl}-3-(pyridin-3-yl)azetidine-1-carboxamide;
N-{4-[1-(cyclohexylmethyl)azetidin-3-yl]phenyl}-3-(pyridin-3-yl)azetidine-1-carboxamide;
N-{4-[1-(3,3-dimethylbutyl)azetidin-3-yl]phenyl}-3-(pyridin-3-yl)azetidine-1-carboxamide;
N-{4-[1-(cyclopropylmethyl)azetidin-3-yl]phenyl}-3-(pyridin-3-yl)azetidine-1-carboxamide;
N-{4-[1-(2-methylpentyl)azetidin-3-yl]phenyl}-3-(pyridin-3-yl)azetidine-1-carboxamide;
3-(pyridin-3-yl)-N-{4-[1-(tetrahydrofuran-2-ylmethyl)azetidin-3-yl]phenyl}azetidine-1-carboxamide;
N-{4-[1-(2-methylpropyl)azetidin-3-yl]phenyl}-3-(pyridin-3-yl)azetidine-1-carboxamide;
N-{4-[1-(3-methylbutyl)azetidin-3-yl]phenyl}-3-(pyridin-3-yl)azetidine-1-carboxamide;
N-{4-[1-(2-ethylbutyl)azetidin-3-yl]phenyl}-3-(pyridin-3-yl)azetidine-1-carboxamide;
N-{4-[1-(2,2-dimethylpropyl)azetidin-3-yl]phenyl}-3-(pyridin-3-yl)azetidine-1-carboxamide;
N-{4-[1-(2-methylbutyl)azetidin-3-yl]phenyl}-3-(pyridin-3-yl)azetidine-1-carboxamide;
3-(pyridin-3-yl)-N-{4-[1-(tetrahydrofuran-3-ylmethyl)azetidin-3-yl]phenyl}azetidine-1-carboxamide;
N-{4-[1-(2,2-dimethylbutyl)azetidin-3-yl]phenyl}-3-(pyridin-3-yl)azetidine-1-carboxamide;
N-[4-(1-pentanoylpyrrolidin-3-yl)phenyl]-3-(pyridin-3-yl)azetidine-1-carboxamide;
N-{4-[1-(3-methylpentanoyl)pyrrolidin-3-yl]phenyl}-3-(pyridin-3-yl)azetidine-1-carboxamide;
N-(4-{1-[(1S,4R)-bicyclo[2.2.1]hept-2-ylacetyl]pyrrolidin-3-yl}phenyl)-3-(pyridin-3-yl)azetidine-1-carboxamide;
N-{4-[1-(cyclopentylacetyl)pyrrolidin-3-yl]phenyl}-3-(pyridin-3-yl)azetidine-1-carboxamide;
N-(4-{1-[(2-methylcyclopropyl)carbonyl]pyrrolidin-3-yl}phenyl)-3-(pyridin-3-yl)azetidine-1-carboxamide;
N-{4-[1-(morpholin-4-ylacetyl)pyrrolidin-3-yl]phenyl}-3-(pyridin-3-yl)azetidine-1-carboxamide;
N-{4-[1-(furan-3-ylcarbonyl)pyrrolidin-3-yl]phenyl}-3-(pyridin-3-yl)azetidine-1-carboxamide;
3-(pyridin-3-yl)-N-{4-[1-(pyrrolidin-1-ylacetyl)pyrrolidin-3-yl]phenyl}azetidine-1-carboxamide;
N-{4-[1-(N,N-dimethyl-beta-alanyl)pyrrolidin-3-yl]phenyl}-3-(pyridin-3-yl)azetidine-1-carboxamide;
3-(pyridin-3-yl)-N-{4-[1-(1,3-thiazol-2-ylcarbonyl)pyrrolidin-3-yl]phenyl}azetidine-1-carboxamide;
3-(pyridin-3-yl)-N-{4-[1-(thiophen-3-ylcarbonyl)pyrrolidin-3-yl]phenyl}azetidine-1-carboxamide;
N-(4-{1-[(1-methylcyclopropyl)carbonyl]pyrrolidin-3-yl}phenyl)-3-(pyridin-3-yl)azetidine-1-carboxamide;
N-(4-{1-[(3-methylthiophen-2-yl)carbonyl]pyrrolidin-3-yl}phenyl)-3-(pyridin-3-yl)azetidine-1-carboxamide;
3-(pyridin-3-yl)-N-{4-[1-(4,4,4-trifluorobutanoyl)pyrrolidin-3-yl]phenyl}azetidine-1-carboxamide;
N-(4-{1-[(4-methylpiperazin-1-yl)acetyl]pyrrolidin-3-yl}phenyl)-3-(pyridin-3-yl)azetidine-1-carboxamide;
N-{4-[1-(5-oxo-L-prolyl)pyrrolidin-3-yl]phenyl}-3-(pyridin-3-yl)azetidine-1-carboxamide;
N-{4-[1-(3-ethoxypropanoyl)pyrrolidin-3-yl]phenyl}-3-(pyridin-3-yl)azetidine-1-carboxamide;
N-{4-[1-(4-methylpentanoyl)pyrrolidin-3-yl]phenyl}-3-(pyridin-3-yl)azetidine-1-carboxamide;
N-(4-{1-[(1-methylcyclohexyl)carbonyl]pyrrolidin-3-yl}phenyl)-3-(pyridin-3-yl)azetidine-1-carboxamide;
N-[4-(1-acetylpyrrolidin-3-yl)phenyl]-3-(pyridin-3-yl)azetidine-1-carboxamide;
N-{4-[1-(cyclohexylacetyl)pyrrolidin-3-yl]phenyl}-3-(pyridin-3-yl)azetidine-1-carboxamide;
N-[4-(1-propanoylpyrrolidin-3-yl)phenyl]-3-(pyridin-3-yl)azetidine-1-carboxamide;
N-(4-{1-[(2-methoxyethoxy)acetyl]pyrrolidin-3-yl}phenyl)-3-(pyridin-3-yl)azetidine-1-carboxamide;
N-(4-{1-[3-(morpholin-4-yl)propanoyl]pyrrolidin-3-yl}phenyl)-3-(pyridin-3-yl)azetidine-1-carboxamide;
N-{4-[1-(2,2-dimethylpropanoyl)pyrrolidin-3-yl]phenyl}-3-(pyridin-3-yl)azetidine-1-carboxamide;

N-(4-{1-[(5-methylthiophen-2-yl)carbonyl]pyrrolidin-3-yl}phenyl)-3-(pyridin-3-yl)azetidine-1-carboxamide;
3-(pyridin-3-yl)-N-{4-[1-(thiophen-2-ylcarbonyl)pyrrolidin-3-yl]phenyl}azetidine-1-carboxamide;
N-(4-{1-[(1-methyl-1H-pyrrol-2-yl)carbonyl]pyrrolidin-3-yl}phenyl)-3-(pyridin-3-yl)azetidine-1-carboxamide;
N-{4-[1-(furan-2-ylcarbonyl)pyrrolidin-3-yl]phenyl}-3-(pyridin-3-yl)azetidine-1-carboxamide;
N-(4-{1-[3-(piperidin-1-yl)propanoyl]pyrrolidin-3-yl}phenyl)-3-(pyridin-3-yl)azetidine-1-carboxamide;
N-{4-[1-(ethoxyacetyl)pyrrolidin-3-yl]phenyl}-3-(pyridin-3-yl)azetidine-1-carboxamide;
N-{4-[1-(3,3-dimethylbutanoyl)pyrrolidin-3-yl]phenyl}-3-(pyridin-3-yl)azetidine-1-carboxamide;
N-{4-[1-(2,2-dimethylbutanoyl)pyrrolidin-3-yl]phenyl}-3-(pyridin-3-yl)azetidine-1-carboxamide;
N-{4-[1-(2-oxopropanoyl)pyrrolidin-3-yl]phenyl}-3-(pyridin-3-yl)azetidine-1-carboxamide;
N-{4-[1-(methoxyacetyl)pyrrolidin-3-yl]phenyl}-3-(pyridin-3-yl)azetidine-1-carboxamide;
N-{4-[1-(cyclohexylcarbonyl)pyrrolidin-3-yl]phenyl}-3-(pyridin-3-yl)azetidine-1-carboxamide;
N-{4-[1-(3-methylbutanoyl)pyrrolidin-3-yl]phenyl}-3-(pyridin-3-yl)azetidine-1-carboxamide;
N-{4-[1-(cyclopentylcarbonyl)pyrrolidin-3-yl]phenyl}-3-(pyridin-3-yl)azetidine-1-carboxamide;
N-{4-[1-(2,3-dimethylbutanoyl)pyrrolidin-3-yl]phenyl}-3-(pyridin-3-yl)azetidine-1-carboxamide;
N-(4-{[(3R)-1-pentanoylpyrrolidin-3-yl]oxy}phenyl)-3-(pyridin-3-yl)azetidine-1-carboxamide;
N-(4-{[(3R)-1-(3-methylpentanoyl)pyrrolidin-3-yl]oxy}phenyl)-3-(pyridin-3-yl)azetidine-1-carboxamide;
N-(4-{[1-(bicyclo[2.2.1]hept-2-ylacetyl)pyrrolidin-3-yl]oxy}phenyl)-3-(pyridin-3-yl)azetidine-1-carboxamide;
N-(4-{[(3R)-1-(cyclopentylacetyl)pyrrolidin-3-yl]oxy}phenyl)-3-(pyridin-3-yl)azetidine-1-carboxamide;
N-[4-({(3R)-1-[(2-methylcyclopropyl)carbonyl]pyrrolidin-3-yl}oxy)phenyl]-3-(pyridin-3-yl)azetidine-1-carboxamide;
N-(4-{[(3R)-1-(morpholin-4-ylacetyl)pyrrolidin-3-yl]oxy}phenyl)-3-(pyridin-3-yl)azetidine-1-carboxamide;
N-(4-{[(3R)-1-(furan-2-ylcarbonyl)pyrrolidin-3-yl]oxy}phenyl)-3-(pyridin-3-yl)azetidine-1-carboxamide;
3-(pyridin-3-yl)-N-(4-{[(3R)-1-(pyrrolidin-1-ylacetyl)pyrrolidin-3-yl]oxy}phenyl)azetidine-1-carboxamide;
N-(4-{[(3R)-1-(5-oxo-D-prolyl)pyrrolidin-3-yl]oxy}phenyl)-3-(pyridin-3-yl)azetidine-1-carboxamide;
N-(4-{[(3R)-1-(N,N-dimethyl-beta-alanyl)pyrrolidin-3-yl]oxy}phenyl)-3-(pyridin-3-yl)azetidine-1-carboxamide;
3-(pyridin-3-yl)-N-(4-{[(3R)-1-(1,3-thiazol-2-ylcarbonyl)pyrrolidin-3-yl]oxy}phenyl)azetidine-1-carboxamide;
3-(pyridin-3-yl)-N-(4-{[(3R)-1-(thiophen-3-ylcarbonyl)pyrrolidin-3-yl]oxy}phenyl)azetidine-1-carboxamide;
N-[4-({(3R)-1-[(1-methylcyclopropyl)carbonyl]pyrrolidin-3-yl}oxy)phenyl]-3-(pyridin-3-yl)azetidine-1-carboxamide;
N-[4-({(3R)-1-[(3-methylthiophen-2-yl)carbonyl]pyrrolidin-3-yl}oxy)phenyl]-3-(pyridin-3-yl)azetidine-1-carboxamide;
3-(pyridin-3-yl)-N-(4-{[(3R)-1-(4,4,4-trifluorobutanoyl)pyrrolidin-3-yl]oxy}phenyl)azetidine-1-carboxamide;
N-[4-({(3R)-1-[(4-methylpiperazin-1-yl)acetyl]pyrrolidin-3-yl}oxy)phenyl]-3-(pyridin-3-yl)azetidine-1-carboxamide;
N-(4-{[(3R)-1-(5-oxo-L-prolyl)pyrrolidin-3-yl]oxy}phenyl)-3-(pyridin-3-yl)azetidine-1-carboxamide;
N-(4-{[(3R)-1-(3-ethoxypropanoyl)pyrrolidin-3-yl]oxy}phenyl)-3-(pyridin-3-yl)azetidine-1-carboxamide;
N-(4-{[(3R)-1-(4-methylpentanoyl)pyrrolidin-3-yl]oxy}phenyl)-3-(pyridin-3-yl)azetidine-1-carboxamide;
N-[4-({(3R)-1-[(1-methylcyclohexyl)carbonyl]pyrrolidin-3-yl}oxy)phenyl]-3-(pyridin-3-yl)azetidine-1-carboxamide;
N-(4-{[(3R)-1-(cyclohexylacetyl)pyrrolidin-3-yl]oxy}phenyl)-3-(pyridin-3-yl)azetidine-1-carboxamide;
N-(4-{[(3R)-1-(N-acetyl-L-leucyl)pyrrolidin-3-yl]oxy}phenyl)-3-(pyridin-3-yl)azetidine-1-carboxamide;
N-(4-{[(3R)-1-propanoylpyrrolidin-3-yl]oxy}phenyl)-3-(pyridin-3-yl)azetidine-1-carboxamide;
N-[4-({(3R)-1-[(2-methoxyethoxy)acetyl]pyrrolidin-3-yl}oxy)phenyl]-3-(pyridin-3-yl)azetidine-1-carboxamide;
N-[4-({(3R)-1-[3-(morpholin-4-yl)propanoyl]pyrrolidin-3-yl}oxy)phenyl]-3-(pyridin-3-yl)azetidine-1-carboxamide;
N-(4-{[(3R)-1-(2,2-dimethylpropanoyl)pyrrolidin-3-yl]oxy}phenyl)-3-(pyridin-3-yl)azetidine-1-carboxamide;
N-[4-({(3R)-1-[(5-methylthiophen-2-yl)carbonyl]pyrrolidin-3-yl}oxy)phenyl]-3-(pyridin-3-yl)azetidine-1-carboxamide;
3-(pyridin-3-yl)-N-(4-{[(3R)-1-(thiophen-2-ylcarbonyl)pyrrolidin-3-yl]oxy}phenyl)azetidine-1-carboxamide;
N-[4-({(3R)-1-[(1-methyl-1H-pyrrol-2-yl)carbonyl]pyrrolidin-3-yl}oxy)phenyl]-3-(pyridin-3-yl)azetidine-1-carboxamide;
N-[4-({(3R)-1-(furan-2-ylcarbonyl)pyrrolidin-3-yl]oxy}phenyl)-3-(pyridin-3-yl)azetidine-1-carboxamide;
N-[4-({(3R)-1-[3-(piperidin-1-yl)propanoyl]pyrrolidin-3-yl}oxy)phenyl]-3-(pyridin-3-yl)azetidine-1-carboxamide;
N-(4-{[(3R)-1-(ethoxyacetyl)pyrrolidin-3-yl]oxy}phenyl)-3-(pyridin-3-yl)azetidine-1-carboxamide;
N-(4-{[(3R)-1-(3,3-dimethylbutanoyl)pyrrolidin-3-yl]oxy}phenyl)-3-(pyridin-3-yl)azetidine-1-carboxamide;
N-(4-{[(3R)-1-(2,2-dimethylbutanoyl)pyrrolidin-3-yl]oxy}phenyl)-3-(pyridin-3-yl)azetidine-1-carboxamide;
N-(4-{[(3R)-1-(methoxyacetyl)pyrrolidin-3-yl]oxy}phenyl)-3-(pyridin-3-yl)azetidine-1-carboxamide;
N-(4-{[(3R)-1-(cyclohexylcarbonyl)pyrrolidin-3-yl]oxy}phenyl)-3-(pyridin-3-yl)azetidine-1-carboxamide;
N-(4-{[(3R)-1-(3-methylbutanoyl)pyrrolidin-3-yl]oxy}phenyl)-3-(pyridin-3-yl)azetidine-1-carboxamide;
N-(4-{[(3R)-1-(cyclopentylcarbonyl)pyrrolidin-3-yl]oxy}phenyl)-3-(pyridin-3-yl)azetidine-1-carboxamide;
N-(4-{[(3R)-1-(2,3-dimethylbutanoyl)pyrrolidin-3-yl]oxy}phenyl)-3-(pyridin-3-yl)azetidine-1-carboxamide;
N-[4-(1-benzoylpiperidin-4-yl)phenyl]-3-(pyridazin-3-yl)azetidine-1-carboxamide;
N-{4-[1-(2-fluorobenzoyl)piperidin-4-yl]phenyl}-3-(pyridazin-3-yl)azetidine-1-carboxamide;
N-{4-[1-(2-methylbenzoyl)piperidin-4-yl]phenyl}-3-(pyridazin-3-yl)azetidine-1-carboxamide;
N-{4-[1-(2,2-dimethylpropanoyl)piperidin-4-yl]phenyl}-3-(pyridazin-3-yl)azetidine-1-carboxamide;
N-{4-[1-(cyclopropylcarbonyl)piperidin-4-yl]phenyl}-3-(pyridazin-3-yl)azetidine-1-carboxamide;
N-[4-(1-acetylpiperidin-4-yl)phenyl]-3-(pyridazin-3-yl)azetidine-1-carboxamide;
N-{4-[1-(3,3-dimethylbutanoyl)piperidin-4-yl]phenyl}-3-(pyridazin-3-yl)azetidine-1-carboxamide;
N-{4-[1-(cyclobutylcarbonyl)piperidin-4-yl]phenyl}-3-(pyridazin-3-yl)azetidine-1-carboxamide;

3-(pyridazin-3-yl)-N-{4-[1-(4,4,4-trifluorobutanoyl)piperidin-4-yl]phenyl}azetidine-1-carboxamide;

3-(pyridazin-3-yl)-N-{4-[1-(3,3,3-trifluoropropanoyl)piperidin-4-yl]phenyl}azetidine-1-carboxamide;

N-(4-{1-[(1-methylcyclopropyl)carbonyl]piperidin-4-yl}phenyl)-3-(pyridazin-3-yl)azetidine-1-carboxamide;

N-{4-[1-(cyclopropylacetyl)piperidin-4-yl]phenyl}-3-(pyridazin-3-yl)azetidine-1-carboxamide;

N-{4-[(1-benzoylpiperidin-4-yl)methyl]phenyl}-3-(pyridazin-3-yl)azetidine-1-carboxamide;

N-(4-{[1-(2-fluorobenzoyl)piperidin-4-yl]methyl}phenyl)-3-(pyridazin-3-yl)azetidine-1-carboxamide;

N-(4-{[1-(2,2-dimethylpropanoyl)piperidin-4-yl]methyl}phenyl)-3-(pyridazin-3-yl)azetidine-1-carboxamide;

N-(4-{[1-(3,3-dimethylbutanoyl)piperidin-4-yl]methyl}phenyl)-3-(pyridazin-3-yl)azetidine-1-carboxamide;

N-(4-{[1-(2-ethylbutanoyl)piperidin-4-yl]methyl}phenyl)-3-(pyridazin-3-yl)azetidine-1-carboxamide;

3-(pyridazin-3-yl)-N-(4-{[1-(4,4,4-trifluorobutanoyl)piperidin-4-yl]methyl}phenyl)azetidine-1-carboxamide;

N-(4-{[1-(2-methylpropanoyl)piperidin-4-yl]methyl}phenyl)-3-(pyridazin-3-yl)azetidine-1-carboxamide;

N-{4-[(1-acetylpiperidin-4-yl)methyl]phenyl}-3-(pyridazin-3-yl)azetidine-1-carboxamide;

N-[4-({1-[(2S)-2-methylbutanoyl]piperidin-4-yl}methyl)phenyl]-3-(pyridazin-3-yl)azetidine-1-carboxamide;

N-[4-({1-[(1-methylcyclopropyl)carbonyl]piperidin-4-yl}methyl)phenyl]-3-(pyridazin-3-yl)azetidine-1-carboxamide; and pharmaceutically acceptable salts thereof.

Embodiments of Formula (IIA)

In another aspect, the present invention provides compounds of Formula (IIA)

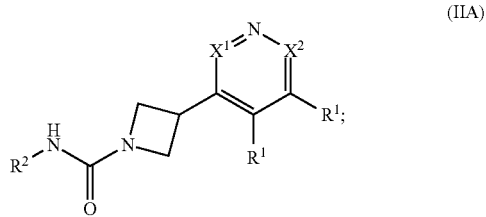

(IIA)

and pharmaceutically acceptable salts thereof; wherein $X^1$, $X^2$, $R^1$ and $R^2$ are as described herein for Formula (IA).

One embodiment of this invention pertains to compounds of Formula (IIA) or pharmaceutically acceptable salts thereof;
wherein
$X^1$ is N and $X^2$ is $CR^1$; or
$X^1$ is $CR^1$ and $X^2$ is N; or
$X^1$ is $CR^1$ and $X^2$ is $CR^1$;

$R^1$, at each occurrence, is independently selected from the group consisting of hydrogen, alkyl, alkenyl, alkynyl, haloalkyl, hydoxyalkyl, alkoxy, OH, $NH_2$, CN, $NO_2$, F, Cl, Br and I;

$R^2$ is independently selected from the group consisting of $C_4$-$C_6$-alkyl, $C_4$-$C_6$-alkenyl, $C_4$-$C_6$-alkynyl, aryl, 3-12 membered heterocyclyl, cycloalkyl, and cycloalkenyl; wherein each $R^2$ $C_4$-$C_6$-alkyl, $C_4$-$C_6$-alkenyl, and $C_4$-$C_6$-alkynyl is substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(N)NH_2$, $C(N)NHR^3$, $C(N)N(R^3)_2$, CNOH, $CNOCH_3$, OH, (O), CN, $N_3$, $NO_2$, F, Cl, Br and I; wherein each $R^2$ aryl, 3-12 membered heterocyclyl, cycloalkyl, and cycloalkenyl is optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I;

$R^3$, at each occurrence, is independently selected from the group consisting of alkyl, alkenyl, alkynyl, aryl, cycloalkyl, cycloalkenyl, and heterocyclyl; wherein each $R^3$ alkyl, alkenyl, and alkynyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, (O), CN, $N_3$, $NO_2$, F, Cl, Br and I; wherein each $R^3$ aryl, cycloalkyl, cycloalkenyl, and heterocyclyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, CNOH, $CNOCH_3$, OH, CN, $N_3$, $NO_2$, F, Cl, Br and I;

$R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, (O), CN, $N_3$, $NO_2$, F, Cl, Br and I;

$R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one or more substituents independently selected from the group consisting of $R^8$, $OR^8$, $SR^8$, $S(O)R^8$, $SO_2R^8$, $NHR^8$, $N(R^8)_2$, C(O)R⁸, C(O)NH₂, C(O)NHR⁸, C(O)N(R⁸)₂, NHC(O)R⁸, NR⁸C(O)R⁸, NHSO₂R⁸, NHC(O)OR⁸, SO₂NH₂, SO₂NHR⁸, SO₂N(R⁸)₂, NHC(O)NH₂, NHC(O)NHR⁸, OH, (O), C(O)OH, N₃, CN, NH₂, F, Cl, Br and I;

R⁶, at each occurrence, is independently selected from the group consisting of alkyl, alkenyl, alkynyl, aryl, heterocyclyl, cycloalkyl, and cycloalkenyl; wherein each R⁶ alkyl, alkenyl, and alkynyl is optionally substituted with one or more substituents independently selected from the group consisting of R⁹, OR⁹, SR⁹, S(O)R⁹, SO₂R⁹, NHR⁹, N(R⁹)₂, C(O)R⁹, C(O)NH₂, C(O)NHR⁹, C(O)N(R⁹)₂, NHC(O)R⁹, NR⁹C(O)R⁹, NHSO₂R⁹, NHC(O)OR⁹, SO₂NH₂, SO₂NHR⁹, SO₂N(R⁹)₂, NHC(O)NH₂, NHC(O)NHR⁹, OH, (O), C(O)OH, N₃, CN, NH₂, CF₃, CF₂CF₃, F, Cl, Br and I;

R⁷, at each occurrence, is independently selected from the group consisting of alkyl, alkenyl, alkynyl, aryl, heterocyclyl, cycloalkyl, and cycloalkenyl;

R⁸, at each occurrence, is independently selected from the group consisting of alkyl, alkenyl, alkynyl, aryl, heterocyclyl, cycloalkyl, and cycloalkenyl;

R⁹, at each occurrence, is independently selected from the group consisting of alkyl, alkenyl, alkynyl, aryl, heterocyclyl, cycloalkyl, and cycloalkenyl;

wherein the cyclic moieties represented by R⁴, R⁵, R⁶, R⁷, R⁸, and R⁹ are independently optionally substituted with one or more substituents independently selected from the group consisting of R¹⁰, OR¹⁰, SR¹⁰, S(O)R¹⁰, C(O)C(O)R¹⁰, SO₂R¹⁰, C(O)R¹⁰, CO(O)R¹⁰, OC(O)R¹⁰, OC(O)OR¹⁰, NH₂, NHR¹⁰, N(R¹⁰)₂, NHC(O)R¹⁰, NR¹⁰C(O)R¹⁰, NHS(O)₂R¹⁰, NR¹⁰S(O)₂R¹⁰, NHC(O)OR¹⁰, NR¹⁰C(O)OR¹⁰, NHC(O)NH₂, NHC(O)NHR¹⁰, NHC(O)N(R¹⁰)₂, NR¹⁰C(O)NHR¹⁰, NR¹⁰C(O)N(R¹⁰)₂, C(O)NH₂, C(O)NHR¹⁰, C(O)N(R¹⁰)₂, C(O)NHOH, C(O)NHOR¹⁰, C(O)NHSO₂R¹⁰, C(O)NR¹⁰SO₂R¹⁰, SO₂NH₂, SO₂NHR¹⁰, SO₂N(R¹⁰)₂, C(O)H, C(O)OH, C(N)NH₂, C(N)NHR¹⁰, C(N)N(R¹⁰)₂, CNOH, CNOCH₃, OH, CN, N₃, NO₂, F, Cl, Br and I;

R¹⁰, at each occurrence, is independently selected from the group consisting of alkyl, alkenyl, alkynyl, aryl, heterocyclyl, cycloalkyl, and cycloalkenyl; wherein each R¹⁰ alkyl, alkenyl, and alkynyl is optionally substituted with one or more substituents independently selected from the group consisting of R¹¹, OR¹¹, SR¹¹, S(O)R¹¹, SO₂R¹¹, C(O)R¹¹, CO(O)R¹¹, OC(O)R¹¹, OC(O)OR¹¹, NH₂, NHR¹¹, N(R¹¹)₂, NHC(O)R¹¹, NR¹¹C(O)R¹¹, NHS(O)₂R¹¹, NR¹¹S(O)₂R¹¹, NHC(O)OR¹¹, NR¹¹C(O)OR¹¹, NHC(O)NH₂, NHC(O)NHR¹¹, NHC(O)N(R¹¹)₂, NR¹¹C(O)NHR¹¹, NR¹¹C(O)N(R¹¹)₂, C(O)NH₂, C(O)NHR¹¹, C(O)N(R¹¹)₂, C(O)NHOH, C(O)NHOR¹¹, C(O)NHSO₂R¹¹, C(O)NR¹¹SO₂R¹¹, SO₂NH₂, SO₂NHR¹¹, SO₂N(R¹¹)₂, C(O)H, C(O)OH, C(N)NH₂, C(N)NHR¹¹, C(N)N(R¹¹)₂, CNOH, CNOCH₃, OH, (O), CN, N₃, NO₂, F, Cl, Br and I; wherein each R¹⁰ aryl, heterocyclyl, cycloalkyl, and cycloalkenyl is optionally substituted with one or more substituents independently selected from the group consisting of R¹², OR¹², SR¹², S(O)R¹², SO₂R¹², C(O)R¹², CO(O)R¹², OC(O)R¹², OC(O)OR¹², NH₂, NHR¹², N(R¹²)₂, NHC(O)R¹², NR¹²C(O)R¹², NHS(O)₂R¹², NR¹²S(O)₂R¹², NHC(O)OR¹², NR¹²C(O)OR¹², NHC(O)NH₂, NHC(O)NHR¹², NHC(O)N(R¹²)₂, NR¹²C(O)NHR¹², NR¹²C(O)N(R¹²)₂, C(O)NH₂, C(O)NHR¹², C(O)N(R¹²)₂, C(O)NHOH, C(O)NHOR¹², C(O)NHSO₂R¹², C(O)NR¹²SO₂R¹², SO₂NH₂, SO₂NHR¹², SO₂N(R¹²)₂, C(O)H, C(O)OH, C(N)NH₂, C(N)NHR¹², C(N)N(R¹²)₂, CNOH, CNOCH₃, OH, CN, N₃, NO₂, F, Cl, Br and I;

R¹¹, at each occurrence, is independently selected from the group consisting of alkyl, alkenyl, alkynyl, aryl, heterocyclyl, cycloalkyl, and cycloalkenyl; wherein each R¹¹ alkyl, alkenyl, and alkynyl is optionally substituted with alkyl or alkoxy; wherein each R¹¹ aryl, heterocyclyl, cycloalkyl, and cycloalkenyl is optionally substituted with alkyl or alkoxy; and R¹², at each occurrence, is independently selected alkyl.

In one embodiment of Formula (IIA), X¹ is N and X² is CR¹. In another embodiment of Formula (IIA), X¹ is CR¹ and X² is N. In another embodiment of Formula (IIA), X¹ is CR¹ and X² is CR¹. In another embodiment of Formula (IIA), X¹ is CR¹ and X² is CR¹, and R¹, at each occurrence, is independently selected from the group consisting of hydrogen, alkyl, alkenyl, alkynyl, haloalkyl, hydoxyalkyl, alkoxy, OH, NH₂, CN, NO₂, F, Cl, Br and I. In another embodiment of Formula (IIA), X¹ is CR¹ and X² is CR¹, and R¹, at each occurrence, is independently selected from the group consisting of hydrogen, alkyl, F, Cl, Br and I. In another embodiment of Formula (IIA), X¹ is CR¹ and X² is CR¹, and R¹, at each occurrence, is hydrogen.

In one embodiment of Formula (IIA), R¹, at each occurrence, is independently selected from the group consisting of hydrogen, alkyl, alkenyl, alkynyl, haloalkyl, hydoxyalkyl, alkoxy, OH, NH₂, CN, NO₂, F, Cl, Br and I. In another embodiment of Formula (IIA), R¹, at each occurrence, is independently selected from the group consisting of hydrogen, alkyl, F, Cl, Br and I. In another embodiment of Formula (IIA), R¹, at each occurrence, is independently selected from the group consisting of hydrogen, alkyl, F, and Cl. In another embodiment of Formula (IIA), R¹, at each occurrence, is hydrogen.

In one embodiment of Formula (IIA), R² is independently selected from the group consisting of C₄-C₆-alkyl, C₄-C₆-alkenyl, C₄-C₆-alkynyl, aryl, 3-12 membered heterocyclyl, cycloalkyl, and cycloalkenyl; wherein each R² C₄-C₆-alkyl, C₄-C₆-alkenyl, and C₄-C₆-alkynyl is substituted with one or more substituents independently selected from the group consisting of R³, OR³, SR³, S(O)R³, SO₂R³, C(O)R³, CO(O)R³, OC(O)R³, OC(O)OR³, NH₂, NHR³, N(R³)₂, NHC(O)R³, NR³C(O)R³, NHS(O)₂R³, NR³S(O)₂R³, NHC(O)OR³, NR³C(O)OR³, NHC(O)NH₂, NHC(O)NHR³, NHC(O)N(R³)₂, NR³C(O)NHR³, NR³C(O)N(R³)₂, C(O)NH₂, C(O)NHR³, C(O)N(R³)₂, C(O)NHOH, C(O)NHOR³, C(O)NHSO₂R³, C(O)NR³SO₂R³, SO₂NH₂, SO₂NHR³, SO₂N(R³)₂, C(O)H, C(O)OH, C(N)NH₂, C(N)NHR³, C(N)N(R³)₂, CNOH, CNOCH₃, OH, CN, N₃, NO₂, F, Cl, Br and I; wherein each R² aryl, 3-12 membered heterocyclyl, cycloalkyl, and cycloalkenyl is optionally substituted with one or more substituents independently selected from the group consisting of R⁴, OR⁴, SR⁴, S(O)R⁴, SO₂R⁴, C(O)R⁴, CO(O)R⁴, OC(O)R⁴, OC(O)OR⁴, NH₂, NHR⁴, N(R⁴)₂, NHC(O)R⁴, NR⁴C(O)R⁴, NHS(O)₂R⁴, NR⁴S(O)₂R⁴, NHC(O)OR⁴, NR⁴C(O)OR⁴, NHC(O)NH₂, NHC(O)NHR⁴, NHC(O)N(R⁴)₂, NR⁴C(O)NHR⁴, NR⁴C(O)N(R⁴)₂, C(O)NH₂, C(O)NHR⁴, C(O)N(R⁴)₂, C(O)NHOH, C(O)NHOR⁴, C(O)NHSO₂R⁴, C(O)NR⁴SO₂R⁴, SO₂NH₂, SO₂NHR⁴, SO₂N(R⁴)₂, C(O)H, C(O)OH, C(N)NH₂, C(N)NHR⁴, C(N)N(R⁴)₂, CNOH, CNOCH₃, OH, CN, N₃, NO₂, F, Cl, Br and I. In another embodiment of Formula (IIA), R² is independently selected from the group consisting of C₄-C₆-alkyl, and aryl; wherein each R² C₄-C₆-alkyl is substituted with one or more substituents independently selected from the group consisting of R³, F, Cl, Br and I; wherein each R² aryl is optionally substituted with one or more substituents independently selected from the group consisting of R⁴, OR⁴, CO(O)R⁴, C(O)NHR⁴, CN, F, Cl, Br and I. In another embodiment of Formula (IIA), R² is independently selected from the group consisting of C₄-C₆-alkyl, and aryl; wherein each $R^2$ $C_4$-$C_6$-alkyl is substituted with one or more $R^3$; wherein each $R^2$ aryl is optionally substituted with one or more substituents independently selected from the group consisting of $R^4$, $OR^4$, $CO(O)R^4$, $C(O)NHR^4$, and CN. In another embodiment of Formula (IIA), $R^2$ is $C_4$-$C_6$-alkyl; wherein each $R^2$ $C_4$-$C_6$-alkyl is substituted with one or more $R^3$. In another embodiment of Formula (IIA), $R^2$ is aryl; wherein each $R^2$ aryl is substituted with one or more substituents independently selected from the group consisting of $R^4$, $OR^4$, $CO(O)R^4$, $C(O)NHR^4$, and CN. In another embodiment of Formula (IIA), $R^2$ is aryl; wherein each $R^2$ aryl is substituted with one $C(O)NHR^4$. In another embodiment of Formula (IIA), $R^2$ is phenyl; wherein each $R^2$ phenyl is substituted with one $C(O)NHR^4$. In another embodiment of Formula (IIA), $R^2$ is phenyl; wherein each $R^2$ phenyl is substituted with one $OR^4$. In another embodiment of Formula (IIA), $R^2$ is phenyl; wherein each $R^2$ phenyl is substituted with one $R^4$.

In one embodiment of Formula (IIA), $R^3$, at each occurrence, is independently selected from the group consisting of alkyl, alkenyl, alkynyl, aryl, cycloalkyl, cycloalkenyl, and heterocyclyl; wherein each $R^3$ alkyl, alkenyl, and alkynyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, (O), CN, $N_3$, $NO_2$, F, Cl, Br and I; wherein each $R^3$ aryl, cycloalkyl, cycloalkenyl, and heterocyclyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, CNOH, $CNOCH_3$, OH, (O), CN, $N_3$, $NO_2$, F, Cl, Br and I. In another embodiment of Formula (IIA), $R^3$, at each occurrence, is independently heterocyclyl; wherein each $R^3$ heterocyclyl is optionally substituted with one or more substituents independently selected from the group consisting of $CO(O)R^6$, F, Cl, Br and I. In another embodiment of Formula (IIA), $R^3$, at each occurrence, is independently heterocyclyl; wherein each $R^3$ heterocyclyl is optionally substituted with one or more $CO(O)R^6$.

In one embodiment of Formula (IIA), $R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one or more substituents independently selected from the group consisting of $R^9$, $OR^9$, $SR^9$, $S(O)R^9$, $SO_2R^9$, $NHR^9$, $N(R^9)_2$, $C(O)R^9$, $C(O)NH_2$, $C(O)NHR^9$, $C(O)N(R^9)_2$, $NHC(O)R^9$, $NR^9C(O)R^9$, $NHSO_2R^9$, $NHC(O)OR^9$, $SO_2NH_2$, $SO_2NHR^9$, $SO_2N(R^9)_2$, $NHC(O)NH_2$, $NHC(O)NHR^9$, OH, (O), $C(O)OH$, $N_3$, CN, $NH_2$, $CF_3$, $CF_2CF_3$, F, Cl, Br and I. In another embodiment of Formula (IIA), $R^6$, at each occurrence, is alkyl.

In one embodiment of Formula (IIA), $R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, (O), CN, $N_3$, $NO_2$, F, Cl, Br and I; wherein the cyclic moiety represented by $R^4$ is independently optionally substituted with one or more substituents independently selected from the group consisting of $R^{10}$, $OR^{10}$, $SR^{10}$, $S(O)R^{10}$, $C(O)C(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I. In another embodiment of Formula (IIA), $R^4$, at each occurrence, is independently selected from the group consisting of alkyl and heterocyclyl; wherein each $R^4$ alkyl is optionally substituted with one or more substituents independently selected from the group consisting of $R^7$, F, Cl, Br and I; wherein the cyclic moiety represented by $R^4$ is independently optionally substituted with one or more substituents independently selected from the group consisting of $R^{10}$, $C(O)C(O)R^{10}$, $C(O)R^{10}$, $CO(O)R^{10}$, F, Cl, Br and I. In another embodiment of Formula (IIA), $R^4$, at each occurrence, is heterocyclyl. In another embodiment of Formula (IIA), $R^4$, at each occurrence, is heterocyclyl; wherein the cyclic moiety represented by $R^4$ is independently optionally substituted with one or more substituents independently selected from the group consisting of $R^{10}$, $C(O)C(O)R^{10}$, $C(O)R^{10}$, $CO(O)R^{10}$, F, Cl, Br and I.

In one embodiment of Formula (IIA), $R^7$, at each occurrence, is independently selected from the group consisting of alkyl, alkenyl, alkynyl, aryl, heterocyclyl, cycloalkyl, and cycloalkenyl. In another embodiment of Formula (IIA), $R^7$, at each occurrence, is independently heterocyclyl. In another embodiment of Formula (IIA), $R^7$, at each occurrence, is heterocyclyl; wherein the cyclic moiety represented by R is independently optionally substituted with one or more substituents independently selected from the group consisting of $R^{10}$, $C(O)C(O)R^{10}$, $C(O)R^{10}$, $CO(O)R^{10}$, F, Cl, Br and I.

In one embodiment of Formula (IIA), $R^{10}$, at each occurrence, is independently selected from the group consisting of alkyl, alkenyl, alkynyl, aryl, heterocyclyl, cycloalkyl, and cycloalkenyl; wherein each $R^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $C(N)NH_2$, $C(N)NHR^{11}$, $C(N)N(R^{11})_2$, CNOH, $CNOCH_3$, OH, (O), CN, $N_3$, $NO_2$, F, Cl, Br and I; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, CNOH, $CNOCH_3$, OH, CN, $N_3$, $NO_2$, F, Cl, Br and I; $R^{11}$, at each occurrence, is independently selected from the group consisting of alkyl, alkenyl, alkynyl, aryl, heterocyclyl, cycloalkyl, and cycloalkenyl; wherein each $R^{11}$ alkyl, alkenyl, and alkynyl is optionally substituted with alkyl or alkoxy; wherein each $R^{11}$ aryl, heterocyclyl, cycloalkyl, and cycloalkenyl is optionally substituted with alkyl or alkoxy; and $R^{12}$, at each occurrence, is independently selected alkyl. In another embodiment of Formula (IIA), $R^{10}$, at each occurrence, is independently selected from the group consisting of alkyl, aryl, heterocyclyl, and cycloalkyl; wherein each $R^{10}$ alkyl is optionally substituted with one or more substituents independently selected from the group consisting of $R^{11}$, $OR^{11}$, $SR^{11}$, $N(R^{11})_2$, $NHC(O)R^{11}$, OH, F, Cl, Br and I; wherein each $R^{10}$ aryl, heterocyclyl, and cycloalkyl is optionally substituted with one or more substituents independently selected from the group consisting of $R^{12}$, $C(O)R^{12}$, F, Cl, Br and I; $R^{11}$, at each occurrence, is independently selected from the group consisting of alkyl, heterocyclyl, and cycloalkyl; wherein each $R^{11}$ alkyl is optionally substituted with alkoxy; wherein each $R^{11}$ heterocyclyl and cycloalkyl is optionally substituted with alkyl; and $R^{12}$, at each occurrence, is independently selected alkyl. In another embodiment of Formula (IIA), $R^{10}$, at each occurrence, is independently selected from the group consisting of alkyl, aryl, heterocyclyl, and cycloalkyl; wherein each $R^{10}$ alkyl is optionally substituted with one or more substituents independently selected from the group consisting of $R^{11}$, $OR^{11}$, $SR^{11}$, $N(R^{11})_2$, $NHC(O)R^{11}$, OH, and F; wherein each $R^{10}$ aryl, heterocyclyl, and cycloalkyl is optionally substituted with one or more substituents independently selected from the group consisting of $R^{12}$, $C(O)R^{12}$, and F; $R^{11}$, at each occurrence, is independently selected from the group consisting of alkyl, heterocyclyl, and cycloalkyl; wherein each $R^{11}$ alkyl is optionally substituted with alkoxy; wherein each $R^{11}$ heterocyclyl and cycloalkyl is optionally substituted with alkyl; and $R^{12}$, at each occurrence, is independently selected alkyl.

One embodiment of this invention pertains to compounds or pharmaceutically acceptable salts thereof, which are useful as inhibitors of NAMPT, the compounds having Formula (IIA)

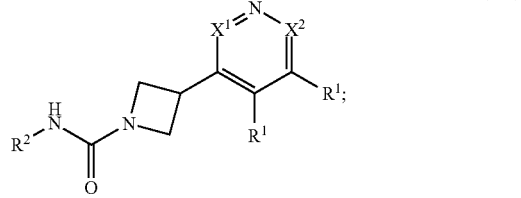

Formula (IIA)

wherein
$X^1$ is $CR^1$ and $X^2$ is $CR^1$;
$R^1$, at each occurrence, is independently selected from the group consisting of hydrogen, alkyl, F, and Cl;

$R^2$ is independently selected from the group consisting of $C_4$-$C_6$-alkyl, and aryl; wherein each $R^2$ $C_4$-$C_6$-alkyl is substituted with one or more $R^3$; wherein each $R^2$ aryl is optionally substituted with one or more substituents independently selected from the group consisting of $R^4$, $OR^4$, $CO(O)R^4$, $C(O)NHR^4$, and CN;

$R^3$, at each occurrence, is heterocyclyl; wherein each $R^3$ heterocyclyl is optionally substituted with one or more $CO(O)R^6$;

$R^4$, at each occurrence, is independently selected from the group consisting of alkyl, and heterocyclyl; wherein each $R^4$ alkyl is optionally substituted with one or more $R^7$;

$R^6$, at each occurrence, is independently alkyl;

$R^7$, at each occurrence, is independently heterocyclyl;

wherein the cyclic moieties represented by $R^4$ and $R^7$ are independently optionally substituted with one or more substituents independently selected from the group consisting of $R^{10}$, $C(O)C(O)R^{10}$, $C(O)R^{10}$, and $CO(O)R^{10}$;

$R^{10}$, at each occurrence, is independently selected from the group consisting of alkyl, aryl, heterocyclyl, and cycloalkyl; wherein each $R^{10}$ alkyl is optionally substituted with one or more substituents independently selected from the group consisting of $R^{11}$, $OR^{11}$, $SR^{11}$, $N(R^{11})_2$, $NHC(O)R^{11}$, OH, and F; wherein each $R^{10}$ aryl, heterocyclyl, and cycloalkyl is optionally substituted with one or more substituents independently selected from the group consisting of $R^{12}$, $C(O)R^{12}$, and F;

$R^{11}$, at each occurrence, is independently selected from the group consisting of alkyl, heterocyclyl, and cycloalkyl; wherein each $R^{11}$ alkyl is optionally substituted with alkoxy; wherein each $R^{11}$ heterocyclyl is optionally substituted with alkyl; and $R^{12}$, at each occurrence, is independently selected alkyl.

Still another embodiment pertains to compounds having Formula (IIA), which include N-[4-({1-[(2S)-2-methylbutanoyl]azetidin-3-yl}oxy)phenyl]-3-(pyridin-3-yl)azetidine-1-carboxamide;

3-(pyridin-3-yl)-N-(4-{[1-(tetrahydro-2H-pyran-4-ylacetyl)piperidin-4-yl]oxy}phenyl)azetidine-1-carboxamide;

3-(5-fluoropyridin-3-yl)-N-(4-{[1-(tetrahydro-2H-pyran-4-ylacetyl)piperidin-4-yl]oxy}phenyl)azetidine-1-carboxamide;

N-[4-({1-[(2S)-2-methylbutanoyl]piperidin-4-yl}oxy)phenyl]-3-(pyridin-3-yl)azetidine-1-carboxamide;

3-(pyridin-3-yl)-N-[4-({1-[(2R)-tetrahydrofuran-2-ylcarbonyl]piperidin-4-yl}oxy)phenyl]azetidine-1-carboxamide;

3-(pyridin-3-yl)-N-(4-{[1-(3,3,3-trifluoropropanoyl)piperidin-4-yl]oxy}phenyl)azetidine-1-carboxamide;

N-(4-{[1-(2-hydroxy-2-methylpropanoyl)piperidin-4-yl]oxy}phenyl)-3-(pyridin-3-yl)azetidine-1-carboxamide;

3-(6-methylpyridin-3-yl)-N-(4-{[1-(tetrahydro-2H-pyran-4-ylacetyl)piperidin-4-yl]oxy}phenyl)azetidine-1-carboxamide;

N-(4-{1-[(2S)-2-methylbutanoyl]-1,2,3,6-tetrahydropyridin-4-yl}phenyl)-3-(pyridin-3-yl)azetidine-1-carboxamide;

3-(pyridin-3-yl)-N-(4-{1-[(2R)-tetrahydrofuran-2-ylcarbonyl]-1,2,3,6-tetrahydropyridin-4-yl}phenyl)azetidine-1-carboxamide;

3-(pyridin-3-yl)-N-(4-{1-[(2S)-tetrahydrofuran-2-ylcarbonyl]-1,2,3,6-tetrahydropyridin-4-yl}phenyl)azetidine-1-carboxamide;

N-{4-[1-(2-hydroxy-2-methylpropanoyl)-1,2,3,6-tetrahydropyridin-4-yl]phenyl}-3-(pyridin-3-yl)azetidine-1-carboxamide;

methyl 4-({[3-(pyridin-3-yl)azetidin-1-yl]carbonyl}amino)benzoate;

N-(4-cyanophenyl)-3-(pyridin-3-yl)azetidine-1-carboxamide;
tert-butyl 4-[4-({[3-(pyridin-3-yl)azetidin-1-yl]carbonyl}amino)butyl]piperidine-1-carboxylate;
N-{4-[1-(2,2-dimethylbutanoyl)-1,2,3,6-tetrahydropyridin-4-yl]phenyl}-3-(pyridin-3-yl)azetidine-1-carboxamide;
N-{4-[1-(3,3-dimethylbutanoyl)-1,2,3,6-tetrahydropyridin-4-yl]phenyl}-3-(pyridin-3-yl)azetidine-1-carboxamide;
3-(pyridin-3-yl)-N-{4-[1-(3,3,3-trifluoropropanoyl)-1,2,3,6-tetrahydropyridin-4-yl]phenyl}azetidine-1-carboxamide;
3-(pyridin-3-yl)-N-{4-[1-(4,4,4-trifluorobutanoyl)-1,2,3,6-tetrahydropyridin-4-yl]phenyl}azetidine-1-carboxamide;
N-{4-[1-(methoxyacetyl)-1,2,3,6-tetrahydropyridin-4-yl]phenyl}-3-(pyridin-3-yl)azetidine-1-carboxamide;
N-(4-{1-[(methylsulfanyl)acetyl]-1,2,3,6-tetrahydropyridin-4-yl}phenyl)-3-(pyridin-3-yl)azetidine-1-carboxamide;
N-{4-[1-(ethoxyacetyl)-1,2,3,6-tetrahydropyridin-4-yl]phenyl}-3-(pyridin-3-yl)azetidine-1-carboxamide;
N-(4-{1-[(2-methoxyethoxy)acetyl]-1,2,3,6-tetrahydropyridin-4-yl}phenyl)-3-(pyridin-3-yl)azetidine-1-carboxamide;
N-(4-{1-[3-(methylsulfanyl)propanoyl]-1,2,3,6-tetrahydropyridin-4-yl}phenyl)-3-(pyridin-3-yl)azetidine-1-carboxamide;
N-{4-[1-(cyclopropylcarbonyl)-1,2,3,6-tetrahydropyridin-4-yl]phenyl}-3-(pyridin-3-yl)azetidine-1-carboxamide;
N-{4-[1-(cyclopropylacetyl)-1,2,3,6-tetrahydropyridin-4-yl]phenyl}-3-(pyridin-3-yl)azetidine-1-carboxamide;
N-{4-[1-(2-methylpropanoyl)-1,2,3,6-tetrahydropyridin-4-yl]phenyl}-3-(pyridin-3-yl)azetidine-1-carboxamide;
3-(pyridin-3-yl)-N-[4-({1-[(2R)-tetrahydrofuran-2-ylcarbonyl]azetidin-3-yl}oxy)phenyl]azetidine-1-carboxamide;
3-(pyridin-3-yl)-N-[4-({1-[(2S)-tetrahydrofuran-2-ylcarbonyl]azetidin-3-yl}oxy)phenyl]azetidine-1-carboxamide;
N-(4-{[1-(2-hydroxy-2-methylpropanoyl)azetidin-3-yl]oxy}phenyl)-3-(pyridin-3-yl)azetidine-1-carboxamide;
3-(pyridin-3-yl)-N-[4-({1-[(2S)-tetrahydrofuran-2-ylcarbonyl]piperidin-4-yl}oxy)phenyl]azetidine-1-carboxamide;
3-(pyridin-3-yl)-N-(4-{[1-(thiophen-2-ylcarbonyl)piperidin-4-yl]oxy}phenyl)azetidine-1-carboxamide;
3-(pyridin-3-yl)-N-(4-{[1-(thiophen-3-ylcarbonyl)piperidin-4-yl]oxy}phenyl)azetidine-1-carboxamide;
N-[4-({1-[(1-acetylpiperidin-4-yl)carbonyl]piperidin-4-yl}oxy)phenyl]-3-(pyridin-3-yl)azetidine-1-carboxamide;
N-[4-({1-[(2-methylcyclopropyl)carbonyl]piperidin-4-yl}oxy)phenyl]-3-(pyridin-3-yl)azetidine-1-carboxamide;
N-[4-({1-[(1-methyl-1H-pyrrol-2-yl)carbonyl]piperidin-4-yl}oxy)phenyl]-3-(pyridin-3-yl)azetidine-1-carboxamide;
N-[4-({1-[3-(morpholin-4-yl)propanoyl]piperidin-4-yl}oxy)phenyl]-3-(pyridin-3-yl)azetidine-1-carboxamide;
N-[4-({1-[3-(4-methylpiperazin-1-yl)propanoyl]piperidin-4-yl}oxy)phenyl]-3-(pyridin-3-yl)azetidine-1-carboxamide;
3-(pyridin-3-yl)-N-[4-({1-[3-(pyrrolidin-1-yl)propanoyl]piperidin-4-yl}oxy)phenyl]azetidine-1-carboxamide;
N-(4-{[1-(cyclopropylacetyl)piperidin-4-yl]oxy}phenyl)-3-(pyridin-3-yl)azetidine-1-carboxamide;
N-(4-{[1-(3-methylpentanoyl)piperidin-4-yl]oxy}phenyl)-3-(pyridin-3-yl)azetidine-1-carboxamide;
N-(4-{[1-(4-methylpentanoyl)piperidin-4-yl]oxy}phenyl)-3-(pyridin-3-yl)azetidine-1-carboxamide;
N-{4-[(1-butanoylpiperidin-4-yl)oxy]phenyl}-3-(pyridin-3-yl)azetidine-1-carboxamide;
N-(4-{[1-(2,2-dimethylpropanoyl)piperidin-4-yl]oxy}phenyl)-3-(pyridin-3-yl)azetidine-1-carboxamide;
N-(4-{[1-(3,3-dimethylbutanoyl)piperidin-4-yl]oxy}phenyl)-3-(pyridin-3-yl)azetidine-1-carboxamide;
N-(4-{[1-(ethoxyacetyl)piperidin-4-yl]oxy}phenyl)-3-(pyridin-3-yl)azetidine-1-carboxamide;
N-(4-{[1-(cyclopropylcarbonyl)piperidin-4-yl]oxy}phenyl)-3-(pyridin-3-yl)azetidine-1-carboxamide;
N-(4-{[1-(methoxyacetyl)piperidin-4-yl]oxy}phenyl)-3-(pyridin-3-yl)azetidine-1-carboxamide;
3-(pyridin-3-yl)-N-{4-[(tetrahydrofuran-3-ylmethyl)carbamoyl]phenyl}azetidine-1-carboxamide;
3-(pyridin-3-yl)-N-{4-[1-(tetrahydro-2H-pyran-4-ylacetyl)piperidin-4-yl]phenyl}azetidine-1-carboxamide;
N-{4-[1-(2-hydroxy-2-methylpropanoyl)piperidin-4-yl]phenyl}-3-(pyridin-3-yl)azetidine-1-carboxamide;
3-(pyridin-3-yl)-N-(4-{1-[(2S)-tetrahydrofuran-2-ylcarbonyl]piperidin-4-yl}phenyl)azetidine-1-carboxamide;
3-(pyridin-3-yl)-N-{4-[1-(tetrahydrofuran-3-ylcarbonyl)piperidin-4-yl]phenyl}azetidine-1-carboxamide;
3-(pyridin-3-yl)-N-(4-{1-[(2R)-tetrahydrofuran-2-ylcarbonyl]piperidin-4-yl}phenyl)azetidine-1-carboxamide;
N-{4-[1-(cyclopropylacetyl)piperidin-4-yl]phenyl}-3-(pyridin-3-yl)azetidine-1-carboxamide;
N-{4-[1-(2-methylpropanoyl)piperidin-4-yl]phenyl}-3-(pyridin-3-yl)azetidine-1-carboxamide;
N-[4-(1-benzoylpiperidin-4-yl)phenyl]-3-(pyridin-3-yl)azetidine-1-carboxamide;
3-(pyridin-3-yl)-N-{4-[1-(3,3,3-trifluoropropanoyl)piperidin-4-yl]phenyl}azetidine-1-carboxamide;
tert-butyl 3-[4-({[3-(pyridin-3-yl)azetidin-1-yl]carbonyl}amino)phenyl]pyrrolidine-1-carboxylate;
tert-butyl (3R)-3-[4-({[3-(pyridin-3-yl)azetidin-1-yl]carbonyl}amino)phenoxy]pyrrolidine-1-carboxylate;
tert-butyl (3S)-3-[4-({[3-(pyridin-3-yl)azetidin-1-yl]carbonyl}amino)phenoxy]pyrrolidine-1-carboxylate;
tert-butyl 3-[4-({[3-(pyridin-3-yl)azetidin-1-yl]carbonyl}amino)phenyl]azetidine-1-carboxylate;
tert-butyl 3-[4-({[3-(pyridin-3-yl)azetidin-1-yl]carbonyl}amino)phenoxy]azetidine-1-carboxylate;
3-(pyridin-3-yl)-N-{4-[1-(tetrahydro-2H-pyran-4-ylacetyl)pyrrolidin-3-yl]phenyl}azetidine-1-carboxamide;
N-{4-[1-(2-methylpropanoyl)pyrrolidin-3-yl]phenyl}-3-(pyridin-3-yl)azetidine-1-carboxamide;
3-(pyridin-3-yl)-N-(4-{1-[(2S)-tetrahydrofuran-2-ylcarbonyl]pyrrolidin-3-yl}phenyl)azetidine-1-carboxamide;
3-(pyridin-3-yl)-N-(4-{1-[(2R)-tetrahydrofuran-2-ylcarbonyl]pyrrolidin-3-yl}phenyl)azetidine-1-carboxamide;
3-(pyridin-3-yl)-N-{4-[1-(tetrahydrofuran-3-ylcarbonyl)pyrrolidin-3-yl]phenyl}azetidine-1-carboxamide;
N-{4-[1-(cyclopropylacetyl)pyrrolidin-3-yl]phenyl}-3-(pyridin-3-yl)azetidine-1-carboxamide;
N-{4-[1-(2-hydroxy-2-methylpropanoyl)pyrrolidin-3-yl]phenyl}-3-(pyridin-3-yl)azetidine-1-carboxamide;
N-[4-(1-benzoylpyrrolidin-3-yl)phenyl]-3-(pyridin-3-yl)azetidine-1-carboxamide;
3-(pyridin-3-yl)-N-{4-[1-(3,3,3-trifluoropropanoyl)pyrrolidin-3-yl]phenyl}azetidine-1-carboxamide;
N-{4-[1-(cyclopropylcarbonyl)pyrrolidin-3-yl]phenyl}-3-(pyridin-3-yl)azetidine-1-carboxamide;
N-{4-[1-[(2S)-2-methylbutanoyl]pyrrolidin-3-yl}phenyl)-3-(pyridin-3-yl)azetidine-1-carboxamide;
N-[4-(1-butanoylpyrrolidin-3-yl)phenyl]-3-(pyridin-3-yl)azetidine-1-carboxamide;
3-(pyridin-3-yl)-N-(4-{[(3R)-1-(tetrahydro-2H-pyran-4-ylacetyl)pyrrolidin-3-yl]oxy}phenyl)azetidine-1-carboxamide;

N-(4-{[(3R)-1-(2-methylpropanoyl)pyrrolidin-3-yl]oxy}phenyl)-3-(pyridin-3-yl)azetidine-1-carboxamide;

3-(pyridin-3-yl)-N-[4-({(3R)-1-[(2S)-tetrahydrofuran-2-ylcarbonyl]pyrrolidin-3-yl}oxy)phenyl]azetidine-1-carboxamide;

3-(pyridin-3-yl)-N-[4-({(3R)-1-[(2R)-tetrahydrofuran-2-ylcarbonyl]pyrrolidin-3-yl}oxy)phenyl]azetidine-1-carboxamide;

3-(pyridin-3-yl)-N-(4-{[(3R)-1-(tetrahydrofuran-3-ylcarbonyl)pyrrolidin-3-yl]oxy}phenyl)azetidine-1-carboxamide;

N-(4-{[(3R)-1-(cyclopropylacetyl)pyrrolidin-3-yl]oxy}phenyl)-3-(pyridin-3-yl)azetidine-1-carboxamide;

N-(4-{[(3R)-1-(2-hydroxy-2-methylpropanoyl)pyrrolidin-3-yl]oxy}phenyl)-3-(pyridin-3-yl)azetidine-1-carboxamide;

N-(4-{[(3R)-1-benzoylpyrrolidin-3-yl]oxy}phenyl)-3-(pyridin-3-yl)azetidine-1-carboxamide;

3-(pyridin-3-yl)-N-(4-{[(3R)-1-(3,3,3-trifluoropropanoyl)pyrrolidin-3-yl]oxy}phenyl)azetidine-1-carboxamide;

N-(4-{[(3R)-1-(cyclopropylcarbonyl)pyrrolidin-3-yl]oxy}phenyl)-3-(pyridin-3-yl)azetidine-1-carboxamide;

N-[4-({(3R)-1-[(2S)-2-methylbutanoyl]pyrrolidin-3-yl}oxy)phenyl]-3-(pyridin-3-yl)azetidine-1-carboxamide;

N-(4-{[(3R)-1-butanoylpyrrolidin-3-yl]oxy}phenyl)-3-(pyridin-3-yl)azetidine-1-carboxamide;

3-(pyridin-3-yl)-N-(4-{[(3S)-1-(tetrahydro-2H-pyran-4-ylacetyl)pyrrolidin-3-yl]oxy}phenyl)azetidine-1-carboxamide;

N-(4-{[(3S)-1-(2-methylpropanoyl)pyrrolidin-3-yl]oxy}phenyl)-3-(pyridin-3-yl)azetidine-1-carboxamide;

3-(pyridin-3-yl)-N-[4-({(3S)-1-[(2S)-tetrahydrofuran-2-ylcarbonyl]pyrrolidin-3-yl}oxy)phenyl]azetidine-1-carboxamide;

3-(pyridin-3-yl)-N-[4-({(3S)-1-[(2R)-tetrahydrofuran-2-ylcarbonyl]pyrrolidin-3-yl}oxy)phenyl]azetidine-1-carboxamide;

3-(pyridin-3-yl)-N-(4-{[(3S)-1-(tetrahydrofuran-3-ylcarbonyl)pyrrolidin-3-yl]oxy}phenyl)azetidine-1-carboxamide;

N-(4-{[(3S)-1-(cyclopropylacetyl)pyrrolidin-3-yl]oxy}phenyl)-3-(pyridin-3-yl)azetidine-1-carboxamide;

N-(4-{[(3S)-1-(2-hydroxy-2-methylpropanoyl)pyrrolidin-3-yl]oxy}phenyl)-3-(pyridin-3-yl)azetidine-1-carboxamide;

N-(4-{[(3S)-1-benzoylpyrrolidin-3-yl]oxy}phenyl)-3-(pyridin-3-yl)azetidine-1-carboxamide;

3-(pyridin-3-yl)-N-(4-{[(3S)-1-(3,3,3-trifluoropropanoyl)pyrrolidin-3-yl]oxy}phenyl)azetidine-1-carboxamide;

N-(4-{[(3S)-1-(cyclopropylcarbonyl)pyrrolidin-3-yl]oxy}phenyl)-3-(pyridin-3-yl)azetidine-1-carboxamide;

N-[4-({(3S)-1-[(2S)-2-methylbutanoyl]pyrrolidin-3-yl}oxy)phenyl]-3-(pyridin-3-yl)azetidine-1-carboxamide;

N-(4-{[(3S)-1-butanoylpyrrolidin-3-yl]oxy}phenyl)-3-(pyridin-3-yl)azetidine-1-carboxamide;

3-(pyridin-3-yl)-N-{4-[1-(tetrahydro-2H-pyran-4-ylacetyl)azetidin-3-yl]phenyl}azetidine-1-carboxamide;

N-{4-[1-(2-methylpropanoyl)azetidin-3-yl]phenyl}-3-(pyridin-3-yl)azetidine-1-carboxamide;

3-(pyridin-3-yl)-N-(4-{1-[(2S)-tetrahydrofuran-2-ylcarbonyl]azetidin-3-yl}phenyl)azetidine-1-carboxamide;

3-(pyridin-3-yl)-N-(4-{1-[(2R)-tetrahydrofuran-2-ylcarbonyl]azetidin-3-yl}phenyl)azetidine-1-carboxamide;

3-(pyridin-3-yl)-N-{4-[1-(tetrahydrofuran-3-ylcarbonyl)azetidin-3-yl]phenyl}azetidine-1-carboxamide;

N-{4-[1-(cyclopropylacetyl)azetidin-3-yl]phenyl}-3-(pyridin-3-yl)azetidine-1-carboxamide;

N-{4-[1-(2-hydroxy-2-methylpropanoyl)azetidin-3-yl]phenyl}-3-(pyridin-3-yl)azetidine-1-carboxamide;

N-[4-(1-benzoylazetidin-3-yl)phenyl]-3-(pyridin-3-yl)azetidine-1-carboxamide;

3-(pyridin-3-yl)-N-{4-[1-(3,3,3-trifluoropropanoyl)azetidin-3-yl]phenyl}azetidine-1-carboxamide;

N-{4-[1-(cyclopropylcarbonyl)azetidin-3-yl]phenyl}-3-(pyridin-3-yl)azetidine-1-carboxamide;

N-(4-{1-[(2S)-2-methylbutanoyl]azetidin-3-yl}phenyl)-3-(pyridin-3-yl)azetidine-1-carboxamide;

N-[4-(1-butanoylazetidin-3-yl)phenyl]-3-(pyridin-3-yl)azetidine-1-carboxamide;

tert-butyl 4-[4-({[3-(2-chloropyridin-3-yl)azetidin-1-yl]carbonyl}amino)phenyl]piperidine-1-carboxylate;

tert-butyl 4-[4-({[3-(4-chloropyridin-3-yl)azetidin-1-yl]carbonyl}amino)phenyl]piperidine-1-carboxylate;

N-(4-{[1-(cyclopropylacetyl)azetidin-3-yl]oxy}phenyl)-3-(pyridin-3-yl)azetidine-1-carboxamide;

N-(4-{[1-(furan-2-ylcarbonyl)azetidin-3-yl]oxy}phenyl)-3-(pyridin-3-yl)azetidine-1-carboxamide;

tert-butyl 4-[4-({[3-(2-fluoropyridin-3-yl)azetidin-1-yl]carbonyl}amino)phenyl]piperidine-1-carboxylate;

N-{4-[(1-pentanoylazetidin-3-yl)oxy]phenyl}-3-(pyridin-3-yl)azetidine-1-carboxamide;

N-[4-({1-[(2-methoxyethoxy)acetyl]azetidin-3-yl}oxy)phenyl]-3-(pyridin-3-yl)azetidine-1-carboxamide;

N-(4-{[1-(ethoxyacetyl)azetidin-3-yl]oxy}phenyl)-3-(pyridin-3-yl)azetidine-1-carboxamide;

N-(4-{[1-(methoxyacetyl)azetidin-3-yl]oxy}phenyl)-3-(pyridin-3-yl)azetidine-1-carboxamide;

N-(4-{[1-(3-methylpentanoyl)azetidin-3-yl]oxy}phenyl)-3-(pyridin-3-yl)azetidine-1-carboxamide;

N-[4-({1-[(1 S,4R)-bicyclo[2.2.1]hept-2-ylacetyl]azetidin-3-yl}oxy)phenyl]-3-(pyridin-3-yl)azetidine-1-carboxamide;

N-(4-{[1-(2,3-dimethylbutanoyl)azetidin-3-yl]oxy}phenyl)-3-(pyridin-3-yl)azetidine-1-carboxamide;

N-(4-{[1-(4-methylpentanoyl)azetidin-3-yl]oxy}phenyl)-3-(pyridin-3-yl)azetidine-1-carboxamide;

N-[4-({1-[(2-methylcyclopropyl)carbonyl]azetidin-3-yl}oxy)phenyl]-3-(pyridin-3-yl)azetidine-1-carboxamide;

3-(pyridin-3-yl)-N-(4-{[1-(4,4,4-trifluorobutanoyl)azetidin-3-yl]oxy}phenyl)azetidine-1-carboxamide;

N-(4-{[1-(2-methylpropanoyl)azetidin-3-yl]oxy}phenyl)-3-(pyridin-3-yl)azetidine-1-carboxamide;

N-(4-{[1-(2,2-dimethylpropanoyl)azetidin-3-yl]oxy}phenyl)-3-(pyridin-3-yl)azetidine-1-carboxamide;

N-{4-[(1-butanoylazetidin-3-yl)oxy]phenyl}-3-(pyridin-3-yl)azetidine-1-carboxamide;

N-{4-[(1-propanoylazetidin-3-yl)oxy]phenyl}-3-(pyridin-3-yl)azetidine-1-carboxamide;

N-(4-{[1-(2,2-dimethylbutanoyl)azetidin-3-yl]oxy}phenyl)-3-(pyridin-3-yl)azetidine-1-carboxamide;

N-(4-{[1-(3-methylbutanoyl)azetidin-3-yl]oxy}phenyl)-3-(pyridin-3-yl)azetidine-1-carboxamide;

N-(4-{[1-(3,3-dimethylbutanoyl)azetidin-3-yl]oxy}phenyl)-3-(pyridin-3-yl)azetidine-1-carboxamide;

3-(pyridin-3-yl)-N-(4-{[1-(3,3,3-trifluoropropanoyl)azetidin-3-yl]oxy}phenyl)azetidine-1-carboxamide;

N-[4-({1-[(1-methylcyclopropyl)carbonyl]azetidin-3-yl}oxy)phenyl]-3-(pyridin-3-yl)azetidine-1-carboxamide;

N-(4-{[1-(2-methylpentanoyl)azetidin-3-yl]oxy}phenyl)-3-(pyridin-3-yl)azetidine-1-carboxamide;

N-{4-[(1-acetylazetidin-3-yl)oxy]phenyl}-3-(pyridin-3-yl)azetidine-1-carboxamide;
N-(4-{[1-(cyclohexylacetyl)azetidin-3-yl]oxy}phenyl)-3-(pyridin-3-yl)azetidine-1-carboxamide;
N-(4-{[1-(cyclohexylcarbonyl)azetidin-3-yl]oxy}phenyl)-3-(pyridin-3-yl)azetidine-1-carboxamide;
N-(4-{[1-(cyclopropylcarbonyl)azetidin-3-yl]oxy}phenyl)-3-(pyridin-3-yl)azetidine-1-carboxamide;
3-(pyridin-3-yl)-N-(4-{[1-(thiophen-2-ylcarbonyl)azetidin-3-yl]oxy}phenyl)azetidine-1-carboxamide;
N-(4-{[1-(cyclopentylcarbonyl)azetidin-3-yl]oxy}phenyl)-3-(pyridin-3-yl)azetidine-1-carboxamide;
N-(4-{[1-(morpholin-4-ylacetyl)azetidin-3-yl]oxy}phenyl)-3-(pyridin-3-yl)azetidine-1-carboxamide;
3-(pyridin-3-yl)-N-(4-{[1-(1,3-thiazol-5-ylcarbonyl)azetidin-3-yl]oxy}phenyl)azetidine-1-carboxamide;
N-[4-({1-[(3,5-dimethyl-1,2-oxazol-4-yl)carbonyl]azetidin-3-yl}oxy)phenyl]-3-(pyridin-3-yl)azetidine-1-carboxamide;
3-(pyridin-3-yl)-N-(4-{[1-(thiophen-3-ylcarbonyl)azetidin-3-yl]oxy}phenyl)azetidine-1-carboxamide;
3-(pyridin-3-yl)-N-(4-{[1-(1,3-thiazol-4-ylcarbonyl)azetidin-3-yl]oxy}phenyl)azetidine-1-carboxamide;
N-(4-{[1-(1,2-oxazol-5-ylcarbonyl)azetidin-3-yl]oxy}phenyl)-3-(pyridin-3-yl)azetidine-1-carboxamide;
N-[4-({1-[(4-methylpiperazin-1-yl)acetyl]azetidin-3-yl}oxy)phenyl]-3-(pyridin-3-yl)azetidine-1-carboxamide;
N-(4-{[1-(N,N-dimethyl-beta-alanyl)azetidin-3-yl]oxy}phenyl)-3-(pyridin-3-yl)azetidine-1-carboxamide;
N-(4-{[1-(furan-3-ylcarbonyl)azetidin-3-yl]oxy}phenyl)-3-(pyridin-3-yl)azetidine-1-carboxamide;
N-[4-({1-[(1-methylcyclohexyl)carbonyl]azetidin-3-yl}oxy)phenyl]-3-(pyridin-3-yl)azetidine-1-carboxamide;
N-(4-{[1-(cyclopentylacetyl)azetidin-3-yl]oxy}phenyl)-3-(pyridin-3-yl)azetidine-1-carboxamide;
3-(pyridin-3-yl)-N-(4-{[1-(1,3-thiazol-2-ylcarbonyl)azetidin-3-yl]oxy}phenyl)azetidine-1-carboxamide;
3-(pyridin-3-yl)-N-(4-{[1-(pyrrolidin-1-ylacetyl)azetidin-3-yl]oxy}phenyl)azetidine-1-carboxamide;
3-(2-fluoropyridin-3-yl)-N-{4-[1-(2-hydroxy-2-methylpropanoyl)piperidin-4-yl]phenyl}azetidine-1-carboxamide;
N-{4-[1-(2-methylpropyl)-1H-pyrazol-4-yl]phenyl}-3-(pyridin-3-yl)azetidine-1-carboxamide;
N-[4-(1-propyl-1H-pyrazol-4-yl)phenyl]-3-(pyridin-3-yl)azetidine-1-carboxamide;
3-(pyridin-3-yl)-N-(4-{1-[(3S)-tetrahydrofuran-3-ylcarbonyl]piperidin-4-yl}phenyl)azetidine-1-carboxamide;
3-(4-chloropyridin-3-yl)-N-(4-{1-[(3S)-tetrahydrofuran-3-ylcarbonyl]piperidin-4-yl}phenyl)azetidine-1-carboxamide;
3-(2-chloropyridin-3-yl)-N-{4-[1-(2-hydroxy-2-methylpropanoyl)piperidin-4-yl]phenyl}azetidine-1-carboxamide;
N-[4-(1-pentanoylpiperidin-4-yl)phenyl]-3-(pyridin-3-yl)azetidine-1-carboxamide;
N-(4-{1-[(2-methylcyclopropyl)carbonyl]piperidin-4-yl}phenyl)-3-(pyridin-3-yl)azetidine-1-carboxamide;
N-(4-{1-[(1S,4R)-bicyclo[2.2.1]hept-2-ylacetyl]piperidin-4-yl}phenyl)-3-(pyridin-3-yl)azetidine-1-carboxamide;
N-{4-[1-(4-methylpentanoyl)piperidin-4-yl]phenyl}-3-(pyridin-3-yl)azetidine-1-carboxamide;
N-{4-[1-(3-methylpentanoyl)piperidin-4-yl]phenyl}-3-(pyridin-3-yl)azetidine-1-carboxamide;
N-{4-[1-(3-ethoxypropanoyl)piperidin-4-yl]phenyl}-3-(pyridin-3-yl)azetidine-1-carboxamide;
N-{4-[1-(2,2-dimethylbutanoyl)piperidin-4-yl]phenyl}-3-(pyridin-3-yl)azetidine-1-carboxamide;
N-{4-[1-(3,3-dimethylbutanoyl)piperidin-4-yl]phenyl}-3-(pyridin-3-yl)azetidine-1-carboxamide;
N-{4-[1-(2,2-dimethylpropanoyl)piperidin-4-yl]phenyl}-3-(pyridin-3-yl)azetidine-1-carboxamide;
N-[4-(1-butanoylpiperidin-4-yl)phenyl]-3-(pyridin-3-yl)azetidine-1-carboxamide;
N-{4-[1-(ethoxyacetyl)piperidin-4-yl]phenyl}-3-(pyridin-3-yl)azetidine-1-carboxamide;
N-{4-[1-(3-methylbutanoyl)piperidin-4-yl]phenyl}-3-(pyridin-3-yl)azetidine-1-carboxamide;
N-{4-[1-(N-acetyl-L-leucyl)piperidin-4-yl]phenyl}-3-(pyridin-3-yl)azetidine-1-carboxamide;
N-(4-{1-[(2-methoxyethoxy)acetyl]piperidin-4-yl}phenyl)-3-(pyridin-3-yl)azetidine-1-carboxamide;
N-{4-[1-(cyclohexylcarbonyl)piperidin-4-yl]phenyl}-3-(pyridin-3-yl)azetidine-1-carboxamide;
N-{4-[1-(cyclohexylacetyl)piperidin-4-yl]phenyl}-3-(pyridin-3-yl)azetidine-1-carboxamide;
3-(pyridin-3-yl)-N-{4-[1-(4,4,4-trifluorobutanoyl)piperidin-4-yl]phenyl}azetidine-1-carboxamide;
N-{4-[1-(cyclopentylcarbonyl)piperidin-4-yl]phenyl}-3-(pyridin-3-yl)azetidine-1-carboxamide;
N-(4-{1-[(1-methylcyclohexyl)carbonyl]piperidin-4-yl}phenyl)-3-(pyridin-3-yl)azetidine-1-carboxamide;
N-{4-[1-(furan-3-ylcarbonyl)piperidin-4-yl]phenyl}-3-(pyridin-3-yl)azetidine-1-carboxamide;
N-[4-(1-acetylpiperidin-4-yl)phenyl]-3-(pyridin-3-yl)azetidine-1-carboxamide;
N-{4-[1-(methoxyacetyl)piperidin-4-yl]phenyl}-3-(pyridin-3-yl)azetidine-1-carboxamide;
3-(pyridin-3-yl)-N-{4-[1-(thiophen-3-ylcarbonyl)piperidin-4-yl]phenyl}azetidine-1-carboxamide;
N-(4-{1-[(3-methylthiophen-2-yl)carbonyl]piperidin-4-yl}phenyl)-3-(pyridin-3-yl)azetidine-1-carboxamide;
N-{4-[1-(morpholin-4-ylacetyl)piperidin-4-yl]phenyl}-3-(pyridin-3-yl)azetidine-1-carboxamide;
3-(pyridin-3-yl)-N-{4-[1-(thiophen-2-ylcarbonyl)piperidin-4-yl]phenyl}azetidine-1-carboxamide;
N-(4-{1-[(5-methylthiophen-2-yl)carbonyl]piperidin-4-yl}phenyl)-3-(pyridin-3-yl)azetidine-1-carboxamide;
N-{4-[1-(furan-2-ylcarbonyl)piperidin-4-yl]phenyl}-3-(pyridin-3-yl)azetidine-1-carboxamide;
N-(4-{1-[(1-methyl-1H-pyrrol-2-yl)carbonyl]piperidin-4-yl}phenyl)-3-(pyridin-3-yl)azetidine-1-carboxamide;
N-[4-(1-propanoylpiperidin-4-yl)phenyl]-3-(pyridin-3-yl)azetidine-1-carboxamide;
N-(4-{1-[(1-methylcyclopropyl)carbonyl]piperidin-4-yl}phenyl)-3-(pyridin-3-yl)azetidine-1-carboxamide;
3-(pyridin-3-yl)-N-{4-[1-(pyrrolidin-1-ylacetyl)piperidin-4-yl]phenyl}azetidine-1-carboxamide;
3-(pyridin-3-yl)-N-{4-[1-(1,3-thiazol-2-ylcarbonyl)piperidin-4-yl]phenyl}azetidine-1-carboxamide;
N-{4-[1-(cyclopentylacetyl)piperidin-4-yl]phenyl}-3-(pyridin-3-yl)azetidine-1-carboxamide;
N-{4-[1-(2,3-dimethylbutanoyl)piperidin-4-yl]phenyl}-3-(pyridin-3-yl)azetidine-1-carboxamide;
N-[4-(1-pentanoylazetidin-3-yl)phenyl]-3-(pyridin-3-yl)azetidine-1-carboxamide;
N-(4-{1-[(2-methylcyclopropyl)carbonyl]azetidin-3-yl}phenyl)-3-(pyridin-3-yl)azetidine-1-carboxamide;
N-(4-{1-[(1S,4R)-bicyclo[2.2.1]hept-2-ylacetyl]azetidin-3-yl}phenyl)-3-(pyridin-3-yl)azetidine-1-carboxamide;
N-{4-[1-(4-methylpentanoyl)azetidin-3-yl]phenyl}-3-(pyridin-3-yl)azetidine-1-carboxamide;

N-{4-[1-(3-methylpentanoyl)azetidin-3-yl]phenyl}-3-(pyridin-3-yl)azetidine-1-carboxamide;
N-{4-[1-(3-ethoxypropanoyl)azetidin-3-yl]phenyl}-3-(pyridin-3-yl)azetidine-1-carboxamide;
N-{4-[1-(2,2-dimethylbutanoyl)azetidin-3-yl]phenyl}-3-(pyridin-3-yl)azetidine-1-carboxamide;
N-{4-[1-(3,3-dimethylbutanoyl)azetidin-3-yl]phenyl}-3-(pyridin-3-yl)azetidine-1-carboxamide;
N-{4-[1-(2,2-dimethylpropanoyl)azetidin-3-yl]phenyl}-3-(pyridin-3-yl)azetidine-1-carboxamide;
N-{4-[1-(ethoxyacetyl)azetidin-3-yl]phenyl}-3-(pyridin-3-yl)azetidine-1-carboxamide;
N-{4-[1-(3-methylbutanoyl)azetidin-3-yl]phenyl}-3-(pyridin-3-yl)azetidine-1-carboxamide;
N-{4-[1-(N-acetyl-L-leucyl)azetidin-3-yl]phenyl}-3-(pyridin-3-yl)azetidine-1-carboxamide;
N-(4-{1-[(2-methoxyethoxy)acetyl]azetidin-3-yl}phenyl)-3-(pyridin-3-yl)azetidine-1-carboxamide;
N-{4-[1-(cyclohexylcarbonyl)azetidin-3-yl]phenyl}-3-(pyridin-3-yl)azetidine-1-carboxamide;
N-{4-[1-(cyclohexylacetyl)azetidin-3-yl]phenyl}-3-(pyridin-3-yl)azetidine-1-carboxamide;
3-(pyridin-3-yl)-N-{4-[1-(4,4,4-trifluorobutanoyl)azetidin-3-yl]phenyl}azetidine-1-carboxamide;
N-{4-[1-(cyclopentylcarbonyl)azetidin-3-yl]phenyl}-3-(pyridin-3-yl)azetidine-1-carboxamide;
N-(4-{1-[(1-methylcyclohexyl)carbonyl]azetidin-3-yl}phenyl)-3-(pyridin-3-yl)azetidine-1-carboxamide;
N-{4-[1-(furan-3-ylcarbonyl)azetidin-3-yl]phenyl}-3-(pyridin-3-yl)azetidine-1-carboxamide;
N-[4-(1-acetylazetidin-3-yl)phenyl]-3-(pyridin-3-yl)azetidine-1-carboxamide;
N-{4-[1-(methoxyacetyl)azetidin-3-yl]phenyl}-3-(pyridin-3-yl)azetidine-1-carboxamide;
3-(pyridin-3-yl)-N-{4-[1-(thiophen-3-ylcarbonyl)azetidin-3-yl]phenyl}azetidine-1-carboxamide;
N-(4-{1-[(3-methylthiophen-2-yl)carbonyl]azetidin-3-yl}phenyl)-3-(pyridin-3-yl)azetidine-1-carboxamide;
N-{4-[1-(morpholin-4-ylacetyl) azetidin-3-yl]phenyl}-3-(pyridin-3-yl)azetidine-1-carboxamide;
3-(pyridin-3-yl)-N-{4-[1-(thiophen-2-ylcarbonyl)azetidin-3-yl]phenyl}azetidine-1-carboxamide;
N-(4-{1-[(5-methylthiophen-2-yl)carbonyl]azetidin-3-yl}phenyl)-3-(pyridin-3-yl)azetidine-1-carboxamide;
N-{4-[1-(furan-2-ylcarbonyl)azetidin-3-yl]phenyl}-3-(pyridin-3-yl)azetidine-1-carboxamide;
N-(4-{1-[(1-methyl-1H-pyrrol-2-yl)carbonyl]azetidin-3-yl}phenyl)-3-(pyridin-3-yl)azetidine-1-carboxamide;
N-[4-(1-propanoylazetidin-3-yl)phenyl]-3-(pyridin-3-yl)azetidine-1-carboxamide;
N-(4-{1-[(1-methylcyclopropyl)carbonyl]azetidin-3-yl}phenyl)-3-(pyridin-3-yl)azetidine-1-carboxamide;
3-(pyridin-3-yl)-N-{4-[1-(1,3-thiazol-2-ylcarbonyl)azetidin-3-yl]phenyl}azetidine-1-carboxamide;
N-{4-[1-(cyclopentylacetyl)azetidin-3-yl]phenyl}-3-(pyridin-3-yl)azetidine-1-carboxamide;
N-{4-[1-(2,3-dimethylbutanoyl)azetidin-3-yl]phenyl}-3-(pyridin-3-yl)azetidine-1-carboxamide;
N-{4-[1-(cyclopentylmethyl)piperidin-4-yl]phenyl}-3-(pyridin-3-yl)azetidine-1-carboxamide;
N-{4-[1-(cyclohexylmethyl)piperidin-4-yl]phenyl}-3-(pyridin-3-yl)azetidine-1-carboxamide;
N-{4-[1-(3,3-dimethylbutyl)piperidin-4-yl]phenyl}-3-(pyridin-3-yl)azetidine-1-carboxamide;
N-{4-[1-(2-methylpentyl)piperidin-4-yl]phenyl}-3-(pyridin-3-yl)azetidine-1-carboxamide;
N-{4-[1-(2-methylpropyl)piperidin-4-yl]phenyl}-3-(pyridin-3-yl)azetidine-1-carboxamide;
N-{4-[1-(3-methylbutyl)piperidin-4-yl]phenyl}-3-(pyridin-3-yl)azetidine-1-carboxamide;
N-{4-[1-(2-ethylbutyl)piperidin-4-yl]phenyl}-3-(pyridin-3-yl)azetidine-1-carboxamide;
N-{4-[1-(2,2-dimethylpropyl)piperidin-4-yl]phenyl}-3-(pyridin-3-yl)azetidine-1-carboxamide;
N-{4-[1-(2-methylbutyl)piperidin-4-yl]phenyl}-3-(pyridin-3-yl)azetidine-1-carboxamide;
N-[4-(1-butylpiperidin-4-yl)phenyl]-3-(pyridin-3-yl)azetidine-1-carboxamide;
N-[4-(1-propylpiperidin-4-yl)phenyl]-3-(pyridin-3-yl)azetidine-1-carboxamide;
N-{4-[1-(2-cyclopropylethyl)piperidin-4-yl]phenyl}-3-(pyridin-3-yl)azetidine-1-carboxamide;
3-(pyridin-3-yl)-N-{4-[1-(tetrahydrofuran-3-ylmethyl)piperidin-4-yl]phenyl}azetidine-1-carboxamide;
N-{4-[1-(2,2-dimethylbutyl)piperidin-4-yl]phenyl}-3-(pyridin-3-yl)azetidine-1-carboxamide;
N-{4-[1-(cyclopentylmethyl)azetidin-3-yl]phenyl}-3-(pyridin-3-yl)azetidine-1-carboxamide;
N-{4-[1-(cyclohexylmethyl)azetidin-3-yl]phenyl}-3-(pyridin-3-yl)azetidine-1-carboxamide;
N-{4-[1-(3,3-dimethylbutyl)azetidin-3-yl]phenyl}-3-(pyridin-3-yl)azetidine-1-carboxamide;
N-{4-[1-(cyclopropylmethyl)azetidin-3-yl]phenyl}-3-(pyridin-3-yl)azetidine-1-carboxamide;
N-{4-[1-(2-methylpentyl)azetidin-3-yl]phenyl}-3-(pyridin-3-yl)azetidine-1-carboxamide;
3-(pyridin-3-yl)-N-{4-[1-(tetrahydrofuran-2-ylmethyl)azetidin-3-yl]phenyl}azetidine-1-carboxamide;
N-{4-[1-(2-methylpropyl)azetidin-3-yl]phenyl}-3-(pyridin-3-yl)azetidine-1-carboxamide;
N-{4-[1-(3-methylbutyl)azetidin-3-yl]phenyl}-3-(pyridin-3-yl)azetidine-1-carboxamide;
N-{4-[1-(2-ethylbutyl)azetidin-3-yl]phenyl}-3-(pyridin-3-yl)azetidine-1-carboxamide;
N-{4-[1-(2,2-dimethylpropyl)azetidin-3-yl]phenyl}-3-(pyridin-3-yl)azetidine-1-carboxamide;
N-{4-[1-(2-methylbutyl)azetidin-3-yl]phenyl}-3-(pyridin-3-yl)azetidine-1-carboxamide;
3-(pyridin-3-yl)-N-{4-[1-(tetrahydrofuran-3-ylmethyl)azetidin-3-yl]phenyl}azetidine-1-carboxamide;
N-{4-[1-(2,2-dimethylbutyl)azetidin-3-yl]phenyl}-3-(pyridin-3-yl)azetidine-1-carboxamide;
N-[4-(1-pentanoylpyrrolidin-3-yl)phenyl]-3-(pyridin-3-yl)azetidine-1-carboxamide;
N-{4-[1-(3-methylpentanoyl)pyrrolidin-3-yl]phenyl}-3-(pyridin-3-yl)azetidine-1-carboxamide;
N-(4-{1-[(1S,4R)-bicyclo[2.2.1]hept-2-ylacetyl]pyrrolidin-3-yl}phenyl)-3-(pyridin-3-yl)azetidine-1-carboxamide;
N-{4-[1-(cyclopentylacetyl)pyrrolidin-3-yl]phenyl}-3-(pyridin-3-yl)azetidine-1-carboxamide;
N-(4-{1-[(2-methylcyclopropyl)carbonyl]pyrrolidin-3-yl}phenyl)-3-(pyridin-3-yl)azetidine-1-carboxamide;
N-{4-[1-(morpholin-4-ylacetyl)pyrrolidin-3-yl]phenyl}-3-(pyridin-3-yl)azetidine-1-carboxamide;
N-{4-[1-(furan-3-ylcarbonyl)pyrrolidin-3-yl]phenyl}-3-(pyridin-3-yl)azetidine-1-carboxamide;
3-(pyridin-3-yl)-N-{4-[1-(pyrrolidin-1-ylacetyl)pyrrolidin-3-yl]phenyl}azetidine-1-carboxamide;
N-{4-[1-(N,N-dimethyl-beta-alanyl)pyrrolidin-3-yl]phenyl}-3-(pyridin-3-yl)azetidine-1-carboxamide;
3-(pyridin-3-yl)-N-{4-[1-(1,3-thiazol-2-ylcarbonyl)pyrrolidin-3-yl]phenyl}azetidine-1-carboxamide;

3-(pyridin-3-yl)-N-{4-[1-(thiophen-3-ylcarbonyl)pyrrolidin-3-yl]phenyl}azetidine-1-carboxamide;
N-(4-{1-[(1-methylcyclopropyl)carbonyl]pyrrolidin-3-yl}phenyl)-3-(pyridin-3-yl)azetidine-1-carboxamide;
N-(4-{1-[(3-methylthiophen-2-yl)carbonyl]pyrrolidin-3-yl}phenyl)-3-(pyridin-3-yl)azetidine-1-carboxamide;
3-(pyridin-3-yl)-N-{4-[1-(4,4,4-trifluorobutanoyl)pyrrolidin-3-yl]phenyl}azetidine-1-carboxamide;
N-(4-{1-[(4-methylpiperazin-1-yl)acetyl]pyrrolidin-3-yl}phenyl)-3-(pyridin-3-yl)azetidine-1-carboxamide;
N-{4-[1-(5-oxo-L-prolyl)pyrrolidin-3-yl]phenyl}-3-(pyridin-3-yl)azetidine-1-carboxamide;
N-{4-[1-(3-ethoxypropanoyl)pyrrolidin-3-yl]phenyl}-3-(pyridin-3-yl)azetidine-1-carboxamide;
N-{4-[1-(4-methylpentanoyl)pyrrolidin-3-yl]phenyl}-3-(pyridin-3-yl)azetidine-1-carboxamide;
N-(4-{1-[(1-methylcyclohexyl)carbonyl]pyrrolidin-3-yl}phenyl)-3-(pyridin-3-yl)azetidine-1-carboxamide;
N-[4-(1-acetylpyrrolidin-3-yl)phenyl]-3-(pyridin-3-yl)azetidine-1-carboxamide;
N-{4-[1-(cyclohexylacetyl)pyrrolidin-3-yl]phenyl}-3-(pyridin-3-yl)azetidine-1-carboxamide;
N-[4-(1-propanoylpyrrolidin-3-yl)phenyl]-3-(pyridin-3-yl)azetidine-1-carboxamide;
N-(4-{1-[(2-methoxyethoxy)acetyl]pyrrolidin-3-yl}phenyl)-3-(pyridin-3-yl)azetidine-1-carboxamide;
N-(4-{1-[3-(morpholin-4-yl)propanoyl]pyrrolidin-3-yl}phenyl)-3-(pyridin-3-yl)azetidine-1-carboxamide;
N-{4-[1-(2,2-dimethylpropanoyl)pyrrolidin-3-yl]phenyl}-3-(pyridin-3-yl)azetidine-1-carboxamide;
N-(4-{1-[(5-methylthiophen-2-yl)carbonyl]pyrrolidin-3-yl}phenyl)-3-(pyridin-3-yl)azetidine-1-carboxamide;
3-(pyridin-3-yl)-N-{4-[1-(thiophen-2-ylcarbonyl)pyrrolidin-3-yl]phenyl}azetidine-1-carboxamide;
N-(4-{1-[(1-methyl-1H-pyrrol-2-yl)carbonyl]pyrrolidin-3-yl}phenyl)-3-(pyridin-3-yl)azetidine-1-carboxamide;
N-{4-[1-(furan-2-ylcarbonyl)pyrrolidin-3-yl]phenyl}-3-(pyridin-3-yl)azetidine-1-carboxamide;
N-(4-{1-[3-(piperidin-1-yl)propanoyl]pyrrolidin-3-yl}phenyl)-3-(pyridin-3-yl)azetidine-1-carboxamide;
N-{4-[1-(ethoxyacetyl)pyrrolidin-3-yl]phenyl}-3-(pyridin-3-yl)azetidine-1-carboxamide;
N-{4-[1-(3,3-dimethylbutanoyl)pyrrolidin-3-yl]phenyl}-3-(pyridin-3-yl)azetidine-1-carboxamide;
N-{4-[1-(2,2-dimethylbutanoyl)pyrrolidin-3-yl]phenyl}-3-(pyridin-3-yl)azetidine-1-carboxamide;
N-{4-[1-(2-oxopropanoyl)pyrrolidin-3-yl]phenyl}-3-(pyridin-3-yl)azetidine-1-carboxamide;
N-{4-[1-(methoxyacetyl)pyrrolidin-3-yl]phenyl}-3-(pyridin-3-yl)azetidine-1-carboxamide;
N-{4-[1-(cyclohexylcarbonyl)pyrrolidin-3-yl]phenyl}-3-(pyridin-3-yl)azetidine-1-carboxamide;
N-{4-[1-(3-methylbutanoyl)pyrrolidin-3-yl]phenyl}-3-(pyridin-3-yl)azetidine-1-carboxamide;
N-{4-[1-(cyclopentylcarbonyl)pyrrolidin-3-yl]phenyl}-3-(pyridin-3-yl)azetidine-1-carboxamide;
N-{4-[1-(2,3-dimethylbutanoyl)pyrrolidin-3-yl]phenyl}-3-(pyridin-3-yl)azetidine-1-carboxamide;
N-(4-{[(3R)-1-pentanoylpyrrolidin-3-yl]oxy}phenyl)-3-(pyridin-3-yl)azetidine-1-carboxamide;
N-(4-{[(3R)-1-(3-methylpentanoyl)pyrrolidin-3-yl]oxy}phenyl)-3-(pyridin-3-yl)azetidine-1-carboxamide;
N-(4-{[1-(bicyclo[2.2.1]hept-2-ylacetyl)pyrrolidin-3-yl]oxy}phenyl)-3-(pyridin-3-yl)azetidine-1-carboxamide;
N-(4-{[(3R)-1-(cyclopentylacetyl)pyrrolidin-3-yl]oxy}phenyl)-3-(pyridin-3-yl)azetidine-1-carboxamide;
N-[4-({(3R)-1-[(2-methylcyclopropyl)carbonyl]pyrrolidin-3-yl}oxy)phenyl]-3-(pyridin-3-yl)azetidine-1-carboxamide;
N-(4-{[(3R)-1-(morpholin-4-ylacetyl)pyrrolidin-3-yl]oxy}phenyl)-3-(pyridin-3-yl)azetidine-1-carboxamide;
N-(4-{[(3R)-1-(furan-3-ylcarbonyl)pyrrolidin-3-yl]oxy}phenyl)-3-(pyridin-3-yl)azetidine-1-carboxamide;
3-(pyridin-3-yl)-N-(4-{[(3R)-1-(pyrrolidin-1-ylacetyl)pyrrolidin-3-yl]oxy}phenyl)azetidine-1-carboxamide;
N-(4-{[(3R)-1-(5-oxo-D-prolyl)pyrrolidin-3-yl]oxy}phenyl)-3-(pyridin-3-yl)azetidine-1-carboxamide;
N-(4-{[(3R)-1-(N,N-dimethyl-beta-alanyl)pyrrolidin-3-yl]oxy}phenyl)-3-(pyridin-3-yl)azetidine-1-carboxamide;
3-(pyridin-3-yl)-N-(4-{[(3R)-1-(1,3-thiazol-2-ylcarbonyl)pyrrolidin-3-yl]oxy}phenyl)azetidine-1-carboxamide;
3-(pyridin-3-yl)-N-(4-{[(3R)-1-(thiophen-3-ylcarbonyl)pyrrolidin-3-yl]oxy}phenyl)azetidine-1-carboxamide;
N-[4-({(3R)-1-[(1-methylcyclopropyl)carbonyl]pyrrolidin-3-yl}oxy)phenyl]-3-(pyridin-3-yl)azetidine-1-carboxamide;
N-[4-({(3R)-1-[(3-methylthiophen-2-yl)carbonyl]pyrrolidin-3-yl}oxy)phenyl]-3-(pyridin-3-yl)azetidine-1-carboxamide;
3-(pyridin-3-yl)-N-(4-{[(3R)-1-(4,4,4-trifluorobutanoyl)pyrrolidin-3-yl]oxy}phenyl)azetidine-1-carboxamide;
N-[4-({(3R)-1-[(4-methylpiperazin-1-yl)acetyl]pyrrolidin-3-yl}oxy)phenyl]-3-(pyridin-3-yl)azetidine-1-carboxamide;
N-(4-{[(3R)-1-(5-oxo-L-prolyl)pyrrolidin-3-yl]oxy}phenyl)-3-(pyridin-3-yl)azetidine-1-carboxamide;
N-(4-{[(3R)-1-(3-ethoxypropanoyl)pyrrolidin-3-yl]oxy}phenyl)-3-(pyridin-3-yl)azetidine-1-carboxamide;
N-(4-{[(3R)-1-(4-methylpentanoyl)pyrrolidin-3-yl]oxy}phenyl)-3-(pyridin-3-yl)azetidine-1-carboxamide;
N-[4-({(3R)-1-[(1-methylcyclohexyl)carbonyl]pyrrolidin-3-yl}oxy)phenyl]-3-(pyridin-3-yl)azetidine-1-carboxamide;
N-(4-{[(3R)-1-(cyclohexylacetyl)pyrrolidin-3-yl]oxy}phenyl)-3-(pyridin-3-yl)azetidine-1-carboxamide;
N-(4-{[(3R)-1-(N-acetyl-L-leucyl)pyrrolidin-3-yl]oxy}phenyl)-3-(pyridin-3-yl)azetidine-1-carboxamide;
N-(4-{[(3R)-1-propanoylpyrrolidin-3-yl]oxy}phenyl)-3-(pyridin-3-yl)azetidine-1-carboxamide;
N-[4-({(3R)-1-[(2-methoxyethoxy)acetyl]pyrrolidin-3-yl}oxy)phenyl]-3-(pyridin-3-yl)azetidine-1-carboxamide;
N-[4-({(3R)-1-[3-(morpholin-4-yl)propanoyl]pyrrolidin-3-yl}oxy)phenyl]-3-(pyridin-3-yl)azetidine-1-carboxamide;
N-(4-{[(3R)-1-(2,2-dimethylpropanoyl)pyrrolidin-3-yl]oxy}phenyl)-3-(pyridin-3-yl)azetidine-1-carboxamide;
N-[4-({(3R)-1-[(5-methylthiophen-2-yl)carbonyl]pyrrolidin-3-yl}oxy)phenyl]-3-(pyridin-3-yl)azetidine-1-carboxamide;
3-(pyridin-3-yl)-N-(4-{[(3R)-1-(thiophen-2-ylcarbonyl)pyrrolidin-3-yl]oxy}phenyl)azetidine-1-carboxamide;
N-[4-({(3R)-1-[(1-methyl-1H-pyrrol-2-yl)carbonyl]pyrrolidin-3-yl}oxy)phenyl]-3-(pyridin-3-yl)azetidine-1-carboxamide;
N-(4-{[(3R)-1-(furan-2-ylcarbonyl)pyrrolidin-3-yl]oxy}phenyl)-3-(pyridin-3-yl)azetidine-1-carboxamide;
N-[4-({(3R)-1-[3-(piperidin-1-yl)propanoyl]pyrrolidin-3-yl}oxy)phenyl]-3-(pyridin-3-yl)azetidine-1-carboxamide;
N-(4-{[(3R)-1-(ethoxyacetyl)pyrrolidin-3-yl]oxy}phenyl)-3-(pyridin-3-yl)azetidine-1-carboxamide;

N-(4-{[(3R)-1-(3,3-dimethylbutanoyl)pyrrolidin-3-yl]oxy}phenyl)-3-(pyridin-3-yl)azetidine-1-carboxamide;
N-(4-{[(3R)-1-(2,2-dimethylbutanoyl)pyrrolidin-3-yl]oxy}phenyl)-3-(pyridin-3-yl)azetidine-1-carboxamide;
N-(4-{[(3R)-1-(methoxyacetyl)pyrrolidin-3-yl]oxy}phenyl)-3-(pyridin-3-yl)azetidine-1-carboxamide;
N-(4-{[(3R)-1-(cyclohexylcarbonyl)pyrrolidin-3-yl]oxy}phenyl)-3-(pyridin-3-yl)azetidine-1-carboxamide;
N-(4-{[(3R)-1-(3-methylbutanoyl)pyrrolidin-3-yl]oxy}phenyl)-3-(pyridin-3-yl)azetidine-1-carboxamide;
N-(4-{[(3R)-1-(cyclopentylcarbonyl)pyrrolidin-3-yl]oxy}phenyl)-3-(pyridin-3-yl)azetidine-1-carboxamide;
N-(4-{[(3R)-1-(2,3-dimethylbutanoyl)pyrrolidin-3-yl]oxy}phenyl)-3-(pyridin-3-yl)azetidine-1-carboxamide;
N-[4-(1-benzoylpiperidin-4-yl)phenyl]-3-(pyridazin-3-yl)azetidine-1-carboxamide;
N-{4-[1-(2-fluorobenzoyl)piperidin-4-yl]phenyl}-3-(pyridazin-3-yl)azetidine-1-carboxamide;
N-{4-[1-(2-methylbenzoyl)piperidin-4-yl]phenyl}-3-(pyridazin-3-yl)azetidine-1-carboxamide;
N-{4-[1-(2,2-dimethylpropanoyl)piperidin-4-yl]phenyl}-3-(pyridazin-3-yl)azetidine-1-carboxamide;
N-{4-[1-(cyclopropylcarbonyl)piperidin-4-yl]phenyl}-3-(pyridazin-3-yl)azetidine-1-carboxamide;
N-[4-(1-acetylpiperidin-4-yl)phenyl]-3-(pyridazin-3-yl)azetidine-1-carboxamide;
N-{4-[1-(3,3-dimethylbutanoyl)piperidin-4-yl]phenyl}-3-(pyridazin-3-yl)azetidine-1-carboxamide;
N-{4-[1-(cyclobutylcarbonyl)piperidin-4-yl]phenyl}-3-(pyridazin-3-yl)azetidine-1-carboxamide;
3-(pyridazin-3-yl)-N-{4-[1-(4,4,4-trifluorobutanoyl)piperidin-4-yl]phenyl}azetidine-1-carboxamide;
3-(pyridazin-3-yl)-N-{4-[1-(3,3,3-trifluoropropanoyl)piperidin-4-yl]phenyl}azetidine-1-carboxamide;
N-(4-{1-[(1-methylcyclopropyl)carbonyl]piperidin-4-yl}phenyl)-3-(pyridazin-3-yl)azetidine-1-carboxamide;
N-{4-[1-(cyclopropylacetyl)piperidin-4-yl]phenyl}-3-(pyridazin-3-yl)azetidine-1-carboxamide;
N-{4-[(1-benzoylpiperidin-4-yl)methyl]phenyl}-3-(pyridazin-3-yl)azetidine-1-carboxamide;
N-(4-{[1-(2-fluorobenzoyl)piperidin-4-yl]methyl}phenyl)-3-(pyridazin-3-yl)azetidine-1-carboxamide;
N-(4-{[1-(2,2-dimethylpropanoyl)piperidin-4-yl]methyl}phenyl)-3-(pyridazin-3-yl)azetidine-1-carboxamide;
N-(4-{[1-(3,3-dimethylbutanoyl)piperidin-4-yl]methyl}phenyl)-3-(pyridazin-3-yl)azetidine-1-carboxamide;
N-(4-{[1-(2-ethylbutanoyl)piperidin-4-yl]methyl}phenyl)-3-(pyridazin-3-yl)azetidine-1-carboxamide;
3-(pyridazin-3-yl)-N-(4-{[1-(4,4,4-trifluorobutanoyl)piperidin-4-yl]methyl}phenyl)azetidine-1-carboxamide;
N-(4-{[1-(2-methylpropanoyl)piperidin-4-yl]methyl}phenyl)-3-(pyridazin-3-yl)azetidine-1-carboxamide;
N-{4-[(1-acetylpiperidin-4-yl)methyl]phenyl}-3-(pyridazin-3-yl)azetidine-1-carboxamide;
N-[4-({1-[(2S)-2-methylbutanoyl]piperidin-4-yl}methyl)phenyl]-3-(pyridazin-3-yl)azetidine-1-carboxamide;
N-[4-({1-[(1-methylcyclopropyl)carbonyl]piperidin-4-yl}methyl)phenyl]-3-(pyridazin-3-yl)azetidine-1-carboxamide; and pharmaceutically acceptable salts thereof.

Embodiments of Formula (IIIA)

In another aspect, the present invention provides compounds of Formula (IIIA)

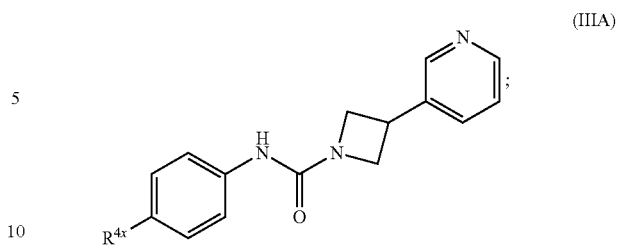

and pharmaceutically acceptable salts thereof; wherein $R^{4x}$ is as described herein for substituents on $R^2$ when $R^2$ is aryl in Formula (IA).

One embodiment of this invention pertains to compounds of Formula (IIIA) or pharmaceutically acceptable salts thereof;
wherein
$R^{4x}$ is independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, $CNOH$, $CNOCH_3$, $OH$, $CN$, $N_3$, $NO_2$, $F$, $Cl$, $Br$ and $I$;

$R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, $CNOH$, $CNOCH_3$, $OH$, $(O)$, $CN$, $N_3$, $NO_2$, $F$, $Cl$, $Br$ and $I$;

$R^7$, at each occurrence, is independently selected from the group consisting of alkyl, alkenyl, alkynyl, aryl, heterocyclyl, cycloalkyl, and cycloalkenyl;

wherein the cyclic moieties represented by $R^4$ and $R^7$ are independently optionally substituted with one or more substituents independently selected from the group consisting of $R^{10}$, $OR^{10}$, $SR^{10}$, $S(O)R^{10}$, $C(O)C(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, $CNOH$, $CNOCH_3$, $OH$, $CN$, $N_3$, $NO_2$, $F$, $Cl$, $Br$ and $I$;

$R^{10}$, at each occurrence, is independently selected from the group consisting of alkyl, alkenyl, alkynyl, aryl, heterocyclyl, cycloalkyl, and cycloalkenyl; wherein each $R^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $C(N)NH_2$, $C(N)NHR^{11}$, $C(N)N(R^{11})_2$, CNOH, $CNOCH_3$, OH, (O), CN, $N_3$, $NO_2$, F, Cl, Br and I; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, CNOH, $CNOCH_3$, OH, CN, $N_3$, $NO_2$, F, Cl, Br and I;

$R^{11}$, at each occurrence, is independently selected from the group consisting of alkyl, alkenyl, alkynyl, aryl, heterocyclyl, cycloalkyl, and cycloalkenyl; wherein each $R^{11}$ alkyl, alkenyl, and alkynyl is optionally substituted with alkyl or alkoxy; wherein each $R^{11}$ aryl, heterocyclyl, cycloalkyl, and cycloalkenyl is optionally substituted with alkyl or alkoxy; and $R^{12}$, at each occurrence, is independently selected alkyl.

In one embodiment of Formula (IIIA), $R^{4x}$ is independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I. In another embodiment of Formula (IIIA), $R^{4x}$ is independently selected from the group consisting of $R^4$, $OR^4$, $CO(O)R^4$, $C(O)NHR^4$, CN, F, Cl, Br and I. In another embodiment of Formula (IIIA), $R^{4x}$ is independently selected from the group consisting of $R^4$, $OR^4$, $CO(O)R^4$, $C(O)NHR^4$, and CN. In another embodiment of Formula (IIIA), $R^{4x}$ is $C(O)NHR^4$. In another embodiment of Formula (IIIA), $R^{4x}$ is $OR^4$. In another embodiment of Formula (IIIA), $R^{4x}$ is $R^4$.

In one embodiment of Formula (IIIA), $R^4$, at each occurrence, is independently selected from the group consisting of alkyl, alkenyl, alkynyl, aryl, heterocyclyl, cycloalkyl, and cycloalkenyl; wherein each $R^4$ alkyl, alkenyl, and alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, (O), CN, $N_3$, $NO_2$, F, Cl, Br and I; wherein the cyclic moiety represented by $R^4$ is independently optionally substituted with one or more substituents independently selected from the group consisting of $R^{10}$, $OR^{10}$, $SR^{10}$, $S(O)R^{10}$, $C(O)C(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$ $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I. In another embodiment of Formula (IIIA), $R^4$, at each occurrence, is independently selected from the group consisting of alkyl and heterocyclyl; wherein each $R^4$ alkyl is optionally substituted with one or more substituents independently selected from the group consisting of $R^7$, F, Cl, Br and I; wherein the cyclic moiety represented by $R^4$ is independently optionally substituted with one or more substituents independently selected from the group consisting of $R^{10}$, $C(O)C(O)R^{10}$, $C(O)R^{10}$, $CO(O)R^{10}$, F, Cl, Br and I. In another embodiment of Formula (IIIA), $R^4$, at each occurrence, is heterocyclyl. In another embodiment of Formula (IIIA), $R^4$, at each occurrence, is heterocyclyl; wherein the cyclic moiety represented by $R^4$ is independently optionally substituted with one or more substituents independently selected from the group consisting of $R^{10}$, $C(O)C(O)R^{10}$, $C(O)R^{10}$, $CO(O)R^{10}$, F, Cl, Br and I.

In one embodiment of Formula (IIIA), $R^7$, at each occurrence, is independently selected from the group consisting of alkyl, alkenyl, alkynyl, aryl, heterocyclyl, cycloalkyl, and cycloalkenyl. In another embodiment of Formula (IIIA), $R^7$, at each occurrence, is independently heterocyclyl. In another embodiment of Formula (IIIA), $R^7$, at each occurrence, is heterocyclyl; wherein the cyclic moiety represented by $R^7$ is independently optionally substituted with one or more substituents independently selected from the group consisting of $R^{10}$, $C(O)C(O)R^{10}$, $C(O)R^{10}$, $CO(O)R^{10}$, F, Cl, Br and I.

In one embodiment of Formula (IIIA), $R^{10}$, at each occurrence, is independently selected from the group consisting of alkyl, alkenyl, alkynyl, aryl, heterocyclyl, cycloalkyl, and cycloalkenyl; wherein each $R^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $C(N)NH_2$, $C(N)NHR^{11}$, $C(N)N(R^{11})_2$, CNOH, $CNOCH_3$, OH, (O), CN, $N_3$, $NO_2$, F, Cl, Br and I; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, CNOH, $CNOCH_3$, OH, CN, $N_3$, $NO_2$, F, Cl, Br and I; $R^{11}$, at each occurrence, is independently selected from the group consisting of alkyl, alkenyl, alkynyl, aryl, heterocyclyl, cycloalkyl, and cycloalkenyl; wherein each $R^{11}$ alkyl, alkenyl, and alkynyl is optionally substituted with alkyl or alkoxy; wherein each $R^{11}$ aryl, heterocyclyl, cycloalkyl, and cycloalkenyl is optionally substituted with alkyl or alkoxy; and $R^{12}$, at each occurrence, is independently selected alkyl.

In another embodiment of Formula (IIIA), $R^{10}$, at each occurrence, is independently selected from the group consisting of alkyl, aryl, heterocyclyl, and cycloalkyl; wherein each $R^{10}$ alkyl is optionally substituted with one or more substituents independently selected from the group consisting of $R^{11}$, $OR^{11}$, $SR^{11}$, $N(R^{11})_2$, $NHC(O)R^{11}$, OH, F, Cl, Br and I; wherein each $R^{10}$ aryl, heterocyclyl, and cycloalkyl is optionally substituted with one or more substituents independently selected from the group consisting of $R^{12}$, C(O)$R^{12}$, F, Cl, Br and I; $R^{11}$, at each occurrence, is independently selected from the group consisting of alkyl, heterocyclyl, and cycloalkyl; wherein each $R^{11}$ alkyl is optionally substituted with alkoxy; wherein each $R^{11}$ heterocyclyl and cycloalkyl is optionally substituted with alkyl; and $R^{12}$, at each occurrence, is independently selected alkyl.

In another embodiment of Formula (IIIA), $R^{10}$, at each occurrence, is independently selected from the group consisting of alkyl, aryl, heterocyclyl, and cycloalkyl; wherein each $R^{10}$ alkyl is optionally substituted with one or more substituents independently selected from the group consisting of $R^{11}$, $OR^{11}$, $SR^{11}$, $N(R^{11})_2$, $NHC(O)R^{11}$, OH, and F; wherein each $R^{10}$ aryl, heterocyclyl, and cycloalkyl is optionally substituted with one or more substituents independently selected from the group consisting of $R^{12}$, C(O)$R^{12}$, and F; $R^{11}$, at each occurrence, is independently selected from the group consisting of alkyl, heterocyclyl, and cycloalkyl; wherein each $R^{11}$ alkyl is optionally substituted with alkoxy; wherein each $R^{11}$ heterocyclyl and cycloalkyl is optionally substituted with alkyl; and $R^{12}$, at each occurrence, is independently selected alkyl.

One embodiment of this invention pertains to compounds or pharmaceutically acceptable salts thereof, which are useful as inhibitors of NAMPT, the compounds having Formula (IIIA)

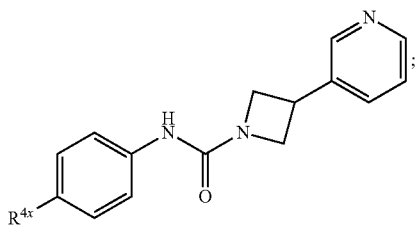

Formula (IIIA)

wherein $R^{4x}$ is independently selected from the group consisting of $R^4$, $OR^4$, $CO(O)R^4$, $C(O)NHR^4$, and CN;

$R^4$, at each occurrence, is independently selected from the group consisting of alkyl, and heterocyclyl; wherein each $R^4$ alkyl is optionally substituted with one or more $R^7$;

$R^7$, at each occurrence, is independently heterocyclyl;

wherein the cyclic moiety represented by $R^4$ and R are independently optionally substituted with one or more substituents independently selected from the group consisting of $R^{10}$, C(O)C(O)$R^{10}$, C(O)$R^{10}$, and CO(O)$R^{10}$;

$R^{10}$, at each occurrence, is independently selected from the group consisting of alkyl, aryl, heterocyclyl, and cycloalkyl; wherein each $R^{10}$ alkyl is optionally substituted with one or more substituents independently selected from the group consisting of $R^{11}$, $OR^{11}$, $SR^{11}$, $N(R^{11})_2$, $NHC(O)R^{11}$, OH, and F; wherein each $R^{10}$ aryl, heterocyclyl, and cycloalkyl is optionally substituted with one or more substituents independently selected from the group consisting of $R^{12}$, C(O)$R^{12}$, and F;

$R^{11}$, at each occurrence, is independently selected from the group consisting of alkyl, heterocyclyl, and cycloalkyl; wherein each $R^{11}$ alkyl is optionally substituted with alkoxy; wherein each $R^{11}$ heterocyclyl is optionally substituted with alkyl; and $R^{12}$, at each occurrence, is independently selected alkyl.

Still another embodiment pertains to compounds having Formula (IIIA), which include N-[4-({1-[(2S)-2-methylbutanoyl]azetidin-3-yl}oxy)phenyl]-3-(pyridin-3-yl)azetidine-1-carboxamide;

3-(pyridin-3-yl)-N-(4-{[1-(tetrahydro-2H-pyran-4-ylacetyl)piperidin-4-yl]oxy}phenyl)azetidine-1-carboxamide;

N-[4-({1-[(2S)-2-methylbutanoyl]piperidin-4-yl}oxy)phenyl]-3-(pyridin-3-yl)azetidine-1-carboxamide;

3-(pyridin-3-yl)-N-[4-({1-[(2R)-tetrahydrofuran-2-ylcarbonyl]piperidin-4-yl}oxy)phenyl]azetidine-1-carboxamide;

3-(pyridin-3-yl)-N-(4-{[1-(3,3,3-trifluoropropanoyl)piperidin-4-yl]oxy}phenyl)azetidine-1-carboxamide;

N-(4-{[1-(2-hydroxy-2-methylpropanoyl)piperidin-4-yl]oxy}phenyl)-3-(pyridin-3-yl)azetidine-1-carboxamide;

N-(4-{1-[(2S)-2-methylbutanoyl]-1,2,3,6-tetrahydropyridin-4-yl}phenyl)-3-(pyridin-3-yl)azetidine-1-carboxamide;

3-(pyridin-3-yl)-N-(4-{1-[(2R)-tetrahydrofuran-2-ylcarbonyl]-1,2,3,6-tetrahydropyridin-4-yl}phenyl)azetidine-1-carboxamide;

3-(pyridin-3-yl)-N-(4-{1-[(2S)-tetrahydrofuran-2-ylcarbonyl]-1,2,3,6-tetrahydropyridin-4-yl}phenyl)azetidine-1-carboxamide;

N-{4-[1-(2-hydroxy-2-methylpropanoyl)-1,2,3,6-tetrahydropyridin-4-yl]phenyl}-3-(pyridin-3-yl)azetidine-1-carboxamide;

methyl 4-({[3-(pyridin-3-yl)azetidin-1-yl]carbonyl}amino)benzoate;

N-(4-cyanophenyl)-3-(pyridin-3-yl)azetidine-1-carboxamide;

N-{4-[1-(2,2-dimethylbutanoyl)-1,2,3,6-tetrahydropyridin-4-yl]phenyl}-3-(pyridin-3-yl)azetidine-1-carboxamide;

N-{4-[1-(3,3-dimethylbutanoyl)-1,2,3,6-tetrahydropyridin-4-yl]phenyl}-3-(pyridin-3-yl)azetidine-1-carboxamide;

3-(pyridin-3-yl)-N-{4-[1-(3,3,3-trifluoropropanoyl)-1,2,3,6-tetrahydropyridin-4-yl]phenyl}azetidine-1-carboxamide;

3-(pyridin-3-yl)-N-{4-[1-(4,4,4-trifluorobutanoyl)-1,2,3,6-tetrahydropyridin-4-yl]phenyl}azetidine-1-carboxamide;

N-{4-[1-(methoxyacetyl)-1,2,3,6-tetrahydropyridin-4-yl]phenyl}-3-(pyridin-3-yl)azetidine-1-carboxamide;

N-(4-{1-[(methylsulfanyl)acetyl]-1,2,3,6-tetrahydropyridin-4-yl}phenyl)-3-(pyridin-3-yl)azetidine-1-carboxamide;

N-{4-[1-(ethoxyacetyl)-1,2,3,6-tetrahydropyridin-4-yl]phenyl}-3-(pyridin-3-yl)azetidine-1-carboxamide;

N-(4-{1-[(2-methoxyethoxy)acetyl]-1,2,3,6-tetrahydropyridin-4-yl}phenyl)-3-(pyridin-3-yl)azetidine-1-carboxamide;

N-(4-{1-[3-(methylsulfanyl)propanoyl]-1,2,3,6-tetrahydropyridin-4-yl}phenyl)-3-(pyridin-3-yl)azetidine-1-carboxamide;

N-{4-[1-(cyclopropylcarbonyl)-1,2,3,6-tetrahydropyridin-4-yl]phenyl}-3-(pyridin-3-yl)azetidine-1-carboxamide;

N-{4-[1-(cyclopropylacetyl)-1,2,3,6-tetrahydropyridin-4-yl]phenyl}-3-(pyridin-3-yl)azetidine-1-carboxamide;

N-{4-[1-(2-methylpropanoyl)-1,2,3,6-tetrahydropyridin-4-yl]phenyl}-3-(pyridin-3-yl)azetidine-1-carboxamide;

3-(pyridin-3-yl)-N-[4-({1-[(2R)-tetrahydrofuran-2-ylcarbonyl]azetidin-3-yl}oxy)phenyl]azetidine-1-carboxamide;

3-(pyridin-3-yl)-N-[4-({1-[(2S)-tetrahydrofuran-2-ylcarbonyl]azetidin-3-yl}oxy)phenyl]azetidine-1-carboxamide;
N-(4-{[1-(2-hydroxy-2-methylpropanoyl)azetidin-3-yl]oxy}phenyl)-3-(pyridin-3-yl)azetidine-1-carboxamide;
3-(pyridin-3-yl)-N-[4-({1-[(2S)-tetrahydrofuran-2-ylcarbonyl]piperidin-4-yl}oxy)phenyl]azetidine-1-carboxamide;
3-(pyridin-3-yl)-N-(4-{[1-(thiophen-2-ylcarbonyl)piperidin-4-yl]oxy}phenyl)azetidine-1-carboxamide;
3-(pyridin-3-yl)-N-(4-{[1-(thiophen-3-ylcarbonyl)piperidin-4-yl]oxy}phenyl)azetidine-1-carboxamide;
N-[4-({1-[(1-acetylpiperidin-4-yl)carbonyl]piperidin-4-yl}oxy)phenyl]-3-(pyridin-3-yl)azetidine-1-carboxamide;
N-[4-({1-[(2-methylcyclopropyl)carbonyl]piperidin-4-yl}oxy)phenyl]-3-(pyridin-3-yl)azetidine-1-carboxamide;
N-[4-({1-[(1-methyl-1H-pyrrol-2-yl)carbonyl]piperidin-4-yl}oxy)phenyl]-3-(pyridin-3-yl)azetidine-1-carboxamide;
N-[4-({1-[3-(morpholin-4-yl)propanoyl]piperidin-4-yl}oxy)phenyl]-3-(pyridin-3-yl)azetidine-1-carboxamide;
N-[4-({1-[3-(4-methylpiperazin-1-yl)propanoyl]piperidin-4-yl}oxy)phenyl]-3-(pyridin-3-yl)azetidine-1-carboxamide;
3-(pyridin-3-yl)-N-[4-({1-[3-(pyrrolidin-1-yl)propanoyl]piperidin-4-yl}oxy)phenyl]azetidine-1-carboxamide;
N-(4-{[1-(cyclopropylacetyl)piperidin-4-yl]oxy}phenyl)-3-(pyridin-3-yl)azetidine-1-carboxamide;
N-(4-{[1-(3-methylpentanoyl)piperidin-4-yl]oxy}phenyl)-3-(pyridin-3-yl)azetidine-1-carboxamide;
N-(4-{[1-(4-methylpentanoyl)piperidin-4-yl]oxy}phenyl)-3-(pyridin-3-yl)azetidine-1-carboxamide;
N-{4-[(1-butanoylpiperidin-4-yl)oxy]phenyl}-3-(pyridin-3-yl)azetidine-1-carboxamide;
N-(4-{[1-(2,2-dimethylpropanoyl)piperidin-4-yl]oxy}phenyl)-3-(pyridin-3-yl)azetidine-1-carboxamide;
N-(4-{[1-(3,3-dimethylbutanoyl)piperidin-4-yl]oxy}phenyl)-3-(pyridin-3-yl)azetidine-1-carboxamide;
N-(4-{[1-(ethoxyacetyl)piperidin-4-yl]oxy}phenyl)-3-(pyridin-3-yl)azetidine-1-carboxamide;
N-(4-{[1-(cyclopropylcarbonyl)piperidin-4-yl]oxy}phenyl)-3-(pyridin-3-yl)azetidine-1-carboxamide;
N-(4-{[1-(methoxyacetyl)piperidin-4-yl]oxy}phenyl)-3-(pyridin-3-yl)azetidine-1-carboxamide;
3-(pyridin-3-yl)-N-{4-[(tetrahydrofuran-3-ylmethyl)carbamoyl]phenyl}azetidine-1-carboxamide;
3-(pyridin-3-yl)-N-{4-[1-(tetrahydro-2H-pyran-4-ylacetyl)piperidin-4-yl]phenyl}azetidine-1-carboxamide;
N-{4-[1-(2-hydroxy-2-methylpropanoyl)piperidin-4-yl]phenyl}-3-(pyridin-3-yl)azetidine-1-carboxamide;
3-(pyridin-3-yl)-N-(4-{1-[(2S)-tetrahydrofuran-2-ylcarbonyl]piperidin-4-yl}phenyl)azetidine-1-carboxamide;
3-(pyridin-3-yl)-N-{4-[1-(tetrahydrofuran-3-ylcarbonyl)piperidin-4-yl]phenyl}azetidine-1-carboxamide;
3-(pyridin-3-yl)-N-(4-{1-[(2R)-tetrahydrofuran-2-ylcarbonyl]piperidin-4-yl}phenyl)azetidine-1-carboxamide;
N-{4-[1-(cyclopropylacetyl)piperidin-4-yl]phenyl}-3-(pyridin-3-yl)azetidine-1-carboxamide;
N-{4-[1-(2-methylpropanoyl)piperidin-4-yl]phenyl}-3-(pyridin-3-yl)azetidine-1-carboxamide;
N-[4-(1-benzoylpiperidin-4-yl)phenyl]-3-(pyridin-3-yl)azetidine-1-carboxamide;
3-(pyridin-3-yl)-N-{4-[1-(3,3,3-trifluoropropanoyl)piperidin-4-yl]phenyl}azetidine-1-carboxamide;
tert-butyl 3-[4-({[3-(pyridin-3-yl)azetidin-1-yl]carbonyl}amino)phenyl]pyrrolidine-1-carboxylate;
tert-butyl (3R)-3-[4-({[3-(pyridin-3-yl)azetidin-1-yl]carbonyl}amino)phenoxy]pyrrolidine-1-carboxylate;
tert-butyl (3S)-3-[4-({[3-(pyridin-3-yl)azetidin-1-yl]carbonyl}amino)phenoxy]pyrrolidine-1-carboxylate;
tert-butyl 3-[4-({[3-(pyridin-3-yl)azetidin-1-yl]carbonyl}amino)phenyl]azetidine-1-carboxylate;
tert-butyl 3-[4-({[3-(pyridin-3-yl)azetidin-1-yl]carbonyl}amino)phenoxy]azetidine-1-carboxylate;
3-(pyridin-3-yl)-N-{4-[1-(tetrahydro-2H-pyran-4-ylacetyl)pyrrolidin-3-yl]phenyl}azetidine-1-carboxamide;
N-{4-[1-(2-methylpropanoyl)pyrrolidin-3-yl]phenyl}-3-(pyridin-3-yl)azetidine-1-carboxamide;
3-(pyridin-3-yl)-N-(4-{1-[(2S)-tetrahydrofuran-2-ylcarbonyl]pyrrolidin-3-yl}phenyl)azetidine-1-carboxamide;
3-(pyridin-3-yl)-N-(4-{1-[(2R)-tetrahydrofuran-2-ylcarbonyl]pyrrolidin-3-yl}phenyl)azetidine-1-carboxamide;
3-(pyridin-3-yl)-N-{4-[1-(tetrahydrofuran-3-ylcarbonyl)pyrrolidin-3-yl]phenyl}azetidine-1-carboxamide;
N-{4-[1-(cyclopropylacetyl)pyrrolidin-3-yl]phenyl}-3-(pyridin-3-yl)azetidine-1-carboxamide;
N-{4-[1-(2-hydroxy-2-methylpropanoyl)pyrrolidin-3-yl]phenyl}-3-(pyridin-3-yl)azetidine-1-carboxamide;
N-[4-(1-benzoylpyrrolidin-3-yl)phenyl]-3-(pyridin-3-yl)azetidine-1-carboxamide;
3-(pyridin-3-yl)-N-{4-[1-(3,3,3-trifluoropropanoyl)pyrrolidin-3-yl]phenyl}azetidine-1-carboxamide;
N-{4-[1-(cyclopropylcarbonyl)pyrrolidin-3-yl]phenyl}-3-(pyridin-3-yl)azetidine-1-carboxamide;
N-(4-{1-[(2S)-2-methylbutanoyl]pyrrolidin-3-yl}phenyl)-3-(pyridin-3-yl)azetidine-1-carboxamide;
N-[4-(1-butanoylpyrrolidin-3-yl)phenyl]-3-(pyridin-3-yl)azetidine-1-carboxamide;
3-(pyridin-3-yl)-N-(4-{[(3R)-1-(tetrahydro-2H-pyran-4-ylacetyl)pyrrolidin-3-yl]oxy}phenyl)azetidine-1-carboxamide;
N-(4-{[(3R)-1-(2-methylpropanoyl)pyrrolidin-3-yl]oxy}phenyl)-3-(pyridin-3-yl)azetidine-1-carboxamide;
3-(pyridin-3-yl)-N-[4-({(3R)-1-[(2S)-tetrahydrofuran-2-ylcarbonyl]pyrrolidin-3-yl}oxy)phenyl]azetidine-1-carboxamide;
3-(pyridin-3-yl)-N-[4-({(3R)-1-[(2R)-tetrahydrofuran-2-ylcarbonyl]pyrrolidin-3-yl}oxy)phenyl]azetidine-1-carboxamide;
3-(pyridin-3-yl)-N-(4-{[(3R)-1-(tetrahydrofuran-3-ylcarbonyl)pyrrolidin-3-yl]oxy}phenyl)azetidine-1-carboxamide;
N-(4-{[(3R)-1-(cyclopropylacetyl)pyrrolidin-3-yl]oxy}phenyl)-3-(pyridin-3-yl)azetidine-1-carboxamide;
N-(4-{[(3R)-1-(2-hydroxy-2-methylpropanoyl)pyrrolidin-3-yl]oxy}phenyl)-3-(pyridin-3-yl)azetidine-1-carboxamide;
N-(4-{[(3R)-1-benzoylpyrrolidin-3-yl]oxy}phenyl)-3-(pyridin-3-yl)azetidine-1-carboxamide;
3-(pyridin-3-yl)-N-(4-{[(3R)-1-(3,3,3-trifluoropropanoyl)pyrrolidin-3-yl]oxy}phenyl)azetidine-1-carboxamide;
N-(4-{[(3R)-1-(cyclopropylcarbonyl)pyrrolidin-3-yl]oxy}phenyl)-3-(pyridin-3-yl)azetidine-1-carboxamide;
N-[4-({(3R)-1-[(2S)-2-methylbutanoyl]pyrrolidin-3-yl}oxy)phenyl]-3-(pyridin-3-yl)azetidine-1-carboxamide;
N-(4-{[(3R)-1-butanoylpyrrolidin-3-yl]oxy}phenyl)-3-(pyridin-3-yl)azetidine-1-carboxamide;
3-(pyridin-3-yl)-N-(4-{[(3S)-1-(tetrahydro-2H-pyran-4-ylacetyl)pyrrolidin-3-yl]oxy}phenyl)azetidine-1-carboxamide;
N-(4-{[(3S)-1-(2-methylpropanoyl)pyrrolidin-3-yl]oxy}phenyl)-3-(pyridin-3-yl)azetidine-1-carboxamide;

3-(pyridin-3-yl)-N-[4-({(3S)-1-[(2S)-tetrahydrofuran-2-yl-carbonyl]pyrrolidin-3-yl}oxy)phenyl]azetidine-1-carboxamide;

3-(pyridin-3-yl)-N-[4-({(3S)-1-[(2R)-tetrahydrofuran-2-yl-carbonyl]pyrrolidin-3-yl}oxy)phenyl]azetidine-1-carboxamide;

3-(pyridin-3-yl)-N-(4-{[(3S)-1-(tetrahydrofuran-3-ylcarbonyl)pyrrolidin-3-yl]oxy}phenyl)azetidine-1-carboxamide;

N-(4-{[(3S)-1-(cyclopropylacetyl)pyrrolidin-3-yl]oxy}phenyl)-3-(pyridin-3-yl)azetidine-1-carboxamide;

N-(4-{[(3S)-1-(2-hydroxy-2-methylpropanoyl)pyrrolidin-3-yl]oxy}phenyl)-3-(pyridin-3-yl)azetidine-1-carboxamide;

N-(4-{[(3S)-1-benzoylpyrrolidin-3-yl]oxy}phenyl)-3-(pyridin-3-yl)azetidine-1-carboxamide;

3-(pyridin-3-yl)-N-(4-{[(3S)-1-(3,3,3-trifluoropropanoyl)pyrrolidin-3-yl]oxy}phenyl)azetidine-1-carboxamide;

N-(4-{[(3S)-1-(cyclopropylcarbonyl)pyrrolidin-3-yl]oxy}phenyl)-3-(pyridin-3-yl)azetidine-1-carboxamide;

N-[4-({(3S)-1-[(2S)-2-methylbutanoyl]pyrrolidin-3-yl}oxy)phenyl]-3-(pyridin-3-yl)azetidine-1-carboxamide;

N-(4-{[(3S)-1-butanoylpyrrolidin-3-yl]oxy}phenyl)-3-(pyridin-3-yl)azetidine-1-carboxamide;

3-(pyridin-3-yl)-N-{4-[1-(tetrahydro-2H-pyran-4-ylacetyl)azetidin-3-yl]phenyl}azetidine-1-carboxamide;

N-{4-[1-(2-methylpropanoyl)azetidin-3-yl]phenyl}-3-(pyridin-3-yl)azetidine-1-carboxamide;

3-(pyridin-3-yl)-N-(4-{1-[(2S)-tetrahydrofuran-2-ylcarbonyl]azetidin-3-yl}phenyl)azetidine-1-carboxamide;

3-(pyridin-3-yl)-N-(4-{1-[(2R)-tetrahydrofuran-2-ylcarbonyl]azetidin-3-yl}phenyl)azetidine-1-carboxamide;

3-(pyridin-3-yl)-N-{4-[1-(tetrahydrofuran-3-ylcarbonyl)azetidin-3-yl]phenyl}azetidine-1-carboxamide;

N-{4-[1-(cyclopropylacetyl)azetidin-3-yl]phenyl}-3-(pyridin-3-yl)azetidine-1-carboxamide;

N-{4-[1-(2-hydroxy-2-methylpropanoyl)azetidin-3-yl]phenyl}-3-(pyridin-3-yl)azetidine-1-carboxamide;

N-[4-(1-benzoylazetidin-3-yl)phenyl]-3-(pyridin-3-yl)azetidine-1-carboxamide;

3-(pyridin-3-yl)-N-{4-[1-(3,3,3-trifluoropropanoyl)azetidin-3-yl]phenyl}azetidine-1-carboxamide;

N-{4-[1-(cyclopropylcarbonyl)azetidin-3-yl]phenyl}-3-(pyridin-3-yl)azetidine-1-carboxamide;

N-(4-{1-[(2S)-2-methylbutanoyl]azetidin-3-yl}phenyl)-3-(pyridin-3-yl)azetidine-1-carboxamide;

N-[4-(1-butanoylazetidin-3-yl)phenyl]-3-(pyridin-3-yl)azetidine-1-carboxamide;

N-(4-{[1-(cyclopropylacetyl)azetidin-3-yl]oxy}phenyl)-3-(pyridin-3-yl)azetidine-1-carboxamide;

N-(4-{[1-(furan-2-ylcarbonyl)azetidin-3-yl]oxy}phenyl)-3-(pyridin-3-yl)azetidine-1-carboxamide;

N-{4-[(1-pentanoylazetidin-3-yl)oxy]phenyl}-3-(pyridin-3-yl)azetidine-1-carboxamide;

N-[4-({1-[(2-methoxyethoxy)acetyl]azetidin-3-yl}oxy)phenyl]-3-(pyridin-3-yl)azetidine-1-carboxamide;

N-[4-{[1-(ethoxyacetyl)azetidin-3-yl]oxy}phenyl]-3-(pyridin-3-yl)azetidine-1-carboxamide;

N-(4-{[1-(methoxyacetyl)azetidin-3-yl]oxy}phenyl)-3-(pyridin-3-yl)azetidine-1-carboxamide;

N-(4-{[1-(3-methylpentanoyl)azetidin-3-yl]oxy}phenyl)-3-(pyridin-3-yl)azetidine-1-carboxamide;

N-[4-({1-[(1 S,4R)-bicyclo[2.2.1]hept-2-ylacetyl]azetidin-3-yl}oxy)phenyl]-3-(pyridin-3-yl)azetidine-1-carboxamide;

N-(4-{[1-(2,3-dimethylbutanoyl)azetidin-3-yl]oxy}phenyl)-3-(pyridin-3-yl)azetidine-1-carboxamide;

N-(4-{[1-(4-methylpentanoyl)azetidin-3-yl]oxy}phenyl)-3-(pyridin-3-yl)azetidine-1-carboxamide;

N-[4-({1-[(2-methylcyclopropyl)carbonyl]azetidin-3-yl}oxy)phenyl]-3-(pyridin-3-yl)azetidine-1-carboxamide;

3-(pyridin-3-yl)-N-(4-{[1-(4,4,4-trifluorobutanoyl)azetidin-3-yl]oxy}phenyl)azetidine-1-carboxamide;

N-(4-{[1-(2-methylpropanoyl)azetidin-3-yl]oxy}phenyl)-3-(pyridin-3-yl)azetidine-1-carboxamide;

N-(4-{[1-(2,2-dimethylpropanoyl)azetidin-3-yl]oxy}phenyl)-3-(pyridin-3-yl)azetidine-1-carboxamide;

N-{4-[(1-butanoylazetidin-3-yl)oxy]phenyl}-3-(pyridin-3-yl)azetidine-1-carboxamide;

N-{4-[(1-propanoylazetidin-3-yl)oxy]phenyl}-3-(pyridin-3-yl)azetidine-1-carboxamide;

N-(4-{[1-(2,2-dimethylbutanoyl)azetidin-3-yl]oxy}phenyl)-3-(pyridin-3-yl)azetidine-1-carboxamide;

N-(4-{[1-(3-methylbutanoyl)azetidin-3-yl]oxy}phenyl)-3-(pyridin-3-yl)azetidine-1-carboxamide;

N-(4-{[1-(3,3-dimethylbutanoyl)azetidin-3-yl]oxy}phenyl)-3-(pyridin-3-yl)azetidine-1-carboxamide;

3-(pyridin-3-yl)-N-(4-{[1-(3,3,3-trifluoropropanoyl)azetidin-3-yl]oxy}phenyl)azetidine-1-carboxamide;

N-[4-({1-[(1-methylcyclopropyl)carbonyl]azetidin-3-yl}oxy)phenyl]-3-(pyridin-3-yl)azetidine-1-carboxamide;

N-(4-{[1-(2-methylpentanoyl)azetidin-3-yl]oxy}phenyl)-3-(pyridin-3-yl)azetidine-1-carboxamide;

N-{4-[(1-acetylazetidin-3-yl)oxy]phenyl}-3-(pyridin-3-yl)azetidine-1-carboxamide;

N-(4-{[1-(cyclohexylacetyl)azetidin-3-yl]oxy}phenyl)-3-(pyridin-3-yl)azetidine-1-carboxamide;

N-(4-{[1-(cyclohexylcarbonyl)azetidin-3-yl]oxy}phenyl)-3-(pyridin-3-yl)azetidine-1-carboxamide;

N-(4-{[1-(cyclopropylcarbonyl)azetidin-3-yl]oxy}phenyl)-3-(pyridin-3-yl)azetidine-1-carboxamide;

3-(pyridin-3-yl)-N-(4-{[1-(thiophen-2-ylcarbonyl)azetidin-3-yl]oxy}phenyl)azetidine-1-carboxamide;

N-(4-{[1-(cyclopentylcarbonyl)azetidin-3-yl]oxy}phenyl)-3-(pyridin-3-yl)azetidine-1-carboxamide;

N-(4-{[1-(morpholin-4-ylacetyl)azetidin-3-yl]oxy}phenyl)-3-(pyridin-3-yl)azetidine-1-carboxamide;

3-(pyridin-3-yl)-N-(4-{[1-(1,3-thiazol-5-ylcarbonyl)azetidin-3-yl]oxy}phenyl)azetidine-1-carboxamide;

N-[4-({1-[(3,5-dimethyl-1,2-oxazol-4-yl)carbonyl]azetidin-3-yl}oxy)phenyl]-3-(pyridin-3-yl)azetidine-1-carboxamide;

3-(pyridin-3-yl)-N-(4-{[1-(thiophen-3-ylcarbonyl)azetidin-3-yl]oxy}phenyl)azetidine-1-carboxamide;

3-(pyridin-3-yl)-N-(4-{[1-(1,3-thiazol-4-ylcarbonyl)azetidin-3-yl]oxy}phenyl)azetidine-1-carboxamide;

N-(4-{[1-(1,2-oxazol-5-ylcarbonyl)azetidin-3-yl]oxy}phenyl)-3-(pyridin-3-yl)azetidine-1-carboxamide;

N-[4-({1-[(4-methylpiperazin-1-yl)acetyl]azetidin-3-yl}oxy)phenyl]-3-(pyridin-3-yl)azetidine-1-carboxamide;

N-(4-{[1-(N,N-dimethyl-beta-alanyl)azetidin-3-yl]oxy}phenyl)-3-(pyridin-3-yl)azetidine-1-carboxamide;

N-(4-{[1-(furan-3-ylcarbonyl)azetidin-3-yl]oxy}phenyl)-3-(pyridin-3-yl)azetidine-1-carboxamide;

N-[4-({1-[(1-methylcyclohexyl)carbonyl]azetidin-3-yl}oxy)phenyl]-3-(pyridin-3-yl)azetidine-1-carboxamide;

N-(4-{[1-(cyclopentylacetyl)azetidin-3-yl]oxy}phenyl)-3-(pyridin-3-yl)azetidine-1-carboxamide;

3-(pyridin-3-yl)-N-(4-{[1-(1,3-thiazol-2-ylcarbonyl)azetidin-3-yl]oxy}phenyl)azetidine-1-carboxamide;
3-(pyridin-3-yl)-N-(4-{[1-(pyrrolidin-1-ylacetyl)azetidin-3-yl]oxy}phenyl)azetidine-1-carboxamide;
N-{4-[1-(2-methylpropyl)-1H-pyrazol-4-yl]phenyl}-3-(pyridin-3-yl)azetidine-1-carboxamide;
N-[4-(1-propyl-1H-pyrazol-4-yl)phenyl]-3-(pyridin-3-yl)azetidine-1-carboxamide;
3-(pyridin-3-yl)-N-(4-{1-[(3S)-tetrahydrofuran-3-ylcarbonyl]piperidin-4-yl}phenyl)azetidine-1-carboxamide;
N-[4-(1-pentanoylpiperidin-4-yl)phenyl]-3-(pyridin-3-yl)azetidine-1-carboxamide;
N-(4-{1-[(2-methylcyclopropyl)carbonyl]piperidin-4-yl}phenyl)-3-(pyridin-3-yl)azetidine-1-carboxamide;
N-(4-{1-[(1S,4R)-bicyclo[2.2.1]hept-2-ylacetyl]piperidin-4-yl}phenyl)-3-(pyridin-3-yl)azetidine-1-carboxamide;
N-{4-[1-(4-methylpentanoyl)piperidin-4-yl]phenyl}-3-(pyridin-3-yl)azetidine-1-carboxamide;
N-{4-[1-(3-methylpentanoyl)piperidin-4-yl]phenyl}-3-(pyridin-3-yl)azetidine-1-carboxamide;
N-{4-[1-(3-ethoxypropanoyl)piperidin-4-yl]phenyl}-3-(pyridin-3-yl)azetidine-1-carboxamide;
N-{4-[1-(2,2-dimethylbutanoyl)piperidin-4-yl]phenyl}-3-(pyridin-3-yl)azetidine-1-carboxamide;
N-{4-[1-(3,3-dimethylbutanoyl)piperidin-4-yl]phenyl}-3-(pyridin-3-yl)azetidine-1-carboxamide;
N-{4-[1-(2,2-dimethylpropanoyl)piperidin-4-yl]phenyl}-3-(pyridin-3-yl)azetidine-1-carboxamide;
N-[4-(1-butanoylpiperidin-4-yl)phenyl]-3-(pyridin-3-yl)azetidine-1-carboxamide;
N-{4-[1-(ethoxyacetyl)piperidin-4-yl]phenyl}-3-(pyridin-3-yl)azetidine-1-carboxamide;
N-{4-[1-(3-methylbutanoyl)piperidin-4-yl]phenyl}-3-(pyridin-3-yl)azetidine-1-carboxamide;
N-{4-[1-(N-acetyl-L-leucyl)piperidin-4-yl]phenyl}-3-(pyridin-3-yl)azetidine-1-carboxamide;
N-(4-{1-[(2-methoxyethoxy)acetyl]piperidin-4-yl}phenyl)-3-(pyridin-3-yl)azetidine-1-carboxamide;
N-{4-[1-(cyclohexylcarbonyl)piperidin-4-yl]phenyl}-3-(pyridin-3-yl)azetidine-1-carboxamide;
N-{4-[1-(cyclohexylacetyl)piperidin-4-yl]phenyl}-3-(pyridin-3-yl)azetidine-1-carboxamide;
3-(pyridin-3-yl)-N-{4-[1-(4,4,4-trifluorobutanoyl)piperidin-4-yl]phenyl}azetidine-1-carboxamide;
N-{4-[1-(cyclopentylcarbonyl)piperidin-4-yl]phenyl}-3-(pyridin-3-yl)azetidine-1-carboxamide;
N-(4-{1-[(1-methylcyclohexyl)carbonyl]piperidin-4-yl}phenyl)-3-(pyridin-3-yl)azetidine-1-carboxamide;
N-{4-[1-(furan-3-ylcarbonyl)piperidin-4-yl]phenyl}-3-(pyridin-3-yl)azetidine-1-carboxamide;
N-[4-(1-acetylpiperidin-4-yl)phenyl]-3-(pyridin-3-yl)azetidine-1-carboxamide;
N-{4-[1-(methoxyacetyl)piperidin-4-yl]phenyl}-3-(pyridin-3-yl)azetidine-1-carboxamide;
3-(pyridin-3-yl)-N-{4-[1-(thiophen-3-ylcarbonyl)piperidin-4-yl]phenyl}azetidine-1-carboxamide;
N-(4-{1-[(3-methylthiophen-2-yl)carbonyl]piperidin-4-yl}phenyl)-3-(pyridin-3-yl)azetidine-1-carboxamide;
N-{4-[1-(morpholin-4-ylacetyl)piperidin-4-yl]phenyl}-3-(pyridin-3-yl)azetidine-1-carboxamide;
3-(pyridin-3-yl)-N-{4-[1-(thiophen-2-ylcarbonyl)piperidin-4-yl]phenyl}azetidine-1-carboxamide;
N-(4-{1-[(5-methylthiophen-2-yl)carbonyl]piperidin-4-yl}phenyl)-3-(pyridin-3-yl)azetidine-1-carboxamide;
N-{4-[1-(furan-2-ylcarbonyl)piperidin-4-yl]phenyl}-3-(pyridin-3-yl)azetidine-1-carboxamide;
N-(4-{1-[(1-methyl-1H-pyrrol-2-yl)carbonyl]piperidin-4-yl}phenyl)-3-(pyridin-3-yl)azetidine-1-carboxamide;
N-[4-(1-propanoylpiperidin-4-yl)phenyl]-3-(pyridin-3-yl)azetidine-1-carboxamide;
N-(4-{1-[(1-methylcyclopropyl)carbonyl]piperidin-4-yl}phenyl)-3-(pyridin-3-yl)azetidine-1-carboxamide;
3-(pyridin-3-yl)-N-{4-[1-(pyrrolidin-1-ylacetyl)piperidin-4-yl]phenyl}azetidine-1-carboxamide;
3-(pyridin-3-yl)-N-{4-[1-(1,3-thiazol-2-ylcarbonyl)piperidin-4-yl]phenyl}azetidine-1-carboxamide;
N-{4-[1-(cyclopentylacetyl)piperidin-4-yl]phenyl}-3-(pyridin-3-yl)azetidine-1-carboxamide;
N-{4-[1-(2,3-dimethylbutanoyl)piperidin-4-yl]phenyl}-3-(pyridin-3-yl)azetidine-1-carboxamide;
N-[4-(1-pentanoylazetidin-3-yl)phenyl]-3-(pyridin-3-yl)azetidine-1-carboxamide;
N-(4-{1-[(2-methylcyclopropyl)carbonyl]azetidin-3-yl}phenyl)-3-(pyridin-3-yl)azetidine-1-carboxamide;
N-(4-{1-[(1S,4R)-bicyclo[2.2.1]hept-2-ylacetyl]azetidin-3-yl}phenyl)-3-(pyridin-3-yl)azetidine-1-carboxamide;
N-{4-[1-(4-methylpentanoyl)azetidin-3-yl]phenyl}-3-(pyridin-3-yl)azetidine-1-carboxamide;
N-{4-[1-(3-methylpentanoyl)azetidin-3-yl]phenyl}-3-(pyridin-3-yl)azetidine-1-carboxamide;
N-{4-[1-(3-ethoxypropanoyl)azetidin-3-yl]phenyl}-3-(pyridin-3-yl)azetidine-1-carboxamide;
N-{4-[1-(2,2-dimethylbutanoyl)azetidin-3-yl]phenyl}-3-(pyridin-3-yl)azetidine-1-carboxamide;
N-{4-[1-(3,3-dimethylbutanoyl)azetidin-3-yl]phenyl}-3-(pyridin-3-yl)azetidine-1-carboxamide;
N-{4-[1-(2,2-dimethylpropanoyl)azetidin-3-yl]phenyl}-3-(pyridin-3-yl)azetidine-1-carboxamide;
N-{4-[1-(ethoxyacetyl)azetidin-3-yl]phenyl}-3-(pyridin-3-yl)azetidine-1-carboxamide;
N-{4-[1-(3-methylbutanoyl)azetidin-3-yl]phenyl}-3-(pyridin-3-yl)azetidine-1-carboxamide;
N-{4-[1-(N-acetyl-L-leucyl)azetidin-3-yl]phenyl}-3-(pyridin-3-yl)azetidine-1-carboxamide;
N-(4-{1-[(2-methoxyethoxy)acetyl]azetidin-3-yl}phenyl)-3-(pyridin-3-yl)azetidine-1-carboxamide;
N-{4-[1-(cyclohexylcarbonyl)azetidin-3-yl]phenyl}-3-(pyridin-3-yl)azetidine-1-carboxamide;
N-{4-[1-(cyclohexylacetyl)azetidin-3-yl]phenyl}-3-(pyridin-3-yl)azetidine-1-carboxamide;
3-(pyridin-3-yl)-N-{4-[1-(4,4,4-trifluorobutanoyl)azetidin-3-yl]phenyl}azetidine-1-carboxamide;
N-{4-[1-(cyclopentylcarbonyl)azetidin-3-yl]phenyl}-3-(pyridin-3-yl)azetidine-1-carboxamide;
N-(4-{1-[(1-methylcyclohexyl)carbonyl]azetidin-3-yl}phenyl)-3-(pyridin-3-yl)azetidine-1-carboxamide;
N-{4-[1-(furan-3-ylcarbonyl)azetidin-3-yl]phenyl}-3-(pyridin-3-yl)azetidine-1-carboxamide;
N-[4-(1-acetylazetidin-3-yl)phenyl]-3-(pyridin-3-yl)azetidine-1-carboxamide;
N-{4-[1-(methoxyacetyl)azetidin-3-yl]phenyl}-3-(pyridin-3-yl)azetidine-1-carboxamide;
3-(pyridin-3-yl)-N-{4-[1-(thiophen-3-ylcarbonyl)azetidin-3-yl]phenyl}azetidine-1-carboxamide;
N-(4-{1-[(3-methylthiophen-2-yl)carbonyl]azetidin-3-yl}phenyl)-3-(pyridin-3-yl)azetidine-1-carboxamide;
N-{4-[1-(morpholin-4-ylacetyl)azetidin-3-yl]phenyl}-3-(pyridin-3-yl)azetidine-1-carboxamide;
3-(pyridin-3-yl)-N-{4-[1-(thiophen-2-ylcarbonyl)azetidin-3-yl]phenyl}azetidine-1-carboxamide;
N-(4-{1-[(5-methylthiophen-2-yl)carbonyl]azetidin-3-yl}phenyl)-3-(pyridin-3-yl)azetidine-1-carboxamide;

N-{4-[1-(furan-2-ylcarbonyl)azetidin-3-yl]phenyl}-3-(pyridin-3-yl)azetidine-1-carboxamide;
N-(4-{1-[(1-methyl-1H-pyrrol-2-yl)carbonyl]azetidin-3-yl}phenyl)-3-(pyridin-3-yl)azetidine-1-carboxamide;
N-[4-(1-propanoylazetidin-3-yl)phenyl]-3-(pyridin-3-yl)azetidine-1-carboxamide;
N-(4-{1-[(1-methylcyclopropyl)carbonyl]azetidin-3-yl}phenyl)-3-(pyridin-3-yl)azetidine-1-carboxamide;
3-(pyridin-3-yl)-N-{4-[1-(1,3-thiazol-2-ylcarbonyl)azetidin-3-yl]phenyl}azetidine-1-carboxamide;
N-{4-[1-(cyclopentylacetyl)azetidin-3-yl]phenyl}-3-(pyridin-3-yl)azetidine-1-carboxamide;
N-{4-[1-(2,3-dimethylbutanoyl)azetidin-3-yl]phenyl}-3-(pyridin-3-yl)azetidine-1-carboxamide;
N-{4-[1-(cyclopentylmethyl)piperidin-4-yl]phenyl}-3-(pyridin-3-yl)azetidine-1-carboxamide;
N-{4-[1-(cyclohexylmethyl)piperidin-4-yl]phenyl}-3-(pyridin-3-yl)azetidine-1-carboxamide;
N-{4-[1-(3,3-dimethylbutyl)piperidin-4-yl]phenyl}-3-(pyridin-3-yl)azetidine-1-carboxamide;
N-{4-[1-(2-methylpentyl)piperidin-4-yl]phenyl}-3-(pyridin-3-yl)azetidine-1-carboxamide;
N-{4-[1-(2-methylpropyl)piperidin-4-yl]phenyl}-3-(pyridin-3-yl)azetidine-1-carboxamide;
N-{4-[1-(3-methylbutyl)piperidin-4-yl]phenyl}-3-(pyridin-3-yl)azetidine-1-carboxamide;
N-{4-[1-(2-ethylbutyl)piperidin-4-yl]phenyl}-3-(pyridin-3-yl)azetidine-1-carboxamide;
N-{4-[1-(2,2-dimethylpropyl)piperidin-4-yl]phenyl}-3-(pyridin-3-yl)azetidine-1-carboxamide;
N-{4-[1-(2-methylbutyl)piperidin-4-yl]phenyl}-3-(pyridin-3-yl)azetidine-1-carboxamide;
N-[4-(1-butylpiperidin-4-yl)phenyl]-3-(pyridin-3-yl)azetidine-1-carboxamide;
N-[4-(1-propylpiperidin-4-yl)phenyl]-3-(pyridin-3-yl)azetidine-1-carboxamide;
N-{4-[1-(2-cyclopropylethyl)piperidin-4-yl]phenyl}-3-(pyridin-3-yl)azetidine-1-carboxamide;
3-(pyridin-3-yl)-N-{4-[1-(tetrahydrofuran-3-ylmethyl)piperidin-4-yl]phenyl}azetidine-1-carboxamide;
N-{4-[1-(2,2-dimethylbutyl)piperidin-4-yl]phenyl}-3-(pyridin-3-yl)azetidine-1-carboxamide;
N-{4-[1-(cyclopentylmethyl)azetidin-3-yl]phenyl}-3-(pyridin-3-yl)azetidine-1-carboxamide;
N-{4-[1-(cyclohexylmethyl)azetidin-3-yl]phenyl}-3-(pyridin-3-yl)azetidine-1-carboxamide;
N-{4-[1-(3,3-dimethylbutyl)azetidin-3-yl]phenyl}-3-(pyridin-3-yl)azetidine-1-carboxamide;
N-{4-[1-(cyclopropylmethyl)azetidin-3-yl]phenyl}-3-(pyridin-3-yl)azetidine-1-carboxamide;
N-{4-[1-(2-methylpentyl)azetidin-3-yl]phenyl}-3-(pyridin-3-yl)azetidine-1-carboxamide;
3-(pyridin-3-yl)-N-{4-[1-(tetrahydrofuran-2-ylmethyl)azetidin-3-yl]phenyl}azetidine-1-carboxamide;
N-{4-[1-(2-methylpropyl)azetidin-3-yl]phenyl}-3-(pyridin-3-yl)azetidine-1-carboxamide;
N-{4-[1-(3-methylbutyl)azetidin-3-yl]phenyl}-3-(pyridin-3-yl)azetidine-1-carboxamide;
N-{4-[1-(2-ethylbutyl)azetidin-3-yl]phenyl}-3-(pyridin-3-yl)azetidine-1-carboxamide;
N-{4-[1-(2,2-dimethylpropyl)azetidin-3-yl]phenyl}-3-(pyridin-3-yl)azetidine-1-carboxamide;
N-{4-[1-(2-methylbutyl)azetidin-3-yl]phenyl}-3-(pyridin-3-yl)azetidine-1-carboxamide;
3-(pyridin-3-yl)-N-{4-[1-(tetrahydrofuran-3-ylmethyl)azetidin-3-yl]phenyl}azetidine-1-carboxamide;
N-{4-[1-(2,2-dimethylbutyl)azetidin-3-yl]phenyl}-3-(pyridin-3-yl)azetidine-1-carboxamide;
N-[4-(1-pentanoylpyrrolidin-3-yl)phenyl]-3-(pyridin-3-yl)azetidine-1-carboxamide;
N-{4-[1-(3-methylpentanoyl)pyrrolidin-3-yl]phenyl}-3-(pyridin-3-yl)azetidine-1-carboxamide;
N-(4-{1-[(1S,4R)-bicyclo[2.2.1]hept-2-ylacetyl]pyrrolidin-3-yl}phenyl)-3-(pyridin-3-yl)azetidine-1-carboxamide;
N-{4-[1-(cyclopentylacetyl)pyrrolidin-3-yl]phenyl}-3-(pyridin-3-yl)azetidine-1-carboxamide;
N-(4-{1-[(2-methylcyclopropyl)carbonyl]pyrrolidin-3-yl}phenyl)-3-(pyridin-3-yl)azetidine-1-carboxamide;
N-{4-[1-(morpholin-4-ylacetyl)pyrrolidin-3-yl]phenyl}-3-(pyridin-3-yl)azetidine-1-carboxamide;
N-{4-[1-(furan-3-ylcarbonyl)pyrrolidin-3-yl]phenyl}-3-(pyridin-3-yl)azetidine-1-carboxamide;
3-(pyridin-3-yl)-N-{4-[1-(pyrrolidin-1-ylacetyl)pyrrolidin-3-yl]phenyl}azetidine-1-carboxamide;
N-{4-[1-(N,N-dimethyl-beta-alanyl)pyrrolidin-3-yl]phenyl}-3-(pyridin-3-yl)azetidine-1-carboxamide;
3-(pyridin-3-yl)-N-{4-[1-(1,3-thiazol-2-ylcarbonyl)pyrrolidin-3-yl]phenyl}azetidine-1-carboxamide;
3-(pyridin-3-yl)-N-{4-[1-(thiophen-3-ylcarbonyl)pyrrolidin-3-yl]phenyl}azetidine-1-carboxamide;
N-(4-{1-[(1-methylcyclopropyl)carbonyl]pyrrolidin-3-yl}phenyl)-3-(pyridin-3-yl)azetidine-1-carboxamide;
N-(4-{1-[(3-methylthiophen-2-yl)carbonyl]pyrrolidin-3-yl}phenyl)-3-(pyridin-3-yl)azetidine-1-carboxamide;
3-(pyridin-3-yl)-N-{4-[1-(4,4,4-trifluorobutanoyl)pyrrolidin-3-yl]phenyl}azetidine-1-carboxamide;
N-(4-{1-[(4-methylpiperazin-1-yl)acetyl]pyrrolidin-3-yl}phenyl)-3-(pyridin-3-yl)azetidine-1-carboxamide;
N-{4-[1-(5-oxo-L-prolyl)pyrrolidin-3-yl]phenyl}-3-(pyridin-3-yl)azetidine-1-carboxamide;
N-{4-[1-(3-ethoxypropanoyl)pyrrolidin-3-yl]phenyl}-3-(pyridin-3-yl)azetidine-1-carboxamide;
N-{4-[1-(4-methylpentanoyl)pyrrolidin-3-yl]phenyl}-3-(pyridin-3-yl)azetidine-1-carboxamide;
N-(4-{1-[(1-methylcyclohexyl)carbonyl]pyrrolidin-3-yl}phenyl)-3-(pyridin-3-yl)azetidine-1-carboxamide;
N-[4-(1-acetylpyrrolidin-3-yl)phenyl]-3-(pyridin-3-yl)azetidine-1-carboxamide;
N-{4-[1-(cyclohexylacetyl)pyrrolidin-3-yl]phenyl}-3-(pyridin-3-yl)azetidine-1-carboxamide;
N-[4-(1-propanoylpyrrolidin-3-yl)phenyl]-3-(pyridin-3-yl)azetidine-1-carboxamide;
N-(4-{1-[(2-methoxyethoxy)acetyl]pyrrolidin-3-yl}phenyl)-3-(pyridin-3-yl)azetidine-1-carboxamide;
N-(4-{1-[3-(morpholin-4-yl)propanoyl]pyrrolidin-3-yl}phenyl)-3-(pyridin-3-yl)azetidine-1-carboxamide;
N-{4-[1-(2,2-dimethylpropanoyl)pyrrolidin-3-yl]phenyl}-3-(pyridin-3-yl)azetidine-1-carboxamide;
N-(4-{1-[(5-methylthiophen-2-yl)carbonyl]pyrrolidin-3-yl}phenyl)-3-(pyridin-3-yl)azetidine-1-carboxamide;
3-(pyridin-3-yl)-N-{4-[1-(thiophen-2-ylcarbonyl)pyrrolidin-3-yl]phenyl}azetidine-1-carboxamide;
N-(4-{1-[(1-methyl-1H-pyrrol-2-yl)carbonyl]pyrrolidin-3-yl}phenyl)-3-(pyridin-3-yl)azetidine-1-carboxamide;
N-{4-[1-(furan-2-ylcarbonyl)pyrrolidin-3-yl]phenyl}-3-(pyridin-3-yl)azetidine-1-carboxamide;
N-(4-{1-[3-(piperidin-1-yl)propanoyl]pyrrolidin-3-yl}phenyl)-3-(pyridin-3-yl)azetidine-1-carboxamide;
N-{4-[1-(ethoxyacetyl)pyrrolidin-3-yl]phenyl}-3-(pyridin-3-yl)azetidine-1-carboxamide;
N-{4-[1-(3,3-dimethylbutanoyl)pyrrolidin-3-yl]phenyl}-3-(pyridin-3-yl)azetidine-1-carboxamide;

N-{4-[1-(2,2-dimethylbutanoyl)pyrrolidin-3-yl]phenyl}-3-(pyridin-3-yl)azetidine-1-carboxamide;
N-{4-[1-(2-oxopropanoyl)pyrrolidin-3-yl]phenyl}-3-(pyridin-3-yl)azetidine-1-carboxamide;
N-{4-[1-(methoxyacetyl)pyrrolidin-3-yl]phenyl}-3-(pyridin-3-yl)azetidine-1-carboxamide;
N-{4-[1-(cyclohexylcarbonyl)pyrrolidin-3-yl]phenyl}-3-(pyridin-3-yl)azetidine-1-carboxamide;
N-{4-[1-(3-methylbutanoyl)pyrrolidin-3-yl]phenyl}-3-(pyridin-3-yl)azetidine-1-carboxamide;
N-{4-[1-(cyclopentylcarbonyl)pyrrolidin-3-yl]phenyl}-3-(pyridin-3-yl)azetidine-1-carboxamide;
N-{4-[1-(2,3-dimethylbutanoyl)pyrrolidin-3-yl]phenyl}-3-(pyridin-3-yl)azetidine-1-carboxamide;
N-(4-{[(3R)-1-pentanoylpyrrolidin-3-yl]oxy}phenyl)-3-(pyridin-3-yl)azetidine-1-carboxamide;
N-(4-{[(3R)-1-(3-methylpentanoyl)pyrrolidin-3-yl]oxy}phenyl)-3-(pyridin-3-yl)azetidine-1-carboxamide;
N-(4-{[1-(bicyclo[2.2.1]hept-2-ylacetyl)pyrrolidin-3-yl]oxy}phenyl)-3-(pyridin-3-yl)azetidine-1-carboxamide;
N-(4-{[(3R)-1-(cyclopentylacetyl)pyrrolidin-3-yl]oxy}phenyl)-3-(pyridin-3-yl)azetidine-1-carboxamide;
N-[4-({(3R)-1-[(2-methylcyclopropyl)carbonyl]pyrrolidin-3-yl}oxy)phenyl]-3-(pyridin-3-yl)azetidine-1-carboxamide;
N-(4-{[(3R)-1-(morpholin-4-ylacetyl)pyrrolidin-3-yl]oxy}phenyl)-3-(pyridin-3-yl)azetidine-1-carboxamide;
N-(4-{[(3R)-1-(furan-3-ylcarbonyl)pyrrolidin-3-yl]oxy}phenyl)-3-(pyridin-3-yl)azetidine-1-carboxamide;
3-(pyridin-3-yl)-N-(4-{[(3R)-1-(pyrrolidin-1-ylacetyl)pyrrolidin-3-yl]oxy}phenyl)azetidine-1-carboxamide;
N-(4-{[(3R)-1-(5-oxo-D-prolyl)pyrrolidin-3-yl]oxy}phenyl)-3-(pyridin-3-yl)azetidine-1-carboxamide;
N-(4-{[(3R)-1-(N,N-dimethyl-beta-alanyl)pyrrolidin-3-yl]oxy}phenyl)-3-(pyridin-3-yl)azetidine-1-carboxamide;
3-(pyridin-3-yl)-N-(4-{[(3R)-1-(1,3-thiazol-2-ylcarbonyl)pyrrolidin-3-yl]oxy}phenyl)azetidine-1-carboxamide;
3-(pyridin-3-yl)-N-(4-{[(3R)-1-(thiophen-3-ylcarbonyl)pyrrolidin-3-yl]oxy}phenyl)azetidine-1-carboxamide;
N-[4-({(3R)-1-[(1-methylcyclopropyl)carbonyl]pyrrolidin-3-yl}oxy)phenyl]-3-(pyridin-3-yl)azetidine-1-carboxamide;
N-[4-({(3R)-1-[(3-methylthiophen-2-yl)carbonyl]pyrrolidin-3-yl}oxy)phenyl]-3-(pyridin-3-yl)azetidine-1-carboxamide;
3-(pyridin-3-yl)-N-(4-{[(3R)-1-(4,4,4-trifluorobutanoyl)pyrrolidin-3-yl]oxy}phenyl)azetidine-1-carboxamide;
N-[4-({(3R)-1-[(4-methylpiperazin-1-yl)acetyl]pyrrolidin-3-yl}oxy)phenyl]-3-(pyridin-3-yl)azetidine-1-carboxamide;
N-(4-{[(3R)-1-(5-oxo-L-prolyl)pyrrolidin-3-yl]oxy}phenyl)-3-(pyridin-3-yl)azetidine-1-carboxamide;
N-(4-{[(3R)-1-(3-ethoxypropanoyl)pyrrolidin-3-yl]oxy}phenyl)-3-(pyridin-3-yl)azetidine-1-carboxamide;
N-(4-{[(3R)-1-(4-methylpentanoyl)pyrrolidin-3-yl]oxy}phenyl)-3-(pyridin-3-yl)azetidine-1-carboxamide;
N-[4-({(3R)-1-[(1-methylcyclohexyl)carbonyl]pyrrolidin-3-yl}oxy)phenyl]-3-(pyridin-3-yl)azetidine-1-carboxamide;
N-(4-{[(3R)-1-(cyclohexylacetyl)pyrrolidin-3-yl]oxy}phenyl)-3-(pyridin-3-yl)azetidine-1-carboxamide;
N-(4-{[(3R)-1-(N-acetyl-L-leucyl)pyrrolidin-3-yl]oxy}phenyl)-3-(pyridin-3-yl)azetidine-1-carboxamide;
N-(4-{[(3R)-1-propanoylpyrrolidin-3-yl]oxy}phenyl)-3-(pyridin-3-yl)azetidine-1-carboxamide;
N-[4-({(3R)-1-[(2-methoxyethoxy)acetyl]pyrrolidin-3-yl}oxy)phenyl]-3-(pyridin-3-yl)azetidine-1-carboxamide;
N-[4-({(3R)-1-[3-(morpholin-4-yl)propanoyl]pyrrolidin-3-yl}oxy)phenyl]-3-(pyridin-3-yl)azetidine-1-carboxamide;
N-(4-{[(3R)-1-(2,2-dimethylpropanoyl)pyrrolidin-3-yl]oxy}phenyl)-3-(pyridin-3-yl)azetidine-1-carboxamide;
N-[4-({(3R)-1-[(5-methylthiophen-2-yl)carbonyl]pyrrolidin-3-yl}oxy)phenyl]-3-(pyridin-3-yl)azetidine-1-carboxamide;
3-(pyridin-3-yl)-N-(4-{[(3R)-1-(thiophen-2-ylcarbonyl)pyrrolidin-3-yl]oxy}phenyl)azetidine-1-carboxamide;
N-[4-({(3R)-1-[(1-methyl-1H-pyrrol-2-yl)carbonyl]pyrrolidin-3-yl}oxy)phenyl]-3-(pyridin-3-yl)azetidine-1-carboxamide;
N-(4-{[(3R)-1-(furan-2-ylcarbonyl)pyrrolidin-3-yl]oxy}phenyl)-3-(pyridin-3-yl)azetidine-1-carboxamide;
N-[4-({(3R)-1-[3-(piperidin-1-yl)propanoyl]pyrrolidin-3-yl}oxy)phenyl]-3-(pyridin-3-yl)azetidine-1-carboxamide;
N-(4-{[(3R)-1-(ethoxyacetyl)pyrrolidin-3-yl]oxy}phenyl)-3-(pyridin-3-yl)azetidine-1-carboxamide;
N-(4-{[(3R)-1-(3,3-dimethylbutanoyl)pyrrolidin-3-yl]oxy}phenyl)-3-(pyridin-3-yl)azetidine-1-carboxamide;
N-(4-{[(3R)-1-(2,2-dimethylbutanoyl)pyrrolidin-3-yl]oxy}phenyl)-3-(pyridin-3-yl)azetidine-1-carboxamide;
N-(4-{[(3R)-1-(methoxyacetyl)pyrrolidin-3-yl]oxy}phenyl)-3-(pyridin-3-yl)azetidine-1-carboxamide;
N-(4-{[(3R)-1-(cyclohexylcarbonyl)pyrrolidin-3-yl]oxy}phenyl)-3-(pyridin-3-yl)azetidine-1-carboxamide;
N-(4-{[(3R)-1-(3-methylbutanoyl)pyrrolidin-3-yl]oxy}phenyl)-3-(pyridin-3-yl)azetidine-1-carboxamide;
N-(4-{[(3R)-1-(cyclopentylcarbonyl)pyrrolidin-3-yl]oxy}phenyl)-3-(pyridin-3-yl)azetidine-1-carboxamide;
N-(4-{[(3R)-1-(2,3-dimethylbutanoyl)pyrrolidin-3-yl]oxy}phenyl)-3-(pyridin-3-yl)azetidine-1-carboxamide;
and pharmaceutically acceptable salts thereof.

Pharmaceutical Compositions, Combination Therapies, Methods of Treatment, and Administration Another embodiment comprises pharmaceutical compositions comprising a compound having Formula (I) and an excipient.

Still another embodiment comprises methods of treating cancer in a mammal comprising administering thereto a therapeutically acceptable amount of a compound having Formula (I).

Still another embodiment pertains to compositions for treating diseases during which NAMPT is expressed, said compositions comprising an excipient and a therapeutically effective amount of the compound having Formula (I).

Still another embodiment pertains to methods of treating disease in a patient during which NAMPT is expressed, said methods comprising administering to the patient a therapeutically effective amount of a compound having Formula (I).

Still another embodiment pertains to compositions for treating inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, atherosclerosis, restenosis, diabetes, glomerulonephritis, cancer, particularly wherein the cancer is selected from breast, prostate, lung, colon, cervix, ovary, skin, CNS, bladder, pancreas, leukemia, lymphoma or Hodgkin's disease, cachexia, inflammation associated with infection and certain viral infections, including Acquired Immune Deficiency Syndrome (AIDS), adult respiratory distress syndrome, and ataxia telengiectasia, said compositions comprising an excipient and a therapeutically effective amount of the compound having Formula (I).

Still another embodiment pertains to methods of treating inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, atherosclerosis, restenosis, diabetes, glomerulonephritis, cancer, particularly wherein the cancer is selected from breast, prostate, lung, colon, cervix, ovary, skin, CNS, bladder, pancreas, leukemia, lymphoma or Hodgkin's disease, cachexia, inflammation associated with infection and certain viral infections, including Acquired Immune Deficiency Syndrome (AIDS), adult respiratory distress syndrome, and ataxia telengiectasia in a patient, said methods comprising administering to the patient a therapeutically effective amount of a compound having Formula (I).

Still another embodiment pertains to compositions for treating diseases during which NAMPT is expressed, said compositions comprising an excipient and a therapeutically effective amount of the compound having Formula (I) and a therapeutically effective amount of one additional therapeutic agent or more than one additional therapeutic agent.

Still another embodiment pertains to methods of treating disease in a patient during which NAMPT is expressed, said methods comprising administering to the patient a therapeutically effective amount of a compound having Formula (I) and a therapeutically effective amount of one additional therapeutic agent or more than one additional therapeutic agent.

Still another embodiment pertains to compositions for treating inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, atherosclerosis, restenosis, diabetes, glomerulonephritis, cancer, particularly wherein the cancer is selected from breast, prostate, lung, colon, cervix, ovary, skin, CNS, bladder, pancreas, leukemia, lymphoma or Hodgkin's disease, cachexia, inflammation associated with infection and certain viral infections, including Acquired Immune Deficiency Syndrome (AIDS), adult respiratory distress syndrome, and ataxia telengiectasia, said compositions comprising an excipient and a therapeutically effective amount of the compound having Formula (I) and a therapeutically effective amount of one additional therapeutic agent or more than one additional therapeutic agent.

Still another embodiment pertains to methods of treating inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, atherosclerosis, restenosis, diabetes, glomerulonephritis, cancer, particularly wherein the cancer is selected from breast, prostate, lung, colon, cervix, ovary, skin, CNS, bladder, pancreas, leukemia, lymphoma or Hodgkin's disease, cachexia, inflammation associated with infection and certain viral infections, including Acquired Immune Deficiency Syndrome (AIDS), adult respiratory distress syndrome, and ataxia telengiectasia in a patient, said methods comprising administering to the patient a therapeutically effective amount of the compound having Formula (I) and a therapeutically effective amount of one additional therapeutic agent or more than one additional therapeutic agent.

Metabolites of compounds having Formula (I), produced by in vitro or in vivo metabolic processes, may also have utility for treating diseases associated with NAMPT.

Certain precursor compounds which may be metabolized in vitro or in vivo to form compounds having Formula (I) may also have utility for treating diseases associated with NAMPT.

Compounds having Formula (I) may exist as acid addition salts, basic addition salts or zwitterions. Salts of the compounds are prepared during isolation or following purification of the compounds. Acid addition salts of the compounds are those derived from the reaction of the compounds with an acid. For example, the acetate, adipate, alginate, bicarbonate, citrate, aspartate, benzoate, benzenesulfonate, bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthalenesulfonate, nicotinate, oxalate, pamoate, pectinate, persulfate, phosphate, picrate, propionate, succinate, tartrate, thiocyanate, trichloroacetic, trifluoroacetic, para-toluenesulfonate, and undecanoate salts of the compounds are contemplated as being embraced by this invention. Basic addition salts of the compounds are those derived from the reaction of the compounds with the hydroxide, carbonate or bicarbonate of cations such as lithium, sodium, potassium, calcium, and magnesium.

The compounds having Formula (I) may be administered, for example, bucally, ophthalmically, orally, osmotically, parenterally (intramuscularly, intraperitoneally intrasternally, intravenously, subcutaneously), rectally, topically, transdermally or vaginally.

Therapeutically effective amounts of compounds having Formula (I) depend on the recipient of the treatment, the disorder being treated and the severity thereof, the composition containing the compound, the time of administration, the route of administration, the duration of treatment, the compound potency, its rate of clearance and whether or not another drug is co-administered. The amount of a compound of this invention having Formula (I) used to make a composition to be administered daily to a patient in a single dose or in divided doses is from about 0.03 to about 200 mg/kg body weight. Single dose compositions contain these amounts or a combination of submultiples thereof.

Compounds having Formula (I) may be administered with or without an excipient. Excipients include, for example, encapsulating materials or additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof.

Excipients for preparation of compositions comprising a compound having Formula (I) to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof. Excipients for preparation of compositions comprising a compound of this invention having Formula (I) to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof. Excipients for preparation of compositions comprising a compound of this invention having Formula (I) to be administered osmotically include, for example, chlorofluorohydrocarbons, ethanol, water and mixtures thereof. Excipients for preparation of compositions comprising a compound of this invention having Formula (I) to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof. Excipients for preparation of compositions comprising a compound of this invention having Formula (I) to be administered rectally or vaginally include, for example, cocoa butter, polyethylene glycol, wax and mixtures thereof.

Compounds having Formula (I) are expected to be useful when used with alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, retinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B.

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, trofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of inhibitors of apoptosis proteins include HGS 1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145 (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474) and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBI- CIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE® (IFN-α), BAM-002 (oxidized glutathione), BEROMUN® (tasonermin), BEXXAR® (tositumobab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-*pseudomonas* exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT®(AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE®(acitretin), staurosporine (*Streptomyces staurospores*), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

Data

Determination of the utility of compounds having Formula (I) as binders to and inhibitors of NAMPT was performed using Time-Resolved Fluorescence Resonance Energy Transfer (TR-FRET) binding assays.

Time-Resolved Fluorescence Resonance Energy Transfer (TR-FRET) Binding Assay of NAMPT Test compounds were serially diluted (typically 11 half log dilutions) in neat DMSO to 50× final concentrations prior to dilution with assay buffer (50 mM HEPES (NaOH), pH 7.5, 100 mM NaCl, 10 mM MgCl$_2$, 1 mM DTT, 1% Glycerol) to 3× and 6% DMSO. Six □L were transferred to 384-well low-volume plates (Owens Corning #3673). To this, 12 □L of a 1.5× solution containing enzyme, probe and antibody were added. Final concentrations in the 18 □L reactions were 1× assay buffer, 2% DMSO, 6.8 nM NAMPT (human, recombinant, C-terminally His-tagged), 200 nM probe (a potent nicotinamide-competitive inhibitor conjugated to Oregon Green 488) and 1 nM Tb-anti-His antibody (Invitrogen #PV5895). Reactions were equilibrated at room temperature for 3 hours prior to reading on an Envision multi-label plate reader (Perkin Elmer; Ex=337 nm, Em=520 and 495 nm). Time-resolved FRET ratios (Em$_{520}$/Em$_{495}$) were normalized to controls, plotted as a function of compound concentration and fit with the four-parameter logistic equation to determine IC50s.

Time-Resolved Fluorescence Resonance Energy Transfer (TR-FRET) Binding Assay of NAMPT with PRPP Compound handling and data processing were identical to the assay in the absence of substrates (above). Final concentrations were 1× assay buffer, 2% DMSO, 2 nM NAMPT, 2 nM probe, 1 nM Tb-anti-His antibody (Invitrogen #PV5895), 200 DM PRPP and 2.5 mM ATP. Reactions were equilibrated for 16 hours prior to measurement to allow for potential enzymatic modification of test compounds.

Table 1 shows the utility of compounds having Formula I to functionally inhibit NAMPT.

TABLE 1

| Example | TR-FRET Binding - IC50 (µM) | TR-FRET Binding - IC50 (with PRPP) (µM) |
| --- | --- | --- |
| 1 | 0.024900 | 0.000873 |
| 2 | 0.125000 | 0.000370 |
| 3 | 1.220000 | 0.007640 |
| 4 | 0.019700 | 0.000195 |
| 5 | 0.056800 | 0.000169 |
| 6 | 0.053400 | 0.000224 |
| 7 | 0.057800 | 0.000344 |
| 8 | 0.617000 | 0.015400 |
| 9 | 0.016300 | 0.000346 |
| 10 | 0.041500 | 0.000250 |
| 11 | 0.015800 | 0.000320 |
| 12 | 0.032100 | 0.000430 |
| 13 | 0.201000 | 0.000374 |
| 14 | 0.879000 | 0.000178 |
| 15 | 0.307000 | 0.000917 |
| 16 | nd | nd |
| 17 | 0.016900 | 0.000568 |
| 18 | 0.036700 | 0.000294 |
| 19 | 0.153000 | 0.000860 |
| 20 | 0.068400 | 0.000500 |
| 21 | 0.032500 | 0.000381 |
| 22 | 0.143000 | 0.000630 |
| 23 | 0.097800 | 0.000551 |
| 24 | 0.170000 | 0.000988 |
| 25 | 0.037400 | 0.000362 |
| 26 | 0.073600 | 0.000724 |
| 27 | 0.013000 | 0.000243 |
| 28 | 0.077200 | 0.000218 |
| 29 | 0.053400 | 0.000243 |
| 30 | 0.069400 | 0.000255 |
| 31 | 0.040600 | 0.000330 |
| 32 | 0.018800 | 0.000209 |
| 33 | 0.056100 | 0.000430 |
| 34 | 0.050700 | 0.000264 |
| 35 | 0.089200 | 0.000492 |
| 36 | 0.027300 | 0.000169 |
| 37 | 0.085400 | 0.000174 |
| 38 | 0.034300 | 0.000201 |
| 39 | 0.090500 | 0.000338 |
| 40 | 0.050500 | 0.000419 |
| 41 | 0.076800 | 0.000448 |
| 42 | 0.043800 | 0.000270 |
| 43 | 0.023700 | 0.000234 |
| 44 | 0.044600 | 0.000315 |
| 45 | 0.034300 | 0.000223 |
| 46 | 0.093100 | 0.000226 |
| 47 | 0.030300 | 0.000268 |
| 48 | 0.206000 | 0.000169 |
| 49 | 0.150000 | 0.000245 |
| 50 | 0.015800 | 0.000169 |
| 51 | 0.017200 | 0.000303 |
| 52 | 0.038900 | 0.000169 |
| 53 | 0.076200 | 0.000194 |
| 54 | 0.117000 | 0.000169 |
| 55 | 0.029300 | 0.000169 |
| 56 | 0.027400 | 0.000169 |
| 57 | 0.006850 | 0.000222 |
| 58 | 0.017400 | 0.000169 |
| 59 | 0.038500 | 0.000364 |
| 60 | 0.055400 | 0.000169 |
| 61 | 0.020900 | 0.000310 |
| 62 | 0.091500 | 0.000467 |
| 63 | 0.044600 | 0.000390 |
| 64 | 0.052100 | 0.000171 |
| 65 | 0.056600 | 0.000169 |
| 66 | 0.086000 | 0.000169 |
| 67 | 0.173000 | 0.000171 |
| 68 | 0.086200 | 0.000169 |
| 69 | 0.044800 | 0.000169 |
| 70 | 0.092200 | 0.000421 |
| 71 | 0.020100 | 0.000184 |
| 72 | 0.065600 | 0.000211 |

TABLE 1-continued

| Example | TR-FRET Binding - IC50 (μM) | TR-FRET Binding - IC50 (with PRPP) (μM) |
|---|---|---|
| 73 | 0.156000 | 0.000663 |
| 74 | 0.031100 | 0.000357 |
| 75 | 0.103000 | 0.000169 |
| 76 | 0.083600 | 0.000169 |
| 77 | 0.061900 | 0.000169 |
| 78 | 0.137000 | 0.000226 |
| 79 | 0.092900 | 0.000169 |
| 80 | 0.122000 | 0.000169 |
| 81 | 0.030900 | 0.000169 |
| 82 | 0.009730 | 0.000169 |
| 83 | 0.007220 | 0.000169 |
| 84 | 0.059400 | 0.000169 |
| 85 | 0.117000 | 0.000325 |
| 86 | 0.027400 | 0.000244 |
| 87 | 0.019800 | 0.000169 |
| 88 | 0.269000 | 0.000580 |
| 89 | 0.227000 | 0.000169 |
| 90 | 0.404000 | 0.000196 |
| 91 | 0.320000 | 0.000169 |
| 92 | 0.387000 | 0.000169 |
| 93 | 0.138000 | 0.000169 |
| 94 | 0.488000 | 0.000213 |
| 95 | 0.079100 | 0.000169 |
| 96 | 0.265000 | 0.000169 |
| 97 | 0.168000 | 0.000169 |
| 98 | 0.616000 | 0.001190 |
| 99 | 0.223000 | 0.000414 |
| 100 | 0.108000 | 0.000309 |
| 101 | 0.143000 | 0.000629 |
| 102 | 0.095700 | 0.000286 |
| 103 | 0.296000 | 0.000287 |
| 104 | 0.188000 | 0.000389 |
| 105 | 0.068300 | 0.000208 |
| 106 | 0.204000 | 0.000553 |
| 107 | 0.012300 | 0.000342 |
| 108 | 0.122000 | 0.000411 |
| 109 | 0.306000 | 0.000596 |
| 110 | 0.035300 | 0.000421 |
| 111 | 0.053900 | 0.000292 |
| 112 | 0.043500 | 0.045900 |
| 113 | 0.075800 | 0.014700 |
| 114 | 0.015800 | 0.000189 |
| 115 | 0.009220 | 0.000169 |
| 116 | 0.026700 | 0.000744 |
| 117 | 0.018800 | 0.000327 |
| 118 | 0.036000 | 0.000324 |
| 119 | 0.117000 | 0.000978 |
| 120 | 0.145000 | 0.000689 |
| 121 | 0.018600 | 0.000497 |
| 122 | 0.016600 | 0.000588 |
| 123 | 0.014700 | 0.000169 |
| 124 | 0.014900 | 0.000375 |
| 125 | 0.029300 | 0.000271 |
| 126 | 0.014400 | 0.000401 |
| 127 | 0.093400 | 0.000603 |
| 128 | 0.030400 | 0.000519 |
| 129 | 0.040000 | 0.000401 |
| 130 | 0.084700 | 0.000559 |
| 131 | 0.007720 | 0.000491 |
| 132 | 0.019100 | 0.000634 |
| 133 | 0.013200 | 0.000358 |
| 134 | 0.054200 | 0.000317 |
| 135 | 0.028100 | 0.000376 |
| 136 | 0.015000 | 0.000544 |
| 137 | 0.098800 | 0.000440 |
| 138 | 0.011400 | 0.000596 |
| 139 | 0.014400 | 0.000442 |
| 140 | 0.043000 | 0.000181 |
| 141 | 0.017600 | 0.000249 |
| 142 | 0.024600 | 0.000339 |
| 143 | 0.136000 | 0.000763 |
| 144 | 0.025600 | 0.000313 |
| 145 | 0.090500 | 0.000600 |
| 146 | 0.015100 | 0.000270 |
| 147 | 0.016700 | 0.000169 |
| 148 | 0.027700 | 0.000321 |
| 149 | 0.022100 | 0.000219 |
| 150 | 0.435000 | 0.002850 |
| 151 | 0.020800 | 0.000169 |
| 152 | 0.005180 | 0.000420 |
| 153 | 0.012400 | 0.000436 |
| 154 | 0.024000 | 0.000169 |
| 155 | 0.399000 | 0.000425 |
| 156 | 0.002710 | 0.000237 |
| 157 | 0.022600 | 0.000169 |
| 158 | 0.026300 | 0.000169 |
| 159 | 0.032400 | 0.000169 |
| 160 | 0.034700 | 0.004270 |
| 161 | 0.008620 | 0.005790 |
| 162 | 0.357000 | 0.000574 |
| 163 | 0.007230 | 0.000295 |
| 164 | 0.015900 | 0.000313 |
| 165 | 0.014400 | 0.000389 |
| 166 | 0.017200 | 0.000337 |
| 167 | 0.008410 | 0.000319 |
| 168 | 0.028900 | 0.000503 |
| 169 | 0.005360 | 0.000304 |
| 170 | 0.007070 | 0.000364 |
| 171 | 0.008740 | 0.000231 |
| 172 | 0.005650 | 0.000206 |
| 173 | 0.090400 | 0.000393 |
| 174 | 0.020800 | 0.000325 |
| 175 | 0.030700 | 0.000403 |
| 176 | 0.065500 | 0.000350 |
| 177 | 0.015800 | 0.000304 |
| 178 | 0.013900 | 0.000420 |
| 179 | 0.032500 | 0.000249 |
| 180 | 0.021300 | 0.000284 |
| 181 | 0.008060 | 0.000256 |
| 182 | 0.003680 | 0.000219 |
| 183 | 0.022000 | 0.000380 |
| 184 | 0.018500 | 0.000305 |
| 185 | 0.003230 | 0.000228 |
| 186 | 0.002930 | 0.000345 |
| 187 | 0.039300 | 0.000292 |
| 188 | 0.002100 | 0.000188 |
| 189 | 0.022600 | 0.000210 |
| 190 | 0.002000 | 0.000282 |
| 191 | 0.004270 | 0.000291 |
| 192 | 0.023000 | 0.000255 |
| 193 | 0.014400 | 0.000243 |
| 194 | 0.248000 | 0.000592 |
| 195 | 0.004190 | 0.000281 |
| 196 | 0.015000 | 0.000281 |
| 197 | 0.017800 | 0.000505 |
| 198 | 0.064200 | 0.000341 |
| 199 | 0.128000 | 0.000356 |
| 200 | 0.036400 | 0.000382 |
| 201 | 0.043200 | 0.000313 |
| 202 | 0.051100 | 0.000327 |
| 203 | 0.250000 | 0.000427 |
| 204 | 0.048600 | 0.000349 |
| 205 | 0.042600 | 0.000242 |
| 206 | 0.049100 | 0.000260 |
| 207 | 0.451000 | 0.000370 |
| 208 | 0.048600 | 0.000473 |
| 209 | 0.024000 | 0.000694 |
| 210 | 0.206000 | 0.000356 |
| 211 | 0.055900 | 0.000341 |
| 212 | 0.040900 | 0.000464 |
| 213 | 0.087300 | 0.000352 |
| 214 | 0.075800 | 0.000289 |
| 215 | 0.027400 | 0.000294 |
| 216 | 0.018400 | 0.000256 |

TABLE 1-continued

| Example | TR-FRET Binding - IC50 (μM) | TR-FRET Binding - IC50 (with PRPP) (μM) |
|---|---|---|
| 217 | 0.278000 | 0.000320 |
| 218 | 0.171000 | 0.000451 |
| 219 | 0.019400 | 0.000290 |
| 220 | 0.010400 | 0.000340 |
| 221 | 0.152000 | 0.000319 |
| 222 | 0.010700 | 0.000183 |
| 223 | 0.021600 | 0.000391 |
| 224 | 0.026000 | 0.000333 |
| 225 | 0.014000 | 0.000268 |
| 226 | 0.169000 | 0.000440 |
| 227 | 0.069200 | 0.000294 |
| 228 | 0.019600 | 0.000310 |
| 229 | 0.040300 | 0.000314 |
| 230 | 0.038800 | 0.000305 |
| 231 | 0.421000 | 0.000225 |
| 232 | 0.352000 | 0.000181 |
| 233 | 0.653000 | 0.000335 |
| 234 | 0.760000 | 0.000529 |
| 235 | 0.649000 | 0.000213 |
| 236 | 0.667000 | 0.000210 |
| 237 | 0.581000 | 0.000257 |
| 238 | 4.010000 | 0.001410 |
| 239 | 1.680000 | 0.000200 |
| 240 | 0.603000 | 0.000466 |
| 241 | 0.359000 | 0.000255 |
| 242 | 0.374000 | 0.000225 |
| 243 | 1.270000 | 0.000326 |
| 244 | 1.170000 | 0.000516 |
| 245 | 0.317000 | 0.000169 |
| 246 | 0.437000 | 0.000213 |
| 247 | 0.871000 | 0.000304 |
| 248 | 0.990000 | 0.000228 |
| 249 | 0.193000 | 0.000169 |
| 250 | 0.865000 | 0.000679 |
| 251 | 0.382000 | 0.000365 |
| 252 | 0.526000 | 0.000296 |
| 253 | 0.538000 | 0.000207 |
| 254 | 0.246000 | 0.000174 |
| 255 | 0.271000 | 0.000173 |
| 256 | 0.830000 | 0.000169 |
| 257 | 0.598000 | 0.000223 |
| 258 | 0.052400 | 0.000359 |
| 259 | 0.054500 | 0.000452 |
| 260 | 0.038400 | 0.000302 |
| 261 | 0.033500 | 0.000194 |
| 262 | 0.060400 | 0.000252 |
| 263 | 0.143000 | 0.000239 |
| 264 | 0.040900 | 0.000188 |
| 265 | 0.191000 | 0.000169 |
| 266 | 0.096200 | 0.000169 |
| 267 | 0.022500 | 0.000297 |
| 268 | 0.036500 | 0.000225 |
| 269 | 0.020100 | 0.000169 |
| 270 | 0.008170 | 0.000196 |
| 271 | 0.046900 | 0.000279 |
| 272 | 0.090700 | 0.000241 |
| 273 | 0.203000 | 0.000169 |
| 274 | 0.082200 | 0.000264 |
| 275 | 0.038300 | 0.000363 |
| 276 | 0.012400 | 0.000347 |
| 277 | 0.076700 | 0.000169 |
| 278 | 0.019700 | 0.000213 |
| 279 | 0.092100 | 0.000204 |
| 280 | 0.101000 | 0.000169 |
| 281 | 0.065600 | 0.000169 |
| 282 | 0.026600 | 0.000219 |
| 283 | 0.033700 | 0.000266 |
| 284 | 0.018300 | 0.000204 |
| 285 | 0.017200 | 0.000169 |
| 286 | 0.009760 | 0.000169 |
| 287 | 0.030100 | 0.000189 |
| 288 | 0.117000 | 0.000227 |
| 289 | 0.029600 | 0.000204 |
| 290 | 0.011100 | 0.000224 |
| 291 | 0.025800 | 0.000207 |
| 292 | 0.268000 | 0.000259 |
| 293 | 0.056600 | 0.000210 |
| 294 | 0.044300 | 0.000200 |
| 295 | 0.050700 | 0.000272 |
| 296 | 0.026400 | 0.000243 |
| 297 | 0.056600 | 0.000236 |
| 298 | 0.035200 | 0.000169 |
| 299 | 0.064900 | 0.000451 |
| 300 | 0.052600 | 0.000341 |
| 301 | 0.059000 | 0.000243 |
| 302 | 0.337000 | 0.000393 |
| 303 | 0.040500 | 0.000595 |
| 304 | 0.594000 | 0.000343 |
| 305 | 0.435000 | 0.000211 |
| 306 | 0.507000 | 0.000169 |
| 307 | 0.024300 | 0.000197 |
| 308 | 0.024200 | 0.000293 |
| 309 | 0.032800 | 0.000262 |
| 310 | 0.004540 | 0.000297 |
| 311 | 0.144000 | 0.000592 |
| 312 | 0.311000 | 0.000290 |
| 313 | 0.369000 | 0.000187 |
| 314 | 0.110000 | 0.000178 |
| 315 | 0.048700 | 0.000169 |
| 316 | 0.013600 | 0.000169 |
| 317 | 0.029900 | 0.000207 |
| 318 | 0.125000 | 0.000419 |
| 319 | 0.070600 | 0.000426 |
| 320 | 0.208000 | 0.000407 |
| 321 | 0.176000 | 0.000246 |
| 322 | 0.034900 | 0.000169 |
| 323 | 0.041400 | 0.000194 |
| 324 | 0.020700 | 0.000360 |
| 325 | 0.018800 | 0.000362 |
| 326 | 0.032200 | 0.000294 |
| 327 | 0.450000 | 0.000169 |
| 328 | 0.159000 | 0.000344 |
| 329 | 0.030400 | 0.000276 |
| 330 | 0.021900 | 0.000364 |
| 331 | 0.081000 | 0.000351 |
| 332 | 0.061700 | 0.000474 |
| 333 | 0.056100 | 0.000416 |
| 334 | 0.094900 | 0.000449 |
| 335 | 0.045700 | 0.000495 | nd = no data

NAMPT Cell Proliferation Assay

PC3 cells were seeded in 96-well black plates (Corning #3904) at 500 cells/well in 90 μl of RPMI media containing 10% heat-inactivated FBS and incubated overnight at 37° C. and 5% $CO_2$ to allow cells to attach to wells. The following day, test compounds were serially diluted in neat DMSO to 1000× final concentrations prior to dilution with RPMI media to 10× and 1% DMSO. Ten μL of the 10× compounds were then transferred to wells containing cells to produce a dose response of 10-fold dilutions from 10 μM to $1\times10^{-5}$ μM. Cells were incubated for 5 days at 37° C. and 5% $CO_2$, then cell viability was measured using Cell Titer Glo reagent (Promega #G7571). Percent inhibition values were calculated and fitted to a sigmoidal dose response curves using Assay Explorer software to determine IC50s. To assess whether inhibition of cell viability was due to NAMPT inhibition, the proliferation assay was also performed in the presence of 0.3 mM nicotinamide mononucleotide.

Table 2 shows the results of the cell proliferation assay.

TABLE 2

| Example | Cell Titer-Glo - IC50 (μM) |
|---|---|
| 1 | 0.0117 |
| 2 | 0.0349 |
| 3 | 4.68 |
| 4 | 0.014 |
| 5 | 0.0283 |
| 6 | 0.0306 |
| 7 | 0.0385 |
| 8 | 7.03 |
| 9 | 0.00682 |
| 10 | 0.0389 |
| 11 | 0.00933 |
| 12 | 0.0101 |
| 13 | 0.514 |
| 14 | 6.68 |
| 15 | 0.0999 |
| 16 | nd |
| 17 | 0.0368 |
| 18 | 0.0658 |
| 19 | 0.192 |
| 20 | 0.123 |
| 21 | 0.0337 |
| 22 | 0.276 |
| 23 | 0.195 |
| 24 | 0.113 |
| 25 | 0.0271 |
| 26 | 0.172 |
| 27 | 0.0092 |
| 28 | 0.0642 |
| 29 | 0.0661 |
| 30 | 0.125 |
| 31 | 0.0389 |
| 32 | 0.0587 |
| 33 | 0.0687 |
| 34 | 0.0624 |
| 35 | 0.0902 |
| 36 | 0.0595 |
| 37 | 0.0729 |
| 38 | 0.0836 |
| 39 | 0.115 |
| 40 | 0.0264 |
| 41 | 0.0698 |
| 42 | 0.10 |
| 43 | 0.028 |
| 44 | 0.0385 |
| 45 | 0.0634 |
| 46 | 0.0442 |
| 47 | 0.064 |
| 48 | 0.0958 |
| 49 | 0.0801 |
| 50 | 0.00857 |
| 51 | 0.00178 |
| 52 | 0.00678 |
| 53 | 0.0138 |
| 54 | 0.0589 |
| 55 | 0.00806 |
| 56 | 0.00883 |
| 57 | 0.00358 |
| 58 | 0.00786 |
| 59 | 0.0685 |
| 60 | 0.0749 |
| 61 | 0.0307 |
| 62 | 0.0697 |
| 63 | 0.012 |
| 64 | 0.0711 |
| 65 | 0.0622 |
| 66 | 0.0822 |
| 67 | 0.0785 |
| 68 | 0.0591 |
| 69 | 0.0613 |
| 70 | 0.0731 |
| 71 | 0.0107 |
| 72 | 0.0777 |
| 73 | 0.0845 |
| 74 | 0.0153 |
| 75 | 0.0693 |
| 76 | 0.0224 |
| 77 | 0.0173 |
| 78 | 0.056 |
| 79 | 0.0414 |
| 80 | 0.0632 |
| 81 | 0.0178 |
| 82 | 0.00724 |
| 83 | 0.00685 |
| 84 | 0.022 |
| 85 | 0.0489 |
| 86 | 0.00548 |
| 87 | 0.00604 |
| 88 | 0.109 |
| 89 | 0.18 |
| 90 | 0.686 |
| 91 | 0.111 |
| 92 | 0.608 |
| 93 | 0.0876 |
| 94 | 0.598 |
| 95 | 0.0662 |
| 96 | 0.171 |
| 97 | 0.0767 |
| 98 | 0.0709 |
| 99 | 0.0493 |
| 100 | 0.0273 |
| 101 | 0.0681 |
| 102 | 0.0679 |
| 103 | 0.0981 |
| 104 | 0.0951 |
| 105 | 0.0609 |
| 106 | 0.576 |
| 107 | 0.00599 |
| 108 | 0.0815 |
| 109 | 0.11 |
| 110 | 0.0118 |
| 111 | 0.0292 |
| 112 | 0.906 |
| 113 | 0.113 |
| 114 | 0.00811 |
| 115 | 0.00611 |
| 116 | 0.135 |
| 117 | 0.00983 |
| 118 | 0.0777 |
| 119 | 0.0769 |
| 120 | 0.078 |
| 121 | 0.00773 |
| 122 | 0.00881 |
| 123 | 0.00881 |
| 124 | 0.00775 |
| 125 | 0.00812 |
| 126 | 0.00738 |
| 127 | 0.071 |
| 128 | 0.00836 |
| 129 | 0.0113 |
| 130 | 0.0787 |
| 131 | 0.00818 |
| 132 | 0.00777 |
| 133 | 0.00443 |
| 134 | 0.0283 |
| 135 | 0.00869 |
| 136 | 0.00742 |
| 137 | 0.0516 |
| 138 | 0.00838 |
| 139 | 0.00781 |
| 140 | 0.0263 |
| 141 | 0.00833 |
| 142 | 0.00791 |
| 143 | 0.0822 |
| 144 | 0.00904 |
| 145 | 0.0739 |
| 146 | 0.00907 |
| 147 | 0.00513 |

TABLE 2-continued

| Example | Cell Titer-Glo - IC50 (μM) |
|---|---|
| 148 | 0.0167 |
| 149 | 0.0765 |
| 150 | 1.05 |
| 151 | 0.0154 |
| 152 | 0.00604 |
| 153 | 0.00803 |
| 154 | 0.00789 |
| 155 | 0.13 |
| 156 | 0.0747 |
| 157 | 0.0378 |
| 158 | 0.0365 |
| 159 | 0.0745 |
| 160 | 0.639 |
| 161 | 0.905 |
| 162 | 0.269 |
| 163 | 0.0344 |
| 164 | 0.0259 |
| 165 | 0.0619 |
| 166 | 0.0664 |
| 167 | 0.0235 |
| 168 | 0.045 |
| 169 | 0.00798 |
| 170 | 0.0148 |
| 171 | 0.022 |
| 172 | 0.0345 |
| 173 | 0.0564 |
| 174 | 0.0244 |
| 175 | 0.0675 |
| 176 | 0.0889 |
| 177 | 0.074 |
| 178 | 0.075 |
| 179 | 0.0769 |
| 180 | 0.0677 |
| 181 | 0.0243 |
| 182 | 0.00695 |
| 183 | 0.0633 |
| 184 | 0.0612 |
| 185 | 0.00918 |
| 186 | 0.00345 |
| 187 | 0.0863 |
| 188 | 0.00225 |
| 189 | 0.0217 |
| 190 | 0.00583 |
| 191 | 0.00746 |
| 192 | 0.0632 |
| 193 | 0.0137 |
| 194 | 0.69 |
| 195 | 0.00866 |
| 196 | 0.0646 |
| 197 | 0.0227 |
| 198 | 0.0476 |
| 199 | nd |
| 200 | 0.017 |
| 201 | nd |
| 202 | 0.0655 |
| 203 | nd |
| 204 | 0.0604 |
| 205 | nd |
| 206 | 0.0634 |
| 207 | nd |
| 208 | 0.0737 |
| 209 | nd |
| 210 | 0.218 |
| 211 | nd |
| 212 | 0.0206 |
| 213 | nd |
| 214 | 0.0437 |
| 215 | nd |
| 216 | 0.0205 |
| 217 | nd |
| 218 | 0.188 |
| 219 | nd |
| 220 | 0.00415 |
| 221 | nd |
| 222 | 0.0119 |
| 223 | nd |
| 224 | 0.0207 |
| 225 | nd |
| 226 | 0.20 |
| 227 | nd |
| 228 | nd |
| 229 | nd |
| 230 | nd |
| 231 | 0.361 |
| 232 | nd |
| 233 | 0.97 |
| 234 | nd |
| 235 | 0.993 |
| 236 | nd |
| 237 | 0.346 |
| 238 | 0.746 |
| 239 | 1.51 |
| 240 | nd |
| 241 | 0.252 |
| 242 | nd |
| 243 | 1.31 |
| 244 | nd |
| 245 | 0.617 |
| 246 | 0.622 |
| 247 | 0.471 |
| 248 | 1.38 |
| 249 | 0.541 |
| 250 | 0.664 |
| 251 | 0.212 |
| 252 | 0.401 |
| 253 | 0.622 |
| 254 | nd |
| 255 | 0.734 |
| 256 | nd |
| 257 | nd |
| 258 | 0.0683 |
| 259 | 0.0647 |
| 260 | 0.0949 |
| 261 | 0.0713 |
| 262 | 0.0516 |
| 263 | 0.365 |
| 264 | 0.0351 |
| 265 | 0.691 |
| 266 | 0.207 |
| 267 | 0.0178 |
| 268 | 0.0228 |
| 269 | 0.0167 |
| 270 | 0.0195 |
| 271 | 0.06037 |
| 272 | 0.22243 |
| 273 | 7.27 |
| 274 | 0.0685 |
| 275 | 0.0345 |
| 276 | 0.01 |
| 277 | 0.0631 |
| 278 | 0.0306 |
| 279 | 0.0476 |
| 280 | 0.114 |
| 281 | 0.125 |
| 282 | 0.0143 |
| 283 | 0.0617 |
| 284 | 0.0223 |
| 285 | 0.0265 |
| 286 | 0.00766 |
| 287 | 0.0374 |
| 288 | 0.084 |
| 289 | 0.0352 |
| 290 | 0.0103 |
| 291 | 0.15 |
| 292 | 0.0878 |
| 293 | 0.0705 |
| 294 | 0.0609 |
| 295 | 0.0665 |
| 296 | 0.0198 |
| 297 | 0.0182 |
| 298 | 0.0112 |
| 299 | 0.0146 |

TABLE 2-continued

| Example | Cell Titer-Glo - IC50 (μM) |
|---|---|
| 300 | 0.0171 |
| 301 | 0.0219 |
| 302 | 0.141 |
| 303 | 0.0135 |
| 304 | 0.262 |
| 305 | 1.82 |
| 306 | 0.298 |
| 307 | 0.00987 |
| 308 | 0.00961 |
| 309 | 0.0111 |
| 310 | 0.00276 |
| 311 | 0.0471 |
| 312 | 0.211 |
| 313 | 4.59 |
| 314 | 0.0839 |
| 315 | 0.05416 |
| 316 | 0.0173 |
| 317 | 0.0554 |
| 318 | 0.156 |
| 319 | 0.0307 |
| 320 | 0.155 |
| 321 | 0.119 |
| 322 | 0.01251 |
| 323 | 0.051 |
| 324 | 0.00624 |
| 325 | 0.0113 |
| 326 | 0.0165 |
| 327 | 0.189 |
| 328 | 0.0527 |
| 329 | 0.0145 |
| 330 | 0.0123 |
| 331 | 0.0424 |
| 332 | 0.0222 |
| 333 | 0.0224 |
| 334 | 0.0324 |
| 335 | 0.0158 |
| 336 | 0.222 |
| 337 | 0.0555 |
| 338 | 0.587 |
| 339 | 0.668 |
| 340 | 2.45 |
| 341 | 8.94 |
| 342 | 0.39 |
| 343 | 0.831 |
| 344 | 7.67 |
| 345 | 1.13 |
| 346 | 0.843 |
| 347 | 1.55 |
| 348 | 0.803 |
| 349 | 0.772 |
| 350 | 0.743 |
| 351 | 0.655 |
| 352 | 0.607 |
| 353 | nd |
| 354 | 0.994 |
| 355 | 7.31 |
| 356 | 0.791 |
| 357 | 0.703 | nd = no data

Compounds which inhibit NAMPT are useful for treating diseases in which activation of NF-KB is implicated. Such methods are useful in the treatment of a variety of diseases including inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, atherosclerosis, restenosis, diabetes, glomerulonephritis, cancer, particularly wherein the cancer is selected from breast, prostate, lung, colon, cervix, ovary, skin, CNS, bladder, pancreas, leukaemia, lymphoma or Hodgkin's disease, cachexia, inflammation associated with infection and certain viral infections, including Acquired Immune Deficiency Syndrome (AIDS), adult respiratory distress syndrome, and ataxia telengiectasia.

Involvement of NAMPT in the treatment of cancer is described in WO 97/48696. Involvement of NAMPT in immuno-suppression is described in WO 97/48397. Involvement of NAMPT for the treatment of diseases involving angiogenesis is described in WO 2003/80054. Involvement of NAMPT for the treatment of rheumatoid arthritis and septic shock is described in WO 2008/025857. Involvement of NAMPT for the prophlaxis and treatment of ischaemia is described in WO 2009/109610.

Cancers include, but are not limited to, hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenström's macroglobulinemia, testicular tumors, uterine cancer, Wilms' tumor and the like.

Schemes and Experimentals

The following abbreviations have the meanings indicated. ADDP means 1,1'-(azodicarbonyl)dipiperidine; AD-mix-β means a mixture of $(DHQD)_2PHAL$, $K_3Fe(CN)_6$, $K_2CO_3$, and $K_2SO_4$; 9-BBN means 9-borabicyclo(3.3.1)nonane; Boc means tert-butoxycarbonyl; (DHQD)$_2$PHAL means hydroquinidine 1,4-phthalazinediyl diethyl ether; DBU means 1,8-diazabicyclo[5.4.0]undec-7-ene; DIBAL means diisobutylaluminum hydride; DIEA means diisopropylethylamine; DMAP means N,N-dimethylaminopyridine; DMF means N,N-dimethylformamide; dmpe means 1,2-bis(dimethylphosphino)ethane; DMSO means dimethylsulfoxide; dppb means 1,4-bis(diphenylphosphino)-butane; dppe means 1,2-bis(diphenylphosphino)ethane; dppf means 1,1'-bis(diphenylphosphino)ferrocene; dppm means 1,1-bis(diphenylphosphino)methane; EDAC.HCl means 1-(3-dimethylaminopropyl)-3-ethylcarbodiimide hydrochloride; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; MP-BH$_3$ means macroporous triethylammonium methylpolystyrene cyanoborohydride; TEA means triethylamine; TFA means trifluoroacetic acid; THF means tetrahydrofuran; NCS means N-chlorosuccinimide; NMM means N-methylmorpholine; NMP means N-methylpyrrolidine; PPh$_3$ means triphenylphosphine.

The following schemes are presented to provide what is believed to be the most useful and readily understood description of procedures and conceptual aspects of this invention. Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

Schemes

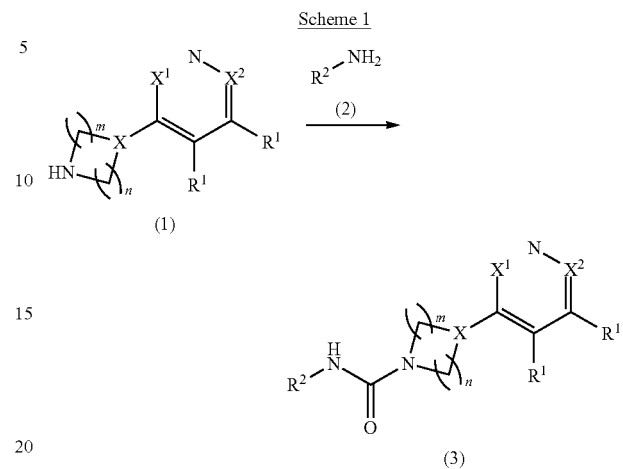

As shown in Scheme 1, compounds of formula (1), wherein $X^1$, $X^2$, and $R^1$ are as described in Formula (I), n is 1 or 2, m is 1 or 2, and X is CH when n is 1 or 2 and m is 1, and X is N or CH when n is 2 and m is 2, can be reacted with compounds of formula (2), wherein $R^2$ is as described herein, in the presence of bis(2,5-dioxopyrrolidin-1-yl) carbonate and a base such as but not limited to diisopropylethylamine to provide compounds of formula (3). The reaction is typically performed at ambient temperature in a solvent such as but not limited to acetonitrile.

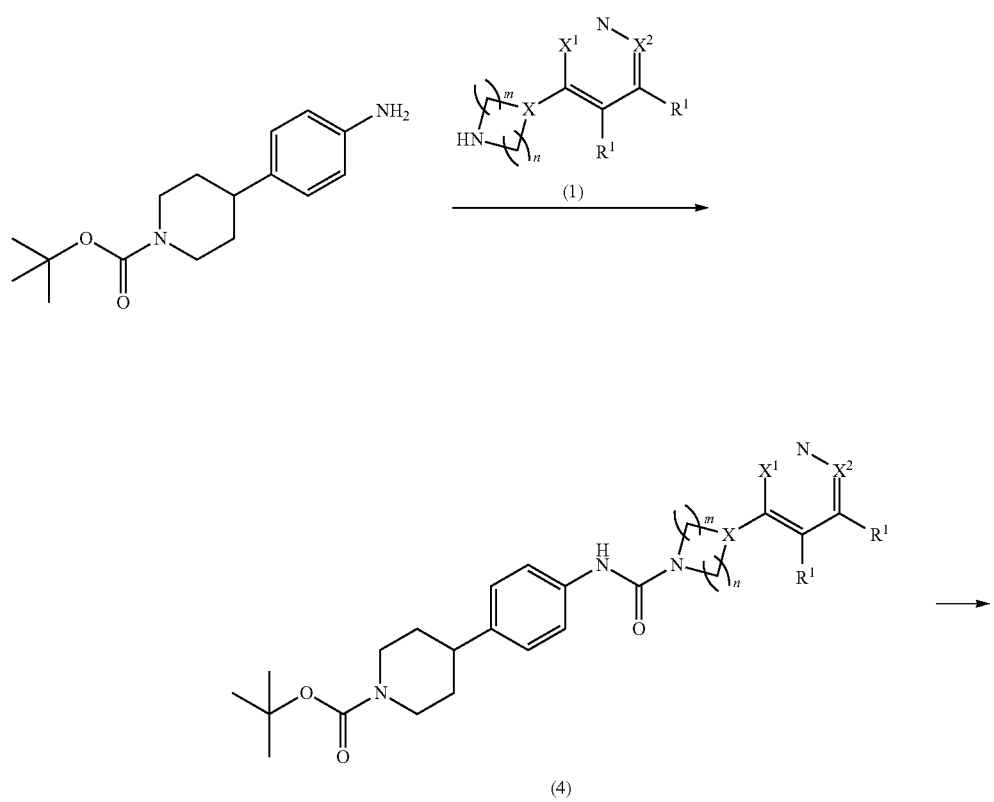

-continued

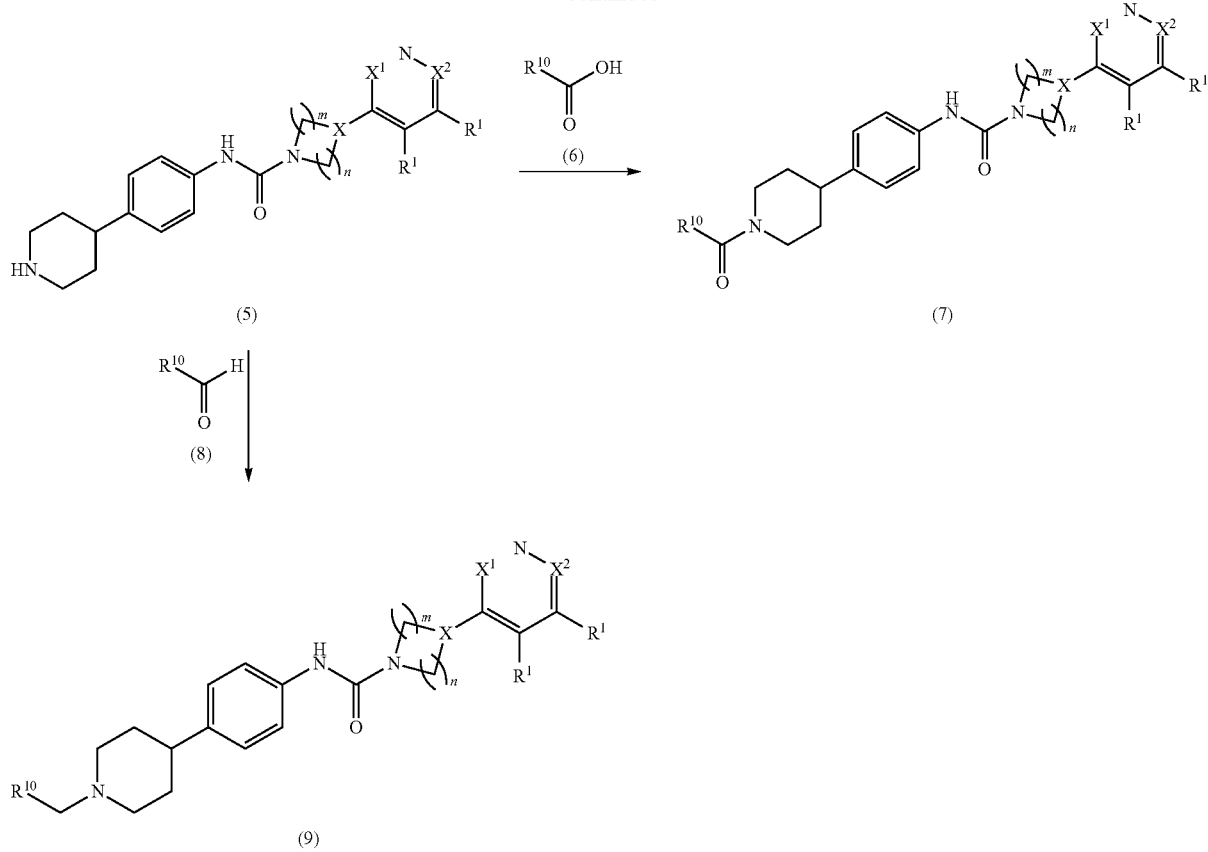

tert-Butyl 4-(4-aminophenyl)piperidine-1-carboxylate can be reacted can be reacted with compounds of formula (1), wherein $X^1$, $X^2$, and $R^1$ are as described in Formula (I), n is 1 or 2, m is 1 or 2, and X is CH when n is 1 or 2 and m is 1, and X is N or CH when n is 2 and m is 2, in the presence of bis(2,5-dioxopyrrolidin-1-yl) carbonate and a base such as but not limited to diisopropylethylamine to provide compounds of formula (4). The reaction is typically performed at ambient temperature in a solvent such as but not limited to acetonitrile. Compounds of formula (5) can be prepared by treating compounds of formula (4) with an acid such as but not limited to trifluoroacetic acid in a solvent such as but not limited to dichloromethane. Compounds of formula (7), which are representative of compounds of Formula (I), can be prepared by reacting compounds of formula (5) with compounds of formula (6), wherein $R^{10}$ is as described herein, in the presence of a base such as but not limited to diisopropylethylamine. The reaction may involve the use of a carboxyl activating agent such as but not limited to N-(3-dimethylaminopropyl)-N'-ethylcarbodiimide hydrochloride, and a ester activating agent such as but not limited to 1-hydroxybenzotriazole hydrate. The reaction is typically performed at ambient temperature in a solvent such as but not limited to N,N-dimethylformamide, N,N-dimethylacetamide, or mixtures thereof. Alternatively, compounds of formula (5) can be reacted with compounds of formula (8), wherein $R^{10}$ is as described herein, to provide compounds of formula (9), which are representative of compounds of Formula (I). The reaction is typically performed in the presence of a reducing agent such as but not limited to sodium triacetoxyborohydride and acetic acid in a solvent such as but not limited to methanol and may be performed at an elevated temperature.

Scheme 3

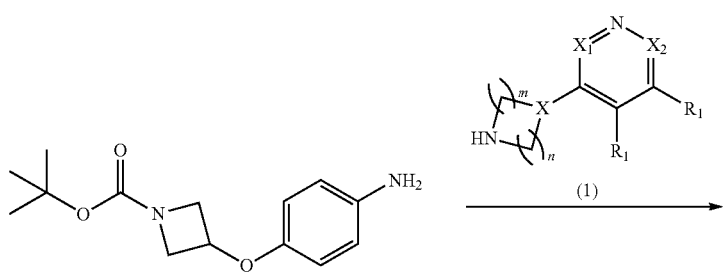

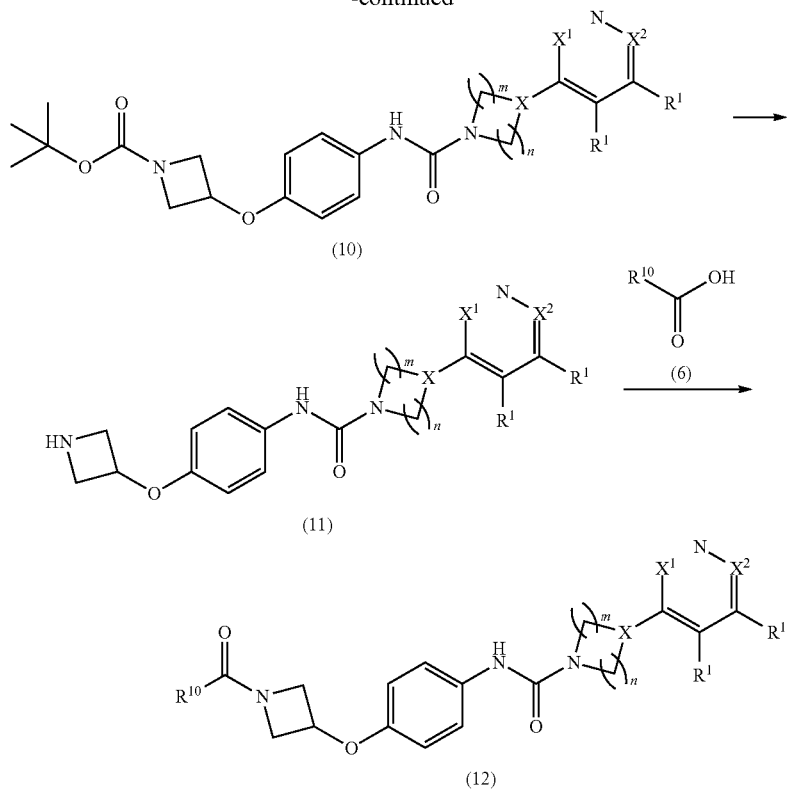

(10)

(11)

(12)

As shown in Scheme 3, tert-butyl 3-(4-aminophenoxy) azetidine-1-carboxylate, can be reacted can be reacted with compounds of formula (1), wherein $X^1$, $X^2$, and $R^1$ are as described in Formula (I), n is 1 or 2, m is 1 or 2, and X is CH when n is 1 or 2 and m is 1, and X is N or CH when n is 2 and m is 2, in the presence of bis(2,5-dioxopyrrolidin-1-yl) carbonate and a base such as but not limited to diisopropylethylamine to provide compounds of formula (10). The reaction is typically performed at ambient temperature in a solvent such as but not limited to acetonitrile. Compounds of formula (11) can be prepared by treating compounds of formula (10) with an acid such as but not limited to trifluoroacetic acid in a solvent such as but not limited to dichloromethane. Compounds of formula (12), which are representative of compounds of Formula (I), can be prepared by reacting compounds of formula (11) with compounds of formula (6), wherein $R^{10}$ is as described herein, in the presence of a base such as but not limited to diisopropylethylamine. The reaction may involve the use of a carboxyl activating agent such as but not limited to N-(3-dimethylaminopropyl)-N'-ethylcarbodiimide hydrochloride, and a ester activating agent such as but not limited to 1-hydroxybenzotriazole hydrate. The reaction is typically performed at ambient temperature in a solvent such as but not limited to N,N-dimethylformamide, N,N-dimethylacetamide, or mixtures thereof.

EXAMPLES

The following examples are presented to provide what is believed to be the most useful and readily understood description of procedures and conceptual aspects of this invention. Each exemplified compound and intermediate was named using ACD/ChemSketch Version 12.5 (20 Apr. 2011), Advanced Chemistry Development Inc., Toronto, Ontario), or ChemDraw Ver. 9.0.7 (CambridgeSoft, Cambridge, Mass.).

EXPERIMENTALS

Example 1

N-[4-({1-[(2S)-2-methylbutanoyl]azetidin-3-yl}oxy) phenyl]-3-(pyridin-3-yl)azetidine-1-carboxamide Example 1A tert-butyl 3-(4-nitrophenoxy)azetidine-1-carboxylate Tert-butyl 3-hydroxyazetidine-1-carboxylate (4.0 g, 23.3 mmol), 1-fluoro-4-nitrobenzene (6.1 g, 43.0 mmol), aqueous potassium hydroxide (35.5 ml of a 5.9 M solution, 209 mmol), and tetrabutylammonium bromide (0.975 g, 3.0 mmol) were combined and stirred at 40° C. overnight. The reaction was cooled, diluted with water and extracted three times with ethyl acetate. The combined organics were dried (sodium sulfate), filtered and concentrated. The residue was purified by regular phase flash column chromatography to give the title compound.

Example 1B tert-butyl 3-(4-aminophenoxy)azetidine-1-carboxylate

Tert-butyl 3-(4-nitrophenoxy)azetidine-1-carboxylate (1 g, 3.40 mmol) and tetrahydrofuran (20 ml) were added to 5% palladium on carbon (wet, 0.200 g, 1.879 mmol) in a 250 mL SS pressure bottle and the mixture was stirred for 1 hour at 30 psi and room temperature. The mixture was filtered through a nylon membrane and the fitrate was concentrated to give the title compound.

Example 1C tert-butyl 3-(4-(3-(pyridin-3-yl)azetidine-1-carboxamido)phenoxy)azetidine-1-carboxylate Tert-butyl 3-(4-aminophenoxy)azetidine-1-carboxylate (1.17 g, 4.43 mmol) and bis(2,5-dioxopyrrolidin-1-yl) carbonate (1.134 g, 4.43 mmol) were combined in acetonitrile (22.13 ml) and stirred for 1 hour at room temperature. 3-(Azetidin-3-yl)pyridine bis hydrochloride (0.948 g, 4.65 mmol) and diisopropylethylamine (3.09 ml, 17.71 mmol) were added and the reaction mixture was stirred overnight. The acetonitrile was removed by rotary evaporation and the residue was taken up in dichloromethane and chromatographed using regular phase chromatography to give the title compound.

Example 1D

N-(4-(azetidin-3-yloxy)phenyl)-3-(pyridin-3-yl)azetidine-1-carboxamide

To a 20 mL vial was added tert-butyl 3-(4-(3-(pyridin-3-yl)azetidine-1-carboxamido)phenoxy) azetidine-1-carboxylate (800 mg, 1.885 mmol) in dichloromethane (9.42 mL). Trifluoroacetic acid (1.4 mL, 18.17 mmol) was added and the reaction mixture was stirred at room temperature for 1.5 hours. The volatiles were removed under vacuum to give the title compound.

Example 1E (S)-N-(4-(1-(2-methylbutanoyl)azetidin-3-yloxy)phenyl)-3-(pyridin-3-yl)azetidine-1-carboxamide N-(4-(azetidin-3-yloxy)phenyl)-3-(pyridin-3-yl)azetidine-1-carboxamide (1 g, 1.805 mmol), (S)-2-methylbutanoic acid (0.221 g, 2.166 mmol), and N-(3-dimethylaminopropyl)-N'-ethylcarbodiimide hydrochloride (0.519 g, 2.71 mmol) were combined in dimethylformamide (9.03 mL) at room temperature. 1-Hydroxybenzotriazole hydrate (0.415 g, 2.71 mmol) and diisopropylethylamine (0.946 ml, 5.42 mmol) were added and the reaction mixture was stirred overnight at room temperature. Water and dichloromethane were added and the organics were removed by pipette. Concentration and reverse phase chromatography gave (S)—N-(4-(1-(2-methylbutanoyl)azetidin-3-yloxy)phenyl)-3-(pyridin-3-yl)azetidine-1-carboxamide. $^1$H NMR (300 MHz, DMSO-$d_6$) δ 8.56 (d, J=2.4 Hz, 1H), 8.48 (dd, J=4.7, 1.6 Hz, 1H), 8.41 (s, 1H), 7.86 (dt, J=7.9, 2.0 Hz, 1H), 7.46-7.37 (m, 3H), 6.76 (d, J=8.9 Hz, 2H), 4.96 (dd, J=6.3, 3.4 Hz, 1H), 4.62-4.53 (m, 1H), 4.36 (d, J=15.9 Hz, 2H), 4.32-4.22 (m, 1H), 4.11-4.02 (m, 1H), 3.98-3.81 (m, 3H), 3.75 (dd, J=10.6, 3.9 Hz, 1H), 2.36-2.20 (m, 1H), 1.59-1.39 (m, 1H), 1.38-1.20 (m, 1H), 0.96 (dd, J=6.8, 3.9 Hz, 3H), 0.82 (q, J=7.2 Hz, 3H); MS (ESI(+)) m/e 409 (M+H)$^+$.

TABLE 1

The following Examples were prepared essentially as described in Example 1, substituting the appropriate alcohol in Example 1A, the appropriate amine in Example 1C and the appropriate carboxylic acid in Example 1E. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 2 | 3-(pyridin-3-yl)-N-(4-{[1-(tetrahydro-2H-pyran-4-ylacetyl)piperidin-4-yl]oxy}phenyl)azetidine-1-carboxamide | $^1$H NMR (300 MHz, DMSO-$d_6$) δ 8.62-8.44 (m, 2H), 8.36 (s, 1H), 7.94-7.78 (m, 1H), 7.49-7.31 (m, 3H), 6.96-6.80 (m, 2H), 4.58-4.25 (m, 3H), 4.02-3.64 (m, 7H), 3.64-3.53 (m, 1H), 3.09-2.85 (m, 1H), 2.84-2.68 (m, 1H), 2.30-2.25 (m, 2H), 2.21-2.13 (m, 1H), 2.00-1.79 (m, 3H), 1.66-1.35 (m, 4H), 1.32-1.11 (m, 2H) | (ESI(+)) m/e 479 (M + H)$^+$ |
| 3 | 3-(5-fluoropyridin-3-yl)-N-(4-{[1-(tetrahydro-2H-pyran-4-ylacetyl)piperidin-4-yl]oxy}phenyl)azetidine-1-carboxamide | $^1$H NMR (300 MHz, DMSO-$d_6$) δ 8.49 (d, J = 2.8 Hz, 1H), 8.46 (t, J = 1.8 Hz, 1H), 8.37 (s, 1H), 7.89-7.80 (m, 1H), 7.43-7.36 (m, 2H), 6.91-6.84 (m, 2H), 4.55-4.43 (m, 1H), 4.39-4.28 (m, 2H), 4.05-3.63 (m, 7H), 3.25-3.14 (m, 2H), 2.27 (d, J = 1.4 Hz, 1H), 2.00-1.77 (m, 3H), 1.66-1.33 (m, 4H), 1.32-1.04 (m, 2H) | (ESI(+)) m/e 497 (M + H)$^+$ |
| 4 | N-[4-({1-[(2S)-2-methylbutanoyl]piperidin-4-yl}oxy)phenyl]-3-(pyridin-3-yl)azetidine-1-carboxamide | $^1$H NMR (300 MHz, DMSO-$d_6$) δ 8.59-8.46 (m, 2H), 8.36 (s, 1H), 7.86 (dt, J = 7.9, 2.0 Hz, 1H), 7.45-7.35 (m, 3H), 6.92-6.85 (m, 2H), 4.51 (dq, J = 7.8, 3.9 Hz, 1H), 4.36 (d, J = 15.9 Hz, 2H), 4.03-3.70 (m, 5H), 2.72 (h, J = 6.7 Hz, 1H), 1.99-1.79 (m, 2H), 1.64-1.36 (m, 3H), 1.38-1.18 (m, 1H), 0.98 (d, J = 6.7 Hz, 3H), 0.80 (d, J = 7.3 Hz, 2H) | (ESI(+)) m/e 437 (M + H)$^+$ |
| 5 | 3-(pyridin-3-yl)-N-[4-({1-[(2R)-tetrahydrofuran-2-ylcarbonyl]piperidin-4-yl}oxy)phenyl]azetidine-1-carboxamide | $^1$H NMR (300 MHz, DMSO-$d_6$) δ 8.56 (d, J = 2.4 Hz, 1H), 8.48 (dd, J = 4.7, 1.6 Hz, 1H), 8.37 (s, 1H), 7.86 (dt, J = 7.9, 2.0 Hz, 1H), 7.45-7.35 (m, 3H), 6.92-6.85 (m, 2H), 4.67 (t, J = 6.6 Hz, 1H), 4.56-4.44 (m, 1H), 4.36 (t, J = 8.1 Hz, 1H), 3.99-3.66 (m, 7H), 2.11-1.69 (m, 6H), 1.64-1.38 (m, 2H) | (ESI(+)) m/e 451 (M + H)$^+$ |

TABLE 1-continued

The following Examples were prepared essentially as described in Example 1, substituting the appropriate alcohol in Example 1A, the appropriate amine in Example 1C and the appropriate carboxylic acid in Example 1E. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 6 | 3-(pyridin-3-yl)-N-(4-{[1-(3,3,3-trifluoropropanoyl)piperidin-4-yl]oxy}phenyl)azetidine-1-carboxamide | $^1$H NMR (300 MHz, DMSO-$d_6$) δ 8.59-8.45 (m, 2H), 8.37 (s, 1H), 7.86 (dt, J = 7.9, 2.0 Hz, 1H), 7.45-7.35 (m, 3H), 6.92-6.85 (m, 2H), 4.58-4.42 (m, 1H), 4.36 (t, J = 8.1 Hz, 1H), 4.01-3.74 (m, 4H), 3.66 (q, J = 11.0 Hz, 3H), 2.00-1.78 (m, 2H), 1.70-1.41 (m, 2H) | (ESI(+)) m/e 463 (M + H)$^+$ |
| 7 | N-(4-{[1-(2-hydroxy-2-methylpropanoyl)piperidin-4-yl]oxy}phenyl)-3-(pyridin-3-yl)azetidine-1-carboxamide | $^1$H NMR (300 MHz, DMSO-$d_6$) δ 16.84-16.76 (m, 1H), 8.56 (d, J = 2.3 Hz, 1H), 8.48 (dd, J = 4.7, 1.6 Hz, 1H), 8.37 (s, 1H), 7.86 (dt, J = 7.9, 2.0 Hz, 1H), 7.45-7.35 (m, 3H), 6.91-6.84 (m, 2H), 5.39 (s, 1H), 4.55-4.43 (m, 1H), 4.36 (d, J = 15.9 Hz, 2H), 4.02 (bs, 1H), 4.02-3.76 (m, 4H), 1.96-1.85 (m, 2H), 1.61-1.40 (m, 2H), 1.31 (s, 6H) | (ESI(+)) m/e 439 (M + H)$^+$ |
| 8 | 3-(6-methylpyridin-3-yl)-N-(4-{[1-(tetrahydro-2H-pyran-4-ylacetyl)piperidin-4-yl]oxy}phenyl)azetidine-1-carboxamide | $^1$H NMR (300 MHz, DMSO-$d_6$) δ 8.41 (d, J = 2.4 Hz, 1H), 8.35 (s, 1H), 7.75 (dd, J = 8.0, 2.4 Hz, 1H), 7.42-7.35 (m, 2H), 7.27 (d, J = 8.0 Hz, 1H), 6.94-6.84 (m, 2H), 4.58-4.43 (m, 1H), 4.33 (t, J = 8.1 Hz, 2H), 3.99-3.57 (m, 9H), 2.45 (s, 1H), 2.27 (d, J = 1.5 Hz, 1H), 2.05-1.79 (m, 4H), 1.66-1.38 (m, 5H), 1.31-1.10 (m, 3H) | (ESI(+)) m/e 493 (M + H)$^+$ |
| 28 | 3-(pyridin-3-yl)-N-[4-({1-[(2R)-tetrahydrofuran-2-ylcarbonyl]azetidin-3-yl}oxy)phenyl]azetidine-1-carboxamide | $^1$H NMR (300 MHz, DMSO-$d_6$) δ 8.56 (d, J = 2.3 Hz, 1H), 8.48 (dd, J = 4.8, 1.6 Hz, 1H), 8.40 (s, 1H), 7.86 (dt, J = 7.9, 2.0 Hz, 1H), 7.45-7.37 (m, 3H), 6.79-6.72 (m, 2H), 5.02-4.91 (m, 1H), 4.73-4.60 (m, 1H), 4.43-4.24 (m, 4H), 4.20-4.07 (m, 1H), 4.09-3.63 (m, 6H), 2.16-1.70 (m, 4H) | (ESI(+)) m/e 423 (M + H)$^+$ |
| 29 | 3-(pyridin-3-yl)-N-[4-({1-[(2S)-tetrahydrofuran-2-ylcarbonyl]azetidin-3-yl}oxy)phenyl]azetidine-1-carboxamide | $^1$H NMR (300 MHz, DMSO-$d_6$) δ 8.56 (d, J = 2.4 Hz, 1H), 8.51-8.39 (m, 1H), 8.40 (s, 1H), 7.86 (dt, J = 7.9, 2.0 Hz, 1H), 7.62-7.37 (m, 3H), 6.79-6.72 (m, 2H), 5.02-4.91 (m, 1H), 4.73-4.60 (m, 1H), 4.42-4.25 (m, 4H), 4.19-4.09 (m, 1H), 4.02-3.63 (m, 6H), 2.14-1.70 (m, 4H) | (ESI(+)) m/e 423 (M + H)$^+$ |
| 30 | N-(4-{[1-(2-hydroxy-2-methylpropanoyl)azetidin-3-yl]oxy}phenyl)-3-(pyridin-3-yl)azetidine-1-carboxamide | $^1$H NMR (300 MHz, DMSO-$d_6$) δ 8.58-8.45 (m, 1H), 8.40 (s, 1H), 7.86 (dt, J = 7.9, 2.0 Hz, 1H), 7.45-7.35 (m, 3H), 6.78-6.71 (m, 2H), 5.13 (s, 1H), 5.00-4.73 (m, 2H), 4.36 (d, J = 15.9 Hz, 2H), 4.29-4.22 (m, 2H), 3.98-3.85 (m, 3H), 3.78-3.69 (m, 1H), 1.25 (s, 6H) | (ESI(+)) m/e 411 (M + H)$^+$ |
| 31 | 3-(pyridin-3-yl)-N-[4-({1-[(2S)-tetrahydrofuran-2-ylcarbonyl]piperidin-4-yl}oxy)phenyl]azetidine-1-carboxamide | $^1$H NMR (300 MHz, DMSO-$d_6$) δ 8.56 (d, J = 2.3 Hz, 1H), 8.48 (dd, J = 4.7, 1.6 Hz, 1H), 8.37 (s, 1H), 7.86 (dt, J = 7.9, 2.0 Hz, 1H), 7.45-7.29 (m, 3H), 6.92-6.85 (m, 2H), 4.67 (t, J = 6.6 Hz, 1H), 4.50 (d, J = 3.1 Hz, 1H), 4.36 (d, J = 15.9 Hz, 2H), 4.01-3.67 (m, 7H), 2.11-1.68 (m, 6H), 1.65-1.33 (m, 2H) | (ESI(+)) m/e 451 (M + H)$^+$ |
| 32 | 3-(pyridin-3-yl)-N-(4-{[1-(thiophen-2-ylcarbonyl)piperidin-4-yl]oxy}phenyl)azetidine-1-carboxamide | $^1$H NMR (300 MHz, DMSO-$d_6$) δ 8.56 (d, J = 2.2 Hz, 1H), 8.59-8.45 (m, 2H), 8.38 (s, 1H), 7.86 (dt, J = 7.9, 2.0 Hz, 1H), 7.80-7.69 (m, 1H), 7.45-7.36 (m, 4H), 7.12 (ddd, J = 5.0, 3.6, 0.5 Hz, 1H), 6.94-6.87 (m, 2H), 4.57 (dq, J = 7.6, 3.8 Hz, 1H), 4.36 (d, J = 15.9 Hz, 2H), 3.99-3.80 (m, 5H), 3.58-3.42 (m, 2H), 2.06-1.84 (m, 2H), 1.73-1.54 (m, 2H) | (ESI(+)) m/e 463 (M + H)$^+$ |
| 33 | 3-(pyridin-3-yl)-N-(4-{[1-(thiophen-3-ylcarbonyl)piperidin-4-yl]oxy}phenyl)azetidine-1-carboxamide | $^1$H NMR (300 MHz, DMSO-$d_6$) δ 8.56 (d, J = 2.1 Hz, 1H), 8.59-8.45 (m, 2H), 8.37 (s, 1H), 7.86 (dt, J = 7.9, 2.0 Hz, 1H), 7.79 (dd, J = 2.9, 1.3 Hz, 1H), 7.61 (dd, J = 4.9, 2.9 Hz, 1H), 7.45-7.35 (m, 3H), 7.21 (dd, J = 4.9, 1.3 Hz, 1H), 6.93-6.86 (m, 2H), 4.53 (dq, J = 7.8, 3.9 Hz, 1H), 4.36 (d, J = 15.9 Hz, 2H), 4.02-3.66 (m, 5H), | (ESI(+)) m/e 463 (M + H)$^+$ |

TABLE 1-continued

The following Examples were prepared essentially as described in Example 1, substituting the appropriate alcohol in Example 1A, the appropriate amine in Example 1C and the appropriate carboxylic acid in Example 1E. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| | | 3.49-3.34 (m, 1H), 1.99-1.86 (m, 2H), 1.72-1.52 (m, 2H) | |
| 34 | N-[4-({1-[(1-acetylpiperidin-4-yl)carbonyl]piperidin-4-yl}oxy)phenyl]-3-(pyridin-3-yl)azetidine-1-carboxamide | $^1$H NMR (300 MHz, DMSO-$d_6$) δ 8.56 (d, J = 2.2 Hz, 1H), 8.59-8.45 (m, 2H), 8.37 (s, 1H), 7.86 (dt, J = 7.9, 2.0 Hz, 1H), 7.45-7.35 (m, 3H), 6.92-6.85 (m, 2H), 4.56-4.42 (m, 1H), 4.36 (t, J = 7.9 Hz, 3H), 4.02-3.71 (m, 6H), 3.15-3.02 (m, 1H), 2.98-2.84 (m, 1H), 2.58 (dd, J = 22.3, 12.2 Hz, 1H), 1.98 (s, 3H), 1.69-1.24 (m, 6H) | (ESI(+)) m/e 506 (M + H)$^+$ |
| 35 | N-[4-({1-[(2-methylcyclopropyl)carbonyl]piperidin-4-yl}oxy)phenyl]-3-(pyridin-3-yl)azetidine-1-carboxamide | $^1$H NMR (300 MHz, DMSO-$d_6$) δ 8.56 (d, J = 2.0 Hz, 1H), 8.59-8.46 (m, 2H), 8.36 (s, 1H), 7.86 (dt, J = 7.9, 2.0 Hz, 1H), 7.45-7.36 (m, 3H), 6.92-6.85 (m, 2H), 4.56-4.45 (m, 1H), 4.36 (d, J = 15.9 Hz, 2H), 4.03-3.76 (m, 6H), 3.48 (bs, 1H), 2.03-1.77 (m, 2H), 1.77-1.67 (m, 1H), 1.49 (bs, 2H), 1.16-1.03 (m, 4H), 1.07 (s, 3H), 0.97-0.83 (m, 1H), 0.57-0.49 (m, 1H) | (ESI(+)) m/e 435 (M + H)$^+$ |
| 36 | N-[4-({1-[(1-methyl-1H-pyrrol-2-yl)carbonyl]piperidin-4-yl}oxy)phenyl]-3-(pyridin-3-yl)azetidine-1-carboxamide | $^1$H NMR (300 MHz, DMSO-$d_6$) δ 8.56 (d, J = 2.3 Hz, 1H), 8.48 (dd, J = 4.7, 1.6 Hz, 1H), 8.37 (s, 1H), 7.86 (dt, J = 7.9, 2.0 Hz, 1H), 7.45-7.36 (m, 3H), 6.93-6.85 (m, 3H), 6.31 (dd, J = 3.7, 1.7 Hz, 1H), 6.02 (dd, J = 3.7, 2.5 Hz, 1H), 4.54 (p, J = 3.8 Hz, 1H), 4.36 (d, J = 15.9 Hz, 2H), 4.00-3.78 (m, 5H), 3.66 (s, 3H), 3.52-3.41 (m, 2H), 2.03-1.85 (m, 2H), 1.70-1.49 (m, 2H) | (ESI(+)) m/e 460 (M + H)$^+$ |
| 37 | N-[4-({1-[3-(morpholin-4-yl)propanoyl]piperidin-4-yl}oxy)phenyl]-3-(pyridin-3-yl)azetidine-1-carboxamide | $^1$H NMR (300 MHz, DMSO-$d_6$) δ 8.57 (dd, J = 6.8, 1.7 Hz, 1H), 8.52-8.42 (m, 1H), 8.37 (s, 1H), 7.86 (dt, J = 7.9, 2.0 Hz, 1H), 7.45-7.29 (m, 3H), 6.91-6.84 (m, 2H), 4.55-4.40 (m, 1H), 4.36 (d, J = 15.9 Hz, 2H), 3.98-3.77 (m, 4H), 3.75-3.65 (m, 1H), 3.59-3.52 (m, 4H), 2.41-2.34 (m, 4H), 2.03-1.74 (m, 1H), 1.67-1.37 (m, 2H) | (ESI(+)) m/e 518 (M + H)$^+$ |
| 38 | N-[4-({1-[3-(4-methylpiperazin-1-yl)propanoyl]piperidin-4-yl}oxy)phenyl]-3-(pyridin-3-yl)azetidine-1-carboxamide | $^1$H NMR (300 MHz, DMSO-$d_6$) δ 8.56 (d, J = 2.4 Hz, 1H), 8.48 (dd, J = 4.7, 1.6 Hz, 1H), 8.37 (s, 1H), 7.94-7.82 (m, 1H), 7.49-7.20 (m, 4H), 6.91-6.84 (m, 2H), 4.55-4.40 (m, 1H), 4.36 (d, J = 15.9 Hz, 2H), 3.98-3.77 (m, 5H), 3.75-3.66 (m, 1H), 2.37-2.18 (m, 5H), 1.91 (s, 1H), 1.65-1.34 (m, 1H) | (ESI(+)) m/e 505 (M + H)$^+$ |
| 39 | 3-(pyridin-3-yl)-N-[4-({1-[3-(pyrrolidin-1-yl)propanoyl]piperidin-4-yl}oxy)phenyl]azetidine-1-carboxamide | $^1$H NMR (300 MHz, DMSO-$d_6$) δ 8.56 (d, J = 2.3 Hz, 1H), 8.48 (dd, J = 4.8, 1.6 Hz, 1H), 8.37 (s, 1H), 7.86 (dt, J = 7.9, 2.0 Hz, 1H), 7.49-7.33 (m, 4H), 6.93-6.81 (m, 3H), 4.54-4.28 (m, 4H), 3.98-3.64 (m, 7H), 2.71-2.62 (m, 2H), 1.98-1.79 (m, 3H), 1.75-1.61 (m, 5H), 1.62-1.39 (m, 3H) | (ESI(+)) m/e 478 (M + H)$^+$ |
| 40 | N-(4-{[1-(cyclopropylacetyl)piperidin-4-yl]oxy}phenyl)-3-(pyridin-3-yl)azetidine-1-carboxamide | $^1$H NMR (300 MHz, DMSO-$d_6$) δ 8.56 (d, J = 2.1 Hz, 1H), 8.48 (dd, J = 4.8, 1.6 Hz, 1H), 8.37 (s, 1H), 7.86 (dt, J = 7.9, 2.0 Hz, 1H), 7.45-7.35 (m, 3H), 6.91-6.84 (m, 2H), 4.55-4.43 (m, 1H), 4.36 (d, J = 15.9 Hz, 2H), 3.98-3.79 (m, 4H), 3.76-3.59 (m, 1H), 3.25-3.15 (m, 1H), 2.27 (d, J = 6.7 Hz, 2H), 1.98-1.80 (m, 2H), 1.63-1.36 (m, 2H), 1.07-0.86 (m, 1H), 0.49-0.35 (m, 2H), 0.20-0.07 (m, 2H) | (ESI(+)) m/e 435 (M + H)$^+$ |
| 41 | N-(4-{[1-(3-methylpentanoyl)piperidin-4-yl]oxy}phenyl)-3-(pyridin-3-yl)azetidine-1-carboxamide | $^1$H NMR (300 MHz, DMSO-$d_6$) δ 8.56 (d, J = 2.2 Hz, 1H), 8.48 (dd, J = 4.7, 1.6 Hz, 1H), 8.37 (s, 1H), 7.86 (dt, J = 7.9, 2.0 Hz, 1H), 7.45-7.35 (m, 3H), 6.91-6.84 (m, 2H), 4.49 (dq, J = 7.8, 3.9 Hz, 1H), 4.36 (d, J = 15.9 Hz, 2H), 3.98-3.80 (m, 4H), 3.77-3.65 (m, 1H), 3.28-3.13 (m, 1H), 2.30 (dt, J = 14.9, 5.4 Hz, 1H), 2.19-2.06 (m, | (ESI(+)) m/e 451 (M + H)$^+$ |

TABLE 1-continued

The following Examples were prepared essentially as described in Example 1, substituting the appropriate alcohol in Example 1A, the appropriate amine in Example 1C and the appropriate carboxylic acid in Example 1E. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
|  |  | 1H), 2.01-1.68 (m, 1H), 1.48 (ddd, J = 24.8, 16.8, 10.2 Hz, 1H), 1.34 (ddd, J = 14.9, 10.2, 6.5 Hz, 1H), 1.14 (tq, J = 14.4, 7.3 Hz, 1H), 0.90-0.73 (m, 6H) |  |
| 42 | N-(4-{[1-(4-methylpentanoyl)piperidin-4-yl]oxy}phenyl)-3-(pyridin-3-yl)azetidine-1-carboxamide | $^1$H NMR (300 MHz, DMSO-d$_6$) δ 8.56 (d, J = 2.2 Hz, 1H), 8.48 (dd, J = 4.7, 1.5 Hz, 1H), 8.37 (s, 1H), 7.86 (dt, J = 7.9, 2.0 Hz, 1H), 7.48-7.34 (m, 3H), 6.91-6.84 (m, 2H), 4.49 (dq, J = 7.8, 3.9 Hz, 1H), 4.36 (d, J = 15.9 Hz, 2H), 3.98-3.77 (m, 4H), 3.76-3.63 (m, 1H), 3.25-3.03 (m, 2H), 2.35-2.26 (m, 2H), 1.98-1.77 (m, 2H), 1.64-1.28 (m, 5H), 0.87 (d, J = 6.5 Hz, 6H) | (ESI(+)) m/e 451 (M + H)$^+$ |
| 43 | N-{4-[(1-butanoylpiperidin-4-yl)oxy]phenyl}-3-(pyridin-3-yl)azetidine-1-carboxamide | $^1$H NMR (300 MHz, DMSO-d$_6$) δ 8.56 (d, J = 2.0 Hz, 1H), 8.48 (dd, J = 4.8, 1.6 Hz, 1H), 8.36 (s, 1H), 7.86 (dt, J = 7.9, 2.0 Hz, 1H), 7.45-7.35 (m, 3H), 6.91-6.84 (m, 2H), 4.54-4.43 (m, 1H), 4.36 (d, J = 15.9 Hz, 2H), 4.02-3.78 (m, 4H), 3.75-3.62 (m, 1H), 3.27-3.07 (m, 1H), 2.29 (t, J = 7.3 Hz, 2H), 1.97-1.80 (m, 2H), 1.63-1.38 (m, 4H), 0.91 (s, 1H), 0.88 (d, J = 7.4 Hz, 2H) | (ESI(+)) m/e 423 (M + H)$^+$ |
| 44 | N-(4-{[1-(2,2-dimethylpropanoyl)piperidin-4-yl]oxy}phenyl)-3-(pyridin-3-yl)azetidine-1-carboxamide | $^1$H NMR (300 MHz, DMSO-d$_6$) δ 8.56 (d, J = 2.0 Hz, 1H), 8.48 (dd, J = 4.8, 1.6 Hz, 1H), 8.37 (s, 1H), 7.86 (dt, J = 7.9, 2.0 Hz, 1H), 7.45-7.35 (m, 3H), 6.91-6.84 (m, 2H), 4.56-4.45 (m, 1H), 4.36 (d, J = 15.9 Hz, 2H), 3.99-3.77 (m, 5H), 1.99-1.83 (m, 2H), 1.62-1.35 (m, 2H), 1.20 (s, 9H) | (ESI(+)) m/e 437 (M + H)$^+$ |
| 45 | N-(4-{[1-(3,3-dimethylbutanoyl)piperidin-4-yl]oxy}phenyl)-3-(pyridin-3-yl)azetidine-1-carboxamide | $^1$H NMR (300 MHz, DMSO-d$_6$) δ 8.56 (d, J = 2.0 Hz, 1H), 8.48 (dd, J = 4.8, 1.6 Hz, 1H), 8.36 (s, 1H), 7.86 (dt, J = 7.9, 2.0 Hz, 1H), 7.45-7.35 (m, 3H), 6.91-6.84 (m, 2H), 4.54-4.42 (m, 1H), 4.36 (d, J = 15.9 Hz, 2H), 4.02-3.70 (m, 5H), 2.24 (s, 2H), 1.98-1.81 (m, 2H), 1.62-1.39 (m, 2H), 0.99 (s, 9H) | (ESI(+)) m/e 451 (M + H)$^+$ |
| 46 | N-(4-{[1-(ethoxyacetyl)piperidin-4-yl]oxy}phenyl)-3-(pyridin-3-yl)azetidine-1-carboxamide | $^1$H NMR (300 MHz, DMSO-d$_6$) δ 8.56 (d, J = 2.1 Hz, 1H), 8.48 (dd, J = 4.8, 1.6 Hz, 1H), 8.37 (s, 1H), 7.86 (dt, J = 7.9, 2.0 Hz, 1H), 7.45-7.35 (m, 3H), 6.92-6.85 (m, 2H), 4.55-4.44 (m, 1H), 4.36 (d, J = 15.9 Hz, 2H), 4.11 (d, J = 1.3 Hz, 2H), 3.98-3.74 (m, 4H), 3.72-3.59 (m, 1H), 3.46 (q, J = 7.0 Hz, 2H), 1.94-1.83 (m, 2H), 1.65-1.40 (m, 2H), 1.13 (t, J = 7.0 Hz, 3H) | (ESI(+)) m/e 439 (M + H)$^+$ |
| 47 | N-(4-{[1-(cyclopropylcarbonyl)piperidin-4-yl]oxy}phenyl)-3-(pyridin-3-yl)azetidine-1-carboxamide | $^1$H NMR (300 MHz, DMSO-d$_6$) δ 8.58-8.45 (m, 2H), 8.36 (s, 1H), 7.86 (dt, J = 7.9, 2.0 Hz, 1H), 7.44-7.35 (m, 3H), 6.92-6.85 (m, 2H), 4.57-4.45 (m, 1H), 4.36 (d, J = 15.9 Hz, 2H), 4.02-3.76 (m, 5H), 3.58-3.38 (m, 1H), 3.28-3.08 (m, 1H), 2.05-1.79 (m, 3H), 1.49 (bs, 2H), 0.77-0.63 (m, 4H) | (ESI(+)) m/e 421 (M + H)$^+$ |
| 48 | N-(4-{[1-(methoxyacetyl)piperidin-4-yl]oxy}phenyl)-3-(pyridin-3-yl)azetidine-1-carboxamide | $^1$H NMR (300 MHz, DMSO-d$_6$) δ 8.56 (d, J = 2.2 Hz, 1H), 8.48 (dd, J = 4.7, 1.6 Hz, 1H), 8.37 (s, 1H), 7.94-7.78 (m, 1H), 7.49-7.31 (m, 3H), 6.96-6.81 (m, 2H), 4.59-4.44 (m, 1H), 4.35 (t, J = 8.0 Hz, 1H), 4.09 (s, 2H), 4.01-3.73 (m, 4H), 3.57 (d, J = 12.9 Hz, 1H), 3.28 (s, 2H), 3.22 (d, J = 19.7 Hz, 1H), 1.90 (s, 2H), 1.50 (s, 2H) | (ESI(+)) m/e 425 (M + H)$^+$ |
| 76 | 3-(pyridin-3-yl)-N-(4-{[(3R)-1-(tetrahydro-2H-pyran-4-ylacetyl)pyrrolidin-3-yl]oxy}phenyl)azetidine-1-carboxamide |  | (ESI(+)) m/e 465 (M + H)$^+$ |

TABLE 1-continued

The following Examples were prepared essentially as described in Example 1, substituting the appropriate alcohol in Example 1A, the appropriate amine in Example 1C and the appropriate carboxylic acid in Example 1E. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 77 | N-(4-{[(3R)-1-(2-methylpropanoyl)pyrrolidin-3-yl]oxy}phenyl)-3-(pyridin-3-yl)azetidine-1-carboxamide | | (ESI(+)) m/e 409 (M + H)$^+$ |
| 78 | 3-(pyridin-3-yl)-N-[4-({(3R)-1-[(2S)-tetrahydrofuran-2-ylcarbonyl]pyrrolidin-3-yl}oxy)phenyl]azetidine-1-carboxamide | | (ESI(+)) m/e 437 (M + H)$^+$ |
| 79 | 3-(pyridin-3-yl)-N-[4-({(3R)-1-[(2R)-tetrahydrofuran-2-ylcarbonyl]pyrrolidin-3-yl}oxy)phenyl]azetidine-1-carboxamide | | (ESI(+)) m/e 437 (M + H)$^+$ |
| 80 | 3-(pyridin-3-yl)-N-(4-{[(3R)-1-(tetrahydrofuran-3-ylcarbonyl)pyrrolidin-3-yl]oxy}phenyl)azetidine-1-carboxamide | | (ESI(+)) m/e 437 (M + H)$^+$ |
| 81 | N-(4-{[(3R)-1-(cyclopropylacetyl)pyrrolidin-3-yl]oxy}phenyl)-3-(pyridin-3-yl)azetidine-1-carboxamide | | (ESI(+)) m/e 421 (M + H)$^+$ |
| 82 | N-(4-{[(3R)-1-(2-hydroxy-2-methylpropanoyl)pyrrolidin-3-yl]oxy}phenyl)-3-(pyridin-3-yl)azetidine-1-carboxamide | | (ESI(+)) m/e 424 (M + H)$^+$ |
| 83 | N-(4-{[(3R)-1-benzoylpyrrolidin-3-yl]oxy}phenyl)-3-(pyridin-3-yl)azetidine-1-carboxamide | | (ESI(+)) m/e 443 (M + H)$^+$ |
| 84 | 3-(pyridin-3-yl)-N-(4-{[(3R)-1-(3,3,3-trifluoropropanoyl)pyrrolidin-3-yl]oxy}phenyl)azetidine-1-carboxamide | $^1$H NMR (400 MHz, DMSO-d$_6$/D$_2$O, Temp = 90° C.) δ 8.73 (d, J = 2.1 Hz, 1H), 8.64 (d, J = 4.4 Hz, 1H), 8.33-8.26 (m, 1H), 7.83-7.76 (m, 1H), 7.42-7.35 (m, 2H), 6.89-6.81 (m, 2H), 5.01-4.90 (m, 1H), 4.47-4.37 (m, 2H), 4.08-3.96 (m, 3H), 3.77-3.50 (m, 3H), 3.52-3.36 (m, 3H), 2.27-1.91 (m, 2H) | (ESI(+)) m/e 449 (M + H)$^+$ |
| 85 | N-(4-{[(3R)-1-(cyclopropylcarbonyl)pyrrolidin-3-yl]oxy}phenyl)-3-(pyridin-3-yl)azetidine-1-carboxamide | $^1$H NMR (300 MHz, DMSO-d$_6$) δ 8.76 (bs, 1H), 8.69-8.62 (m, 1H), 8.41 (s, 1H), 8.26 (dd, J = 5.0, 3.0 Hz, 1H), 7.73 (ddd, J = 7.6, 5.2, 2.2 Hz, 1H), 7.41 (dd, J = 9.0, 2.0 Hz, 2H), 6.87 (dd, J = 9.0, 7.5 Hz, 2H), 4.98 (d, J = 32.2 Hz, 2H), 4.49-4.23 (m, 2H), 4.08-3.88 (m, 3H), 3.91-3.64 (m, 2H), 3.34 (dd, J = 19.2, 9.5 Hz, 1H), 2.31-1.91 (m, 2H), 1.74 (ddd, J = 12.8, 10.5, 6.5 Hz, 1H), 0.84-0.36 (m, 4H) | (ESI(+)) m/e 407 (M + H)$^+$ |
| 86 | N-[4-({(3R)-1-[(2S)-2-methylbutanoyl]pyrrolidin-3-yl}oxy)phenyl]-3- | $^1$H NMR (300 MHz, DMSO-d$_6$) δ 8.80-8.64 (m, 2H), 8.68 (d, J = 4.3 Hz, 1H), 8.41 (s, 1H), 8.34-8.25 (m, 1H), 7.77 (ddd, J = 7.9, 5.3, 2.5 Hz, 1H), 7.45-7.37 (m, 2H), 6.91-6.79 (m, 2H), 4.95 (d, J = 23.5 Hz, | (ESI(+)) m/e 423 (M + H)$^+$ |

TABLE 1-continued

The following Examples were prepared essentially as described in Example 1, substituting the appropriate alcohol in Example 1A, the appropriate amine in Example 1C and the appropriate carboxylic acid in Example 1E. Some products were purified by flash chromatography while others were purified by reverse-phase HPLC. Accordingly, some Examples were isolated as trifluoroacetic acid salts.

| Ex | Name | $^1$H NMR | MS |
|----|------|-----------|-----|
|    | (pyridin-3-yl)azetidine-1-carboxamide | 1H), 4.43-4.27 (m, 2H), 3.99 (dd, J = 6.5, 4.7 Hz, 3H), 3.82-3.30 (m, 2H), 2.20-1.96 (m, 2H), 1.61-1.42 (m, 1H), 1.28 (tt, J = 14.1, 7.1 Hz, 1H), 1.00 (d, J = 6.7 Hz, 2H), 0.93 (d, J = 6.7 Hz, 2H), 0.82 (td, J = 7.4, 2.2 Hz, 4H) |  |
| 87 | N-(4-{[(3R)-1-butanoylpyrrolidin-3-yl]oxy}phenyl)-3-(pyridin-3-yl)azetidine-1-carboxamide | $^1$H NMR (300 MHz, DMSO-d$_6$) δ 8.76 (bs, 1H), 8.66 (dd, J = 5.2, 1.4 Hz, 1H), 8.41 (s, 1H), 8.30-8.22 (m, 1H), 7.78-7.69 (m, 1H), 7.42 (d, J = 1.0 Hz, 2H), 6.90-6.80 (m, 2H), 4.95 (d, J = 22.7 Hz, 1H), 4.45-4.24 (m, 2H), 4.08-3.90 (m, 3H), 3.63-3.44 (m, 3H), 2.29-1.97 (m, 3H), 1.60-1.42 (m, 3H), 0.93-0.83 (m, 4H) | (ESI(+)) m/e 409 (M + H)$^+$ |
| 88 | 3-(pyridin-3-yl)-N-(4-{[(3S)-1-(tetrahydro-2H-pyran-4-ylacetyl)pyrrolidin-3-yl]oxy}phenyl)azetidine-1-carboxamide | $^1$H NMR (300 MHz, DMSO-d$_6$) δ 8.76 (s, 1H), 8.66 (d, J = 4.5 Hz, 1H), 8.41 (s, 1H), 8.27 (d, J = 7.9 Hz, 1H), 7.83-7.57 (m, 1H), 7.45-7.37 (m, 2H), 6.89-6.80 (m, 2H), 4.95 (d, J = 22.0 Hz, 2H), 4.80-4.39 (m, 4H), 4.38 (q, J = 5.7 Hz, 3H), 4.10-3.87 (m, 2H), 3.71-3.44 (m, 2H), 3.38-3.15 (m, 2H), 2.21 (d, J = 6.8 Hz, 2H), 2.18-1.84 (m, 1H), 1.64-1.51 (m, 2H), 1.30-0.95 (m, 2H) | (ESI(+)) m/e 465 (M + H)$^+$ |
| 89 | N-(4-{[(3S)-1-(2-methylpropanoyl)pyrrolidin-3-yl]oxy}phenyl)-3-(pyridin-3-yl)azetidine-1-carboxamide | $^1$H NMR (300 MHz, DMSO-d$_6$) δ 8.78 (bs, 1H), 8.68 (d, J = 4.9 Hz, 1H), 8.41 (s, 1H), 8.35-8.27 (m, 1H), 7.82-7.73 (m, 1H), 7.49-7.26 (m, 2H), 6.91-6.80 (m, 2H), 4.95 (d, J = 25.5 Hz, 1H), 4.43-4.32 (m, 2H), 4.06-3.90 (m, 3H), 3.63-3.47 (m, 3H), 2.81-2.54 (m, 1H), 2.29-1.94 (m, 3H), 1.09-0.89 (m, 6H) | (ESI(+)) m/e 409 (M + H)$^+$ |
| 90 | 3-(pyridin-3-yl)-N-[4-({(3S)-1-[(2S)-tetrahydrofuran-2-ylcarbonyl]pyrrolidin-3-yl}oxy)phenyl]azetidine-1-carboxamide | $^1$H NMR (300 MHz, DMSO-d$_6$) δ 8.79 (bs, 1H), 8.68 (d, J = 5.3 Hz, 1H), 8.41 (s, 1H), 8.35-8.27 (m, 1H), 7.82-7.73 (m, 1H), 7.45-7.38 (m, 2H), 6.91-6.78 (m, 2H), 4.96 (d, J = 23.1 Hz, 1H), 4.58-4.31 (m, 3H), 4.08-3.92 (m, 3H), 3.86-3.44 (m, 6H), 2.28-1.70 (m, 6H) | (ESI(+)) m/e 437 (M + H)$^+$ |
| 91 | 3-(pyridin-3-yl)-N-[4-({(3S)-1-[(2R)-tetrahydrofuran-2-ylcarbonyl]pyrrolidin-3-yl}oxy)phenyl]azetidine-1-carboxamide |  | (ESI(+)) m/e 437 (M + H)$^+$ |
| 92 | 3-(pyridin-3-yl)-N-(4-{[(3S)-1-(tetrahydrofuran-3-ylcarbonyl)pyrrolidin-3-yl]oxy}phenyl)azetidine-1-carboxamide | $^1$H NMR (300 MHz, DMSO-d$_6$) δ 8.81 (bs, 1H), 8.70 (d, J = 5.4 Hz, 1H), 8.42 (s, 1H), 8.36 (dd, J = 9.0, 2.5 Hz, 1H), 7.86-7.77 (m, 1H), 7.45-7.38 (m, 2H), 6.94-6.72 (m, 2H), 5.75 (s, 1H), 5.03-4.89 (m, 1H), 4.40-4.33 (m, 2H), 4.07-3.73 (m, 6H), 3.55-3.49 (m, 2H), 3.43-3.09 (m, 2H), 2.29-1.86 (m, 5H) | (ESI(+)) m/e 437 (M + H)$^+$ |
| 93 | N-(4-{[(3S)-1-(cyclopropylacetyl)pyrrolidin-3-yl]oxy}phenyl)-3-(pyridin-3-yl)azetidine-1-carboxamide | $^1$H NMR (300 MHz, DMSO-d$_6$) δ 8.80 (bs, 1H), 8.69 (d, J = 5.3 Hz, 1H), 8.41 (s, 1H), 8.38-8.29 (m, 1H), 7.79 (ddd, J = 7.9, 5.4, 2.3 Hz, 1H), 7.44-7.37 (m, 2H), 6.91-6.76 (m, 2H), 6.71-5.35 (m, 2H), 5.01-4.88 (m, 1H), 4.40-4.33 (m, 2H), 4.06-3.93 (m, 3H), 3.76-3.26 (m, 2H), 2.30-1.90 (m, 4H), 1.04-0.86 (m, 1H), 0.49-0.35 (m, 2H), 0.17-0.07 (m, 2H) | (ESI(+)) m/e 421 (M + H)$^+$ |
| 94 | N-(4-{[(3S)-1-(2-hydroxy-2-methylpropanoyl)pyrrolidin-3-yl]oxy}phenyl)-3-(pyridin-3-yl)azetidine-1-carboxamide | $^1$H NMR (300 MHz, DMSO-d$_6$) δ 8.78 (d, J = 2.1 Hz, 1H), 8.67 (dd, J = 5.2, 1.4 Hz, 1H), 8.41 (s, 1H), 8.34-8.26 (m, 1H), 7.81-7.73 (m, 1H), 7.31 (dd, J = 56.7, 9.0 Hz, 2H), 6.89-6.81 (m, 2H), 4.92 (d, J = 25.9 Hz, 1H), 4.43-4.31 (m, 2H), 4.13-3.92 (m, 4H), 3.87-3.56 (m, 2H), 3.44 (dd, J = 22.1, 12.9 Hz, 2H), 2.15-1.90 (m, 2H), 1.34-1.23 (m, 4H), 1.20 (s, 1H) | (ESI(+)) m/e 425 (M + H)$^+$ |

TABLE 1-continued

The following Examples were prepared essentially as described in Example 1, substituting the appropriate alcohol in Example 1A, the appropriate amine in Example 1C and the appropriate carboxylic acid in Example 1E. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 95 | N-(4-{[(3S)-1-benzoylpyrrolidin-3-yl]oxy}phenyl)-3-(pyridin-3-yl)azetidine-1-carboxamide | $^1$H NMR (300 MHz, DMSO-$d_6$) δ 8.80-8.74 (m, 1H), 8.70-8.63 (m, 1H), 8.45-8.36 (m, 1H), 8.33-8.24 (m, 1H), 7.81-7.71 (m, 1H), 7.58-7.30 (m, 7H), 6.90 (d, J = 8.6 Hz, 1H), 6.81 (d, J = 8.6 Hz, 1H), 4.96 (d, J = 25.8 Hz, 2H), 4.40-4.33 (m, 2H), 3.98 (d, J = 2.8 Hz, 2H), 3.86-3.75 (m, 1H), 3.71-3.34 (m, 3H), 2.27-1.99 (m, 2H) | (ESI(+)) m/e 443 (M + H)$^+$ |
| 96 | 3-(pyridin-3-yl)-N-(4-{[(3S)-1-(3,3,3-trifluoropropanoyl)pyrrolidin-3-yl]oxy}phenyl)azetidine-1-carboxamide | $^1$H NMR (300 MHz, DMSO-$d_6$) δ 8.76 (bs, 1H), 8.66 (d, J = 5.1 Hz, 1H), 8.41 (s, 1H), 8.30-8.22 (m, 1H), 7.78-7.69 (m, 1H), 7.45-7.38 (m, 2H), 6.91-6.81 (m, 2H), 4.97 (d, J = 20.8 Hz, 2H), 4.40-4.32 (m, 2H), 4.04-3.91 (m, 3H), 3.83-3.20 (m, 5H), 2.29-1.97 (m, 2H) | (ESI(+)) m/e 449 (M + H)$^+$ |
| 97 | N-(4-{[(3S)-1-(cyclopropylcarbonyl)pyrrolidin-3-yl]oxy}phenyl)-3-(pyridin-3-yl)azetidine-1-carboxamide | $^1$H NMR (300 MHz, DMSO-$d_6$) δ 8.78 (s, 1H), 8.68 (d, J = 5.3 Hz, 1H), 8.41 (s, 1H), 8.34-8.26 (m, 1H), 7.81-7.72 (m, 1H), 7.45-7.37 (m, 2H), 6.92-6.81 (m, 2H), 6.67-4.84 (m, 4H), 4.43-4.31 (m, 2H), 3.91-3.63 (m, 2H), 3.58-3.46 (m, 2H), 2.29-1.96 (m, 2H), 1.93-1.66 (m, 1H), 0.80-0.64 (m, 4H) | (ESI(+)) m/e 407 (M + H)$^+$ |
| 98 | N-[4-({(3S)-1-[(2S)-2-methylbutanoyl]pyrrolidin-3-yl}oxy)phenyl]-3-(pyridin-3-yl)azetidine-1-carboxamide | $^1$H NMR (300 MHz, DMSO-$d_6$) δ 8.78 (bs, 1H), 8.68 (d, J = 5.3 Hz, 1H), 8.41 (s, 1H), 8.35-8.27 (m, 1H), 7.82-7.73 (m, 2H), 7.40 (t, J = 6.2 Hz, 2H), 6.90-6.80 (m, 2H), 4.95 (d, J = 24.2 Hz, 2H), 4.43-4.32 (m, 2H), 4.01 (dd, J = 12.9, 5.8 Hz, 3H), 3.80-3.46 (m, 3H), 2.28-1.95 (m, 2H), 1.65-1.40 (m, 1H), 1.39-1.17 (m, 1H), 0.98 (dd, J = 6.7, 3.2 Hz, 3H), 0.83 (t, J = 7.4 Hz, 2H), 0.75 (d, J = 7.4 Hz, 1H) | (ESI(+)) m/e 423 (M + H)$^+$ |
| 99 | N-(4-{[(3S)-1-butanoylpyrrolidin-3-yl]oxy}phenyl)-3-(pyridin-3-yl)azetidine-1-carboxamide | $^1$H NMR (300 MHz, DMSO-$d_6$) δ 8.80 (bs, 1H), 8.69 (d, J = 5.3 Hz, 1H), 8.42 (s, 1H), 8.38-8.30 (m, 1H), 7.94-7.75 (m, 1H), 7.42 (ddd, J = 9.6, 7.6, 1.8 Hz, 2H), 7.01-6.71 (m, 2H), 5.03-4.89 (m, 2H), 4.43-4.29 (m, 2H), 4.07-3.89 (m, 3H), 3.74 (dd, J = 11.6, 4.5 Hz, 1H), 3.64-3.40 (m, 2H), 3.40-3.20 (m, 1H), 2.30-2.07 (m, 2H), 2.07-1.93 (m, 1H), 1.61-1.38 (m, 2H), 0.97-0.77 (m, 3H) | (ESI(+)) m/e 409 (M + H)$^+$ |
| 114 | N-(4-{[1-(cyclopropylacetyl)azetidin-3-yl]oxy}phenyl)-3-(pyridin-3-yl)azetidine-1-carboxamide | $^1$H NMR (400 MHz, DMSO-$d_6$/D$_2$O) □ ppm 8.56 (d, J = 1.83 Hz, 1 H) 8.48 (dd, J = 4.58, 1.53 Hz, 1 H) 8.40 (s, 1 H) 7.84-7.88 (m, 1 H) 7.39-7.43 (m, 3 H) 6.75 (d, J = 9.16 Hz, 2 H) 4.92-4.97 (m, 1 H) 4.51 (dd, J = 9.00, 6.87 Hz, 1 H) 4.36 (t, J = 8.24 Hz, 2 H) 4.26 (dd, J = 10.53, 6.56 Hz, 1 H) 4.03 (dd, J = 9.46, 3.36 Hz, 1 H) 3.92-3.96 (m, 2 H) 3.83-3.91 (m, 1 H) 3.74 (dd, J = 10.53, 3.51 Hz, 1 H) 2.02 (d, J = 6.71 Hz, 2 H) 0.88-0.97 (m, 1 H) 0.41-0.46 (m, 2 H) 0.08-0.12 (m, 2 H) | (ESI(+)) m/e 407 (M + H)$^+$ |
| 115 | N-(4-{[1-(furan-2-ylcarbonyl)azetidin-3-yl]oxy}phenyl)-3-(pyridin-3-yl)azetidine-1-carboxamide | $^1$H NMR (400 MHz, DMSO-$d_6$/D$_2$O) □ ppm 8.58 (s, 1 H) 8.50 (d, J = 4.27 Hz, 1 H) 8.41 (s, 1 H) 7.84-7.91 (m, 2 H) 7.42-7.46 (m, 3 H) 7.07-7.08 (m, 1 H) 6.76-6.81 (m, 2 H) 6.64 (dd, J = 3.66, 1.83 Hz, 1 H) 4.44-4.51 (m, 1 H) 4.36 (t, J = 8.24 Hz, 3 H) 3.93-3.97 (m, 2 H) 3.84-3.92 (m, 2 H) | (ESI(+)) m/e 419 (M + H)$^+$ |
| 117 | N-{4-[(1-pentanoylazetidin-3-yl)oxy]phenyl}-3-(pyridin-3-yl)azetidine-1-carboxamide | $^1$H NMR (400 MHz, DMSO-$d_6$/D$_2$O Temp = 90° C.) δ ppm 8.59-8.39 (m, 2H), 7.88-7.67 (m, 1H), 7.48-7.23 (m, 3H), 6.89-6.63 (m, 2H), 5.15-4.84 (m, 1H), 4.51-4.26 (m, 3H), 4.07-3.84 (m, 4H), 2.21-2.00 (m, 2H), 1.61-1.41 (m, 2H), 1.41-1.16 (m, 2H), 0.87 (t, J = 7.3 Hz, 3H) | (ESI(+)) m/e 409 (M + H)$^+$ |

TABLE 1-continued

The following Examples were prepared essentially as described in Example 1, substituting the appropriate alcohol in Example 1A, the appropriate amine in Example 1C and the appropriate carboxylic acid in Example 1E. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 118 | N-[4-({1-[(2-methoxyethoxy)acetyl]azetidin-3-yl}oxy)phenyl]-3-(pyridin-3-yl)azetidine-1-carboxamide | $^1$H NMR (400 MHz, DMSO-$d_6$/$D_2O$, Temp = 90° C.) δ ppm 8.61-8.40 (m, 2H), 7.90-7.73 (m, 1H), 7.51-7.31 (m, 3H), 6.89-6.66 (m, 2H), 5.09-4.88 (m, 1H), 4.39 (t, J = 8.3 Hz, 4H), 4.08-3.83 (m, 7H), 3.57 (dd, J = 5.8, 3.7 Hz, 2H), 3.52-3.40 (m, 2H) | (ESI(+)) m/e 441 (M + H)$^+$ |
| 119 | N-(4-{[1-(ethoxyacetyl)azetidin-3-yl]oxy}phenyl)-3-(pyridin-3-yl)azetidine-1-carboxamide | $^1$H NMR (400 MHz, DMSO-$d_6$/$D_2O$, Temp = 90° C.) δ ppm 8.66-8.29 (m, 2H), 7.81 (dt, J = 7.9, 2.0 Hz, 1H), 7.57-7.35 (m, 3H), 6.84-6.65 (m, 2H), 5.19-4.85 (m, 1H), 4.39 (t, J = 8.4 Hz, 4H), 4.06-3.82 (m, 7H), 3.49 (q, J = 7.0 Hz, 2H), 1.13 (t, J = 7.0 Hz, 3H) | (ESI(+)) m/e 411 (M + H)$^+$ |
| 120 | N-(4-{[1-(methoxyacetyl)azetidin-3-yl]oxy}phenyl)-3-(pyridin-3-yl)azetidine-1-carboxamide | $^1$H NMR (400 MHz, DMSO-$d_6$/$D_2O$, Temp = 90° C.) δ ppm 8.65-8.38 (m, 2H), 7.91-7.72 (m, 1H), 7.49-7.32 (m, 3H), 6.81-6.65 (m, 2H), 5.11-4.92 (m, 1H), 4.46-4.33 (m, 3H), 4.06-3.85 (m, 6H), 3.30 (s, 3H) | (ESI(+)) m/e 397 (M + H)$^+$ |
| 121 | N-(4-{[1-(3-methylpentanoyl)azetidin-3-yl]oxy}phenyl)-3-(pyridin-3-yl)azetidine-1-carboxamide | $^1$H NMR (400 MHz, DMSO-$d_6$/$D_2O$, Temp = 90° C.) δ ppm 8.61-8.52 (m, 1H), 8.52-8.41 (m, 1H), 7.88-7.72 (m, 1H), 7.49-7.24 (m, 3H), 6.87-6.69 (m, 2H), 5.09-4.84 (m, 1H), 4.51-4.28 (m, 4H), 4.07-3.83 (m, 5H), 2.18-2.02 (m, 1H), 1.93 (t, J = 6.6 Hz, 1H), 1.84-1.67 (m, 1H), 1.43-1.28 (m, 1H), 1.28-1.12 (m, 1H), 1.00-0.74 (m, 7H) | (ESI(+)) m/e 423 (M + H)$^+$ |
| 122 | N-[4-({1-[(1S,4R)-bicyclo[2.2.1]hept-2-ylacetyl]azetidin-3-yl}oxy)phenyl]-3-(pyridin-3-yl)azetidine-1-carboxamide | $^1$H NMR (400 MHz, DMSO-$d_6$/$D_2O$, Temp = 90° C.) δ ppm 8.54 (d, J = 2.1 Hz, 1H), 8.46 (dd, J = 4.8, 1.4 Hz, 1H), 7.81 (dt, J = 7.9, 1.9 Hz, 1H), 7.44-7.31 (m, 3H), 6.85-6.71 (m, 3H), 5.03-4.87 (m, 1H), 4.39 (t, J = 8.3 Hz, 4H), 4.02-3.85 (m, 5H), 2.33-2.06 (m, 3H), 1.87-1.63 (m, 2H), 1.34-1.24 (m, 2H), 1.20-1.07 (m, 4H), 1.04 (t, J = 10.8 Hz, 4H) | (ESI(+)) m/e 461 (M + H)$^+$ |
| 123 | N-(4-{[1-(2,3-dimethylbutanoyl)azetidin-3-yl]oxy}phenyl)-3-(pyridin-3-yl)azetidine-1-carboxamide | $^1$H NMR (400 MHz, DMSO-$d_6$/$D_2O$, Temp = 90° C.) δ ppm 8.54 (t, J = 3.5 Hz, 1H), 8.48-8.41 (m, 1H), 7.95-7.69 (m, 1H), 7.50-7.31 (m, 3H), 6.81-6.69 (m, 2H), 5.04-4.87 (m, 1H), 4.46-4.24 (m, 4H), 4.06-3.81 (m, 5H), 2.22-2.08 (m, 1H), 1.78-1.57 (m, 1H), 0.97 (d, J = 6.8 Hz, 3H), 0.93-0.82 (m, 6H) | (ESI(+)) m/e 423 (M + H)$^+$ |
| 124 | N-(4-{[1-(4-methylpentanoyl)azetidin-3-yl]oxy}phenyl)-3-(pyridin-3-yl)azetidine-1-carboxamide | $^1$H NMR (400 MHz, DMSO-$d_6$/$D_2O$, Temp = 90° C.) δ ppm 8.55 (t, J = 3.7 Hz, 1H), 8.49-8.40 (m, 1H), 7.92-7.72 (m, 1H), 7.55-7.32 (m, 3H), 6.86-6.54 (m, 2H), 5.06-4.85 (m, 1H), 4.50-4.25 (m, 4H), 4.02-3.82 (m, 5H), 2.07 (dd, J = 13.9, 6.0 Hz, 2H), 1.64-1.48 (m, 1H), 1.40 (dd, J = 15.2, 6.9 Hz, 2H), 0.87 (d, J = 6.5 Hz, 6H) | (ESI(+)) m/e 423 (M + H)$^+$ |
| 125 | N-[4-({1-[(2-methylcyclopropyl)carbonyl]azetidin-3-yl}oxy)phenyl]-3-(pyridin-3-yl)azetidine-1-carboxamide | $^1$H NMR (400 MHz, DMSO-$d_6$/$D_2O$, Temp = 90° C.) δ ppm 8.54 (t, J = 3.8 Hz, 1H), 8.52-8.43 (m, 1H), 7.89-7.74 (m, 1H), 7.47-7.32 (m, 3H), 6.92-6.69 (m, 2H), 5.10-4.89 (m, 1H), 4.48-4.33 (m, 4H), 4.05-3.82 (m, 5H), 1.34-1.11 (m, 2H), 1.09-1.05 (m, 3H), 1.03-0.89 (m, 1H), 0.70-0.46 (m, 1H) | (ESI(+)) m/e 407 (M + H)$^+$ |
| 126 | 3-(pyridin-3-yl)-N-(4-{[1-(4,4,4-trifluorobutanoyl)azetidin-3-yl]oxy}phenyl)azetidine-1-carboxamide | $^1$H NMR (400 MHz, DMSO-$d_6$/$D_2O$, Temp = 90° C.) δ ppm 8.55 (t, J = 3.6 Hz, 1H), 8.52-8.39 (m, 1H), 7.89-7.74 (m, 1H), 7.43-7.28 (m, 3H), 6.83-6.69 (m, 2H), 5.10-4.88 (m, 1H), 4.48-4.30 (m, 3H), 4.06-3.78 (m, 5H), 2.51-2.44 (m, 2H), 2.36 (dd, J = 13.3, 5.7 Hz, 2H) | (ESI(+)) m/e 449 (M + H)$^+$ |

TABLE 1-continued

The following Examples were prepared essentially as described in Example 1,
substituting the appropriate alcohol in Example 1A, the appropriate amine in Example 1C and
the appropriate carboxylic acid in Example 1E. Some products were purified by flash
chromatography while others were purified by reverse-phase HPLC. Accordingly, some
Examples were isolated as trifluoroacetic acid salts.

| Ex | Name | $^1$H NMR | MS |
|---|---|---|---|
| 127 | N-(4-{[1-(2-methylpropanoyl)azetidin-3-yl]oxy}phenyl)-3-(pyridin-3-yl)azetidine-1-carboxamide | $^1$H NMR (400 MHz, DMSO-$d_6$/$D_2$O, Temp = 90° C.) δ ppm 8.54 (d, J = 2.1 Hz, 1H), 8.51-8.38 (m, 1H), 7.88-7.76 (m, 1H), 7.51-7.31 (m, 3H), 6.79-6.65 (m, 2H), 5.04-4.88 (m, 1H), 4.39 (t, J = 8.4 Hz, 4H), 3.97 (dd, J = 8.0, 6.0 Hz, 3H), 3.93-3.77 (m, 2H), 2.48 (d, J = 6.8 Hz, 1H), 1.00 (d, J = 6.8 Hz, 6H) | (ESI(+)) m/e 395 (M + H)$^+$ |
| 128 | N-(4-{[1-(2,2-dimethylpropanoyl)azetidin-3-yl]oxy}phenyl)-3-(pyridin-3-yl)azetidine-1-carboxamide | $^1$H NMR (400 MHz, DMSO-$d_6$/$D_2$O, Temp = 90° C.) δ ppm 8.55 (dd, J = 6.6, 1.8 Hz, 1H), 8.52-8.43 (m, 1H), 7.88-7.74 (m, 1H), 7.47-7.27 (m, 3H), 6.85-6.60 (m, 2H), 5.05-4.91 (m, 1H), 4.66-4.46 (m, 2H), 4.39 (dd, J = 10.5, 6.3 Hz, 2H), 4.11-3.94 (m, 4H), 3.93-3.80 (m, 1H), 1.13 (s, 9H) | (ESI(+)) m/e 409 (M + H)$^+$ |
| 129 | N-{4-[(1-butanoylazetidin-3-yl)oxy]phenyl}-3-(pyridin-3-yl)azetidine-1-carboxamide | $^1$H NMR (400 MHz, DMSO-$d_6$/$D_2$O, Temp = 90° C.) δ ppm 8.54 (d, J = 2.1 Hz, 1H), 8.46 (dd, J = 4.8, 1.5 Hz, 1H), 7.81 (dt, J = 7.8, 1.9 Hz, 1H), 7.46-7.35 (m, 3H), 6.85-6.67 (m, 2H), 5.02-4.89 (m, 1H), 4.39 (t, J = 8.4 Hz, 4H), 4.01-3.84 (m, 4H), 2.06 (t, J = 7.3 Hz, 2H), 1.52 (h, J = 7.3 Hz, 2H), 0.89 (t, J = 7.4 Hz, 3H) | (ESI(+)) m/e 395 (M + H)$^+$ |
| 130 | N-{4-[(1-propanoylazetidin-3-yl)oxy]phenyl}-3-(pyridin-3-yl)azetidine-1-carboxamide | $^1$H NMR (400 MHz, DMSO-$d_6$/$D_2$O, Temp = 90° C.) δ ppm 8.54 (d, J = 3.3 Hz, 1H), 8.51-8.41 (m, 1H), 7.93-7.70 (m, 1H), 7.50-7.31 (m, 3H), 6.84-6.72 (m, 2H), 5.00-4.88 (m, 1H), 4.49-4.32 (m, 4H), 4.08-3.82 (m, 5H), 2.19-2.02 (m, 2H), 1.00 (t, J = 7.5 Hz, 3H) | (ESI(+)) m/e 381 (M + H)$^+$ |
| 131 | N-(4-{[1-(2,2-dimethylbutanoyl)azetidin-3-yl]oxy}phenyl)-3-(pyridin-3-yl)azetidine-1-carboxamide | $^1$H NMR (400 MHz, DMSO-$d_6$/$D_2$O, Temp = 90° C.) δ ppm 8.54 (t, J = 2.6 Hz, 1H), 8.51-8.38 (m, 1H), 7.92-7.73 (m, 1H), 7.46-7.34 (m, 3H), 6.86-6.67 (m, 2H), 5.02-4.88 (m, 1H), 4.64-4.46 (m, 2H), 4.39 (t, J = 8.4 Hz, 2H), 4.07-3.96 (m, 4H), 3.92-3.84 (m, 1H), 1.49 (q, J = 7.4 Hz, 2H), 1.09 (s, 6H), 0.80 (t, J = 7.4 Hz, 3H) | (ESI(+)) m/e 423 (M + H)$^+$ |
| 132 | N-(4-{[1-(3-methylbutanoyl)azetidin-3-yl]oxy}phenyl)-3-(pyridin-3-yl)azetidine-1-carboxamide | $^1$H NMR (400 MHz, DMSO-$d_6$/$D_2$O, Temp = 90° C.) δ ppm 8.54 (d, J = 2.1 Hz, 1H), 8.46 (dd, J = 4.7, 1.4 Hz, 1H), 7.89-7.73 (m, 1H), 7.48-7.30 (m, 3H), 6.87-6.74 (m, 2H), 5.00-4.89 (m, 1H), 4.39 (t, J = 8.4 Hz, 4H), 4.08-3.79 (m, 5H), 1.99-1.86 (m, 3H), 1.02-0.85 (m, 6H) | (ESI(+)) m/e 409 (M + H)$^+$ |
| 133 | N-(4-{[1-(3,3-dimethylbutanoyl)azetidin-3-yl]oxy}phenyl)-3-(pyridin-3-yl)azetidine-1-carboxamide | $^1$H NMR (400 MHz, DMSO-$d_6$/$D_2$O, Temp = 90° C.) δ ppm 8.54 (d, J = 2.1 Hz, 1H), 8.46 (dd, J = 4.8, 1.4 Hz, 1H), 7.94-7.74 (m, 1H), 7.47-7.26 (m, 3H), 6.76 (d, J = 9.0 Hz, 2H), 5.04-4.83 (m, 1H), 4.39 (t, J = 8.3 Hz, 3H), 3.96 (dd, J = 16.5, 8.5 Hz, 3H), 3.88 (dd, J = 14.3, 6.0 Hz, 2H), 1.98 (s, 2H), 0.99 (s, 9H) | (ESI(+)) m/e 423 (M + H)$^+$ |
| 134 | 3-(pyridin-3-yl)-N-(4-{[1-(3,3,3-trifluoropropanoyl)azetidin-3-yl]oxy}phenyl)azetidine-1-carboxamide | $^1$H NMR (400 MHz, DMSO-$d_6$/$D_2$O, Temp = 90° C.) δ ppm 8.54 (d, J = 2.1 Hz, 1H), 8.51-8.38 (m, 1H), 7.97-7.74 (m, 1H), 7.52-7.27 (m, 3H), 6.87-6.68 (m, 2H), 5.12-4.93 (m, 1H), 4.58 (s, 1H), 4.44-4.31 (m, 3H), 4.14 (s, 1H), 4.03-3.80 (m, 4H), 3.33-3.26 (m, 2H) | (ESI(+)) m/e 435 (M + H)$^+$ |
| 135 | N-[4-({1-[(1-methylcyclopropyl)carbonyl]azetidin-3-yl}oxy)phenyl]-3-(pyridin-3-yl)azetidine-1-carboxamide | $^1$H NMR (400 MHz, DMSO-$d_6$/$D_2$O, Temp = 90° C.) δ ppm 8.62-8.52 (m, 1H), 8.52-8.36 (m, 1H), 7.90-7.72 (m, 1H), 7.46-7.33 (m, 3H), 6.83-6.70 (m, 2H), 5.06-4.84 (m, 1H), 4.59-4.46 (m, 2H), 4.46-4.29 (m, 2H), 4.05-3.95 (m, 4H), 3.91-3.80 (m, 1H), 1.25 (s, 3H), 1.09-0.81 (m, 2H), 0.63-0.39 (m, 2H) | (ESI(+)) m/e 407 (M + H)$^+$ |

TABLE 1-continued

The following Examples were prepared essentially as described in Example 1, substituting the appropriate alcohol in Example 1A, the appropriate amine in Example 1C and the appropriate carboxylic acid in Example 1E. Some products were purified by flash chromatography while others were purified by reverse-phase HPLC. Accordingly, some Examples were isolated as trifluoroacetic acid salts.

| Ex | Name | $^1$H NMR | MS |
|----|------|-----------|-----|
| 136 | N-(4-{[1-(2-methylpentanoyl)azetidin-3-yl]oxy}phenyl)-3-(pyridin-3-yl)azetidine-1-carboxamide | $^1$H NMR (400 MHz, DMSO-d$_6$/D$_2$O, Temp = 90° C.) δ ppm 8.54 (s, 1H), 8.46 (d, J = 4.7 Hz, 1H), 7.81 (d, J = 7.9 Hz, 1H), 7.40 (t, J = 7.5 Hz, 3H), 6.76 (d, J = 8.8 Hz, 2H), 4.97 (s, 1H), 4.39 (t, J = 8.2 Hz, 4H), 4.12-3.78 (m, 5H), 2.37 (dd, J = 12.8, 6.3 Hz, 1H), 1.63-1.41 (m, 1H), 1.26 (s, 4H), 0.99 (d, J = 6.7 Hz, 3H), 0.86 (t, J = 6.9 Hz, 3H) | (ESI(+)) m/e 423 (M + H)$^+$ |
| 137 | N-{4-[(1-acetylazetidin-3-yl)oxy]phenyl}-3-(pyridin-3-yl)azetidine-1-carboxamide | $^1$H NMR (400 MHz, DMSO-d$_6$/D$_2$O, Temp = 90° C.) δ ppm 8.54 (d, J = 2.1 Hz, 1H), 8.46 (dd, J = 4.8, 1.5 Hz, 1H), 7.85-7.77 (m, 1H), 7.46-7.33 (m, 3H), 6.81-6.69 (m, 2H), 5.05-4.84 (m, 1H), 4.39 (t, J = 8.4 Hz, 4H), 4.03-3.93 (m, 3H), 3.93-3.83 (m, 1H), 1.80 (s, 3H) | (ESI(+)) m/e 367 (M + H)$^+$ |
| 138 | N-(4-{[1-(cyclohexylacetyl)azetidin-3-yl]oxy}phenyl)-3-(pyridin-3-yl)azetidine-1-carboxamide | $^1$H NMR (400 MHz, DMSO-d$_6$/D$_2$O, Temp = 90° C.) δ ppm 8.54 (d, J = 2.1 Hz, 1H), 8.52-8.36 (m, 1H), 7.85-7.73 (m, 1H), 7.43-7.26 (m, 3H), 6.77-6.70 (m, 2H), 5.13-4.90 (m, 1H), 4.41 (dd, J = 24.5, 16.0 Hz, 4H), 4.04-3.77 (m, 5H), 1.96 (t, J = 6.8 Hz, 2H), 1.72-1.66 (m, 4H), 1.28-1.13 (m, 4H), 1.03-0.91 (m, 3H) | (ESI(+)) m/e 449 (M + H)$^+$ |
| 139 | N-(4-{[1-(cyclohexylcarbonyl)azetidin-3-yl]oxy}phenyl)-3-(pyridin-3-yl)azetidine-1-carboxamide | $^1$H NMR (400 MHz, DMSO-d$_6$/D$_2$O, Temp = 90° C.) δ ppm 8.54 (d, J = 2.2 Hz, 1H), 8.51-8.42 (m, 1H), 7.88-7.74 (m, 1H), 7.50-7.28 (m, 3H), 6.83-6.66 (m, 2H), 5.04-4.87 (m, 1H), 4.39 (t, J = 8.4 Hz, 4H), 4.04-3.82 (m, 5H), 2.31-2.15 (m, 1H), 1.76-1.57 (m, 6H), 1.38-1.24 (m, 4H) | (ESI(+)) m/e 435 (M + H)$^+$ |
| 140 | N-(4-{[1-(cyclopropylcarbonyl)azetidin-3-yl]oxy}phenyl)-3-(pyridin-3-yl)azetidine-1-carboxamide | $^1$H NMR (400 MHz, DMSO-d$_6$/D$_2$O, Temp = 90° C.) δ ppm 8.54 (d, J = 2.1 Hz, 1H), 8.49-8.30 (m, 1H), 7.91-7.72 (m, 1H), 7.48-7.34 (m, 3H), 6.85-6.68 (m, 2H), 5.12-4.93 (m, 1H), 4.55-4.34 (m, 4H), 4.08-3.84 (m, 5H), 1.63-1.47 (m, 1H), 0.82-0.66 (m, 5H) | (ESI(+)) m/e 393 (M + H)$^+$ |
| 141 | 3-(pyridin-3-yl)-N-(4-{[1-(thiophen-2-ylcarbonyl)azetidin-3-yl]oxy}phenyl)azetidine-1-carboxamide | $^1$H NMR (400 MHz, DMSO-d$_6$/D$_2$O, Temp = 90° C.) δ ppm 8.55 (d, J = 1.9 Hz, 1H), 8.47 (dd, J = 4.8, 1.3 Hz, 1H), 7.82 (d, J = 7.9 Hz, 1H), 7.75 (dd, J = 5.0, 1.0 Hz, 1H), 7.53 (dd, J = 3.7, 1.0 Hz, 1H), 7.49-7.35 (m, 3H), 7.16 (dd, J = 4.9, 3.8 Hz, 1H), 6.86-6.70 (m, 2H), 5.18-4.96 (m, 1H), 4.68 (s, 2H), 4.40 (t, J = 8.4 Hz, 2H), 4.19 (s, 1H), 4.03-3.83 (m, 4H) | (ESI(+)) m/e 435 (M + H)$^+$ |
| 142 | N-(4-{[1-(cyclopentylcarbonyl)azetidin-3-yl]oxy}phenyl)-3-(pyridin-3-yl)azetidine-1-carboxamide | $^1$H NMR (400 MHz, DMSO-d$_6$/D$_2$O, Temp = 90° C.) δ ppm 8.54 (d, J = 2.1 Hz, 1H), 8.46 (dd, J = 4.8, 1.5 Hz, 1H), 7.81 (dt, J = 7.8, 1.9 Hz, 1H), 7.47-7.31 (m, 3H), 6.83-6.70 (m, 2H), 5.05-4.90 (m, 1H), 4.39 (t, J = 8.4 Hz, 4H), 4.07-3.81 (m, 5H), 2.65 (dt, J = 15.1, 7.7 Hz, 1H), 1.83-1.70 (m, 2H), 1.70-1.45 (m, 6H) | (ESI(+)) m/e 421 (M + H)$^+$ |
| 143 | N-(4-{[1-(morpholin-4-ylacetyl)azetidin-3-yl]oxy}phenyl)-3-(pyridin-3-yl)azetidine-1-carboxamide | $^1$H NMR (400 MHz, DMSO-d$_6$/D$_2$O, Temp = 90° C.) δ ppm 8.68-8.50 (m, 1H), 8.52-8.39 (m, 1H), 7.94-7.73 (m, 1H), 7.46-7.33 (m, 3H), 6.86-6.63 (m, 2H), 5.03-4.89 (m, 1H), 4.61-4.31 (m, 4H), 4.02-3.83 (m, 5H), 3.65-3.47 (m, 4H), 2.57-2.49 (m, 2H), 2.49-2.38 (m, 4H) | (ESI(+)) m/e 452 (M + H)$^+$ |
| 144 | 3-(pyridin-3-yl)-N-(4-{[1-(1,3-thiazol-5-ylcarbonyl)azetidin-3-yl]oxy}phenyl)azetidine-1-carboxamide | $^1$H NMR (400 MHz, DMSO-d$_6$/D$_2$O, Temp = 90° C.) δ ppm 9.19 (s, 1H), 8.55 (d, J = 2.1 Hz, 1H), 8.46 (dd, J = 4.8, 1.5 Hz, 1H), 8.26 (s, 1H), 7.81 (d, J = 7.9 Hz, 1H), 7.49-7.32 (m, 3H), 6.87-6.72 (m, 2H), 5.18-4.97 (m, 1H), 4.69 (s, 2H), 4.40 (t, J = 8.4 Hz, 2H), 4.21 (s, 2H), 4.03-3.94 (m, 2H), 3.89 (dt, J = 8.6, 7.2 Hz, 1H), 3.20 (s, 1H) | (ESI(+)) m/e 436 (M + H)$^+$ |

TABLE 1-continued

The following Examples were prepared essentially as described in Example 1, substituting the appropriate alcohol in Example 1A, the appropriate amine in Example 1C and the appropriate carboxylic acid in Example 1E. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 145 | N-[4-({1-[(3,5-dimethyl-1,2-oxazol-4-yl)carbonyl]azetidin-3-yl}oxy)phenyl]-3-(pyridin-3-yl)azetidine-1-carboxamide | $^1$H NMR (400 MHz, DMSO-d$_6$/D$_2$O, Temp = 90° C.) δ ppm 8.55 (t, J = 4.4 Hz, 1H), 8.50-8.41 (m, 1H), 7.85-7.76 (m, 1H), 7.44-7.32 (m, 3H), 6.80-6.72 (m, 2H), 5.03 (tt, J = 6.4, 4.1 Hz, 1H), 4.50-4.36 (m, 4H), 4.06-3.92 (m, 4H), 3.92-3.82 (m, 1H), 3.20 (s, 1H), 2.44 (s, 3H), 2.24 (s, 3H) | (ESI(+)) m/e 436 (M + H)$^+$ |
| 146 | 3-(pyridin-3-yl)-N-(4-{[1-(thiophen-3-ylcarbonyl)azetidin-3-yl]oxy}phenyl)azetidine-1-carboxamide | $^1$H NMR (400 MHz, DMSO-d$_6$/D$_2$O, Temp = 90° C.) δ ppm 8.54 (d, J = 1.9 Hz, 1H), 8.53-8.43 (m, 1H), 7.96 (dd, J = 2.9, 1.2 Hz, 1H), 7.81 (dd, J = 7.9, 1.8 Hz, 1H), 7.55 (dd, J = 5.1, 2.9 Hz, 1H), 7.43-7.34 (m, 4H), 6.82-6.74 (m, 2H), 5.09-5.00 (m, 1H), 4.62 (s, 2H), 4.39 (t, J = 8.3 Hz, 2H), 4.15 (s, 2H), 4.02-3.93 (m, 2H), 3.94-3.86 (m, 1H) | (ESI(+)) m/e 435 (M + H)$^+$ |
| 147 | 3-(pyridin-3-yl)-N-(4-{[1-(1,3-thiazol-4-ylcarbonyl)azetidin-3-yl]oxy}phenyl)azetidine-1-carboxamide | $^1$H NMR (400 MHz, DMSO-d$_6$/D$_2$O, Temp = 90° C.) δ ppm 9.08 (d, J = 2.0 Hz, 1H), 8.54 (d, J = 2.1 Hz, 1H), 8.46 (dd, J = 4.8, 1.5 Hz, 1H), 8.28 (d, J = 2.1 Hz, 1H), 7.91-7.73 (m, 1H), 7.50-7.30 (m, 3H), 6.85-6.72 (m, 2H), 5.13-4.98 (m, 1H), 4.58 (s, 2H), 4.40 (t, J = 8.4 Hz, 3H), 4.31-4.01 (m, 1H), 3.98 (dd, J = 8.0, 6.0 Hz, 2H), 3.93-3.80 (m, 1H) | (ESI(+)) m/e 436 (M + H)$^+$ |
| 148 | N-(4-{[1-(1,2-oxazol-5-ylcarbonyl)azetidin-3-yl]oxy}phenyl)-3-(pyridin-3-yl)azetidine-1-carboxamide | $^1$H NMR (400 MHz, DMSO-d$_6$/D$_2$O, Temp = 90° C.) δ ppm 8.61 (t, J = 12.7 Hz, 1H), 8.55 (d, J = 2.0 Hz, 1H), 8.47 (dd, J = 4.7, 1.3 Hz, 1H), 7.82 (d, J = 7.9 Hz, 1H), 7.47-7.38 (m, 3H), 6.96 (d, J = 1.9 Hz, 1H), 6.86-6.72 (m, 2H), 5.16-5.06 (m, 1H), 4.58 (s, 2H), 4.40 (t, J = 8.4 Hz, 3H), 3.97 (dt, J = 15.9, 7.8 Hz, 3H), 3.93-3.84 (m, 1H) | (ESI(+)) m/e 420 (M + H)$^+$ |
| 149 | N-[4-({1-[(4-methylpiperazin-1-yl)acetyl]azetidin-3-yl}oxy)phenyl]-3-(pyridin-3-yl)azetidine-1-carboxamide | $^1$H NMR (400 MHz, DMSO-d$_6$/D$_2$O, Temp = 90° C.) δ ppm 8.59-8.51 (m, 1H), 8.51-8.38 (m, 1H), 7.85-7.78 (m, 1H), 7.44-7.33 (m, 3H), 6.80-6.71 (m, 2H), 5.02-4.91 (m, 1H), 4.71-4.50 (m, 1H), 4.46-4.32 (m, 3H), 4.06-3.95 (m, 3H), 3.93-3.82 (m, 2H), 3.06-2.93 (m, 2H), 2.49-2.39 (m, 5H), 2.38-2.28 (m, 5H), 2.16 (s, 4H) | (ESI(+)) m/e 465 (M + H)$^+$ |
| 150 | N-(4-{[1-(N,N-dimethyl-beta-alanyl)azetidin-3-yl]oxy}phenyl)-3-(pyridin-3-yl)azetidine-1-carboxamide | $^1$H NMR (400 MHz, DMSO-d$_6$/D$_2$O, Temp = 90° C.) δ ppm 8.54 (s, 1H), 8.46 (d, J = 4.8 Hz, 1H), 7.80 (d, J = 7.8 Hz, 1H), 7.45-7.29 (m, 3H), 6.76 (dd, J = 11.5, 4.7 Hz, 2H), 5.05-4.93 (m, 1H), 4.52 (s, 1H), 4.39 (t, J = 8.4 Hz, 3H), 4.11 (s, 2H), 4.05-3.94 (m, 2H), 3.90 (dd, J = 14.3, 8.1 Hz, 1H), 2.73 (s, 6H), 2.56 (d, J = 6.7 Hz, 2H) | (ESI(+)) m/e 424 (M + H)$^+$ |
| 151 | N-(4-{[1-(furan-3-ylcarbonyl)azetidin-3-yl]oxy}phenyl)-3-(pyridin-3-yl)azetidine-1-carboxamide | $^1$H NMR (500 MHz, DMSO-d$_6$, Temp = 90° C.) δ ppm 8.57 (d, J = 2.1 Hz, 1H), 8.54-8.47 (m, 1H), 8.43 (s, 1H), 8.19 (s, 1H), 7.92-7.84 (m, 1H), 7.76 (t, J = 1.6 Hz, 1H), 7.48-7.40 (m, 3H), 6.80-6.75 (m, 2H), 5.09-4.99 (m, 1H), 4.78-4.71 (m, 1H), 4.50-4.41 (m, 1H), 4.37 (t, J = 8.3 Hz, 2H), 4.32 (d, J = 7.2 Hz, 1H), 3.94 (dd, J = 7.9, 6.1 Hz, 2H), 3.92-3.77 (m, 2H) | (ESI(+)) m/e 419 (M + H)$^+$ |
| 152 | N-[4-({1-[(1-methylcyclohexyl)carbonyl]azetidin-3-yl}oxy)phenyl]-3-(pyridin-3-yl)azetidine-1-carboxamide | $^1$H NMR (400 MHz, DMSO-d$_6$/D$_2$O, Temp = 90° C.) δ ppm 8.60-8.53 (m, 1H), 8.52-8.42 (m, 1H), 7.81 (ddd, J = 7.9, 4.7, 1.5 Hz, 1H), 7.46-7.32 (m, 3H), 6.80-6.71 (m, 3H), 4.98-4.90 (m, 1H), 4.56-4.42 (m, 2H), 4.40 (dd, J = 10.9, 5.8 Hz, 2H), 4.00 (ddd, J = 14.0, 10.2, 8.8 Hz, 3H), 3.93-3.82 (m, 1H), 1.55-1.29 (m, 8H), 1.31-1.15 (m, 4H), 1.09 (s, 4H) | (ESI(+)) m/e 449 (M + H)$^+$ |

TABLE 1-continued

The following Examples were prepared essentially as described in Example 1, substituting the appropriate alcohol in Example 1A, the appropriate amine in Example 1C and the appropriate carboxylic acid in Example 1E. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 153 | N-(4-{[1-(cyclopentylacetyl)azetidin-3-yl]oxy}phenyl)-3-(pyridin-3-yl)azetidine-1-carboxamide | $^1$H NMR (400 MHz, DMSO-d$_6$/D$_2$O, Temp = 90° C.) δ ppm 8.54 (d, J = 2.2 Hz, 1H), 8.46 (dd, J = 4.8, 1.5 Hz, 1H), 7.81 (dt, J = 7.9, 1.9 Hz, 1H), 7.47-7.33 (m, 3H), 6.83-6.72 (m, 3H), 5.04-4.85 (m, 1H), 4.39 (t, J = 8.4 Hz, 3H), 3.99-3.93 (m, 2H), 3.93-3.79 (m, 2H), 2.14 (dt, J = 11.5, 5.8 Hz, 1H), 2.08 (d, J = 1.9 Hz, 1H), 1.82-1.69 (m, 2H), 1.64-1.40 (m, 5H), 1.24-1.01 (m, 2H) | (ESI(+)) m/e 435 (M + H)$^+$ |
| 154 | 3-(pyridin-3-yl)-N-(4-{[1-(1,3-thiazol-2-ylcarbonyl)azetidin-3-yl]oxy}phenyl)azetidine-1-carboxamide | $^1$H NMR (400 MHz, DMSO-d$_6$/D$_2$O, Temp = 90° C.) δ ppm 8.55 (d, J = 1.9 Hz, 1H), 8.52-8.40 (m, 1H), 7.99 (d, J = 3.1 Hz, 1H), 7.92 (d, J = 3.2 Hz, 1H), 7.81 (dt, J = 7.9, 1.9 Hz, 1H), 7.48-7.38 (m, 3H), 6.85-6.77 (m, 2H), 5.10 (td, J = 6.2, 3.2 Hz, 1H), 4.51 (s, 1H), 4.40 (t, J = 8.4 Hz, 3H), 4.07 (s, 1H), 4.06-3.93 (m, 3H), 3.89 (dt, J = 8.5, 7.1 Hz, 1H) | (ESI(+)) m/e 436 (M + H)$^+$ |
| 155 | 3-(pyridin-3-yl)-N-(4-{[1-(pyrrolidin-1-ylacetyl)azetidin-3-yl]oxy}phenyl)azetidine-1-carboxamide | $^1$H NMR (400 MHz, DMSO-d$_6$/D$_2$O, Temp = 90° C.) δ ppm 8.54 (s, 1H), 8.46 (d, J = 4.3 Hz, 1H), 7.81 (dd, J = 7.9, 1.9 Hz, 1H), 7.49-7.34 (m, 3H), 6.81-6.72 (m, 2H), 5.05-4.94 (m, 1H), 4.52 (s, 1H), 4.39 (t, J = 8.4 Hz, 3H), 4.11 (s, 1H), 3.97 (dd, J = 8.0, 6.0 Hz, 3H), 3.94-3.88 (m, 1H), 3.78 (s, 2H), 3.11 (s, 4H), 2.00-1.81 (m, 4H) | (ESI(+)) m/e 436 (M + H)$^+$ |
| 297 | N-(4-{[(3R)-1-pentanoylpyrrolidin-3-yl]oxy}phenyl)-3-(pyridin-3-yl)azetidine-1-carboxamide | | (ESI(+)) m/e 423 (M + H)$^+$ |
| 298 | N-(4-{[(3R)-1-(3-methylpentanoyl)pyrrolidin-3-yl]oxy}phenyl)-3-(pyridin-3-yl)azetidine-1-carboxamide | | (ESI(+)) m/e 437 (M + H)$^+$ |
| 299 | N-(4-{[1-(bicyclo[2.2.1]hept-2-ylacetyl)pyrrolidin-3-yl]oxy}phenyl)-3-(pyridin-3-yl)azetidine-1-carboxamide | | (ESI(+)) m/e 475 (M + H)$^+$ |
| 300 | N-(4-{[(3R)-1-(cyclopentylacetyl)pyrrolidin-3-yl]oxy}phenyl)-3-(pyridin-3-yl)azetidine-1-carboxamide | | (ESI(+)) m/e 449 (M + H)$^+$ |
| 301 | N-[4-({(3R)-1-[(2-methylcyclopropyl)carbonyl]pyrrolidin-3-yl}oxy)phenyl]-3-(pyridin-3-yl)azetidine-1-carboxamide | | (ESI(+)) m/e 421 (M + H)$^+$ |
| 302 | N-(4-{[(3R)-1-(morpholin-4-ylacetyl)pyrrolidin-3-yl]oxy}phenyl)-3-(pyridin-3-yl)azetidine-1-carboxamide | | (ESI(+)) m/e 466 (M + H)$^+$ |
| 303 | N-(4-{[(3R)-1-(furan-3-ylcarbonyl)pyrrolidin- | | (ESI(+)) m/e 433 (M + H)$^+$ |

TABLE 1-continued

The following Examples were prepared essentially as described in Example 1, substituting the appropriate alcohol in Example 1A, the appropriate amine in Example 1C and the appropriate carboxylic acid in Example 1E. Some products were purified by flash chromatography while others were purified by reverse-phase HPLC. Accordingly, some Examples were isolated as trifluoroacetic acid salts.

| Ex  | Name | $^1$H NMR | MS |
|-----|------|-----------|-----|
|     | 3-yl]oxy}phenyl)-3-(pyridin-3-yl)azetidine-1-carboxamide | | |
| 304 | 3-(pyridin-3-yl)-N-(4-{[(3R)-1-(pyrrolidin-1-ylacetyl)pyrrolidin-3-yl]oxy}phenyl)azetidine-1-carboxamide | | (ESI(+)) m/e 450 (M + H)$^+$ |
| 305 | N-(4-{[(3R)-1-(5-oxo-D-prolyl)pyrrolidin-3-yl]oxy}phenyl)-3-(pyridin-3-yl)azetidine-1-carboxamide | | (ESI(+)) m/e 450 (M + H)$^+$ |
| 306 | N-(4-{[(3R)-1-(N,N-dimethyl-beta-alanyl)pyrrolidin-3-yl]oxy}phenyl)-3-(pyridin-3-yl)azetidine-1-carboxamide | | (ESI(+)) m/e 438 (M + H)$^+$ |
| 307 | 3-(pyridin-3-yl)-N-(4-{[(3R)-1-(1,3-thiazol-2-ylcarbonyl)pyrrolidin-3-yl]oxy}phenyl)azetidine-1-carboxamide | | (ESI(+)) m/e 450 (M + H)$^+$ |
| 308 | 3-(pyridin-3-yl)-N-(4-{[(3R)-1-(thiophen-3-ylcarbonyl)pyrrolidin-3-yl]oxy}phenyl)azetidine-1-carboxamide | | (ESI(+)) m/e 449 (M + H)$^+$ |
| 309 | N-[4-({(3R)-1-[(1-methylcyclopropyl)carbonyl]pyrrolidin-3-yl}oxy)phenyl]-3-(pyridin-3-yl)azetidine-1-carboxamide | | (ESI(+)) m/e 421 (M + H)$^+$ |
| 310 | N-[4-({(3R)-1-[(3-methylthiophen-2-yl)carbonyl]pyrrolidin-3-yl}oxy)phenyl]-3-(pyridin-3-yl)azetidine-1-carboxamide | | (ESI(+)) m/e 463 (M + H)$^+$ |
| 311 | 3-(pyridin-3-yl)-N-(4-{[(3R)-1-(4,4,4-trifluorobutanoyl)pyrrolidin-3-yl]oxy}phenyl)azetidine-1-carboxamide | | (ESI(+)) m/e 463 (M + H)$^+$ |
| 312 | N-[4-({(3R)-1-[(4-methylpiperazin-1-yl)acetyl]pyrrolidin-3-yl}oxy)phenyl]-3-(pyridin-3-yl)azetidine-1-carboxamide | | (ESI(+)) m/e 479 (M + H)$^+$ |
| 313 | N-(4-{[(3R)-1-(5-oxo-L-prolyl)pyrrolidin-3-yl]oxy}phenyl)-3-(pyridin-3-yl)azetidine-1-carboxamide | | (ESI(+)) m/e 450 (M + H)$^+$ |

TABLE 1-continued

The following Examples were prepared essentially as described in Example 1, substituting the appropriate alcohol in Example 1A, the appropriate amine in Example 1C and the appropriate carboxylic acid in Example 1E. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 314 | N-(4-{[(3R)-1-(3-ethoxypropanoyl)pyrrolidin-3-yl]oxy}phenyl)-3-(pyridin-3-yl)azetidine-1-carboxamide | | (ESI(+)) m/e 439 (M + H)$^+$ |
| 315 | N-(4-{[(3R)-1-(4-methylpentanoyl)pyrrolidin-3-yl]oxy}phenyl)-3-(pyridin-3-yl)azetidine-1-carboxamide | | (ESI(+)) m/e 437 (M + H)$^+$ |
| 316 | N-[4-({(3R)-1-[(1-methylcyclohexyl)carbonyl]pyrrolidin-3-yl}oxy)phenyl]-3-(pyridin-3-yl)azetidine-1-carboxamide | | (ESI(+)) m/e 463 (M + H)$^+$ |
| 317 | N-(4-{[(3R)-1-(cyclohexylacetyl)pyrrolidin-3-yl]oxy}phenyl)-3-(pyridin-3-yl)azetidine-1-carboxamide | | (ESI(+)) m/e 463 (M + H)$^+$ |
| 318 | N-(4-{[(3R)-1-(N-acetyl-L-leucyl)pyrrolidin-3-yl]oxy}phenyl)-3-(pyridin-3-yl)azetidine-1-carboxamide | | (ESI(+)) m/e 494 (M + H)$^+$ |
| 319 | N-(4-{[(3R)-1-propanoylpyrrolidin-3-yl]oxy}phenyl)-3-(pyridin-3-yl)azetidine-1-carboxamide | | (ESI(+)) m/e 395 (M + H)$^+$ |
| 320 | N-[4-({(3R)-1-[(2-methoxyethoxy)acetyl]pyrrolidin-3-yl}oxy)phenyl]-3-(pyridin-3-yl)azetidine-1-carboxamide | | (ESI(+)) m/e 455 (M + H)$^+$ |
| 321 | N-[4-({(3R)-1-[3-(morpholin-4-yl)propanoyl]pyrrolidin-3-yl}oxy)phenyl]-3-(pyridin-3-yl)azetidine-1-carboxamide | | (ESI(+)) m/e 480 (M + H)$^+$ |
| 322 | N-(4-{[(3R)-1-(2,2-dimethylpropanoyl)pyrrolidin-3-yl]oxy}phenyl)-3-(pyridin-3-yl)azetidine-1-carboxamide | | (ESI(+)) m/e 423 (M + H)$^+$ |
| 323 | N-[4-({(3R)-1-[(5-methylthiophen-2-yl)carbonyl]pyrrolidin-3-yl}oxy)phenyl]-3-(pyridin-3-yl)azetidine-1-carboxamide | | (ESI(+)) m/e 463 (M + H)$^+$ |
| 324 | 3-(pyridin-3-yl)-N-(4-{[(3R)-1-(thiophen-2- | | (ESI(+)) m/e 449 (M + H)$^+$ |

TABLE 1-continued

The following Examples were prepared essentially as described in Example 1, substituting the appropriate alcohol in Example 1A, the appropriate amine in Example 1C and the appropriate carboxylic acid in Example 1E. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
|  | ylcarbonyl)pyrrolidin-3-yl]oxy}phenyl)azetidine-1-carboxamide |  |  |
| 325 | N-[4-({(3R)-1-[(1-methyl-1H-pyrrol-2-yl)carbonyl]pyrrolidin-3-yl}oxy)phenyl]-3-(pyridin-3-yl)azetidine-1-carboxamide |  | (ESI(+)) m/e 446 (M + H)$^+$ |
| 326 | N-(4-{[(3R)-1-(furan-2-ylcarbonyl)pyrrolidin-3-yl]oxy}phenyl)-3-(pyridin-3-yl)azetidine-1-carboxamide |  | (ESI(+)) m/e 433 (M + H)$^+$ |
| 327 | N-[4-({(3R)-1-[3-(piperidin-1-yl)propanoyl]pyrrolidin-3-yl}oxy)phenyl]-3-(pyridin-3-yl)azetidine-1-carboxamide |  | (ESI(+)) m/e 478 (M + H)$^+$ |
| 328 | N-(4-{[(3R)-1-(ethoxyacetyl)pyrrolidin-3-yl]oxy}phenyl)-3-(pyridin-3-yl)azetidine-1-carboxamide |  | (ESI(+)) m/e 425 (M + H)$^+$ |
| 329 | N-(4-{[(3R)-1-(3,3-dimethylbutanoyl)pyrrolidin-3-yl]oxy}phenyl)-3-(pyridin-3-yl)azetidine-1-carboxamide |  | (ESI(+)) m/e 437 (M + H)$^+$ |
| 330 | N-(4-{[(3R)-1-(2,2-dimethylbutanoyl)pyrrolidin-3-yl]oxy}phenyl)-3-(pyridin-3-yl)azetidine-1-carboxamide |  | (ESI(+)) m/e 437 (M + H)$^+$ |
| 331 | N-(4-{[(3R)-1-(methoxyacetyl)pyrrolidin-3-yl]oxy}phenyl)-3-(pyridin-3-yl)azetidine-1-carboxamide |  | (ESI(+)) m/e 411 (M + H)$^+$ |
| 332 | N-(4-{[(3R)-1-(cyclohexylcarbonyl)pyrrolidin-3-yl]oxy}phenyl)-3-(pyridin-3-yl)azetidine-1-carboxamide |  | (ESI(+)) m/e 449 (M + H)$^+$ |
| 333 | N-(4-{[(3R)-1-(3-methylbutanoyl)pyrrolidin-3-yl]oxy}phenyl)-3-(pyridin-3-yl)azetidine-1-carboxamide |  | (ESI(+)) m/e 423 (M + H)$^+$ |
| 334 | N-(4-{[(3R)-1-(cyclopentylcarbonyl)pyrrolidin-3-yl]oxy}phenyl)-3-(pyridin-3- |  | (ESI(+)) m/e 435 (M + H)$^+$ |

TABLE 1-continued

The following Examples were prepared essentially as described in Example 1, substituting the appropriate alcohol in Example 1A, the appropriate amine in Example 1C and the appropriate carboxylic acid in Example 1E. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| | yl)azetidine-1-carboxamide | | |
| 335 | N-(4-{[(3R)-1-(2,3-dimethylbutanoyl)pyrrolidin-3-yl]oxy}phenyl)-3-(pyridin-3-yl)azetidine-1-carboxamide | | (ESI(+)) m/e 437 (M + H)$^+$ |

Example 9

N-(4-{1-[(2S)-2-methylbutanoyl]-1,2,3,6-tetrahydropyridin-4-yl}phenyl)-3-(pyridin-3-yl)azetidine-1-carboxamide

Example 9A tert-butyl 4-(4-nitrophenyl)-5,6-dihydropyridine-1(2H)-carboxylate In a 350 mL sealed pressure flask were mixed 1-bromo-4-nitrobenzene (4.00 g, 19.80 mmol), tert-butyl 4-(4,4,5,5-tetramethyl-1,3,2-dioxaborolan-2-yl)-5,6-dihydropyridine-1(2H)-carboxylate (6.74 g, 21.78 mmol), and sodium carbonate (4.41 g, 41.6 mmol) in tetrahydrofuran (60 ml), water (30 ml), and methanol (10 ml). The mixture was put through three vacuum/nitrogen purge cycles. [1,1'-Bis(diphenylphosphino)ferrocene]dichloropalladium(II) dichloromethane (0.485 g, 0.594 mmol) was added, and the reaction mixture was heated overnight at 70° C. under nitrogen. The reaction mixture was cooled, diluted with ethyl acetate and water, and the layers were separated. The aqueous layer was extracted with ethyl acetate and the combined organic layers were concentrated. Normal phase chromatography provided the title compound.

Example 9B tert-butyl 4-(4-aminophenyl)-5,6-dihydropyridine-1(2H)-carboxylate The title compound was prepared as described in Example 1B, substituting tert-butyl 4-(4-nitrophenyl)-5,6-dihydropyridine-1(2H)-carboxylate for tert-butyl 3-(4-nitrophenoxy)azetidine-1-carboxylate.

Example 9C tert-butyl 4-(4-(3-(pyridin-3-yl)azetidine-1-carboxamido)phenyl)-5,6-dihydropyridine-1(2H)-carboxylate The title compound was prepared as described in Example 1C, substituting tert-butyl 4-(4-aminophenyl)-5,6-dihydropyridine-1(2H)-carboxylate for tert-butyl 3-(4-aminophenoxy)azetidine-1-carboxylate.

Example 9D 3-(pyridin-3-yl)-N-(4-(1,2,3,6-tetrahydropyridin-4-yl)phenyl)azetidine-1-carboxamide The title compound was prepared as described in Example 1D, substituting tert-butyl 4-(4-(3-(pyridin-3-yl)azetidine-1-carboxamido)phenyl)piperidine-1-carboxylate for tert-butyl 3-(4-(3-(pyridin-3-yl)azetidine-1-carboxamido)phenoxy)azetidine-1-carboxylate.

Example 9E

N-(4-{1-[(2S)-2-methylbutanoyl]-1,2,3,6-tetrahydropyridin-4-yl}phenyl)-3-(pyridin-3-yl)azetidine-1-carboxamide The title compound was prepared as described in Example 1E, substituting 3-(pyridin-3-yl)-N-(4-(1,2,3,6-tetrahydropyridin-4-yl)phenyl)azetidine-1-carboxamide for N-(4-(azetidin-3-yloxy)phenyl)-3-(pyridin-3-yl)azetidine-1-carboxamide. $^1$H NMR (300 MHz, DMSO-d$_6$) δ 8.59-8.53 (m, 2H), 8.52-8.45 (m, 1H), 7.99-7.83 (m, 1H), 7.57-7.45 (m, 2H), 7.41 (ddd, J=7.8, 4.8, 0.9 Hz, 1H), 7.39-7.30 (m, 2H), 6.10 (bs, 1H), 4.39 (d, J=16.4 Hz, 2H), 4.23-4.14 (m, 1H), 4.13-4.06 (m, 1H), 4.07-3.82 (m, 3H), 3.72-3.65 (m, 2H), 2.86-2.56 (m, 1H), 1.67-1.46 (m, 1H), 1.41-1.22 (m, 1H), 1.00 (t, J=6.8 Hz, 3H), 0.92-0.76 (m, 3H); MS (ESI(+)) m/e 419 (M+H).

TABLE 2

The following Examples were prepared essentially as described in Example 9, substituting the appropriate carboxylic acid in Example 9E. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 10 | 3-(pyridine-3-yl)-N-(4-{1-[(2R)- | $^1$H NMR (300 MHz, DMSO-d$_6$) δ 8.57 (d, J = 2.3 Hz, 1H), 8.48 (dd, J = 4.7, 1.6 Hz, | (ESI(+)) m/e 433 |

TABLE 2-continued

The following Examples were prepared essentially as described in Example 9, substituting the appropriate carboxylic acid in Example 9E. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
|  | tetrahydrofuran-2-ylcarbonyl]-1,2,3,6-tetrahydropyridin-4-yl}phenyl)azetidine-1-carboxamide | 1H), 7.87 (dt, J = 7.9, 2.0 Hz, 1H), 7.54-7.47 (m, 2H), 7.45-7.37 (m, 1H), 7.32 (d, J = 2.1 Hz, 1H), 6.09 (bs, 1H), 4.70 (ddd, J = 16.9, 7.5, 5.6 Hz, 1H), 4.38 (t, J = 8.2 Hz, 2H), 4.25-3.55 (m, 5H), 2.16-1.91 (m, 2H), 1.92-1.75 (m, 2H) | (M + H)$^+$ |
| 11 | 3-(pyridine-3-yl)-N-(4-{1-[(2S)-tetrahydrofuran-2-ylcarbonyl]-1,2,3,6-tetrahydropyridin-4-yl}phenyl)azetidine-1-carboxamide | $^1$H NMR (300 MHz, DMSO-d$_6$) δ 8.57 (d, J = 2.3 Hz, 1H), 8.48 (dd, J = 4.7, 1.6 Hz, 1H), 7.87 (dt, J = 7.9, 2.0 Hz, 1H), 7.55-7.27 (m, 5H), 6.09 (bs, 1H), 4.77-4.63 (m, 1H), 4.39 (t, J = 8.2 Hz, 2H), 4.23-3.48 (m, 2H), 2.19-1.72 (m, 4H) | (ESI(+)) m/e 433 (M + H)$^+$ |
| 12 | N-{4-[1-(2-hydroxy-2-methylpropanoyl)-1,2,3,6-tetrahydropyridin-4-yl]phenyl}-3-(pyridin-3-yl)azetidine-1-carboxamide | $^1$H NMR (300 MHz, DMSO-d$_6$) δ 8.57 (d, J = 2.3 Hz, 2H), 8.48 (dd, J = 4.7, 1.6 Hz, 1H), 7.87 (dt, J = 7.9, 2.0 Hz, 1H), 7.52 (s, 1H), 7.45-7.37 (m, 1H), 7.33 (s, 1H), 6.14-6.08 (m, 1H), 5.43 (s, 1H), 4.38 (t, J = 8.2 Hz, 2H), 4.22-3.76 (m, 6H), 1.40-1.23 (m, 6H) | (ESI(+)) m/e 421 (M + H)$^+$ |
| 16 | N-{4-[1-(2,2-dimethylbutanoyl)-1,2,3,6-tetrahydropyridin-4-yl]phenyl}-3-(pyridin-3-yl)azetidine-1-carboxamide | $^1$H NMR (400 MHz, DMSO-d$_6$/D$_2$O Temp = 90° C.) ☐ ppm 8.47-8.61 (m, 2 H) 7.88 (d, 1 H) 7.39-7.52 (m, J = 8.54 Hz, 3 H) 7.27-7.38 (m, J = 8.54 Hz, 2 H) 6.09 (s, 1 H) 4.42 (t, J = 8.24 Hz, 2 H) 4.12-4.19 (m, 2 H) 3.88-4.06 (m, 3 H) 3.74 (t, J = 5.80 Hz, 2 H) 2.93 (d, J = 4.58 Hz, 2 H) 1.56-1.70 (m, J = 7.32 Hz, 2 H) 1.20 (s, 6 H) 0.81 (t, J = 7.32 Hz, 3 H) | (APCI(+)) m/e 433 (M + H)$^+$ |
| 17 | N-{4-[1-(3,3-dimethylbutanoyl)-1,2,3,6-tetrahydropyridin-4-yl]phenyl}-3-(pyridin-3-yl)azetidine-1-carboxamide | $^1$H NMR (400 MHz, DMSO-d$_6$/D$_2$O Temp = 90° C.) ☐ ppm 8.61 (d, 2 H) 7.95 (d, 1 H) 7.50-7.58 (m, J = 12.82 Hz, 1 H) 7.43-7.49 (m, J = 8.54 Hz, 2 H) 7.25-7.35 (m, 2 H) 6.06 (s, 1 H) 4.42 (t, J = 8.24 Hz, 2 H) 4.13 (s, 2 H) 3.97-4.06 (m, 2 H) 3.69 (t, J = 5.65 Hz, 3 H) 2.92 (s, 2 H) 2.29 (s, 2 H) 1.01 (s, 9 H) | (APCI(+)) m/e 433 (M + H)$^+$ |
| 18 | 3-(pyridin-3-yl)-N-{4-[1-(3,3,3-trifluoropropanoyl)-1,2,3,6-tetrahydropyridin-4-yl]phenyl}azetidine-1-carboxamide | $^1$H NMR (400 MHz, DMSO-d$_6$/D$_2$O Temp = 90° C.) ☐ ppm 8.61 (d, 2 H) 7.96 (d, 1 H) 7.39-7.60 (m, 3 H) 7.26-7.36 (m, 2 H) 6.06 (s, 1 H) 4.43 (t, J = 8.24 Hz, 2 H) 4.13 (s, 2 H) 3.89-4.05 (m, 3 H) 3.49-3.75 (m, 4 H) 2.93 (s, 2 H) | (APCI(+)) m/e 445 (M + H)$^+$ |
| 19 | 3-(pyridin-3-yl)-N-{4-[1-(4,4,4-trifluorobutanoyl)-1,2,3,6-tetrahydropyridin-4-yl]phenyl}azetidine-1-carboxamide | $^1$H NMR (400 MHz, DMSO-d$_6$/D$_2$O Temp = 90° C.) ☐ ppm 8.61 (d, 2 H) 7.95 (d, 1 H) 7.50-7.57 (m, 1 H) 7.47 (d, J = 8.54 Hz, 2 H) 7.32 (d, J = 8.85 Hz, 2 H) 6.06 (s, 1 H) 4.42 (t, J = 8.24 Hz, 2 H) 4.13 (s, 2 H) 3.89-4.05 (m, 3 H) 3.68 (t, J = 5.49 Hz, 3 H) 2.93 (s, 1 H) 2.56-2.72 (m, J = 25.94 Hz, 4 H) | (APCI(+)) m/e 459 (M + H)$^+$ |
| 20 | N-{4-[1-(methoxyacetyl)-1,2,3,6-tetrahydropyridin-4-yl]phenyl}-3-(pyridin-3-yl)azetidine-1-carboxamide | $^1$H NMR (400 MHz, DMSO-d$_6$/D$_2$O) ☐ ppm 8.64 (d, 2 H) 8.02 (d, 1 H) 7.55-7.61 (m, 1 H) 7.46 (d, J = 8.85 Hz, 2 H) 7.31 (d, 2 H) 6.06 (s, 1 H) 4.43 (t, J = 8.24 Hz, 2 H) 4.06-4.16 (m, 4 H) 3.91-4.05 (m, 3 H) 3.64 (t, J = 5.65 Hz, 2 H) 3.33 (s, 3 H) 2.92 (s, 2 H) | (APCI(+)) m/e 407 (M + H)$^+$ |
| 21 | N-(4-{1-[(methylsulfanyl)acetyl]-1,2,3,6-tetrahydropyridin-4-yl}phenyl)-3-(pyridin-3-yl)azetidine-1-carboxamide | $^1$H NMR (400 MHz, DMSO-d$_6$) ☐ ppm 8.64 (d, 2 H) 8.03 (d, J = 8.24 Hz, 1 H) 7.53-7.61 (m, J = 12.82 Hz, 1 H) 7.47 (d, J = 8.54 Hz, 2 H) 7.27-7.37 (m, 2 H) 6.07 (s, 1 H) 4.43 (t, J = 8.24 Hz, 2 H) 4.14 (s, 2 H) 3.94-4.06 (m, 3 H) 3.68 (t, J = 5.65 Hz, 2 H) 3.42 (s, 2 H) 2.93 (s, 2 H) 2.12 (s, 3 H) | (APCI(+)) m/e 423 (M + H)$^+$ |
| 22 | N-{4-[1-(ethoxyacetyl)-1,2,3,6-tetrahydropyridin-4- | $^1$H NMR (400 MHz, DMSO-d$_6$) ☐ ppm 8.63 (d, 2 H) 8.00 (d, 1 H) 7.53-7.63 (m, J = 13.12 Hz, 1 H) 7.46 (d, J = 8.54 Hz, 2 H) 7.32 (d, J = 8.54 Hz, 2 H) 6.06 (s, 1 H) | (APCI(+)) m/e 421 (M + H)$^+$ |

TABLE 2-continued

The following Examples were prepared essentially as described in Example 9, substituting the appropriate carboxylic acid in Example 9E. Some products were purified by flash chromatography while others were purified by reverse-phase HPLC. Accordingly, some Examples were isolated as trifluoroacetic acid salts.

| Ex | Name | ¹H NMR | MS |
|---|---|---|---|
|  | yl]phenyl}-3-(pyridin-3-yl)azetidine-1-carboxamide | 4.43 (t, J = 8.24 Hz, 2 H) 4.08-4.20 (m, 4 H) 3.92-4.07 (m, 3 H) 3.66 (t, J = 5.80 Hz, 2 H) 3.45-3.56 (m, 2 H) 2.92 (s, 2 H) 1.10-1.20 (m, 3 H) |  |
| 23 | N-(4-{1-[(2-methoxyethoxy)acetyl]-1,2,3,6-tetrahydropyridin-4-yl}phenyl)-3-(pyridin-3-yl)azetidine-1-carboxamide | ¹H NMR (400 MHz, DMSO-d₆) □ ppm 8.63 (d, 2 H) 8.00 (d, 1 H) 7.52-7.60 (m, 1 H) 7.46 (d, J = 8.85 Hz, 2 H) 7.32 (d, J = 8.85 Hz, 2 H) 6.06 (s, 1 H) 4.43 (t, J = 8.24 Hz, 2 H) 4.19 (s, 2 H) 4.10 (s, 3 H) 3.92-4.05 (m, 3 H) 3.56-3.71 (m, 5 H) 3.47-3.53 (m, 3 H) 2.92 (s, 2 H) | (APCI(+)) m/e 451 (M + H)⁺ |
| 24 | N-(4-{1-[3-(methylsulfanyl)propanoyl]-1,2,3,6-tetrahydropyridin-4-yl}phenyl)-3-(pyridin-3-yl)azetidine-1-carboxamide | ¹H NMR (400 MHz, DMSO-d₆) □ ppm 8.61 (d, 2 H) 7.96 (d, 1 H) 7.50-7.56 (m, 1 H) 7.47 (d, J = 8.54 Hz, 2 H) 7.32 (d, J = 8.54 Hz, 2 H) 6.06 (s, 1 H) 4.42 (t, J = 8.39 Hz, 2 H) 4.12 (s, 2 H) 3.91-4.04 (m, 3 H) 3.67 (t, J = 5.65 Hz, 2 H) 2.92 (s, 2 H) 2.65-2.76 (m, J = 16.33, 5.65 Hz, 4 H) 2.08 (s, 3 H) | (APCI(+)) m/e 437 (M + H)⁺ |
| 25 | N-{4-[1-(cyclopropylcarbonyl)-1,2,3,6-tetrahydropyridin-4-yl]phenyl}-3-(pyridin-3-yl)azetidine-1-carboxamide | ¹H NMR (400 MHz, DMSO-d₆) □ ppm 8.64 (d, 2 H) 8.03 (d, 1 H) 7.58 (dd, J = 7.63, 5.49 Hz, 1 H) 7.47 (d, J = 8.85 Hz, 2 H) 7.32 (d, 2 H) 6.08 (s, 1 H) 4.43 (t, J = 8.24 Hz, 2 H) 4.22 (s, 2 H) 3.91-4.07 (m, 3 H) 3.78 (s, 2 H) 2.93 (s, 2 H) 1.90-2.01 (m, 1 H) 0.71-0.82 (m, 4 H) | (APCI(+)) m/e 403 (M + H)⁺ |
| 26 | N-{4-[1-(cyclopropylacetyl)-1,2,3,6-tetrahydropyridin-4-yl]phenyl}-3-(pyridin-3-yl)azetidine-1-carboxamide | ¹H NMR (400 MHz, DMSO-d₆) □ ppm 8.62 (d, 2 H) 7.96 (d, 1 H) 7.50-7.55 (m, J = 12.21 Hz, 1 H) 7.46 (d, J = 8.54 Hz, 2 H) 7.32 (d, J = 8.54 Hz, 2 H) 6.06 (s, 1 H) 4.42 (t, J = 8.24 Hz, 2 H) 4.08-4.12 (m, J = 2.44 Hz, 2 H) 3.90-4.04 (m, 3 H) 3.66 (t, J = 5.65 Hz, 2 H) 2.92 (s, 2 H) 2.32 (d, J = 6.71 Hz, 2 H) 0.95-1.06 (m, 1 H) 0.42-0.51 (m, 2 H) 0.09-0.20 (m, 2 H) | (APCI(+)) m/e 417 (M + H)⁺ |
| 27 | N-{4-[1-(2-methylpropanoyl)-1,2,3,6-tetrahydropyridin-4-yl]phenyl}-3-(pyridin-3-yl)azetidine-1-carboxamide | ¹H NMR (300 MHz, DMSO-d₆) δ 8.57 (d, J = 2.4 Hz, 1H), 8.48 (dd, J = 4.7, 1.6 Hz, 1H), 7.87 (dt, J = 7.9, 2.0 Hz, 1H), 7.54-7.30 (m, 5H), 6.10 (bs, 1H), 4.39 (t, J = 8.2 Hz, 2H), 4.23-4.15 (m, 1H), 4.11-4.04 (m, 1H), 4.01-3.86 (m, 3H), 3.72-3.63 (m, 2H), 3.06-2.83 (m, 1H), 2.40 (s, 1H), 1.06-0.97 (m, 6H) | (ESI(+)) m/e 405 (M + H)⁺ |

Example 13 methyl 4-({[3-(pyridin-3-yl)azetidin-1-yl]carbonyl}amino)benzoate

To a 20 mL vial was added 3-(azetidin-3-yl)pyridine, bistrifluoroacetic acid (75 mg, 0.207 mmol) and diisopropylethylamine (0.109 ml, 0.622 mmol) in dichloromethane (2072 µl). Methyl 4-isocyanatobenzoate (47.7 mg, 0.269 mmol) was added, and the mixture was stirred at room temperature for 2 hours and concentrated by rotary evaporation. The residue was purified by regular phase chromatography to give the title compound. ¹H NMR (300 MHz, DMSO-d₆) δ 8.90 (s, 1H), 8.57 (d, J=2.1 Hz, 1H), 8.48 (dd, J=4.8, 1.6 Hz, 1H), 7.91-7.82 (m, 3H), 7.71-7.64 (m, 2H), 7.41 (ddd, J=7.9, 4.7, 0.8 Hz, 1H), 4.42 (t, J=8.4 Hz, 2H), 4.05-3.96 (m, 2H), 3.89 (dt, J=8.1, 7.0 Hz, 1H), 3.81 (s, 1H); MS (ESI(+)) m/e 312 (M+H).

Example 14

N-(4-cyanophenyl)-3-(pyridin-3-yl)azetidine-1-carboxamide

The title compound was prepared as described in Example 13, substituting 4-isocyanatobenzonitrile for methyl 4-isocyanatobenzoate. ¹H NMR (300 MHz, DMSO-d₆) δ 8.99 (s, 1H), 8.57 (d, J=2.1 Hz, 1H), 8.48 (dd, J=4.7, 1.6 Hz, 1H), 7.88 (dt, J=7.9, 2.0 Hz, 1H), 7.79-7.65 (m, 4H), 7.41 (ddd, J=7.9, 4.7, 0.8 Hz, 1H), 4.42 (t, J=8.4 Hz, 2H), 4.11-3.84 (m, 3H); MS (ESI(+)) m/e 279 (M+H).

Example 15 tert-butyl 4-[4-({[3-(pyridin-3-yl)azetidin-1-yl]carbonyl}amino)butyl]piperidine-1-carboxylate The title compound was prepared as described in Example 1C, substituting tert-butyl 4-(4-aminobutyl)piperidine-1-carboxylate for tert-butyl 3-(4-aminophenoxy)azetidine-1- carboxylate. $^1$H NMR (300 MHz, DMSO-d$_6$) δ 8.54-8.43 (m, 1H), 7.99-7.68 (m, 1H), 7.39 (dd, J=7.9, 4.8 Hz, 1H), 6.34 (t, J=5.6 Hz, 1H), 4.24-4.14 (m, 1H), 4.09-3.67 (m, 4H), 3.12-2.88 (m, 2H), 2.80-2.59 (m, 2H), 1.65-1.40 (m, 3H), 1.43-1.13 (m, 7H), 1.06-0.80 (m, 2H); MS (ESI(+)) m/e 417 (M+H).

Example 49

3-(pyridin-3-yl)-N-{4-[(tetrahydrofuran-3-ylmethyl)carbamoyl]phenyl}azetidine-1-carboxamide

Example 49A 4-amino-N-((tetrahydrofuran-3-yl)methyl)benzamide

The title compound was prepared as described in Example 1E, substituting (tetrahydrofuran-3-yl)methanamine for N-(4-(azetidin-3-yloxy)phenyl)-3-(pyridin-3-yl)azetidine-1-carboxamide and 4-aminobenzoic acid for (S)-2-methylbutanoic acid.

Example 49B 3-(pyridin-3-yl)-N-{4-[(tetrahydrofuran-3-ylmethyl)carbamoyl]phenyl}azetidine-1-carboxamide The title compound was prepared as described in Example 1C, substituting 4-amino-N-((tetrahydrofuran-3-yl)methyl)benzamide for tert-butyl 3-(4-aminophenoxy)azetidine-1-carboxylate. $^1$H NMR (400 MHz, DMSO-d$_6$/D$_2$O Temp=90° C.) δ ppm 8.77 (d, J=1.7 Hz, 1H), 8.69-8.58 (m, 1H), 8.39 (d, J=8.1 Hz, 1H), 7.87 (dd, J=8.0, 5.4 Hz, 1H), 7.79-7.67 (m, 2H), 7.67-7.30 (m, 2H), 4.62-4.36 (m, 2H), 4.16-4.02 (m, 3H), 3.78-3.68 (m, 2H), 3.64 (dd, J=14.9, 7.8 Hz, 1H), 3.47 (dd, J=8.5, 5.6 Hz, 1H), 3.35-3.24 (m, 2H), 2.12-1.83 (m, 1H), 1.81-1.47 (m, 1H); MS (ESI(+)) m/e 381 (M+H)$^+$.

Example 50

3-(pyridin-3-yl)-N-{4-[1-(tetrahydro-2H-pyran-4-ylacetyl)piperidin-4-yl]phenyl}azetidine-1-carboxamide

Example 50A tert-butyl 4-(4-(3-(pyridin-3-yl)azetidine-1-carboxamido)phenyl)piperidine-1-carboxylate The title compound was prepared as described in Example 1C, substituting tert-butyl 4-(4-aminophenyl)piperidine-1-carboxylate for tert-butyl 3-(4-aminophenoxy)azetidine-1-carboxylate.

Example 50B

N-(4-(piperidin-4-yl)phenyl)-3-(pyridin-3-yl)azetidine-1-carboxamide

The title compound was prepared as described in Example 1D, substituting tert-butyl 4-(4-(3-(pyridin-3-yl)azetidine-1-carboxamido)phenyl)piperidine-1-carboxylate for tert-butyl 3-(4-(3-(pyridin-3-yl)azetidine-1-carboxamido)phenoxy)azetidine-1-carboxylate.

Example 50C

N-(4-{1-[(2S)-2-methylbutanoyl]-1,2,3,6-tetrahydropyridin-4-yl}phenyl)-3-(pyridin-3-yl)azetidine-1-carboxamide The title compound was prepared as described in Example 1E, substituting N-(4-(piperidin-4-yl)phenyl)-3-(pyridin-3-yl)azetidine-1-carboxamide for N-(4-(azetidin-3-yloxy)phenyl)-3-(pyridin-3-yl)azetidine-1-carboxamide and tetrahydro-2H-pyran-4-ylacetic acid for (S)-2-methylbutanoic acid. $^1$H NMR (300 MHz, DMSO-d$_6$) δ ppm 8.58 (d, J=1.7 Hz, 1H), 8.49 (d, J=3.4 Hz, 1H), 8.44 (s, 1H), 7.89 (dt, J=7.9, 1.9 Hz, 1H), 7.43 (dd, J=7.9, 5.6 Hz, 3H), 7.10 (d, J=8.6 Hz, 2H), 4.55 (d, J=12.8 Hz, 1H), 4.37 (t, J=8.1 Hz, 2H), 4.04-3.76 (m, 6H), 3.08 (dd, J=17.1, 9.4 Hz, 1H), 2.74-2.55 (m, 2H), 2.27 (d, J=6.9 Hz, 2H), 1.92 (ddd, J=14.8, 7.4, 3.8 Hz, 1H), 1.76 (t, J=11.6 Hz, 2H), 1.65-1.08 (m, 7H); MS (ESI(+)) m/e 463 (M+H).

TABLE 3

The following Examples were prepared essentially as described in Example 50, substituting the appropriate amine in Example 50A and the appropriate carboxylic acid in Example 50C. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 51 | N-{4-[1-(2-hydroxy-2-methylpropanoyl)piperidin-4-yl]phenyl}-3-(pyridin-3-yl)azetidine-1-carboxamide | $^1$H NMR (300 MHz, DMSO-d$_6$) δ 8.56 (d, J = 2.3 Hz, 1H), 8.48 (dd, J = 4.7, 1.6 Hz, 1H), 8.45 (s, 1H), 7.86 (dt, J = 7.9, 2.0 Hz, 1H), 7.46-7.37 (m, 3H), 7.10 (d, J = 8.6 Hz, 1H), 4.76 (bs, 1H), 4.37 (d, J = 16.2 Hz, 2H), 3.99-3.81 (m, 3H), 2.81-2.60 (m, 1H), 1.81-1.71 (m, 2H), 1.60-1.36 (m, 2H), 1.33 (s, 6H) | (ESI(+)) m/e 423 (M + H)$^+$ |
| 52 | 3-(pyridin-3-yl)-N-(4-{1-[(2S)-tetrahydrofuran-2-ylcarbonyl]piperidin-4-yl}phenyl)azetidine-1-carboxamide | $^1$H NMR (300 MHz, DMSO-d$_6$) δ 8.56 (d, J = 2.3 Hz, 1H), 8.48 (dd, J = 4.7, 1.6 Hz, 1H), 8.45 (s, 1H), 7.86 (dt, J = 7.9, 1.9 Hz, 1H), 7.46-7.37 (m, 3H), 7.14-7.07 (m, 2H), 4.68 (dd, J = 7.5, 5.7 Hz, 1H), 4.53-4.43 (m, 1H), 4.37 (t, J = 8.1 Hz, 2H), 4.15-4.05 (m, 1H), 4.03-3.68 (m, 5H), 3.17-2.98 (m, 1H), 2.80-2.59 (m, 2H), 2.29-1.93 (m, 2H), 1.94-1.70 (m, 4H), 1.62-1.31 (m, 2H) | (ESI(+)) m/e 435 (M + H)$^+$ |

TABLE 3-continued

The following Examples were prepared essentially as described in Example 50, substituting the appropriate amine in Example 50A and the appropriate carboxylic acid in Example 50C. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 53 | 3-(pyridin-3-yl)-N-{4-[1-(tetrahydrofuran-3-ylcarbonyl)piperidin-4-yl]phenyl}azetidine-1-carboxamide | $^1$H NMR (300 MHz, DMSO-d$_6$) δ 8.56 (d, J = 2.3 Hz, 1H), 8.52-8.37 (m, 1H), 7.86 (dt, J = 7.9, 2.0 Hz, 1H), 7.46-7.37 (m, 3H), 7.15-7.08 (m, 2H), 4.59-4.48 (m, 1H), 4.37 (t, J = 8.1 Hz, 2H), 4.11-4.01 (m, 1H), 4.00-3.80 (m, 4H), 3.78-3.62 (m, 3H), 3.46-3.34 (m, 1H), 3.20-3.02 (m, 1H), 2.77-2.59 (m, 2H), 2.10-1.91 (m, 2H), 1.93-1.70 (m, 2H), 1.61-1.29 (m, 2H) | (ESI(+)) m/e 435 (M + H)$^+$ |
| 54 | 3-(pyridin-3-yl)-N-(4-{1-[(2R)-tetrahydrofuran-2-ylcarbonyl]piperidin-4-yl}phenyl)azetidine-1-carboxamide | $^1$H NMR (400 MHz, DMSO-d$_6$) δ 8.56 (d, J = 2.3 Hz, 1H), 8.48 (dd, J = 4.7, 1.6 Hz, 1H), 8.45 (s, 1H), 7.86 (dt, J = 7.9, 1.9 Hz, 1H), 8.05-7.64 (m, 4H), 7.46-7.38 (m, 4H), 7.14-7.07 (m, 3H), 4.68 (dd, J = 7.6, 5.7 Hz, 1H), 4.52-4.44 (m, 1H), 4.37 (t, J = 8.3 Hz, 3H), 4.14-4.05 (m, 1H), 4.02-3.68 (m, 7H), 3.17-3.00 (m, 2H), 2.76-2.56 (m, 3H), 2.13-1.91 (m, 3H), 1.92-1.70 (m, 5H), 1.60-1.31 (m, 3H), 1.26 (d, J = 6.4 Hz, 1H) | (ESI(+)) m/e 435 (M + H)$^+$ |
| 55 | N-{4-[1-(cyclopropylacetyl)piperidin-4-yl]phenyl}-3-(pyridin-3-yl)azetidine-1-carboxamide | $^1$H NMR (400 MHz, DMSO-d$_6$) δ 8.45 (d, J = 2.3 Hz, 1H), 8.40-8.35 (m, 1H), 8.34 (s, 1H), 7.75 (dt, J = 7.9, 1.9 Hz, 1H), 7.35-7.27 (m, 3H), 7.03-6.96 (m, 2H), 4.48-4.39 (m, 1H), 4.26 (t, J = 8.2 Hz, 2H), 3.89-3.71 (m, 4H), 3.02-2.91 (m, 1H), 2.66-2.41 (m, 2H), 2.17 (d, J = 6.7 Hz, 2H), 1.70-1.59 (m, 2H), 1.48-1.18 (m, 2H), 0.93-0.79 (m, 1H), 0.38-0.27 (m, 2H), 0.02 (q, J = 4.8 Hz, 1H) | (ESI(+)) m/e 419 (M + H)$^+$ |
| 56 | N-{4-[1-(2-methylpropanoyl)piperidin-4-yl]phenyl}-3-(pyridin-3-yl)azetidine-1-carboxamide | $^1$H NMR (300 MHz, DMSO-d$_6$) δ 8.56 (d, J = 2.3 Hz, 1H), 8.48 (dd, J = 4.7, 1.6 Hz, 1H), 8.44 (s, 1H), 7.86 (dt, J = 7.9, 2.0 Hz, 1H), 7.47-7.36 (m, 3H), 7.15-7.07 (m, 2H), 4.60-4.49 (m, 1H), 4.37 (d, J = 16.2 Hz, 2H), 4.13-3.81 (m, 4H), 3.20-2.81 (m, 2H), 2.76-2.58 (m, 2H), 1.85-1.70 (m, 2H), 1.60-1.28 (m, 2H), 1.09-0.93 (m, 6H) | (ESI(+)) m/e 407 (M + H)$^+$ |
| 57 | N-[4-(1-benzoylpiperidin-4-yl)phenyl]-3-(pyridin-3-yl)azetidine-1-carboxamide | $^1$H NMR (300 MHz, DMSO-d$_6$) δ 8.56 (d, J = 2.3 Hz, 1H), 8.48 (dd, J = 4.7, 1.6 Hz, 1H), 8.44 (s, 1H), 7.86 (dt, J = 7.9, 2.0 Hz, 1H), 7.52-7.36 (m, 8H), 7.19-7.11 (m, 2H), 4.76-4.48 (m, 1H), 4.37 (d, J = 16.2 Hz, 2H), 4.03-3.81 (m, 3H), 3.77-3.50 (m, 1H), 3.23-2.63 (m, 3H), 1.97-1.46 (m, 4H) | (ESI(+)) m/e 441 (M + H)$^+$ |
| 58 | 3-(pyridin-3-yl)-N-{4-[1-(3,3,3-trifluoropropanoyl)piperidin-4-yl]phenyl}azetidine-1-carboxamide | $^1$H NMR (300 MHz, DMSO-d$_6$) δ 8.56 (d, J = 2.1 Hz, 1H), 8.48 (dd, J = 4.8, 1.6 Hz, 1H), 8.44 (s, 1H), 7.86 (dt, J = 7.9, 2.0 Hz, 1H), 7.50-7.35 (m, 3H), 7.14-7.07 (m, 2H), 4.56-4.46 (m, 1H), 4.37 (d, J = 16.2 Hz, 2H), 4.03-3.81 (m, 4H), 3.65 (q, J = 11.0 Hz, 1H), 3.20-3.04 (m, 1H), 2.77-2.57 (m, 2H), 1.82-1.72 (m, 2H), 1.64-1.22 (m, 2H) | (ESI(+)) m/e 447 (M + H)$^+$ |
| 64 | 3-(pyridin-3-yl)-N-{4-[1-(tetrahydro-2H-pyran-4-ylacetyl)pyrrolidin-3-yl]phenyl}azetidine-1-carboxamide | $^1$H NMR (300 MHz, DMSO-d$_6$) δ 8.77 (d, J = 2.1 Hz, 1H), 8.67 (dd, J = 5.2, 1.4 Hz, 1H), 8.51 (d, J = 2.4 Hz, 1H), 8.29 (dd, J = 8.2, 2.1 Hz, 1H), 7.80-7.71 (m, 1H), 7.46 (dd, J = 8.4, 3.6 Hz, 2H), 7.17 (t, J = 8.6 Hz, 2H), 4.47-4.31 (m, 2H), 4.06-3.90 (m, 3H), 3.92-3.72 (m, 3H), 3.69-3.41 (m, 2H), 3.39-3.20 (m, 4H), 2.20 (d, J = 7.5 Hz, 2H), 2.05-1.77 (m, 2H), 1.65-1.54 (m, 2H), 1.31-1.10 (m, 2H) | (ESI(+)) m/e 449 (M + H)$^+$ |
| 65 | N-{4-[1-(2-methylpropanoyl)pyrrolidin-3-yl]phenyl}-3-(pyridin-3-yl)azetidine-1-carboxamide | $^1$H NMR (300 MHz, DMSO-d$_6$) δ 8.57 (d, J = 2.3 Hz, 1H), 8.51-8.45 (m, 2H), 7.86 (dt, J = 7.9, 2.0 Hz, 1H), 7.50-7.37 (m, 3H), 7.23-7.12 (m, 2H), 4.38 (t, J = 8.1 Hz, 2H), 4.04-3.79 (m, 4H), 3.80-3.64 (m, 1H), 3.62-3.46 (m, 1H), 3.26-3.03 (m, 1H), 2.75-2.62 (m, 1H), 2.32-2.10 (m, 1H), 2.08-1.81 (m, 1H), 1.05-0.97 (m, 6H) | (ESI(+)) m/e 393 (M + H)$^+$ |
| 66 | 3-(pyridin-3-yl)-N-(4-{1-[(2S)-tetrahydrofuran-2- | $^1$H NMR (300 MHz, DMSO-d$_6$) δ 8.57 (d, J = 2.4 Hz, 1H), 8.51-8.45 (m, 2H), 7.86 (dt, J = 7.9, 2.0 Hz, 1H), 7.50-7.37 (m, 3H), 7.21-7.12 (m, 2H), 4.58-4.48 (m, 1H), 4.38 (t, J = 8.1 Hz, | (ESI(+)) m/e 421 (M + H)$^+$ |

TABLE 3-continued

The following Examples were prepared essentially as described in Example 50, substituting the appropriate amine in Example 50A and the appropriate carboxylic acid in Example 50C. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
|  | ylcarbonyl]pyrrolidin-3-yl}phenyl)azetidine-1-carboxamide | 2H), 4.07-3.38 (m, 9H), 3.25-3.05 (m, 1H), 2.31-2.08 (m, 1H), 2.11-1.71 (m, 5H) |  |
| 67 | 3-(pyridin-3-yl)-N-(4-{1-[(2R)-tetrahydrofuran-2-ylcarbonyl]pyrrolidin-3-yl}phenyl)azetidine-1-carboxamide | $^1$H NMR (300 MHz, DMSO-d$_6$) δ 8.57 (d, J = 2.4 Hz, 1H), 8.51-8.45 (m, 2H), 7.86 (dt, J = 7.9, 2.0 Hz, 1H), 7.50-7.37 (m, 3H), 7.21-7.12 (m, 2H), 4.58-4.48 (m, 1H), 4.38 (t, J = 8.1 Hz, 2H), 4.07-3.38 (m, 9H), 3.25-3.05 (m, 1H), 2.31-2.08 (m, 1H), 2.11-1.71 (m, 5H) | (ESI(+)) m/e 421 (M + H)$^+$ |
| 68 | 3-(pyridin-3-yl)-N-{4-[1-(tetrahydrofuran-3-ylcarbonyl)pyrrolidin-3-yl]phenyl}azetidine-1-carboxamide | $^1$H NMR (300 MHz, DMSO-d$_6$) δ 8.57 (d, J = 2.4 Hz, 1H), 8.51-8.45 (m, 2H), 7.86 (dt, J = 7.9, 2.0 Hz, 1H), 7.52-7.37 (m, 3H), 7.23-7.13 (m, 2H), 4.38 (t, J = 8.1 Hz, 2H), 4.04-3.40 (m, 10H), 3.24-2.87 (m, 2H), 2.33-2.11 (m, 1H), 2.12-1.79 (m, 3H) | (ESI(+)) m/e 421 (M + H)$^+$ |
| 69 | N-{4-[1-(cyclopropylacetyl)pyrrolidin-3-yl]phenyl}-3-(pyridin-3-yl)azetidine-1-carboxamide | $^1$H NMR (300 MHz, DMSO-d$_6$) δ 8.56 (d, J = 2.3 Hz, 1H), 8.51-8.45 (m, 2H), 7.86 (dt, J = 7.9, 2.0 Hz, 1H), 7.50-7.37 (m, 3H), 7.21-7.12 (m, 2H), 4.38 (d, J = 16.3 Hz, 2H), 4.04-3.75 (m, 4H), 3.66-3.40 (m, 2H), 3.24-2.96 (m, 2H), 2.34-2.10 (m, 3H), 2.04-1.80 (m, 1H), 1.05-0.92 (m, 1H), 0.50-0.35 (m, 2H), 0.20-0.08 (m, 2H) | (ESI(+)) m/e 405 (M + H)$^+$ |
| 70 | N-{4-[1-(2-hydroxy-2-methylpropanoyl)pyrrolidin-3-yl]phenyl}-3-(pyridin-3-yl)azetidine-1-carboxamide | $^1$H NMR (300 MHz, DMSO-d$_6$) δ 8.57 (d, J = 2.4 Hz, 1H), 8.51-8.45 (m, 2H), 7.86 (dt, J = 7.9, 2.0 Hz, 1H), 7.50-7.38 (m, 3H), 7.21-7.13 (m, 2H), 5.14 (d, J = 3.3 Hz, 1H), 4.43-4.23 (m, 3H), 4.12-3.81 (m, 4H), 3.75-3.39 (m, 2H), 2.26-2.06 (m, 1H), 1.95-1.75 (m, 1H), 1.34-1.27 (m, 6H) | (ESI(+)) m/e 409 (M + H)$^+$ |
| 71 | N-[4-(1-benzoylpyrrolidin-3-yl)phenyl]-3-(pyridin-3-yl)azetidine-1-carboxamide | $^1$H NMR (300 MHz, DMSO-d$_6$) δ 8.76 (bs, 1H), 8.66 (d, J = 6.2 Hz, 1H), 8.51 (d, J = 8.7 Hz, 1H), 8.31-8.22 (m, 1H), 7.78-7.69 (m, 1H), 7.60-7.32 (m, 7H), 7.22 (d, J = 8.2 Hz, 1H), 7.14 (d, J = 8.3 Hz, 1H), 4.39 (d, J = 5.1 Hz, 1H), 4.05-3.87 (m, 4H), 3.74-3.14 (m, 5H), 2.32-2.14 (m, 1H), 2.11-1.87 (m, 1H) | (ESI(+)) m/e 427 (M + H)$^+$ |
| 72 | 3-(pyridin-3-yl)-N-{4-[1-(3,3,3-trifluoropropanoyl)pyrrolidin-3-yl]phenyl}azetidine-1-carboxamide | $^1$H NMR (400 MHz, DMSO-d$_6$) δ 8.56 (bs, 1H), 8.49 (d, J = 9.5 Hz, 2H), 7.86 (dt, J = 7.9, 1.9 Hz, 1H), 7.51-7.34 (m, 3H), 7.17 (dd, J = 8.3, 5.2 Hz, 2H), 4.38 (t, J = 8.3 Hz, 2H), 4.04-3.75 (m, 4H), 3.74-3.46 (m, 4H), 3.30-3.13 (m, 2H), 2.35-2.14 (m, 1H), 2.29-1.81 (m, 1H) | (ESI(+)) m/e 433 (M + H)$^+$ |
| 73 | N-{4-[1-(cyclopropylcarbonyl)pyrrolidin-3-yl]phenyl}-3-(pyridin-3-yl)azetidine-1-carboxamide | $^1$H NMR (300 MHz, DMSO-d$_6$) δ 8.57 (d, J = 2.4 Hz, 1H), 8.51-8.45 (m, 2H), 7.86 (dt, J = 7.9, 1.9 Hz, 1H), 7.51-7.37 (m, 3H), 7.19 (dd, J = 12.4, 8.4 Hz, 2H), 4.38 (t, J = 8.1 Hz, 2H), 4.12-3.75 (m, 5H), 3.71-3.37 (m, 2H), 3.25-3.04 (m, 2H), 2.34-1.66 (m, 3H), 0.80-0.63 (m, 4H) | (ESI(+)) m/e 391 (M + H)$^+$ |
| 74 | N-(4-{1-[(2S)-2-methylbutanoyl]pyrrolidin-3-yl}phenyl)-3-(pyridin-3-yl)azetidine-1-carboxamide | $^1$H NMR (300 MHz, DMSO-d$_6$) δ 8.75 (bs, 1H), 8.65 (d, J = 5.3 Hz, 1H), 8.51 (d, J = 2.1 Hz, 1H), 8.24 (dd, J = 8.5, 2.3 Hz, 1H), 7.76-7.67 (m, 1H), 7.46 (dd, J = 8.5, 3.1 Hz, 2H), 7.23-7.12 (m, 2H), 4.47-4.30 (m, 3H), 4.06-3.88 (m, 4H), 3.84-3.43 (m, 2H), 3.43-3.01 (m, 2H), 2.31-2.11 (m, 1H), 2.07-1.80 (m, 1H), 1.66-1.46 (m, 1H), 1.40-1.20 (m, 1H), 1.04-0.95 (m, 3H), 0.88-0.77 (m, 3H) | (ESI(+)) m/e 467 (M + H)$^+$ |
| 75 | N-[4-(1-butanoylpyrrolidin-3-yl)phenyl]-3- |  | (ESI(+)) m/e 393 (M + H)$^+$ |

TABLE 3-continued

The following Examples were prepared essentially as described in Example 50, substituting the appropriate amine in Example 50A and the appropriate carboxylic acid in Example 50C. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
|  | (pyridin-3-yl)azetidine-1-carboxamide |  |  |
| 100 | 3-(pyridin-3-yl)-N-{4-[1-(tetrahydro-2H-pyran-4-ylacetyl)azetidin-3-yl]phenyl}azetidine-1-carboxamide | $^1$H NMR (300 MHz, DMSO-$d_6$) δ 8.77 (d, J = 2.2 Hz, 1H), 8.66 (dd, J = 5.2, 1.5 Hz, 1H), 8.55 (s, 1H), 8.32-8.24 (m, 1H), 7.75 (dd, J = 8.0, 5.2 Hz, 1H), 7.54-7.47 (m, 2H), 7.30-7.11 (m, 2H), 4.47 (dd, J = 14.6, 6.5 Hz, 2H), 4.43-4.32 (m, 1H), 4.30-4.11 (m, 1H), 4.12-3.92 (m, 4H), 3.86-3.65 (m, 4H), 3.34-3.22 (m, 2H), 2.06-1.83 (m, 3H), 1.63-1.52 (m, 2H), 1.29-1.06 (m, 2H) | (ESI(+)) m/e 435 (M + H)$^+$ |
| 101 | N-{4-[1-(2-methylpropanoyl)azetidin-3-yl]phenyl}-3-(pyridin-3-yl)azetidine-1-carboxamide | $^1$H NMR (400 MHz, DMSO-$d_6$/D$_2$O Temp = 90° C.) δ 8.73 (d, J = 2.2 Hz, 1H), 8.64 (dd, J = 5.3, 1.4 Hz, 1H), 8.31-8.24 (m, 1H), 7.77 (dd, J = 8.0, 5.3 Hz, 1H), 7.50-7.44 (m, 2H), 7.24-7.18 (m, 2H), 4.51-4.15 (m, 4H), 4.15-3.72 (m, 6H), 3.89-3.70 (m, 1H), 1.02 (d, J = 6.8 Hz, 6H) | (ESI(+)) m/e 379 (M + H)$^+$ |
| 102 | 3-(pyridin-3-yl)-N-(4-{1-[(2S)-tetrahydrofuran-2-ylcarbonyl]azetidin-3-yl}phenyl)azetidine-1-carboxamide | $^1$H NMR (300 MHz, DMSO-$d_6$) δ 8.78 (d, J = 2.1 Hz, 1H), 8.68 (dd, J = 5.2, 1.4 Hz, 1H), 8.55 (s, 1H), 8.30 (d, J = 8.6 Hz, 1H), 7.77 (dd, J = 8.0, 5.2 Hz, 1H), 7.52 (t, J = 9.0 Hz, 2H), 7.27-7.20 (m, 2H), 4.67-4.55 (m, 1H), 4.45-4.30 (m, 3H), 4.31-4.11 (m, 3H), 4.07-3.93 (m, 4H), 3.86-3.65 (m, 1H), 2.11-1.92 (m, 2H), 1.92-1.74 (m, 3H) | (ESI(+)) m/e 407 (M + H)$^+$ |
| 103 | 3-(pyridin-3-yl)-N-(4-{1-[(2R)-tetrahydrofuran-2-ylcarbonyl]azetidin-3-yl}phenyl)azetidine-1-carboxamide | $^1$H NMR (300 MHz, DMSO-$d_6$) δ 8.76 (t, J = 6.1 Hz, 1H), 8.66 (dt, J = 9.5, 4.8 Hz, 1H), 8.57 (d, J = 10.0 Hz, 1H), 8.28 (d, J = 8.1 Hz, 1H), 7.75 (dd, J = 7.9, 5.3 Hz, 1H), 7.50 (d, J = 8.4 Hz, 2H), 7.23 (d, J = 8.3 Hz, 2H), 4.69-4.46 (m, 1H), 4.47-4.29 (m, 3H), 4.08-3.88 (m, 3H), 3.88-3.58 (m, 3H), 2.29-1.72 (m, 4H) | (ESI(+)) m/e 407 (M + H)$^+$ |
| 104 | 3-(pyridin-3-yl)-N-{4-[1-(tetrahydrofuran-3-ylcarbonyl)azetidin-3-yl]phenyl}azetidine-1-carboxamide | $^1$H NMR (300 MHz, DMSO-$d_6$) δ 8.75 (d, J = 2.0 Hz, 1H), 8.64 (dd, J = 5.2, 1.4 Hz, 1H), 8.55 (s, 1H), 8.23 (d, J = 8.0 Hz, 1H), 7.71 (dd, J = 8.0, 5.2 Hz, 1H), 7.51 (d, J = 8.4 Hz, 1H), 7.24 (d, J = 8.4 Hz, 2H), 4.53 (dd, J = 15.0, 8.1 Hz, 2H), 4.47-4.33 (m, 2H), 4.16 (ddd, J = 14.1, 10.1, 4.6 Hz, 3H), 4.08-3.93 (m, 3H), 3.91-3.71 (m, 3H), 3.71-3.56 (m, 2H), 3.14-2.93 (m, 1H), 2.10-1.87 (m, 2H) | (ESI(+)) m/e 407 (M + H)$^+$ |
| 105 | N-{4-[1-(cyclopropylacetyl)azetidin-3-yl]phenyl}-3-(pyridin-3-yl)azetidine-1-carboxamide | $^1$H NMR (300 MHz, DMSO-$d_6$) δ 8.71 (d, J = 1.9 Hz, 1H), 8.61 (dd, J = 5.1, 1.5 Hz, 1H), 8.54 (s, 1H), 8.17 (d, J = 8.0 Hz, 1H), 7.66 (dd, J = 8.0, 5.1 Hz, 1H), 7.53-7.47 (m, 2H), 7.23 (d, J = 8.5 Hz, 2H), 4.53-4.31 (m, 2H), 4.20 (dd, J = 14.1, 6.7 Hz, 1H), 4.09-3.90 (m, 2H), 3.85-3.42 (m, 2H), 2.11 (d, J = 7.0 Hz, 2H), 2.03 (d, J = 6.8 Hz, 1H), 1.00-0.86 (m, 1H), 0.49-0.36 (m, 3H), 0.18-0.07 (m, 3H) | (ESI(+)) m/e 391 (M + H)$^+$ |
| 106 | N-{4-[1-(2-hydroxy-2-methylpropanoyl)azetidin-3-yl]phenyl}-3-(pyridin-3-yl)azetidine-1-carboxamide | $^1$H NMR (300 MHz, DMSO-$d_6$) δ 8.75 (d, J = 2.2 Hz, 1H), 8.64 (dd, J = 5.2, 1.5 Hz, 1H), 8.54 (s, 1H), 8.27-8.20 (m, 1H), 7.71 (dd, J = 8.0, 5.2 Hz, 1H), 7.57-7.40 (m, 2H), 7.28-7.14 (m, 2H), 4.86-4.65 (m, 2H), 4.45-4.30 (m, 3H), 4.21 (d, J = 8.2 Hz, 1H), 4.09-3.86 (m, 3H), 3.87-3.57 (m, 2H), 1.27 (s, 6H) | (ESI(+)) m/e 395 (M + H)$^+$ |
| 107 | N-[4-(1-benzoylazetidin-3-yl)phenyl]-3-(pyridin-3-yl)azetidine-1-carboxamide | $^1$H NMR (300 MHz, DMSO-$d_6$) δ 8.76 (d, J = 2.1 Hz, 1H), 8.66 (dd, J = 5.2, 1.5 Hz, 1H), 8.55 (s, 1H), 8.30-8.22 (m, 1H), 7.77-7.64 (m, 3H), 7.57-7.41 (m, 5H), 7.32-7.09 (m, 2H), 4.65 (t, J = 8.7 Hz, 2H), 4.50-4.31 (m, 3H), 4.28 (d, J = 7.1 Hz, 1H), 4.00 (q, J = 5.6 Hz, 3H), 3.91-3.71 (m, 1H) | (ESI(+)) m/e 413 (M + H)$^+$ |
| 108 | 3-(pyridin-3-yl)-N-{4-[1-(3,3,3- | $^1$H NMR (400 MHz, DMSO-$d_6$/D$_2$O Temp = 90° C.) δ 8.69 (d, J = 2.2 Hz, 1H), 8.63-8.54 (m, | (ESI(+)) m/e 419 |

TABLE 3-continued

The following Examples were prepared essentially as described in Example 50, substituting the appropriate amine in Example 50A and the appropriate carboxylic acid in Example 50C. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
|  | trifluoropropanoyl)azetidin-3-yl]phenyl}azetidine-1-carboxamide | 1H), 8.24-7.99 (m, 1H), 7.77-7.55 (m, 1H), 7.55-7.44 (m, 2H), 7.30-7.19 (m, 2H), 4.62-4.24 (m, 6H), 4.21-3.63 (m, 6H) | (M + H)$^+$ |
| 109 | N-{4-[1-(cyclopropylcarbonyl)azetidin-3-yl]phenyl}-3-(pyridin-3-yl)azetidine-1-carboxamide | $^1$H NMR (300 MHz, DMSO-d$_6$) δ 8.76 (d, J = 2.2 Hz, 1H), 8.66 (dd, J = 5.2, 1.5 Hz, 1H), 8.55 (s, 1H), 8.30-8.22 (m, 1H), 7.73 (dd, J = 8.0, 5.2 Hz, 1H), 7.55-7.48 (m, 2H), 7.33-7.11 (m, 2H), 4.62 (t, J = 8.1 Hz, 1H), 4.54-4.31 (m, 2H), 4.32-4.09 (m, 2H), 3.93 (dq, J = 10.9, 5.1 Hz, 2H), 3.92-3.61 (m, 2H), 1.63-1.51 (m, 1H), 0.73 (d, J = 2.0 Hz, 2H) | (ESI(+)) m/e 377 (M + H)$^+$ |
| 110 | N-(4-{1-[(2S)-2-methylbutanoyl]azetidin-3-yl}phenyl)-3-(pyridin-3-yl)azetidine-1-carboxamide | $^1$H NMR (300 MHz, DMSO-d$_6$) δ 8.78-8.68 (m, 1H), 8.67-8.61 (m, 1H), 8.54 (s, 1H), 8.27-8.19 (m, 1H), 7.75-7.67 (m, 1H), 7.54-7.47 (m, 2H), 7.33-7.14 (m, 2H), 4.99 (bs, 3H), 4.56-4.12 (m, 2H), 4.11-3.88 (m, 3H), 3.84-3.75 (m, 2H), 2.36-2.22 (m, 1H), 1.60-1.43 (m, 1H), 1.39-1.17 (m, 1H), 1.02-0.95 (m, 3H), 0.84 (t, J = 7.4 Hz, 3H) | (ESI(+)) m/e 393 (M + H)$^+$ |
| 111 | N-[4-(1-butanoylazetidin-3-yl)phenyl]-3-(pyridin-3-yl)azetidine-1-carboxamide | $^1$H NMR (300 MHz, DMSO-d$_6$) δ 8.75 (d, J = 2.2 Hz, 1H), 8.65 (dd, J = 5.2, 1.5 Hz, 1H), 8.55 (s, 1H), 8.24 (dt, J = 8.0, 1.8 Hz, 1H), 7.72 (dd, J = 8.0, 5.2 Hz, 1H), 7.54-7.47 (m, 2H), 7.20 (dd, J = 16.0, 8.6 Hz, 2H), 4.52-4.33 (m, 2H), 4.26-4.15 (m, 1H), 4.11-3.94 (m, 3H), 3.82-3.66 (m, 2H), 2.06 (t, J = 7.3 Hz, 2H), 1.59-1.50 (m, 1H), 1.52-1.43 (m, 2H), 1.02-0.74 (m, 4H) | (ESI(+)) m/e 379 (M + H)$^+$ |
| 156 | 3-(2-fluoropyridin-3-yl)-N-{4-[1-(2-hydroxy-2-methylpropanoyl)piperidin-4-yl]phenyl}azetidine-1-carboxamide | $^1$H NMR (300 MHz, DMSO-d$_6$) δ 8.44 (s, 1H), 8.14 (dt, J = 4.8, 1.5 Hz, 1H), 8.09-7.98 (m, 1H), 7.49-7.34 (m, 3H), 7.14-7.06 (m, 2H), 5.35 (s, 1H), 4.73 (bs, 1H), 4.39-4.28 (m, 2H), 4.08-3.92 (m, 4H), 3.23-2.59 (m, 3H), 1.80-1.70 (m, 2H), 1.71-1.36 (m, 2H), 1.33 (s, 6H) | (ESI(+)) m/e 441 (M + H)$^+$ |
| 159 | 3-(pyridin-3-yl)-N-(4-{1-[(3S)-tetrahydrofuran-3-ylcarbonyl]piperidin-4-yl}phenyl)azetidine-1-carboxamide | $^1$H NMR (500 MHz, DMSO-d$_6$) δ 8.57 (d, J = 2.3 Hz, 1H), 8.49 (dd, J = 4.8, 1.6 Hz, 1H), 8.47 (s, 1H), 7.88 (dt, J = 7.9, 1.9 Hz, 1H), 7.46-7.40 (m, 3H), 7.11 (d, J = 8.6 Hz, 2H), 4.57-4.50 (m, 1H), 4.37 (t, J = 8.3 Hz, 2H), 4.09-4.02 (m, 1H), 3.98-3.92 (m, 2H), 3.93-3.79 (m, 2H), 3.81-3.52 (m, 2H), 3.16-3.04 (m, 1H), 2.75-2.65 (m, 1H), 2.60 (d, J = 7.6 Hz, 1H), 2.10-1.94 (m, 2H), 1.83-1.72 (m, 2H), 1.59-1.32 (m, 2H), 1.34-1.21 (m, 2H) | (ESI(+)) m/e 435 (M + H)$^+$ |
| 160 | 3-(4-chloropyridin-3-yl)-N-(4-{1-[(3S)-tetrahydrofuran-3-ylcarbonyl]piperidin-4-yl}phenyl)azetidine-1-carboxamide | $^1$H NMR (500 MHz, DMSO-d$_6$) δ 8.70 (s, 1H), 8.58-8.38 (m, 2H), 7.57 (d, J = 5.2 Hz, 1H), 7.44-7.39 (m, 2H), 7.14-7.08 (m, 2H), 4.57-4.50 (m, 1H), 4.45-4.33 (m, 2H), 4.20-4.00 (m, 4H), 3.88 (dt, J = 12.2, 8.1 Hz, 1H), 3.78-3.63 (m, 3H), 3.20-3.04 (m, 1H), 2.75-2.56 (m, 2H), 2.10-1.94 (m, 2H), 1.82-1.71 (m, 2H), 1.56-1.32 (m, 2H) | (ESI(+)) m/e 469 (M + H)$^+$ |
| 161 | 3-(2-chloropyridin-3-yl)-N-{4-[1-(2-hydroxy-2-methylpropanoyl)piperidin-4-yl]phenyl}azetidine-1-carboxamide | $^1$H NMR (500 MHz, DMSO-d$_6$) δ 8.46 (s, 1H), 8.41-8.30 (m, 1H), 8.01 (dd, J = 7.7, 1.8 Hz, 1H), 7.56-7.43 (m, 1H), 7.44-7.39 (m, 2H), 7.13-7.07 (m, 2H), 5.37 (s, 1H), 5.03-4.45 (m, 2H), 4.42-4.30 (m, 2H), 4.12-3.99 (m, 3H), 3.29-2.58 (m, 3H), 1.79-1.72 (m, 2H), 1.63-1.40 (m, 2H), 1.33 (s, 6H) | (ESI(+)) m/e 457 (M + H)$^+$ |
| 163 | N-[4-(1-pentanoylpiperidin-4-yl)phenyl]-3- | $^1$H NMR (500 MHz, DMSO-d$_6$/D$_2$O Temp = 25° C.) ☐ ppm 8.88 (s, 1 H) 8.78 (d, J = 5.19 Hz, 1 H) 8.60 (d, J = 8.24 Hz, 1 H) 8.02 (dd, J = 7.93, | (ESI(+)) m/e 421 (M + H)$^+$ |

TABLE 3-continued

The following Examples were prepared essentially as described in Example 50, substituting the appropriate amine in Example 50A and the appropriate carboxylic acid in Example 50C. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
|  | (pyridin-3-yl)azetidine-1-carboxamide | 5.80 Hz, 1 H) 7.41 (d, J = 8.54 Hz, 2 H) 7.12 (d, J = 8.54 Hz, 2 H) 4.52 (d, J = 12.82 Hz, 1 H) 4.42 (t, J = 8.09 Hz, 2 H) 3.94-4.13 (m, 4 H) 3.09 (t, J = 12.21 Hz, 1 H) 2.54-2.76 (m, 2 H) 2.33 (t, 2 H) 1.72-1.82 (m, 2 H) 1.41-1.55 (m, 3 H) 1.25-1.41 (m, 3 H) 0.89 (t, J = 7.32 Hz, 3 H) |  |
| 164 | N-(4-{1-[(2-methylcyclopropyl)carbonyl]piperidin-4-yl}phenyl)-3-(pyridin-3-yl)azetidine-1-carboxamide | $^1$H NMR (500 MHz, DMSO-d$_6$/D$_2$O Temp = 25° C.) □ ppm 8.87 (s, 1 H) 8.76 (d, J = 5.49 Hz, 1 H) 8.56 (d, J = 7.93 Hz, 1 H) 7.99 (dd, J = 8.09, 5.65 Hz, 1 H) 7.41 (d, J = 8.54 Hz, 2 H) 7.13 (d, J = 8.54 Hz, 2 H) 4.28-4.54 (m, 4 H) 3.98-4.13 (m, 3 H) 3.09-3.22 (m, 1 H) 2.73 (t, J = 11.90 Hz, 1 H) 2.66 (t, 1 H) 1.68-1.92 (m, 3 H) 1.32-1.58 (m, 2 H) 1.10-1.24 (m, 1 H) 1.04-1.09 (m, 3 H) 0.89-1.00 (m, J = 31.89, 6.26 Hz, 1 H) 0.53-0.59 (m, 1 H) | (ESI(+)) m/e 419 (M + H)$^+$ |
| 165 | N-(4-{1-[(1S,4R)-bicyclo[2.2.1]hept-2-ylacetyl]piperidin-4-yl}phenyl)-3-(pyridin-3-yl)azetidine-1-carboxamide | $^1$H NMR (500 MHz, DMSO-d$_6$/D$_2$O Temp = 25° C.) □ ppm 8.88 (s, 1 H) 8.77 (d, J = 5.19 Hz, 1 H) 8.58 (d, J = 7.94 Hz, 1 H) 8.01 (dd, J = 7.93, 5.49 Hz, 1 H) 7.41 (d, J = 8.54 Hz, 2 H) 7.12 (d, J = 8.24 Hz, 2 H) 4.52 (d, J = 12.82 Hz, 1 H) 4.42 (t, J = 8.09 Hz, 2 H) 3.97-4.12 (m, 4 H) 3.08 (t, J = 12.05 Hz, 1 H) 2.65-2.76 (m, 1 H) 2.54-2.62 (m, 1 H) 2.32 (dd, J = 15.26, 7.93 Hz, 1 H) 2.12-2.21 (m, 2 H) 1.95 (d, J = 4.58 Hz, 1 H) 1.71-1.84 (m, 3 H) 1.31-1.55 (m, 6 H) 0.98-1.21 (m, 4 H) | (ESI(+)) m/e 473 (M + H)$^+$ |
| 166 | N-{4-[1-(4-methylpentanoyl)piperidin-4-yl]phenyl}-3-(pyridin-3-yl)azetidine-1-carboxamide | $^1$H NMR (500 MHz, DMSO-d$_6$/D$_2$O Temp = 25° C.) □ ppm 8.88 (s, 1 H) 8.77 (d, J = 5.49 Hz, 1 H) 8.58 (d, J = 7.93 Hz, 1 H) 8.01 (dd, J = 7.93, 5.80 Hz, 1 H) 7.41 (d, J = 8.54 Hz, 2 H) 7.11 (d, 2 H) 4.52 (d, J = 12.82 Hz, 1 H) 4.42 (t, J = 8.09 Hz, 2 H) 3.93-4.13 (m, 4 H) 3.04-3.15 (m, 1 H) 2.66-2.75 (m, 1 H) 2.55-2.62 (m, 1 H) 2.30-2.36 (m, 2 H) 1.78 (dd, J = 25.02, 12.82 Hz, 2 H) 1.45-1.63 (m, 2 H) 1.30-1.46 (m, 3 H) 0.88 (d, J = 6.41 Hz, 6 H) | (ESI(+)) m/e 435 (M + H)$^+$ |
| 167 | N-{4-[1-(3-methylpentanoyl)piperidin-4-yl]phenyl}-3-(pyridin-3-yl)azetidine-1-carboxamide | $^1$H NMR (500 MHz, DMSO-d$_6$/D$_2$O Temp = 25° C.) □ ppm 8.88 (s, 1 H) 8.77 (d, J = 5.49 Hz, 1 H) 8.58 (d, J = 8.24 Hz, 1 H) 8.01 (dd, J = 7.93, 5.49 Hz, 1 H) 7.41 (d, J = 8.54 Hz, 2 H) 7.12 (d, J = 8.54 Hz, 2 H) 4.55 (d, J = 12.82 Hz, 1 H) 4.42 (t, J = 8.09 Hz, 2 H) 3.96-4.13 (m, 4 H) 3.10 (t, J = 12.21 Hz, 1 H) 2.66-2.76 (m, 1 H) 2.55-2.62 (m, 1 H) 2.28-2.35 (m, 1 H) 2.11-2.20 (m, 1 H) 1.72-1.85 (m, 3 H) 1.42-1.56 (m, 1 H) 1.30-1.41 (m, 2 H) 1.09-1.24 (m, 1 H) 0.83-0.91 (m, 6 H) | (ESI(+)) m/e 435 (M + H)$^+$ |
| 168 | N-{4-[1-(3-ethoxypropanoyl)piperidin-4-yl]phenyl}-3-(pyridin-3-yl)azetidine-1-carboxamide | $^1$H NMR (500 MHz, DMSO-d$_6$/D$_2$O Temp = 25° C.) □ ppm 8.88 (s, 1 H) 8.77 (d, J = 5.19 Hz, 1 H) 8.58 (d, J = 8.24 Hz, 1 H) 8.01 (dd, J = 7.93, 5.80 Hz, 1 H) 7.41 (d, J = 8.54 Hz, 2 H) 7.12 (d, J = 8.54 Hz, 2 H) 4.52 (d, J = 12.82 Hz, 1 H) 4.42 (t, J = 8.24 Hz, 2 H) 3.97-4.15 (m, 4 H) 3.61 (t, J = 6.71 Hz, 2 H) 3.43 (q, J = 7.02 Hz, 2 H) 3.09 (t, J = 12.05 Hz, 1 H) 2.66-2.78 (m, 1 H) 2.54-2.66 (m, 3 H) 1.71-1.81 (m, 2 H) 1.47-1.58 (m, 1 H) 1.30-1.43 (m, 1 H) 1.10 (t, J = 7.02 Hz, 3 H) | (ESI(+)) m/e 437 (M + H)$^+$ |
| 169 | N-{4-[1-(2,2-dimethylbutanoyl)piperidin-4-yl]phenyl}-3-(pyridin-3-yl)azetidine-1-carboxamide | $^1$H NMR (500 MHz, DMSO-d$_6$/D$_2$O Temp = 25° C.) □ ppm 8.85 (s, 1 H) 8.75 (d, J = 5.19 Hz, 1 H) 8.53 (d, J = 7.93 Hz, 1 H) 7.97 (dd, J = 8.09, 5.65 Hz, 1 H) 7.39-7.44 (m, 2 H) 7.12 (d, J = 8.54 Hz, 2 H) 4.41 (t, J = 7.93 Hz, 4 H) 3.99-4.10 (m, 3 H) 2.85 (t, J = 12.97 Hz, 2 H) 2.68-2.77 (m, 1 H) 1.80 (d, J = 12.82 Hz, 2 H) 1.57-1.67 (m, 2 H) 1.34-1.49 (m, 2 H) 1.17 (s, 6 H) 0.83 (t, J = 7.32 Hz, 3 H) | (ESI(+)) m/e 435 (M + H)$^+$ |
| 170 | N-{4-[1-(3,3-dimethylbutanoyl)piperidin-4-yl]phenyl}-3- | $^1$H NMR (500 MHz, DMSO-d$_6$/D$_2$O Temp = 25° C.) □ ppm 8.87 (s, 1 H) 8.76 (d, J = 5.49 Hz, 1 H) 8.56 (d, J = 7.93 Hz, 1 H) 7.99 (dd, J = 8.09, 5.65 Hz, 1 H) 7.41 (d, J = 8.54 Hz, 2 H) 7.12 (d, | (ESI(+)) m/e 435 (M + H)$^+$ |

TABLE 3-continued

The following Examples were prepared essentially as described in Example 50, substituting the appropriate amine in Example 50A and the appropriate carboxylic acid in Example 50C. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
|  | (pyridin-3-yl)azetidine-1-carboxamide | J = 8.54 Hz, 2 H) 4.60 (d, J = 13.12 Hz, 1 H) 4.42 (t, J = 8.09 Hz, 2 H) 4.00-4.13 (m, 4 H) 3.09 (t, J = 12.05 Hz, 1 H) 2.67-2.77 (m, 1 H) 2.54-2.61 (m, 1 H) 2.17-2.36 (m, 2 H) 1.78 (t, J = 12.66 Hz, 2 H) 1.31-1.55 (m, 2 H) 1.00 (s, 9 H) |  |
| 171 | N-{4-[1-(2,2-dimethylpropanoyl)piperidin-4-yl]phenyl}-3-(pyridin-3-yl)azetidine-1-carboxamide | $^1$H NMR (500 MHz, DMSO-$d_6$/D$_2$O Temp = 25° C.) □ ppm 8.86 (s, 1 H) 8.76 (d, J = 5.49 Hz, 1 H) 8.50-8.62 (m, 1 H) 7.94-7.99 (m, 1 H) 7.41 (d, J = 8.54 Hz, 2 H) 7.13 (d, J = 8.54 Hz, 2 H) 4.41 (t, J = 7.93 Hz, 4 H) 3.99-4.12 (m, 3 H) 2.80-2.97 (m, 2 H) 2.66-2.78 (m, 1 H) 1.79 (d, J = 12.82 Hz, 2 H) 1.37-1.51 (m, 2 H) 1.22 (s, 9 H) | (ESI(+)) m/e 421 (M + H)$^+$ |
| 172 | N-[4-(1-butanoylpiperidin-4-yl)phenyl]-3-(pyridin-3-yl)azetidine-1-carboxamide | $^1$H NMR (500 MHz, DMSO-$d_6$/D$_2$O Temp = 25° C.) □ ppm 8.88 (s, 1 H) 8.78 (d, J = 5.49 Hz, 1 H) 8.59 (d, J = 8.24 Hz, 1 H) 8.01 (dd, J = 8.09, 5.65 Hz, 1 H) 7.41 (d, J = 8.54 Hz, 2 H) 7.12 (d, J = 8.54 Hz, 2 H) 4.53 (d, J = 13.12 Hz, 1 H) 4.42 (t, J = 8.24 Hz, 2 H) 3.96-4.13 (m, 4 H) 3.09 (t, J = 12.05 Hz, 1 H) 2.66-2.76 (m, 1 H) 2.55-2.63 (m, 1 H) 2.32 (t, J = 7.32 Hz, 2 H) 1.71-1.90 (m, 2 H) 1.42-1.59 (m, 3 H) 1.32-1.43 (m, 1 H) 0.90 (t, J = 7.32 Hz, 3 H) | (ESI(+)) m/e 407 (M + H)$^+$ |
| 173 | N-{4-[1-(ethoxyacetyl)piperidin-4-yl]phenyl}-3-(pyridin-3-yl)azetidine-1-carboxamide | $^1$H NMR (500 MHz, DMSO-$d_6$/D$_2$O Temp = 25° C.) □ ppm 8.88 (s, 1 H) 8.77 (d, J = 5.49 Hz, 1 H) 8.59 (d, J = 8.24 Hz, 1 H) 8.01 (dd, J = 8.09, 5.65 Hz, 1 H) 7.41 (d, J = 8.54 Hz, 2 H) 7.12 (d, J = 8.54 Hz, 2 H) 4.38-4.51 (m, 3 H) 3.88-4.20 (m, 6 H) 3.43-3.54 (m, 2 H) 3.07 (t, J = 12.21 Hz, 1 H) 2.60-2.78 (m, 2 H) 1.78 (d, J = 12.51 Hz, 2 H) 1.33-1.60 (m, 2 H) 1.14 (t, J = 7.02 Hz, 3 H) | (ESI(+)) m/e 423 (M + H)$^+$ |
| 174 | N-{4-[1-(3-methylbutanoyl)piperidin-4-yl]phenyl}-3-(pyridin-3-yl)azetidine-1-carboxamide | $^1$H NMR (500 MHz, DMSO-$d_6$/D$_2$O Temp = 25° C.) □ ppm 8.88 (s, 1 H) 8.78 (d, J = 5.19 Hz, 1 H) 8.60 (d, J = 8.24 Hz, 1 H) 8.02 (dd, J = 8.09, 5.65 Hz, 1 H) 7.41 (d, J = 8.54 Hz, 2 H) 7.12 (d, J = 8.54 Hz, 2 H) 4.54 (d, J = 13.12 Hz, 1 H) 4.42 (t, J = 8.24 Hz, 2 H) 3.96-4.14 (m, 4 H) 3.09 (t, J = 12.05 Hz, 1 H) 2.66-2.76 (m, 1 H) 2.55-2.63 (m, 1 H) 2.17-2.27 (m, 2 H) 1.94-2.04 (m, 1 H) 1.76 (d, J = 17.09 Hz, 2 H) 1.32-1.53 (m, 2 H) 0.92 (dd, J = 6.56, 1.98 Hz, 6 H) | (ESI(+)) m/e 421 (M + H)$^+$ |
| 175 | N-{4-[1-(N-acetyl-L-leucyl)piperidin-4-yl]phenyl}-3-(pyridin-3-yl)azetidine-1-carboxamide | $^1$H NMR (500 MHz, DMSO-$d_6$/D$_2$O Temp = 25° C.) □ ppm 8.89 (s, 1 H) 8.79 (d, J = 5.49 Hz, 1 H) 8.62 (d, J = 8.24 Hz, 1 H) 8.03 (dd, J = 7.93, 5.80 Hz, 1 H) 7.42 (d, J = 8.54 Hz, 2 H) 7.12 (dd, J = 11.29, 8.54 Hz, 2 H) 4.80 (dd, J = 9.77, 4.58 Hz, 1 H) 4.49 (d, 1 H) 4.42 (t, J = 8.24 Hz, 2 H) 3.97-4.17 (m, 4 H) 3.11-3.20 (m, 1 H) 2.74 (t, J = 11.90 Hz, 1 H) 2.65 (t, J = 11.75 Hz, 1 H) 1.85 (d, J = 4.88 Hz, 3 H) 1.78 (t, J = 13.73 Hz, 2 H) 1.27-1.65 (m, 5 H) 0.84-0.94 (m, 6 H) | (ESI(+)) m/e 492 (M + H)$^+$ |
| 176 | N-(4-{1-[(2-methoxyethoxy)acetyl]piperidin-4-yl}phenyl)-3-(pyridin-3-yl)azetidine-1-carboxamide | $^1$H NMR (500 MHz, DMSO-$d_6$/D$_2$O Temp = 25° C.) □ ppm 8.88 (s, 1 H) 8.77 (d, J = 5.49 Hz, 1 H) 8.58 (d, J = 8.24 Hz, 1 H) 8.01 (dd, J = 8.09, 5.65 Hz, 1 H) 7.41 (d, J = 8.54 Hz, 2 H) 7.12 (d, J = 8.54 Hz, 2 H) 4.37-4.51 (m, 3 H) 3.99-4.25 (m, 5 H) 3.89 (d, J = 12.82 Hz, 1 H) 3.51-3.64 (m, 2 H) 3.44-3.50 (m, 2 H) 3.24-3.29 (m, 3 H) 3.07 (t, J = 12.21 Hz, 1 H) 2.59-2.79 (m, 2 H) 1.77 (d, J = 12.51 Hz, 2 H) 1.47-1.64 (m, 1 H) 1.31-1.48 (m, 1 H) | (ESI(+)) m/e 453 (M + H)$^+$ |
| 177 | N-{4-[1-(cyclohexylcarbonyl)piperidin-4-yl]phenyl}-3-(pyridin-3-yl)azetidine-1-carboxamide | $^1$H NMR (500 MHz, DMSO-$d_6$/D$_2$O Temp = 25° C.) □ ppm 8.85 (s, 1 H) 8.75 (d, J = 5.19 Hz, 1 H) 8.53 (d, J = 8.24 Hz, 1 H) 7.97 (dd, J = 8.09, 5.65 Hz, 1 H) 7.41 (d, J = 8.54 Hz, 2 H) 7.13 (d, J = 8.54 Hz, 2 H) 4.53 (d, 1 H) 4.41 (t, J = 7.93 Hz, 2 H) 3.98-4.11 (m, 4 H) 2.98-3.16 (m, 1 H) 2.64-2.75 (m, 1 H) 2.58-2.63 (m, 2 H) 1.64 (d, J = 9.77 Hz, 7 H) 1.05-1.53 (m, 7 H) | (ESI(+)) m/e 447 (M + H)$^+$ |

TABLE 3-continued

The following Examples were prepared essentially as described in Example 50, substituting the appropriate amine in Example 50A and the appropriate carboxylic acid in Example 50C. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 178 | N-{4-[1-(cyclohexylacetyl)piperidin-4-yl]phenyl}-3-(pyridin-3-yl)azetidine-1-carboxamide | $^1$H NMR (500 MHz, DMSO-$d_6$/$D_2$O Temp = 25° C.) ☐ ppm 8.83 (s, 1 H) 8.73 (d, J = 5.19 Hz, 1 H) 8.48 (d, J = 7.94 Hz, 1 H) 7.93 (dd, J = 7.93, 5.49 Hz, 1 H) 7.41 (d, J = 8.54 Hz, 2 H) 7.12 (d, J = 8.54 Hz, 2 H) 4.54 (d, J = 13.12 Hz, 1 H) 4.36-4.45 (m, 2 H) 3.92-4.13 (m, 4 H) 3.09 (t, J = 12.05 Hz, 1 H) 2.66-2.78 (m, 1 H) 2.56-2.65 (m, 1 H) 2.22 (d, J = 6.71 Hz, 2 H) 1.55-1.91 (m, 8 H) 1.30-1.54 (m, 2 H) 1.05-1.28 (m, 3 H) 0.88-0.99 (m, J = 11.90, 11.90 Hz, 2 H) | (ESI(+)) m/e 461 (M + H)$^+$ |
| 179 | 3-(pyridin-3-yl)-N-{4-[1-(4,4,4-trifluorobutanoyl)piperidin-4-yl]phenyl}azetidine-1-carboxamide | $^1$H NMR (500 MHz, DMSO-$d_6$/$D_2$O Temp = 25° C.) ☐ ppm 8.88 (s, 1 H) 8.77 (d, J = 5.49 Hz, 1 H) 8.58 (d, J = 8.24 Hz, 1 H) 8.01 (dd, J = 8.09, 5.65 Hz, 1 H) 7.41 (d, J = 8.54 Hz, 2 H) 7.13 (d, J = 8.85 Hz, 2 H) 4.52 (d, J = 12.82 Hz, 1 H) 4.42 (t, J = 8.24 Hz, 2 H) 3.93-4.13 (m, 4 H) 3.11 (t, J = 12.05 Hz, 1 H) 2.54-2.76 (m, 5 H) 2.43-2.50 (m, 1 H) 1.77 (t, J = 11.90 Hz, 2 H) 1.34-1.63 (m, 2 H) | (ESI(+)) m/e 461 (M + H)$^+$ |
| 180 | N-{4-[1-(cyclopentylcarbonyl)piperidin-4-yl]phenyl}-3-(pyridin-3-yl)azetidine-1-carboxamide | $^1$H NMR (500 MHz, DMSO-$d_6$/$D_2$O Temp = 25° C.) ☐ ppm 8.89 (s, 1 H) 8.78 (d, J = 5.49 Hz, 1 H) 8.56-8.63 (m, 1 H) 8.03 (dd, J = 8.09, 5.65 Hz, 1 H) 7.41 (d, J = 8.54 Hz, 2 H) 7.13 (d, J = 8.54 Hz, 2 H) 4.53 (d, J = 12.82 Hz, 1 H) 4.42 (t, J = 8.24 Hz, 2 H) 4.00-4.15 (m, 4 H) 2.95-3.15 (m, 2 H) 2.67-2.76 (m, 1 H) 2.57-2.65 (m, 1 H) 1.29-1.86 (m, 12 H) | (ESI(+)) m/e 433 (M + H)$^+$ |
| 181 | N-(4-{1-[(1-methylcyclohexyl)carbonyl]piperidin-4-yl}phenyl)-3-(pyridin-3-yl)azetidine-1-carboxamide | $^1$H NMR (500 MHz, DMSO-$d_6$/$D_2$O Temp = 25° C.) ☐ ppm 8.85 (s, 1 H) 8.75 (d, J = 5.49 Hz, 1 H) 8.54 (d, J = 7.93 Hz, 1 H) 7.97 (dd, J = 7.93, 5.49 Hz, 1 H) 7.41 (d, J = 8.24 Hz, 2 H) 7.12 (d, J = 8.54 Hz, 2 H) 4.41 (t, J = 7.93 Hz, 4 H) 3.97-4.18 (m, 3 H) 2.67-2.97 (m, 3 H) 1.97 (d, J = 7.93 Hz, 2 H) 1.79 (d, J = 12.21 Hz, 2 H) 1.25-1.57 (m, 10 H) 1.20 (s, 3 H) | (ESI(+)) m/e 461 (M + H)$^+$ |
| 182 | N-{4-[1-(furan-3-ylcarbonyl)piperidin-4-yl]phenyl}-3-(pyridin-3-yl)azetidine-1-carboxamide | $^1$H NMR (500 MHz, DMSO-$d_6$/$D_2$O Temp = 25° C.) ☐ ppm 8.88 (s, 1 H) 8.77 (d, J = 5.49 Hz, 1 H) 8.58 (d, J = 7.93 Hz, 1 H) 7.97-8.05 (m, 2 H) 7.68-7.79 (m, 1 H) 7.42 (d, J = 8.54 Hz, 2 H) 7.15 (d, J = 8.54 Hz, 2 H) 6.68 (s, 1 H) 4.57 (s, 1 H) 4.42 (t, J = 8.24 Hz, 2 H) 3.99-4.15 (m, 4 H) 3.17 (s, 1 H) 2.63-2.87 (m, 2 H) 1.80 (s, 2 H) 1.55 (s, 2 H) | (ESI(+)) m/e 431 (M + H)$^+$ |
| 183 | N-[4-(1-acetylpiperidin-4-yl)phenyl]-3-(pyridin-3-yl)azetidine-1-carboxamide | $^1$H NMR (500 MHz, DMSO-$d_6$/$D_2$O Temp = 25° C.) ☐ ppm 8.88 (s, 1 H) 8.78 (d, J = 5.49 Hz, 1 H) 8.60 (d, J = 7.94 Hz, 1 H) 8.02 (dd, J = 8.09, 5.65 Hz, 1 H) 7.41 (d, J = 8.54 Hz, 2 H) 7.13 (d, J = 8.54 Hz, 2 H) 4.50 (d, J = 13.12 Hz, 1 H) 4.42 (t, J = 8.24 Hz, 2 H) 4.00-4.14 (m, 3 H) 3.91 (d, J = 13.73 Hz, 1 H) 3.06-3.17 (m, 1 H) 2.63-2.74 (m, 1 H) 2.56-2.64 (m, 1 H) 2.04 (s, 3 H) 1.76 (t, J = 15.56 Hz, 2 H) 1.47-1.60 (m, 1 H) 1.32-1.45 (m, 1 H) | (ESI(+)) m/e 379 (M + H)$^+$ |
| 184 | N-{4-[1-(methoxyacetyl)piperidin-4-yl]phenyl}-3-(pyridin-3-yl)azetidine-1-carboxamide | $^1$H NMR (500 MHz, DMSO-$d_6$/$D_2$O Temp = 25° C.) ☐ ppm 8.88 (s, 1 H) 8.78 (d, J = 5.49 Hz, 1 H) 8.60 (d, J = 8.24 Hz, 1 H) 8.02 (dd, J = 8.09, 5.65 Hz, 1 H) 7.41 (d, J = 8.54 Hz, 2 H) 7.13 (d, J = 8.54 Hz, 2 H) 4.36-4.55 (m, 3 H) 3.97-4.20 (m, 5 H) 3.85 (d, J = 13.43 Hz, 1 H) 3.30 (s, 3 H) 3.07 (t, J = 12.36 Hz, 1 H) 2.57-2.78 (m, 2 H) 1.77 (d, J = 12.51 Hz, 2 H) 1.34-1.61 (m, 2 H) | (ESI(+)) m/e 409 (M + H)$^+$ |
| 185 | 3-(pyridin-3-yl)-N-{4-[1-(thiophen-3-ylcarbonyl)piperidin-4-yl]phenyl}azetidine-1-carboxamide | $^1$H NMR (500 MHz, DMSO-$d_6$/$D_2$O Temp = 25° C.) ☐ ppm 8.86 (s, 1 H) 8.75 (d, J = 5.19 Hz, 1 H) 8.54 (d, J = 8.24 Hz, 1 H) 7.97 (dd, J = 8.09, 5.65 Hz, 1 H) 7.77 (d, J = 1.83 Hz, 1 H) 7.61 (dd, J = 4.88, 3.05 Hz, 1 H) 7.43 (d, J = 8.54 Hz, 2 H) 7.20-7.25 (m, 1 H) 7.16 (d, J = 8.54 Hz, 2 H) 4.58 (s, 1 H) 4.42 (t, J = 7.93 Hz, 2 H) 3.99-4.14 (m, 3 H) 3.84-3.95 (m, 1 H) 3.14-3.27 (m, 1 H) 2.69-2.94 (m, 2 H) 1.67-1.97 (m, J = 17.09 Hz, 2 H) 1.46-1.64 (m, 2 H) | (ESI(+)) m/e 447 (M + H)$^+$ |

TABLE 3-continued

The following Examples were prepared essentially as described in Example 50, substituting the appropriate amine in Example 50A and the appropriate carboxylic acid in Example 50C. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 186 | N-(4-{1-[(3-methylthiophen-2-yl)carbonyl]piperidin-4-yl}phenyl)-3-(pyridin-3-yl)azetidine-1-carboxamide | $^1$H NMR (500 MHz, DMSO-$d_6$/D$_2$O Temp = 25° C.) □ ppm 8.87 (s, 1 H) 8.76 (d, J = 5.19 Hz, 1 H) 8.56 (d, J = 8.24 Hz, 1 H) 7.99 (dd, J = 7.93, 5.49 Hz, 1 H) 7.55 (d, J = 5.19 Hz, 1 H) 7.42 (d, J = 8.85 Hz, 2 H) 7.14 (d, J = 8.54 Hz, 2 H) 6.95 (d, J = 4.88 Hz, 1 H) 4.42 (t, J = 8.09 Hz, 2 H) 3.98-4.31 (m, 5 H) 3.04 (d, J = 6.10 Hz, 2 H) 2.70-2.84 (m, 1 H) 2.21 (s, 3 H) 1.82 (d, J = 12.51 Hz, 2 H) 1.42-1.56 (m, 2 H) | (ESI(+)) m/e 461 (M + H)$^+$ |
| 187 | N-{4-[1-(morpholin-4-ylacetyl)piperidin-4-yl]phenyl}-3-(pyridin-3-yl)azetidine-1-carboxamide | $^1$H NMR (500 MHz, DMSO-$d_6$/D$_2$O Temp = 25° C.) □ ppm 8.86 (s, 1 H) 8.76 (d, J = 5.49 Hz, 1 H) 8.54 (d, J = 7.93 Hz, 1 H) 7.98 (dd, J = 8.09, 5.65 Hz, 1 H) 7.43 (d, J = 8.54 Hz, 2 H) 7.13 (d, J = 8.55 Hz, 2 H) 4.27-4.54 (m, 5 H) 3.92-4.12 (m, 6 H) 3.78-3.88 (m, 2 H) 3.38-3.53 (m, 2 H) 3.10-3.23 (m, 3 H) 2.77 (t, J = 12.05 Hz, 2 H) 1.83 (d, J = 13.12 Hz, 2 H) 1.55-1.69 (m, 1 H) 1.38-1.50 (m, 1 H) | (ESI(+)) m/e 464 (M + H)$^+$ |
| 188 | 3-(pyridin-3-yl)-N-{4-[1-(thiophen-2-ylcarbonyl)piperidin-4-yl]phenyl}azetidine-1-carboxamide | $^1$H NMR (500 MHz DMSO-$d_6$/D$_2$O Temp = 25° C.) □ ppm 8.84 (s, 1 H) 8.74 (d, J = 5.19 Hz, 1 H) 8.51 (d, J = 7.93 Hz, 1 H) 7.95 (dd, J = 7.93, 5.49 Hz, 1 H) 7.69-7.80 (m, 1 H) 7.39-7.46 (m, 3 H) 7.10-7.19 (m, 3 H) 4.19-4.57 (m, 4 H) 3.99-4.13 (m, 3 H) 2.92-3.38 (m, 2 H) 2.71-2.86 (m, 1 H) 1.83 (d, J = 12.82 Hz, 2 H) 1.48-1.65 (m, 2 H) | (ESI(+)) m/e 447 (M + H)$^+$ |
| 189 | N-(4-{1-[(5-methylthiophen-2-yl)carbonyl]piperidin-4-yl}phenyl)-3-(pyridin-3-yl)azetidine-1-carboxamide | $^1$H NMR (500 MHz, DMSO-$d_6$/D$_2$O Temp = 25° C.) □ ppm 8.88 (s, 1 H) 8.77 (d, J = 5.19 Hz, 1 H) 8.58 (d, J = 8.24 Hz, 1 H) 8.01 (dd, J = 8.09, 5.65 Hz, 1 H) 7.42 (d, J = 8.54 Hz, 2 H) 7.23 (d, J = 3.66 Hz, 1 H) 7.16 (d, J = 8.54 Hz, 2 H) 6.83 (d, J = 2.75 Hz, 1 H) 4.42 (t, J = 8.09 Hz, 4 H) 3.98-4.16 (m, 3 H) 2.97-3.16 (m, 2 H) 2.71-2.85 (m, 1 H) 2.47 (s, 3 H) 1.82 (d, J = 12.51 Hz, 2 H) 1.47-1.63 (m, 2 H) | (ESI(+)) m/e 461 (M + H)$^+$ |
| 190 | N-{4-[1-(furan-2-ylcarbonyl)piperidin-4-yl]phenyl}-3-(pyridin-3-yl)azetidine-1-carboxamide | $^1$H NMR (500 MHz, DMSO-$d_6$/D$_2$O Temp = 25° C.) □ ppm 8.87 (s, 1 H) 8.77 (d, J = 5.49 Hz, 1 H) 8.58 (d, J = 8.24 Hz, 1 H) 8.00 (dd, J = 7.93, 5.49 Hz, 1 H) 7.81 (s, 1 H) 7.42 (d, J = 8.54 Hz, 2 H) 7.11-7.21 (m, 2 H) 6.99 (d, J = 3.66 Hz, 1 H) 6.63 (dd, J = 3.51, 1.68 Hz, 1 H) 4.42 (t, J = 8.09 Hz, 4 H) 3.99-4.15 (m, 3 H) 2.84-3.35 (m, 2 H) 2.74-2.83 (m, 1 H) 1.85 (d, J = 12.51 Hz, 2 H) 1.56 (d, J = 10.07 Hz, 2 H) | (ESI(+)) m/e 431 (M + H)$^+$ |
| 191 | N-(4-{1-[(1-methyl-1H-pyrrol-2-yl)carbonyl]piperidin-4-yl}phenyl)-3-(pyridin-3-yl)azetidine-1-carboxamide | $^1$H NMR (500 MHz, DMSO-$d_6$/D$_2$O Temp = 25° C.) □ ppm 8.87 (s, 1 H) 8.76 (d, J = 5.19 Hz, 1 H) 8.56 (d, J = 8.24 Hz, 1 H) 7.99 (dd, J = 7.93, 5.80 Hz, 1 H) 7.42 (d, J = 8.54 Hz, 2 H) 7.16 (d, J = 8.85 Hz, 2 H) 6.88 (d, J = 1.83 Hz, 1 H) 6.33 (dd, J = 3.66, 1.53 Hz, 1 H) 6.01-6.06 (m, 1 H) 4.33-4.48 (m, J = 8.09, 8.09 Hz, 4 H) 4.01-4.10 (m, 3 H) 3.66-3.67 (m, 3 H) 2.96-3.08 (m, 2 H) 2.71-2.82 (m, 1 H) 1.81 (d, J = 12.21 Hz, 2 H) 1.47-1.61 (m, 2 H) | (ESI(+)) m/e 444 (M + H)$^+$ |
| 192 | N-[4-(1-propanoylpiperidin-4-yl)phenyl]-3-(pyridin-3-yl)azetidine-1-carboxamide | $^1$H NMR (500 MHz, DMSO-$d_6$/D$_2$O Temp = 25° C.) □ ppm 8.89 (s, 1 H) 8.78 (d, J = 5.49 Hz, 1 H) 8.53-8.65 (m, 1 H) 8.03 (dd, J = 8.09, 5.65 Hz, 1 H) 7.31-7.47 (m, 2 H) 7.08-7.17 (m, 2 H) 4.52 (d, J = 12.51 Hz, 1 H) 4.42 (t, J = 8.24 Hz, 2 H) 3.92-4.16 (m, 4 H) 3.08 (t, J = 12.05 Hz, 1 H) 2.57-2.76 (m, 2 H) 2.35 (q, J = 7.53 Hz, 2 H) 1.77 (t, J = 15.26 Hz, 2 H) 1.29-1.58 (m, 2 H) 1.01 (t, J = 7.48 Hz, 3 H) | (ESI(+)) m/e 393 (M + H)$^+$ |
| 193 | N-(4-{1-[(1-methylcyclopropyl)carbonyl]piperidin-4-yl}phenyl)-3-(pyridin-3-yl)azetidine-1-carboxamide | $^1$H NMR (500 MHz, DMSO-$d_6$/D$_2$O Temp = 25° C.) □ ppm 8.89 (s, 1 H) 8.78 (d, J = 5.19 Hz, 1 H) 8.60 (t, J = 7.93 Hz, 1 H) 8.03 (dd, J = 7.93, 5.80 Hz, 1 H) 7.41 (d, J = 8.54 Hz, 2 H) 7.14 (d, J = 8.54 Hz, 2 H) 4.30-4.49 (m, 4 H) 3.99-4.18 (m, 3 H) 2.65-3.18 (m, 3 H) 1.79 (d, J = 12.51 Hz, 2 H) 1.33-1.57 (m, 2 H) 1.25 (s, 3 H) 0.78-0.88 (m, 2 H) 0.50-0.60 (m, 2 H) | (ESI(+)) m/e 419 (M + H)$^+$ |

TABLE 3-continued

The following Examples were prepared essentially as described in Example 50, substituting the appropriate amine in Example 50A and the appropriate carboxylic acid in Example 50C. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 194 | 3-(pyridin-3-yl)-N-{4-[1-(pyrrolidin-1-ylacetyl)piperidin-4-yl]phenyl}azetidine-1-carboxamide | $^1$H NMR (500 MHz, DMSO-$d_6$/$D_2$O Temp = 25° C.) ☐ ppm 8.83 (s, 1 H) 8.73 (d, J = 5.19 Hz, 1 H) 8.47 (d, J = 8.24 Hz, 1 H) 7.93 (dd, J = 7.93, 5.80 Hz, 1 H) 7.42 (d, J = 8.54 Hz, 2 H) 7.13 (d, J = 8.54 Hz, 2 H) 4.26-4.52 (m, 5 H) 3.97-4.10 (m, 3 H) 3.64-3.67 (m, 1 H) 3.59 (d, J = 6.41 Hz, 2 H) 2.96-3.24 (m, 3 H) 2.76 (t, J = 12.36 Hz, 2 H) 1.77-2.09 (m, 6 H) 1.36-1.66 (m, 2 H) | (ESI(+)) m/e 448 (M + H)$^+$ |
| 195 | 3-(pyridin-3-yl)-N-{4-[1-(1,3-thiazol-2-ylcarbonyl)piperidin-4-yl]phenyl}azetidine-1-carboxamide | $^1$H NMR (500 MHz, DMSO-$d_6$/$D_2$O Temp = 25° C.) ☐ ppm 8.86 (s, 1 H) 8.76 (d, J = 5.49 Hz, 1 H) 8.55 (d, J = 8.24 Hz, 1 H) 7.94-8.04 (m, 3 H) 7.42 (d, J = 8.54 Hz, 2 H) 7.16 (d, J = 8.85 Hz, 2 H) 5.35 (d, J = 12.82 Hz, 1 H) 4.61 (d, J = 11.90 Hz, 1 H) 4.42 (t, J = 7.93 Hz, 2 H) 3.99-4.10 (m, 3 H) 3.27 (t, J = 12.66 Hz, 1 H) 2.78-2.99 (m, 2 H) 1.80-1.91 (m, 2 H) 1.52-1.69 (m, 2 H) | (ESI(+)) m/e 448 (M + H)$^+$ |
| 196 | N-{4-[1-(cyclopentylacetyl)piperidin-4-yl]phenyl}-3-(pyridin-3-yl)azetidine-1-carboxamide | $^1$H NMR (500 MHz, DMSO-$d_6$/$D_2$O Temp = 25° C.) ☐ ppm 8.88 (s, 1 H) 8.77 (d, J = 5.49 Hz, 1 H) 8.59 (d, J = 8.24 Hz, 1 H) 8.01 (dd, J = 8.09, 5.65 Hz, 1 H) 7.41 (d, J = 8.54 Hz, 2 H) 7.12 (d, J = 8.54 Hz, 2 H) 4.53 (d, J = 13.12 Hz, 1 H) 4.42 (t, J = 8.09 Hz, 2 H) 3.92-4.14 (m, 4 H) 3.09 (t, J = 12.05 Hz, 1 H) 2.55-2.79 (m, 2 H) 2.36 (d, J = 7.32 Hz, 2 H) 2.04-2.22 (m, 1 H) 1.30-1.90 (m, 10 H) 1.05-1.20 (m, 2 H) | (ESI(+)) m/e 447 (M + H)$^+$ |
| 197 | N-{4-[1-(2,3-dimethylbutanoyl)piperidin-4-yl]phenyl}-3-(pyridin-3-yl)azetidine-1-carboxamide | $^1$H NMR (500 MHz, DMSO-$d_6$/$D_2$O Temp = 25° C.) ☐ ppm 8.87 (s, 1 H) 8.76 (d, J = 5.19 Hz, 1 H) 8.56 (d, J = 8.24 Hz, 1 H) 7.99 (dd, J = 7.93, 5.80 Hz, 1 H) 7.38-7.45 (m, 2 H) 7.06-7.16 (m, 2 H) 4.54-4.63 (m, 1 H) 4.42 (t, J = 8.09 Hz, 2 H) 3.99-4.18 (m, 4 H) 3.11 (t, J = 12.21 Hz, 1 H) 2.69-2.80 (m, 1 H) 2.54-2.63 (m, 2 H) 1.70-1.93 (m, 3 H) 1.29-1.56 (m, 2 H) 0.93-1.07 (m, 3 H) 0.78-0.90 (m, 6 H) | (ESI(+)) m/e 435 (M + H)$^+$ |
| 198 | N-[4-(1-pentanoylazetidin-3-yl)phenyl]-3-(pyridin-3-yl)azetidine-1-carboxamide | $^1$H NMR (400 MHz, DMSO-$d_6$/$D_2$O Temp = 90° C.) ☐ ppm 8.71 (d, J = 2.14 Hz, 1 H) 8.60-8.65 (m, 1 H) 8.24 (d, J = 7.93 Hz, 1 H) 7.75 (dd, J = 8.09, 5.34 Hz, 1 H) 7.47 (d, J = 8.54 Hz, 2 H) 7.21 (d, J = 8.54 Hz, 2 H) 4.31-4.53 (m, 4 H) 3.97-4.09 (m, 4 H) 3.71-3.85 (m, 2 H) 2.08 (t, J = 7.32 Hz, 2 H) 1.45-1.57 (m, 2 H) 1.25-1.37 (m, 2 H) 0.88 (t, J = 7.32 Hz, 3 H) | (ESI(+)) m/e 393 (M + H)$^+$ |
| 199 | N-(4-{1-[(2-methylcyclopropyl)carbonyl]azetidin-3-yl}phenyl)-3-(pyridin-3-yl)azetidine-1-carboxamide | $^1$H NMR (400 MHz, DMSO-$d_6$/$D_2$O Temp = 90° C.) ☐ ppm 8.71 (d, J = 1.83 Hz, 1 H) 8.62 (d, J = 5.19 Hz, 1 H) 8.23 (d, J = 8.24 Hz, 1 H) 7.74 (dd, J = 7.93, 5.49 Hz, 1 H) 7.48 (d, J = 8.54 Hz, 2 H) 7.19-7.25 (m, 2 H) 4.36-4.50 (m, 4 H) 3.92-4.11 (m, 4 H) 3.76-3.89 (m, 2 H) 1.25-1.33 (m, 1 H) 1.12-1.20 (m, 1 H) 1.04-1.10 (m, 3 H) 0.88-0.98 (m, 1 H) 0.53-0.63 (m, 1 H) | (ESI(+)) m/e 391 (M + H)$^+$ |
| 200 | N-(4-{1-[(1S,4R)-bicyclo[2.2.1]hept-2-ylacetyl]azetidin-3-yl}phenyl)-3-(pyridin-3-yl)azetidine-1-carboxamide | $^1$H NMR (400 MHz, DMSO-$d_6$/$D_2$O Temp = 90° C.) ☐ ppm 8.71 (d, J = 1.83 Hz, 1 H) 8.59-8.66 (m, 1 H) 8.24 (d, J = 7.93 Hz, 1 H) 7.74 (dd, J = 7.93, 5.19 Hz, 1 H) 7.42-7.51 (m, 2 H) 7.20 (d, J = 8.85 Hz, 2 H) 4.31-4.61 (m, 4 H) 3.92-4.13 (m, 4 H) 3.66-3.82 (m, 2 H) 2.17 (s, 1 H) 2.01-2.11 (m, 1 H) 1.88-2.00 (m, 2 H) 1.75-1.86 (m, 1 H) 1.37-1.52 (m, 3 H) 1.29-1.35 (m, 1 H) 1.00-1.22 (m, 4 H) | (ESI(+)) m/e 445 (M + H)$^+$ |
| 201 | N-{4-[1-(4-methylpentanoyl)azetidin-3-yl]phenyl}-3-(pyridin-3-yl)azetidine-1-carboxamide | $^1$H NMR (400 MHz, DMSO-$d_6$/$D_2$O Temp = 90° C.) ☐ ppm 8.72 (d, J = 1.83 Hz, 1 H) 8.63 (dd, J = 5.34, 1.37 Hz, 1 H) 8.27 (d, J = 8.24 Hz, 1 H) 7.77 (dd, J = 7.93, 5.19 Hz, 1 H) 7.47 (d, J = 8.54 Hz, 2 H) 7.21 (d, J = 8.54 Hz, 2 H) 4.25-4.58 (m, 4 H) 3.96-4.13 (m, 4 H) 3.72-3.86 (m, 2 H) 2.05-2.11 (m, 2 H) 1.49-1.66 (m, 1 H) 1.38-1.46 (m, 2 H) 0.88 (d, J = 6.71 Hz, 6 H) | (ESI(+)) m/e 407 (M + H)$^+$ |

TABLE 3-continued

The following Examples were prepared essentially as described in Example 50, substituting the appropriate amine in Example 50A and the appropriate carboxylic acid in Example 50C. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 202 | N-{4-[1-(3-methylpentanoyl)azetidin-3-yl]phenyl}-3-(pyridin-3-yl)azetidine-1-carboxamide | $^1$H NMR (400 MHz, DMSO-$d_6$/$D_2O$ Temp = 90° C.) ☐ ppm 8.71 (d, J = 1.83 Hz, 1 H) 8.58-8.64 (m, 1 H) 8.25 (d, J = 7.93 Hz, 1 H) 7.76 (dd, J = 7.93, 5.19 Hz, 1 H) 7.47 (d, J = 8.54 Hz, 2 H) 7.20 (d, J = 8.54 Hz, 2 H) 4.29-4.64 (m, 4 H) 3.95-4.18 (m, 4 H) 3.68-3.88 (m, 2 H) 1.99-2.14 (m, 1 H) 1.87-1.96 (m, 1 H) 1.73-1.86 (m, 1 H) 1.29-1.46 (m, 1 H) 1.14-1.27 (m, 1 H) 0.83-0.92 (m, 6 H) | (ESI(+)) m/e 407 (M + H)$^+$ |
| 203 | N-{4-[1-(3-ethoxypropanoyl)azetidin-3-yl]phenyl}-3-(pyridin-3-yl)azetidine-1-carboxamide | $^1$H NMR (400 MHz, DMSO-$d_6$/$D_2O$ Temp = 90° C.) ☐ ppm 8.70 (d, J = 1.83 Hz, 1 H) 8.57-8.65 (m, 1 H) 8.22 (d, J = 8.24 Hz, 1 H) 7.73 (dd, J = 7.93, 5.19 Hz, 1 H) 7.47 (d, J = 8.54 Hz, 2 H) 7.21 (d, J = 8.54 Hz, 2 H) 4.28-4.62 (m, 4 H) 3.93-4.22 (m, 4 H) 3.70-3.83 (m, 2 H) 3.61 (t, J = 6.41 Hz, 2 H) 3.44 (q, J = 7.02 Hz, 2 H) 2.28-2.38 (m, 2 H) 1.11 (t, J = 6.87 Hz, 3 H) | (ESI(+)) m/e 409 (M + H)$^+$ |
| 204 | N-{4-[1-(2,2-dimethylbutanoyl)azetidin-3-yl]phenyl}-3-(pyridin-3-yl)azetidine-1-carboxamide | $^1$H NMR (400 MHz, DMSO-$d_6$/$D_2O$ Temp = 90° C.) ☐ ppm 8.71 (d, J = 2.14 Hz, 1 H) 8.63 (dd, J = 5.34, 1.37 Hz, 1 H) 8.25 (d, J = 8.24 Hz, 1 H) 7.76 (dd, J = 7.93, 5.49 Hz, 1 H) 7.47 (d, J = 8.54 Hz, 2 H) 7.20 (d, J = 8.54 Hz, 2 H) 4.33-4.64 (m, 4 H) 3.93-4.12 (m, 5 H) 3.70-3.81 (m, 1 H) 1.51 (q, J = 7.32 Hz, 2 H) 1.11 (s, 6 H) 0.83 (t, J = 7.48 Hz, 3 H); ) | (ESI(+)) m/e 407 (M + H)$^+$ |
| 205 | N-{4-[1-(3,3-dimethylbutanoyl)azetidin-3-yl]phenyl}-3-(pyridin-3-yl)azetidine-1-carboxamide | $^1$H NMR (400 MHz, DMSO-$d_6$/$D_2O$ Temp = 90° C.) ☐ ppm 8.72 (d, J = 1.83 Hz, 1 H) 8.63 (dd, J = 5.49, 1.22 Hz, 1 H) 8.26 (d, J = 8.24 Hz, 1 H) 7.76 (dd, J = 7.93, 5.19 Hz, 1 H) 7.47 (d, J = 8.54 Hz, 2 H) 7.20 (d, J = 8.54 Hz, 2 H) 4.19-4.62 (m, 4 H) 3.90-4.05 (m, 4 H) 3.59-3.85 (m, 2 H) 1.98 (s, 2 H) 1.01 (s, 9 H) | (ESI(+)) m/e 407 (M + H)$^+$ |
| 206 | N-{4-[1-(2,2-dimethylpropanoyl)azetidin-3-yl]phenyl}-3-(pyridin-3-yl)azetidine-1-carboxamide | $^1$H NMR (400 MHz, DMSO-$d_6$/$D_2O$ Temp = 90° C.) ☐ ppm 8.73 (d, J = 1.83 Hz, 1 H) 8.64 (d, J = 5.49 Hz, 1 H) 8.28 (d, J = 7.93 Hz, 1 H) 7.78 (dd, J = 8.09, 5.34 Hz, 1 H) 7.47 (d, J = 8.54 Hz, 2 H) 7.20 (d, J = 8.54 Hz, 2 H) 4.36-4.57 (m, 4 H) 3.93-4.14 (m, 5 H) 3.67-3.84 (m, 1 H) 1.15 (s, 9 H) | (ESI(+)) m/e 393 (M + H)$^+$ |
| 207 | N-{4-[1-(ethoxyacetyl)azetidin-3-yl]phenyl}-3-(pyridin-3-yl)azetidine-1-carboxamide | $^1$H NMR (400 MHz, DMSO-$d_6$/$D_2O$ Temp = 90° C.) ☐ ppm 8.72 (d, J = 1.83 Hz, 1 H) 8.63 (d, J = 5.19 Hz, 1 H) 8.26 (d, J = 7.93 Hz, 1 H) 7.76 (dd, J = 7.93, 5.19 Hz, 1 H) 7.44-7.51 (m, 2 H) 7.17-7.25 (m, J = 8.09, 8.09 Hz, 2 H) 4.21-4.64 (m, 4 H) 3.97-4.18 (m, 5 H) 3.95 (s, 2 H) 3.78-3.87 (m, 1 H) 3.50 (q, J = 6.92 Hz, 2 H) 1.10-1.18 (m, 3 H) | (ESI(+)) m/e 395 (M + H)$^+$ |
| 208 | N-{4-[1-(3-methylbutanoyl)azetidine-3-yl]phenyl}-3-(pyridin-3-yl)azetidine-1-carboxamide | $^1$H NMR (400 MHz, DMSO-$d_6$/$D_2O$ Temp = 90° C.) ☐ ppm 8.72 (d, J = 1.83 Hz, 1 H) 8.61-8.65 (m, 1 H) 8.28 (d, J = 8.24 Hz, 1 H) 7.77 (dd, J = 7.93, 5.49 Hz, 1 H) 7.47 (d, J = 8.54 Hz, 2 H) 7.20 (d, J = 8.54 Hz, 2 H) 4.23-4.59 (m, 4 H) 3.95-4.24 (m, 4 H) 3.71-3.83 (m, 2 H) 1.92-2.05 (m, 3 H) 0.92 (d, J = 6.10 Hz, 6 H) | (ESI(+)) m/e 393 (M + H)$^+$ |
| 209 | N-{4-[1-(N-acetyl-L-leucyl)azetidin-3-yl]phenyl}-3-(pyridin-3-yl)azetidine-1-carboxamide | $^1$H NMR (400 MHz, DMSO-$d_6$/$D_2O$ Temp = 90° C.) ☐ ppm 8.73 (d, J = 2.14 Hz, 1 H) 8.62-8.65 (m, 1 H) 8.28 (d, J = 8.24 Hz, 1 H) 7.73-7.79 (m, 1 H) 7.47 (d, J = 8.54 Hz, 2 H) 7.21 (d, J = 8.54 Hz, 2 H) 4.20-4.87 (m, 4 H) 3.91-4.21 (m, 4 H) 3.65-3.92 (m, 2 H) 1.84-1.88 (m, 3 H) 1.55-1.71 (m, 1 H) 1.42-1.55 (m, 2 H) 0.82-0.97 (m, 7 H) | (ESI(+)) m/e 464 (M + H)$^+$ |
| 210 | N-(4-{1-[(2-methoxyethoxy)acetyl]azetidin-3-yl}phenyl)-3-(pyridin-3-yl)azetidine-1-carboxamide | $^1$H NMR (400 MHz, DMSO-$d_6$/$D_2O$ Temp = 90° C.) ☐ ppm 8.71 (d, J = 1.83 Hz, 1 H) 8.62 (dd, J = 5.19, 1.22 Hz, 1 H) 8.24 (d, J = 7.93 Hz, 1 H) 7.74 (dd, J = 7.93, 5.19 Hz, 1 H) 7.47 (d, J = 8.54 Hz, 2 H) 7.22 (d, J = 8.54 Hz, 2 H) 4.20-4.80 (m, 5 H) 3.91-4.14 (m, 8 H) 3.75-3.91 (m, 2 H) 3.56-3.61 (m, 2 H) 3.45-3.51 (m, 2 H) | (ESI(+)) m/e 425 (M + H)$^+$ |

TABLE 3-continued

The following Examples were prepared essentially as described in Example 50, substituting the appropriate amine in Example 50A and the appropriate carboxylic acid in Example 50C. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 211 | N-{4-[1-(cyclohexylcarbonyl)azetidin-3-yl]phenyl}-3-(pyridin-3-yl)azetidine-1-carboxamide | $^1$H NMR (400 MHz, DMSO-$d_6$/$D_2O$ Temp = 90° C.) ☐ ppm 8.72 (d, J = 1.53 Hz, 1 H) 8.63 (d, J = 4.27 Hz, 1 H) 8.26 (d, J = 7.93 Hz, 1 H) 7.73-7.77 (m, 1 H) 7.47 (d, J = 8.54 Hz, 2 H) 7.20 (d, J = 8.54 Hz, 2 H) 4.18-4.63 (m, 4 H) 3.90-4.15 (m, 4 H) 3.67-3.87 (m, 2 H) 2.15-2.31 (m, 1 H) 1.53-1.88 (m, 5 H) 1.08-1.46 (m, 5 H) | (ESI(+)) m/e 419 (M + H)$^+$ |
| 212 | N-{4-[1-(cyclohexylacetyl)azetidin-3-yl]phenyl}-3-(pyridin-3-yl)azetidine-1-carboxamide | $^1$H NMR (400 MHz, DMSO-$d_6$/$D_2O$ Temp = 90° C.) ☐ ppm 8.74 (d, J = 1.83 Hz, 1 H) 8.61-8.68 (m, 1 H) 8.31 (d, J = 8.24 Hz, 1 H) 7.80 (dd, J = 7.93, 5.19 Hz, 1 H) 7.47 (d, J = 8.54 Hz, 2 H) 7.20 (d, J = 8.54 Hz, 2 H) 4.21-4.72 (m, 4 H) 3.87-4.20 (m, 4 H) 3.62-3.84 (m, 2 H) 1.97 (d, J = 6.41 Hz, 2 H) 1.52-1.79 (m, 6 H) 1.07-1.33 (m, 3 H) 0.91-1.06 (m, 2 H) | (ESI(+)) m/e 433 (M + H)$^+$ |
| 213 | 3-(pyridin-3-yl)-N-{4-[1-(4,4,4-trifluorobutanoyl)azetidin-3-yl]phenyl}azetidine-1-carboxamide | $^1$H NMR (400 MHz, DMSO-$d_6$/$D_2O$ Temp = 90° C.) ☐☐ ppm 8.72 (d, J = 1.83 Hz, 1 H) 8.63 (d, J = 4.27 Hz, 1 H) 8.26 (d, J = 7.93 Hz, 1 H) 7.76 (dd, J = 7.93, 5.19 Hz, 1 H) 7.47 (d, J = 8.54 Hz, 2 H) 7.22 (d, J = 8.54 Hz, 2 H) 4.18-4.81 (m, 4 H) 3.96-4.16 (m, 4 H) 3.73-3.89 (m, 2 H) 2.42-2.50 (m, 2 H) 2.32-2.40 (m, 2 H) | (ESI(+)) m/e 433 (M + H)$^+$ |
| 214 | N-{4-[1-(cyclopentylcarbonyl)azetidin-3-yl]phenyl}-3-(pyridin-3-yl)azetidine-1-carboxamide | $^1$H NMR (400 MHz, DMSO-$d_6$/$D_2O$ Temp = 90° C.) ☐ ppm 8.74 (d, J = 1.83 Hz, 1 H) 8.65 (d, J = 5.49 Hz, 1 H) 8.31 (d, J = 7.93 Hz, 1 H) 7.80 (dd, J = 7.93, 5.49 Hz, 1 H) 7.47 (d, J = 8.54 Hz, 2 H) 7.21 (d, J = 8.54 Hz, 2 H) 4.12-4.74 (m, 4 H) 3.85-4.23 (m, 4 H) 3.71-3.86 (m, 2 H) 2.61-2.73 (m, 1 H) 1.38-1.87 (m, 8 H) | (ESI(+)) m/e 405 (M + H)$^+$ |
| 215 | N-(4-{1-[(1-methylcyclohexyl)carbonyl]azetidin-3-yl}phenyl)-3-(pyridin-3-yl)azetidine-1-carboxamide | $^1$H NMR (400 MHz, DMSO-$d_6$/$D_2O$ Temp = 90° C.) ☐ ppm 8.73 (d, J = 1.83 Hz, 1 H) 8.64 (d, J = 5.19 Hz, 1 H) 8.28 (d, J = 7.93 Hz, 1 H) 7.78 (dd, J = 8.09, 5.34 Hz, 1 H) 7.47 (d, J = 8.54 Hz, 2 H) 7.20 (d, J = 8.54 Hz, 2 H) 4.35-4.68 (m, 4 H) 3.89-4.13 (m, 5 H) 3.70-3.80 (m, 1 H) 1.88-1.99 (m, 2 H) 1.15-1.66 (m, 8 H) 1.11 (s, 3 H) | (ESI(+)) m/e 433 (M + H)$^+$ |
| 216 | N-{4-[1-(furan-3-ylcarbonyl)azetidin-3-yl]phenyl}-3-(pyridin-3-yl)azetidine-1-carboxamide | $^1$H NMR (400 MHz, DMSO-$d_6$/$D_2O$ Temp = 90° C.) ☐ ppm 8.72 (d, J = 2.14 Hz, 1 H) 8.62-8.66 (m, 1 H) 8.27 (d, J = 7.94 Hz, 1 H) 8.06 (s, 1 H) 7.77 (dd, J = 7.93, 5.49 Hz, 1 H) 7.65-7.68 (m, 1 H) 7.48 (d, J = 8.54 Hz, 2 H) 7.25 (d, J = 8.85 Hz, 2 H) 6.73 (d, J = 1.83 Hz, 1 H) 4.32-4.84 (m, 4 H) 3.96-4.25 (m, 5 H) 3.84-3.93 (m, 1 H) | (ESI(+)) m/e 403 (M + H)$^+$ |
| 217 | N-[4-(1-acetylazetidin-3-yl)phenyl]-3-(pyridin-3-yl)azetidine-1-carboxamide | $^1$H NMR (400 MHz, DMSO-$d_6$/$D_2O$ Temp = 90° C.) ☐ ppm 8.73 (d, J = 1.83 Hz, 1 H) 8.60-8.67 (m, 1 H) 8.29 (d, J = 7.93 Hz, 1 H) 7.78 (dd, J = 7.93, 5.49 Hz, 1 H) 7.47 (d, J = 8.54 Hz, 2 H) 7.22 (d, J = 8.54 Hz, 2 H) 4.13-4.65 (m, 4 H) 3.89-4.21 (m, 4 H) 3.67-3.90 (m, 2 H) 1.80 (s, 3 H) | (ESI(+)) m/e 351 (M + H)$^+$ |
| 218 | N-{4-[1-(methoxyacetyl)azetidin-3-yl]phenyl}-3-(pyridin-3-yl)azetidine-1-carboxamide | $^1$H NMR (400 MHz, DMSO-$d_6$/$D_2O$ Temp = 90° C.) ☐ ppm 8.72 (d, J = 2.14 Hz, 1 H) 8.63 (dd, J = 5.19, 1.22 Hz, 1 H) 8.26 (d, J = 8.24 Hz, 1 H) 7.76 (dd, J = 7.93, 5.19 Hz, 1 H) 7.47 (d, J = 8.54 Hz, 2 H) 7.22 (d, J = 8.54 Hz, 2 H) 4.33-4.52 (m, 4 H) 3.96-4.11 (m, 5 H) 3.92 (s, 2 H) 3.80-3.89 (m, 1 H) 3.31 (s, 3 H) | (ESI(+)) m/e 381 (M + H)$^+$ |
| 219 | 3-(pyridin-3-yl)-N-{4-[1-(thiophen-3-ylcarbonyl)azetidin-3-yl]phenyl}azetidine-1-carboxamide | $^1$H NMR (400 MHz, DMSO-$d_6$/$D_2O$ Temp = 90° C.) ☐ ppm 8.73 (d, J = 1.83 Hz, 1 H) 8.64 (dd, J = 5.19, 1.22 Hz, 1 H) 8.28 (d, J = 7.93 Hz, 1 H) 7.97 (dd, J = 3.05, 1.22 Hz, 1 H) 7.78 (dd, J = 8.09, 5.34 Hz, 1 H) 7.54 (dd, J = 5.04, 2.90 Hz, 1 H) 7.48 (d, J = 8.54 Hz, 2 H) 7.39 (dd, J = 4.88, 1.22 Hz, 1 H) 7.25 (d, J = 8.54 Hz, 2 H) 4.38-4.76 (m, 4 H) 3.99-4.25 (m, 5 H) 3.85-3.94 (m, 1 H) | (ESI(+)) m/e 419 (M + H)$^+$ |
| 220 | N-(4-{1-[(3-methylthiophen-2-yl)carbonyl]azetidin-3-yl}phenyl)- | $^1$H NMR (400 MHz, DMSO-$d_6$/$D_2O$ Temp = 90° C.) ☐ ppm 8.73 (d, J = 2.14 Hz, 1 H) 8.64 (dd, J = 5.49, 1.22 Hz, 1 H) 8.29 (d, J = 7.94 Hz, 1 H) 7.78 (dd, J = 8.09, 5.34 Hz, 1 H) 7.56 (d, J = 5.19 Hz, 1 H) 7.48 (d, J = 8.54 Hz, 2 H) 7.23 (d, | (ESI(+)) m/e 433 (M + H)$^+$ |

TABLE 3-continued

The following Examples were prepared essentially as described in Example 50, substituting the appropriate amine in Example 50A and the appropriate carboxylic acid in Example 50C. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| | 3-(pyridin-3-yl)azetidine-1-carboxamide | J = 8.54 Hz, 2 H) 6.98 (d, J = 4.88 Hz, 1 H) 4.53 (t, J = 9.00 Hz, 2 H) 4.38-4.48 (m, 2 H) 3.96-4.16 (m, 5 H) 3.81-3.92 (m, 1 H) 2.41 (s, 3 H) | |
| 221 | N-{4-[1-(morpholin-4-ylacetyl)azetidin-3-yl]phenyl}-3-(pyridin-3-yl)azetidine-1-carboxamide | $^1$H NMR (400 MHz, DMSO-d$_6$/D$_2$O Temp = 90° C.) □ ppm 8.68 (d, J = 1.83 Hz, 1 H) 8.60 (dd, J = 5.19, 1.22 Hz, 1 H) 8.15 (d, J = 7.93 Hz, 1 H) 7.68 (dd, J = 7.93, 5.19 Hz, 1 H) 7.49 (d, J = 8.54 Hz, 2 H) 7.24 (d, J = 8.54 Hz, 2 H) 4.27-5.16 (m, 4 H) 3.95-4.29 (m, 7 H) 3.81-3.95 (m, 5 H) 3.30-3.36 (m, 4 H) | (ESI(+)) m/e 436 (M + H)$^+$ |
| 222 | 3-(pyridin-3-yl)-N-{4-[1-(thiophen-2-ylcarbonyl)azetidin-3-yl]phenyl}azetidine-1-carboxamide | $^1$H NMR (400 MHz, DMSO-d$_6$/D$_2$O Temp = 90° C.) □ ppm 8.72 (d, J = 1.83 Hz, 1 H) 8.61-8.65 (m, 1 H) 8.27 (d, J = 7.93 Hz, 1 H) 7.71-7.80 (m, 2 H) 7.54 (d, J = 2.75 Hz, 1 H) 7.49 (d, J = 8.54 Hz, 2 H) 7.26 (d, J = 8.54 Hz, 2 H) 7.16 (dd, J = 4.88, 3.66 Hz, 1 H) 4.65 (s, 2 H) 4.39-4.49 (m, 2 H) 4.21 (s, 2 H) 3.97-4.09 (m, 3 H) 3.87-3.96 (m, 1 H) | (ESI(+)) m/e 419 (M + H)$^+$ |
| 223 | N-(4-{1-[(5-methylthiophen-2-yl)carbonyl]azetidin-3-yl}phenyl)-3-(pyridin-3-yl)azetidine-1-carboxamide | $^1$H NMR (400 MHz, DMSO-d$_6$/D$_2$O Temp = 90° C.) □ ppm 8.71 (d, J = 1.83 Hz, 1 H) 8.63 (d, J = 4.27 Hz, 1 H) 8.25 (d, J = 8.24 Hz, 1 H) 7.75 (dd, J = 7.93, 5.19 Hz, 1 H) 7.48 (d, J = 8.54 Hz, 2 H) 7.34 (d, J = 3.66 Hz, 1 H) 7.25 (d, J = 8.54 Hz, 2 H) 6.85 (d, J = 3.66 Hz, 1 H) 4.62 (t, J = 8.39 Hz, 2 H) 4.37-4.48 (m, 2 H) 4.18 (t, J = 6.41 Hz, 2 H) 3.97-4.09 (m, 3 H) 3.86-3.94 (m, 1 H) 2.47 (s, 3 H) | (ESI(+)) m/e 433 (M + H)$^+$ |
| 224 | N-{4-[1-(furan-2-ylcarbonyl)azetidin-3-yl]phenyl}-3-(pyridin-3-yl)azetidine-1-carboxamide | $^1$H NMR (400 MHz, DMSO-d$_6$/D$_2$O Temp = 90° C.) □ ppm 8.73 (d, J = 2.14 Hz, 1 H) 8.64 (dd, J = 5.19, 1.22 Hz, 1 H) 8.28 (d, J = 7.93 Hz, 1 H) 7.70-7.82 (m, 2 H) 7.48 (d, J = 8.54 Hz, 2 H) 7.25 (d, J = 8.54 Hz, 2 H) 7.02 (d, J = 3.66 Hz, 1 H) 6.60 (dd, J = 3.51, 1.68 Hz, 1 H) 4.64 (s, 2 H) 4.34-4.52 (m, 2 H) 4.20 (s, 2 H) 3.98-4.10 (m, 3 H) 3.86-3.97 (m, 1 H) | (ESI(+)) m/e 403 (M + H)$^+$ |
| 225 | N-(4-{1-[(1-methyl-1H-pyrrol-2-yl)carbonyl]azetidin-3-yl}phenyl)-3-(pyridin-3-yl)azetidine-1-carboxamide | $^1$H NMR (400 MHz, DMSO-d$_6$/D$_2$O Temp = 90° C.) □ ppm 8.72 (d, J = 1.83 Hz, 1 H) 8.63 (d, J = 5.19 Hz, 1 H) 8.26 (d, J = 7.93 Hz, 1 H) 7.76 (dd, J = 8.09, 5.34 Hz, 1 H) 7.48 (d, J = 8.54 Hz, 2 H) 7.24 (d, J = 8.54 Hz, 2 H) 6.88 (d, J = 2.14 Hz, 1 H) 6.52 (dd, J = 3.97, 1.53 Hz, 1 H) 6.06 (dd, J = 3.81, 2.59 Hz, 1 H) 4.54 (t, J = 8.85 Hz, 2 H) 4.37-4.47 (m, 2 H) 4.10 (t, J = 9.00, 6.26 Hz, 2 H) 3.98-4.06 (m, 3 H) 3.85-3.89 (m, 1 H) 3.84 (s, 3 H) | (ESI(+)) m/e 416 (M + H)$^+$ |
| 226 | N-[4-(1-propanoylazetidin-3-yl)phenyl]-3-(pyridin-3-yl)azetidine-1-carboxamide | $^1$H NMR (400 MHz, DMSO-d$_6$/D$_2$O Temp = 90° C.) □ ppm 8.72 (d, J = 1.83 Hz, 1 H) 8.64 (dd, J = 5.19, 1.22 Hz, 1 H) 8.28 (d, J = 8.24 Hz, 1 H) 7.78 (dd, J = 7.93, 5.49 Hz, 1 H) 7.47 (d, J = 8.54 Hz, 2 H) 7.21 (d, J = 8.54 Hz, 2 H) 4.19-4.68 (m, 4 H) 3.90-4.14 (m, 4 H) 3.70-3.87 (m, 2 H) 2.10 (q, J = 7.53 Hz, 2 H) 1.01 (t, J = 7.63 Hz, 3 H) | (ESI(+)) m/e 365 (M + H)$^+$ |
| 227 | N-(4-{1-[(1-methylcyclopropyl)carbonyl]azetidin-3-yl}phenyl)-3-(pyridin-3-yl)azetidine-1-carboxamide | $^1$H NMR (400 MHz, DMSO-d$_6$/D$_2$O Temp = 90° C.) □ ppm 8.73 (d, J = 2.14 Hz, 1 H) 8.64 (d, J = 5.19 Hz, 1 H) 8.29 (d, J = 7.93 Hz, 1 H) 7.75-7.80 (m, 1 H) 7.48 (d, J = 8.54 Hz, 2 H) 7.21 (d, J = 8.54 Hz, 2 H) 4.37-4.52 (m, 4 H) 3.97-4.12 (m, 5 H) 3.72-3.87 (m, 1 H) 1.27 (s, 3 H) 0.88-0.97 (m, 2 H) 0.44-0.53 (m, 2 H) | (ESI(+)) m/e 391 (M + H)$^+$ |
| 228 | 3-(pyridin-3-yl)-N-{4-[1-(1,3-thiazol-2-ylcarbonyl)azetidin-3-yl]phenyl}azetidine-1-carboxamide | $^1$H NMR (400 MHz, DMSO-d$_6$/D$_2$O Temp = 90° C.) □ ppm 8.72 (d, J = 1.83 Hz, 1 H) 8.63 (dd, J = 5.34, 1.37 Hz, 1 H) 8.26 (d, J = 8.24 Hz, 1 H) 7.99 (d, J = 3.05 Hz, 1 H) 7.91 (d, J = 3.05 Hz, 1 H) 7.76 (dd, J = 7.93, 5.19 Hz, 1 H) 7.49 (d, J = 8.54 Hz, 2 H) 7.24-7.30 (m, 2 H) 5.01 (s, 1 H) 4.35-4.79 (m, 4 H) 3.86-4.24 (m, 5 H) | (ESI(+)) m/e 420 (M + H)$^+$ |
| 229 | N-{4-[1-(cyclopentylacetyl)azetidin-3-yl]phenyl}-3- | $^1$H NMR (400 MHz, DMSO-d$_6$/D$_2$O Temp = 90° C.) □ ppm 8.71 (d, J = 1.83 Hz, 1 H) 8.63 (dd, J = 5.49, 1.22 Hz, 1 H) 8.25 (d, J = 7.93 Hz, 1 H) 7.75 (dd, J = 8.09, 5.34 Hz, 1 H) 7.47 (d, J = 8.54 Hz, | (ESI(+)) m/e 419 (M + H)$^+$ |

TABLE 3-continued

The following Examples were prepared essentially as described in Example 50, substituting the appropriate amine in Example 50A and the appropriate carboxylic acid in Example 50C. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
|  | (pyridin-3-yl)azetidine-1-carboxamide | 2 H) 7.20 (d, J = 8.54 Hz, 2 H) 4.14-4.78 (m, 4 H) 3.82-4.18 (m, 4 H) 3.62-3.86 (m, 2 H) 2.05-2.22 (m, 3 H) 1.68-1.83 (m, 2 H) 1.40-1.65 (m, 4 H) 1.09-1.21 (m, 2 H) |  |
| 230 | N-{4-[1-(2,3-dimethylbutanoyl)azetidin-3-yl]phenyl}-3-(pyridin-3-yl)azetidine-1-carboxamide | $^1$H NMR (400 MHz, DMSO-d$_6$/D$_2$O Temp = 90° C.) ☐ ppm 8.73 (d, J = 1.83 Hz, 1 H) 8.62-8.67 (m, 1 H) 8.30 (d, J = 8.24 Hz, 1 H) 7.80 (dd, J = 7.93, 5.19 Hz, 1 H) 7.47 (d, J = 8.54 Hz, 2 H) 7.20 (d, J = 8.54 Hz, 2 H) 4.16-4.68 (m, 4 H) 3.90-4.26 (m, 5 H) 3.66-3.89 (m, 1 H) 2.01-2.19 (m, 1 H) 1.65-1.85 (m, 1 H) 0.98 (d, J = 6.71 Hz, 3 H) 0.89 (dd, J = 6.56, 4.12 Hz, 6 H) | (ESI(+)) m/e 407 (M + H)$^+$ |
| 258 | N-[4-(1-pentanoylpyrrolidin-3-yl)phenyl]-3-(pyridin-3-yl)azetidine-1-carboxamide |  | (ESI(+)) m/e 407 (M + H)$^+$ |
| 259 | N-{4-[1-(3-methylpentanoyl)pyrrolidin-3-yl]phenyl}-3-(pyridin-3-yl)azetidine-1-carboxamide |  | (ESI(+)) m/e 421 (M + H)$^+$ |
| 260 | N-(4-{1-[(1S,4R)-bicyclo[2.2.1]hept-2-ylacetyl]pyrrolidin-3-yl}phenyl)-3-(pyridin-3-yl)azetidine-1-carboxamide |  | (ESI(+)) m/e 459 (M + H)$^+$ |
| 261 | N-{4-[1-(cyclopentylacetyl)pyrrolidin-3-yl]phenyl}-3-(pyridin-3-yl)azetidine-1-carboxamide |  | (ESI(+)) m/e 433 (M + H)$^+$ |
| 262 | N-(4-{1-[(2-methylcyclopropyl)carbonyl]pyrrolidin-3-yl}phenyl)-3-(pyridin-3-yl)azetidine-1-carboxamide |  | (ESI(+)) m/e 405 (M + H)$^+$ |
| 263 | N-{4-[1-(morpholin-4-ylacetyl)pyrrolidin-3-yl]phenyl}-3-(pyridin-3-yl)azetidine-1-carboxamide |  | (ESI(+)) m/e 450 (M + H)$^+$ |
| 264 | N-{4-[1-(furan-3-ylcarbonyl)pyrrolidin-3-yl]phenyl}-3-(pyridin-3-yl)azetidine-1-carboxamide |  | (ESI(+)) m/e 417 (M + H)$^+$ |
| 265 | 3-(pyridin-3-yl)-N-{4-[1-(pyrrolidin-1-ylacetyl)pyrrolidin-3-yl]phenyl}azetidine-1-carboxamide |  | (ESI(+)) m/e 434 (M + H)$^+$ |

TABLE 3-continued

The following Examples were prepared essentially as described in Example 50, substituting the appropriate amine in Example 50A and the appropriate carboxylic acid in Example 50C. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 266 | N-{4-[1-(N,N-dimethyl-beta-alanyl)pyrrolidin-3-yl]phenyl}-3-(pyridin-3-yl)azetidine-1-carboxamide | | (ESI(+)) m/e 422 (M + H)$^+$ |
| 267 | 3-(pyridin-3-yl)-N-{4-[1-(1,3-thiazol-2-ylcarbonyl)pyrrolidin-3-yl]phenyl}azetidine-1-carboxamide | | (ESI(+)) m/e 434 (M + H)$^+$ |
| 268 | 3-(pyridin-3-yl)-N-{4-[1-(thiophen-3-ylcarbonyl)pyrrolidin-3-yl]phenyl}azetidine-1-carboxamide | | (ESI(+)) m/e 433 (M + H)$^+$ |
| 269 | N-(4-{1-[(1-methylcyclopropyl)carbonyl]pyrrolidin-3-yl}phenyl)-3-(pyridin-3-yl)azetidine-1-carboxamide | | (ESI(+)) m/e 405 (M + H)$^+$ |
| 270 | N-(4-{1-[(3-methylthiophen-2-yl)carbonyl]pyrrolidin-3-yl}phenyl)-3-(pyridin-3-yl)azetidine-1-carboxamide | | (ESI(+)) m/e 447 (M + H)$^+$ |
| 271 | 3-(pyridin-3-yl)-N-{4-[1-(4,4,4-trifluorobutanoyl)pyrrolidin-3-yl]phenyl}azetidine-1-carboxamide | | (ESI(+)) m/e 447 (M + H)$^+$ |
| 272 | N-(4-{1-[(4-methylpiperazin-1-yl)acetyl]pyrrolidin-3-yl}phenyl)-3-(pyridin-3-yl)azetidine-1-carboxamide | | (ESI(+)) m/e 463 (M + H)$^+$ |
| 273 | N-{4-[1-(5-oxo-L-prolyl)pyrrolidin-3-yl]phenyl}-3-(pyridin-3-yl)azetidine-1-carboxamide | | (ESI(+)) m/e 434 (M + H)$^+$ |
| 274 | N-{4-[1-(3-ethoxypropanoyl)pyrrolidin-3-yl]phenyl}-3-(pyridin-3-yl)azetidine-1-carboxamide | | (ESI(+)) m/e 423 (M + H)$^+$ |
| 275 | N-{4-[1-(4-methylpentanoyl)pyrrolidin-3-yl]phenyl}-3- | | (ESI(+)) m/e 421 (M + H)$^+$ |

TABLE 3-continued

The following Examples were prepared essentially as described in Example 50, substituting the appropriate amine in Example 50A and the appropriate carboxylic acid in Example 50C. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
|  | (pyridin-3-yl)azetidine-1-carboxamide |  |  |
| 276 | N-(4-{1-[(1-methylcyclohexyl)carbonyl]pyrrolidin-3-yl}phenyl)-3-(pyridin-3-yl)azetidine-1-carboxamide |  | (ESI(+)) m/e 447 (M + H)$^+$ |
| 277 | N-[4-(1-acetylpyrrolidin-3-yl)phenyl]-3-(pyridin-3-yl)azetidine-1-carboxamide |  | (ESI(+)) m/e 365 (M + H)$^+$ |
| 278 | N-{4-[1-(cyclohexylacetyl)pyrrolidin-3-yl]phenyl}-3-(pyridin-3-yl)azetidine-1-carboxamide |  | (ESI(+)) m/e 447 (M + H)$^+$ |
| 279 | N-[4-(1-propanoylpyrrolidin-3-yl)phenyl]-3-(pyridin-3-yl)azetidine-1-carboxamide |  | (ESI(+)) m/e 379 (M + H)$^+$ |
| 280 | N-(4-{1-[(2-methoxyethoxy)acetyl]pyrrolidin-3-yl}phenyl)-3-(pyridin-3-yl)azetidine-1-carboxamide |  | (ESI(+)) m/e 439 (M + H)$^+$ |
| 281 | N-(4-{1-[3-(morpholin-4-yl)propanoyl]pyrrolidin-3-yl}phenyl)-3-(pyridin-3-yl)azetidine-1-carboxamide |  | (ESI(+)) m/e 464 (M + H)$^+$ |
| 282 | N-{4-[1-(2,2-dimethylpropanoyl)pyrrolidin-3-yl]phenyl}-3-(pyridin-3-yl)azetidine-1-carboxamide |  | (ESI(+)) m/e 407 (M + H)$^+$ |
| 283 | N-(4-{1-[(5-methylthiophen-2-yl)carbonyl]pyrrolidin-3-yl}phenyl)-3-(pyridin-3-yl)azetidine-1-carboxamide |  | (ESI(+)) m/e 447 (M + H)$^+$ |
| 284 | 3-(pyridin-3-yl)-N-{4-[1-(thiophen-2-ylcarbonyl)pyrrolidin-3-yl]phenyl}azetidine-1-carboxamide |  | (ESI(+)) m/e 433 (M + H)$^+$ |
| 285 | N-(4-{1-[(1-methyl-1H-pyrrol-2-yl)carbonyl]pyrrolidin-3-yl}phenyl)-3- |  | (ESI(+)) m/e 430 (M + H)$^+$ |

TABLE 3-continued

The following Examples were prepared essentially as described in Example 50, substituting the appropriate amine in Example 50A and the appropriate carboxylic acid in Example 50C. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| | (pyridin-3-yl)azetidine-1-carboxamide | | |
| 286 | N-{4-[1-(furan-2-ylcarbonyl)pyrrolidin-3-yl]phenyl}-3-(pyridin-3-yl)azetidine-1-carboxamide | | (ESI(+)) m/e 417 (M + H)$^+$ |
| 287 | N-(4-{1-[3-(piperidin-1-yl)propanoyl]pyrrolidin-3-yl}phenyl)-3-(pyridin-3-yl)azetidine-1-carboxamide | | (ESI(+)) m/e 462 (M + H)$^+$ |
| 288 | N-{4-[1-(ethoxyacetyl)pyrrolidin-3-yl]phenyl}-3-(pyridin-3-yl)azetidine-1-carboxamide | | (ESI(+)) m/e 409 (M + H)$^+$ |
| 289 | N-{4-[1-(3,3-dimethylbutanoyl)pyrrolidin-3-yl]phenyl}-3-(pyridin-3-yl)azetidine-1-carboxamide | | (ESI(+)) m/e 421 (M + H)$^+$ |
| 290 | N-{4-[1-(2,2-dimethylbutanoyl)pyrrolidin-3-yl]phenyl}-3-(pyridin-3-yl)azetidine-1-carboxamide | | (ESI(+)) m/e 421 (M + H)$^+$ |
| 291 | N-{4-[1-(2-oxopropanoyl)pyrrolidin-3-yl]phenyl}-3-(pyridin-3-yl)azetidine-1-carboxamide | | (ESI(+)) m/e 393 (M + H)$^+$ |
| 292 | N-{4-[1-(methoxyacetyl)pyrrolidin-3-yl]phenyl}-3-(pyridin-3-yl)azetidine-1-carboxamide | | (ESI(+)) m/e 395 (M + H)$^+$ |
| 293 | N-{4-[1-(cyclohexylcarbonyl)pyrrolidin-3-yl]phenyl}-3-(pyridin-3-yl)azetidine-1-carboxamide | | (ESI(+)) m/e 433 (M + H)$^+$ |
| 294 | N-{4-[1-(3-methylbutanoyl)pyrrolidin-3-yl]phenyl}-3-(pyridin-3-yl)azetidine-1-carboxamide | | (ESI(+)) m/e 407 (M + H)$^+$ |

TABLE 3-continued

The following Examples were prepared essentially as described in Example 50, substituting the appropriate amine in Example 50A and the appropriate carboxylic acid in Example 50C. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 295 | N-{4-[1-(cyclopentylcarbonyl)pyrrolidin-3-yl]phenyl}-3-(pyridin-3-yl)azetidine-1-carboxamide | | (ESI(+)) m/e 419 (M + H)$^+$ |
| 296 | N-{4-[1-(2,3-dimethylbutanoyl)pyrrolidin-3-yl]phenyl}-3-(pyridin-3-yl)azetidine-1-carboxamide | | (ESI(+)) m/e 421 (M + H)$^+$ |

Example 59 tert-butyl 3-[4-({[3-(pyridin-3-yl)azetidin-1-yl]carbonyl}amino)phenyl]pyrrolidine-1-carboxylate The title compound was prepared as described in Example 1C, substituting tert-butyl 3-(4-aminophenyl)pyrrolidine-1-carboxylate for tert-butyl 3-(4-aminophenoxy)azetidine-1-carboxylate. $^1$H NMR (300 MHz, DMSO-d$_6$) δ 8.56 (d, J=2.3 Hz, 1H), 8.52-8.45 (m, 2H), 7.86 (dt, J=7.9, 2.0 Hz, 1H), 7.49-7.37 (m, 3H), 7.19-7.12 (m, 2H), 4.38 (d, J=16.3 Hz, 2H), 4.03-3.81 (m, 3H), 3.66 (dd, J=10.1, 7.4 Hz, 1H), 3.51-3.40 (m, 1H), 3.29-3.19 (m, 2H), 3.10 (t, J=9.8 Hz, 1H), 2.21-2.05 (m, 1H), 1.99-1.80 (m, 1H), 1.43-1.38 (m, 8H), 1.26 (t, J=5.3 Hz, 1H); MS (ESI(+)) m/e 423 (M+H).

Example 60 tert-butyl (3R)-3-[4-({[3-(pyridin-3-yl)azetidin-1-yl]carbonyl}amino)phenoxy]pyrrolidine-1-carboxylate The title compound was prepared as in Example 1A-C, substituting (R)-tert-butyl 3-hydroxypyrrolidine-1-carboxylate for tert-butyl 3-hydroxyazetidine-1-carboxylate in Example 1A. $^1$H NMR (300 MHz, DMSO-d$_6$) δ 8.56 (d, J=2.3 Hz, 1H), 8.48 (dd, J=4.8, 1.6 Hz, 1H), 8.37 (s, 1H), 7.86 (dt, J=7.9, 2.0 Hz, 1H), 7.47-7.33 (m, 3H), 6.88-6.81 (m, 2H), 4.90 (bs, 1H), 4.36 (d, J=16.0 Hz, 2H), 4.08-3.80 (m, 3H), 3.57-3.33 (m, 1H), 2.11-1.96 (m, 2H), 1.42-1.36 (m, 9H); MS (ESI(+)) m/e 439 (M+H).

Example 61 tert-butyl (3S)-3-[4-({[3-(pyridin-3-yl)azetidin-1-yl]carbonyl}amino)phenoxy]pyrrolidine-1-carboxylate The title compound was prepared as in Example 1A-C, substituting (S)-tert-butyl 3-hydroxypyrrolidine-1-carboxylate for tert-butyl 3-hydroxyazetidine-1-carboxylate in Example 1A. $^1$H NMR (300 MHz, DMSO-d$_6$) δ 8.56 (d, J=2.3 Hz, 1H), 8.48 (dd, J=4.8, 1.6 Hz, 1H), 8.37 (s, 1H), 7.86 (dt, J=7.9, 2.0 Hz, 1H), 7.45-7.34 (m, 3H), 6.88-6.81 (m, 2H), 4.90 (bs, 1H), 4.36 (d, J=16.0 Hz, 2H), 4.08-3.80 (m, 3H), 3.58-3.31 (m, 1H), 2.11-1.96 (m, 2H), 1.42-1.36 (m, 9H); MS (ESI(+)) m/e 439 (M+H).

Example 62 tert-butyl 3-[4-({[3-(pyridin-3-yl)azetidin-1-yl]carbonyl}amino)phenyl]azetidine-1-carboxylate The title compound was prepared as described in Example 1C, substituting tert-butyl 3-(4-aminophenyl)azetidine-1-carboxylate for tert-butyl 3-(4-aminophenoxy)azetidine-1-carboxylate. $^1$H NMR (300 MHz, DMSO-d$_6$) δ 8.57 (d, J=2.3 Hz, 1H), 8.51 (s, 1H), 8.53-8.45 (m, 2H), 7.87 (dt, J=7.9, 2.0 Hz, 1H), 7.53-7.46 (m, 2H), 7.41 (ddd, J=7.9, 4.7, 0.8 Hz, 1H), 7.20 (d, J=8.6 Hz, 1H), 4.38 (d, J=16.4 Hz, 2H), 4.21 (t, J=8.1 Hz, 2H), 4.13-3.63 (m, 6H), 1.40 (s, 9H); MS (ESI(+)) m/e 409 (M+H).

Example 63 tert-butyl 3-[4-({[3-(pyridin-3-yl)azetidin-1-yl]carbonyl}amino)phenoxy]azetidine-1-carboxylate The title compound was prepared as described in Example 1C. $^1$H NMR (300 MHz, DMSO-d$_6$) δ 8.56 (d, J=2.3 Hz, 1H), 8.48 (dd, J=4.7, 1.6 Hz, 1H), 8.39 (s, 1H), 7.86 (dt, J=7.9, 2.0 Hz, 1H), 7.45-7.37 (m, 3H), 6.77-6.70 (m, 2H), 4.96-4.85 (m, 1H), 4.36 (d, J=16.0 Hz, 2H), 4.31-4.22 (m, 2H), 4.12-3.81 (m, 4H), 3.76 (dd, J=9.5, 3.9 Hz, 2H), 1.39 (s, 9H); MS (ESI(+)) m/e 425 (M+H).

Example 112 tert-butyl 4-[4-({[3-(2-chloropyridin-3-yl)azetidin-1-yl]carbonyl}amino)phenyl]piperidine-1-carboxylate The title compound was prepared as described in Example 1C, substituting tert-butyl 4-(4-aminophenyl)piperidine-1-carboxylate for tert-butyl 3-(4-aminophenoxy)azetidine-1-carboxylate and 3-(azetidin-3-yl)-2-chloropyridine for 3-(azetidin-3-yl)pyridine bis hydrochloride. $^1$H NMR (300 MHz, DMSO-d$_6$) δ 8.45 (s, 1H), 8.42-8.30 (m, 1H), 8.01 (dd, J=7.7, 1.9 Hz, 1H), 7.56-7.42 (m, 2H), 7.44-7.37 (m, 2H), 7.14-7.06 (m, 2H), 4.43-4.29 (m, 2H), 4.14-3.83 (m, 4H), 2.91-2.66 (m, 2H), 1.76-1.59 (m, 2H), 1.47 (dd, J=12.6, 4.1 Hz, 1H), 1.41 (s, 10H), 1.33-1.07 (m, 1H); MS (ESI(+)) m/e 415 (M+H)$^+$.

Example 113 tert-butyl 4-[4-({[3-(4-chloropyridin-3-yl)azetidin-1-yl]carbonyl}amino)phenyl]piperidine-1-carboxylate The title compound was prepared as described in Example 1C, substituting tert-butyl 4-(4-aminophenyl)piperidine-1-carboxylate for tert-butyl 3-(4-aminophenoxy)azetidine-1-carboxylate and 3-(azetidin-3-yl)-4-chloropyridine for 3-(azetidin-3-yl)pyridine bis hydrochloride. $^1$H NMR (300 MHz, DMSO-$d_6$) δ 8.70 (s, 1H), 8.47 (d, J=5.3 Hz, 2H), 8.47-8.43 (m, 2H), 7.57 (d, J=5.2 Hz, 1H), 7.45-7.38 (m, 2H), 7.10 (d, J=8.6 Hz, 2H), 4.45-4.32 (m, 2H), 4.19-3.97 (m, 5H), 2.88-2.66 (m, 2H), 1.77-1.66 (m, 2H), 1.41 (s, 10H); MS (ESI(+)) m/e 470 (M+H)$^+$.

Example 116 tert-butyl 4-[4-({[3-(2-fluoropyridin-3-yl)azetidin-1-yl]carbonyl}amino)phenyl]piperidine-1-carboxylate The title compound was prepared as described in Example 1C, substituting tert-butyl 4-(4-aminophenyl)piperidine-1-carboxylate for tert-butyl 3-(4-aminophenoxy)azetidine-1-carboxylate and 3-(azetidin-3-yl)-2-fluoropyridine for 3-(azetidin-3-yl)pyridine bis hydrochloride. $^1$H NMR (300 MHz, DMSO-$d_6$) δ 8.44 (s, 1H), 8.17-8.11 (m, 1H), 8.09-7.99 (m, 1H), 7.48-7.30 (m, 3H), 7.10 (d, J=8.6 Hz, 2H), 4.39-4.28 (m, 2H), 4.12-3.90 (m, 6H), 2.89-2.65 (m, 2H), 1.77-1.66 (m, 2H), 1.41 (s, 11H); MS (ESI(+)) m/e 399 (M+H)$^+$.

Example 157

N-{4-[1-(2-methylpropyl)-1H-pyrazol-4-yl]phenyl}-3-(pyridin-3-yl)azetidine-1-carboxamide

Example 157A

N-(4-bromophenyl)-3-(pyridin-3-yl)azetidine-1-carboxamide

The title compound was prepared as described in Example 13, substituting 1-bromo-4-isocyanatobenzene for methyl 4-isocyanatobenzoate.

Example 157B

N-{4-[1-(2-methylpropyl)-1H-pyrazol-4-yl]phenyl}-3-(pyridin-3-yl)azetidine-1-carboxamide The title compound was prepared as described in Example 9A, substituting 1-isobutyl-4-(4,4,5,5-tetramethyl-1,3,2-dioxaborolan-2-yl)-1H-pyrazole for tert-butyl 4-(4,4,5,5-tetramethyl-1,3,2-dioxaborolan-2-yl)-5,6-dihydropyridine-1(2H)-carboxylate and N-(4-bromophenyl)-3-(pyridin-3-yl)azetidine-1-carboxamide for 1-bromo-4-nitrobenzene. $^1$H NMR (300 MHz, DMSO-$d_6$) δ 8.58 (t, J=3.4 Hz, 1H), 8.53-8.43 (m, 1H), 8.04 (d, J=0.8 Hz, 1H), 7.92-7.83 (m, 1H), 7.81-7.72 (m, 1H), 7.57-7.33 (m, 5H), 4.39 (t, J=8.2 Hz, 2H), 4.04-3.81 (m, 6H), 2.21-2.03 (m, 1H), 0.89-0.82 (m, 6H); MS (ESI(+)) m/e 376 (M+H)$^+$.

Example 158

N-[4-(1-propyl-1H-pyrazol-4-yl)phenyl]-3-(pyridin-3-yl)azetidine-1-carboxamide

The title compound was prepared as described in Example 157, substituting 1-propyl-4-(4,4,5,5-tetramethyl-1,3,2-dioxaborolan-2-yl)-1H-pyrazole for 1-isobutyl-4-(4,4,5,5-tetramethyl-1,3,2-dioxaborolan-2-yl)-1H-pyrazole in Example 157B. $^1$H NMR (500 MHz, DMSO-$d_6$) δ 8.60-8.55 (m, 1H), 8.52 (bs, 1H), 8.49 (dd, J=4.7, 1.6 Hz, 1H), 8.06 (s, 1H), 7.92-7.84 (m, 1H), 7.78 (s, 1H), 7.51 (d, J=8.7 Hz, 2H), 7.49-7.23 (m, 3H), 4.39 (t, J=8.4 Hz, 2H), 4.05 (t, J=6.9 Hz, 2H), 3.97 (dt, J=17.7, 8.8 Hz, 2H), 3.93-3.83 (m, 1H), 1.87-1.72 (m, 2H), 0.86 (s, 1H), 0.85 (s, 1H), 0.86-0.80 (m, 1H); MS (ESI(+)) m/e 362 (M+H)$^+$.

Example 162

4-(pyridin-3-yl)-N-(4-{[1-(tetrahydro-2H-pyran-4-ylacetyl)piperidin-4-yl]oxy}phenyl)piperazine-1-carboxamide

Example 162A 4-(piperidin-4-yloxy)aniline

The title compound was prepared as described in Example 1D, substituting tert-butyl 4-(4-aminophenoxy)piperidine-1-carboxylate for tert-butyl 3-(4-(3-(pyridin-3-yl)azetidine-1-carboxamido)phenoxy) azetidine-1-carboxylate.

Example 162B 1-(4-(4-aminophenoxy)piperidin-1-yl)-2-(tetrahydro-2H-pyran-4-yl)ethanone The title compound was prepared as described in Example 1E, substituting 4-(piperidin-4-yloxy)aniline for N-(4-(azetidin-3-yloxy)phenyl)-3-(pyridin-3-yl)azetidine-1-carboxamide and 2-(tetrahydro-2H-pyran-4-yl)acetic acid for (S)-2-methylbutanoic acid.

Example 162C 4-(pyridin-3-yl)-N-(4-{[1-(tetrahydro-2H-pyran-4-ylacetyl)piperidin-4-yl]oxy}phenyl)piperazine-1-carboxamide The title compound was prepared as described in Example 1C, substituting 1-(4-(4-aminophenoxy)piperidin-1-yl)-2-(tetrahydro-2H-pyran-4-yl)ethanone for tert-butyl 3-(4-aminophenoxy)azetidine-1-carboxylate and 1-(pyridin-3-yl)piperazine for 3-(azetidin-3-yl)pyridine bis hydrochloride. $^1$H NMR (400 MHz, DMSO-$d_6$/$D_2O$) δ ppm 8.40-8.29 (m, 1H), 8.12 (d, J=5.2 Hz, 1H), 7.97 (dd, J=8.9, 2.8 Hz, 1H), 7.77 (dd, J=8.9, 5.3 Hz, 1H), 7.39-7.30 (m, 2H), 6.91-6.83 (m, 2H), 4.52-4.43 (m, 1H), 3.86-3.73 (m, 4H), 3.65 (dd, J=11.2, 6.3 Hz, 4H), 3.52-3.41 (m, 4H), 3.36-3.33 (m, 2H), 3.31-3.27 (m, 2H), 2.28 (d, J=6.9 Hz, 2H), 2.00-1.80 (m, 4H), 1.71-1.49 (m, 4H), 1.36-1.16 (m, 2H); MS (ESI(+)) m/e 508 (M+H)$^+$.

Example 231

N-{4-[1-(cyclopentylmethyl)piperidin-4-yl]phenyl}-3-(pyridin-3-yl)azetidine-1-carboxamide

Example 231A tert-butyl 4-(4-(3-(pyridin-3-yl)azetidine-1-carboxamido)phenyl)piperidine-1-carboxylate The title compound was prepared as described in Example 1C, substituting tert-butyl 4-(4-aminophenyl)piperidine-1-carboxylate for tert-butyl 3-(4-aminophenoxy)azetidine-1-carboxylate.

Example 231B

N-(4-(piperidin-4-yl)phenyl)-3-(pyridin-3-yl)azetidine-1-carboxamide

The title compound was prepared as described in Example 1D, substituting tert-butyl 4-(4-(3-(pyridin-3-yl)azetidine-1-carboxamido)phenyl)piperidine-1-carboxylate for tert-butyl 3-(4-(3-(pyridin-3-yl)azetidine-1-carboxamido)phenoxy)azetidine-1-carboxylate.

Example 231C

N-{4-[1-(cyclopentylmethyl)piperidin-4-yl]phenyl}-3-(pyridin-3-yl)azetidine-1-carboxamide In a 20 mL vial was added N-(4-(piperidin-4-yl)phenyl)-3-(pyridin-3-yl)azetidine-1-carboxamide, bistrifluoroacetic acid (67 mg, 0.12 mmol) dissolved in methanol, (2.0 mL) followed by the addition of cyclopentanecarbaldehyde (13 mg, 0.13 mmol) dissolved in methanol (0.45 mL), followed by the addition of acetic acid neat (68 µL, 1.2 mmol). The reaction mixture was shaken for 1 hour at 70° C. After that, MP-cyanoborohydride (272 mg, 2-3 mmol/g) resin was added and the resulting mixture was shaken at 70° C. overnight. The reaction mixture was filtered and concentrated to dryness. The residues were dissolved in 1:1 DMSO/methanol and purified by reverse phase chromatography. $^1$H NMR (500 MHz, pyridine/$d_5$-$D_2O$ Temp=90° C.) δ ppm 8.55 (dd, J=4.73, 1.68 Hz, 1 H) 8.40-8.48 (m, 1 H) 7.75 (d, J=8.54 Hz, 2 H) 7.56-7.61 (m, 1 H) 7.21 (d, J=8.54 Hz, 2 H) 7.16-7.19 (m, 1 H) 4.46 (t, J=8.24 Hz, 2 H) 4.10 (dd, J=8.09, 5.95 Hz, 2 H) 3.64-3.74 (m, 1 H) 3.28 (d, 2 H) 2.39-2.66 (m, 5 H) 2.02-2.26 (m, 3 H) 1.75-1.88 (m, 4 H) 1.40-1.59 (m, 4 H) 1.20-1.31 (m, 2 H); (ESI) m/z 419 (M+H).

TABLE 4

The following Examples were prepared essentially as described in Example 231, substituting the appropriate amine in Example 231A and the appropriate aldehyde in Example 231C. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 232 | N-{4-[1-(cyclohexylmethyl)piperidin-4-yl]phenyl}-3-(pyridin-3-yl)azetidine-1-carboxamide | $^1$H NMR (500 MHz, pyridine-$d_5$/$D_2O$ Temp = 90° C.) ☐ ppm 8.55 (dd, J = 4.58, 1.53 Hz, 1 H) 8.40-8.46 (m, 1 H) 7.75 (d, J = 8.54 Hz, 2 H) 7.56-7.60 (m, 1 H) 7.21 (d, J = 8.54 Hz, 2 H) 7.16-7.18 (m, 1 H) 4.46 (t, J = 8.24 Hz, 2 H) 4.05-4.15 (m, J = 7.93, 5.80 Hz, 2 H) 3.64-3.74 (m, 1 H) 3.16 (m, 2 H) 2.48-2.62 (m, 1 H) 2.37-2.43 (m, 2 H) 2.24-2.37 (m, 2 H) 1.94-2.11 (m, 2 H) 1.76-1.90 (m, 4 H) 1.53-1.72 (m, 4 H) 1.07-1.32 (m, 3 H) 0.88-1.02 (m, 2 H) | (ESI(+)) m/e 433 (M + H)⁺ |
| 233 | N-{4-[1-(3,3-dimethylbutyl)piperidin-4-yl]phenyl}-3-(pyridin-3-yl)azetidine-1-carboxamide | $^1$H NMR (500 MHz, pyridine-$d_5$/$D_2O$ Temp = 90° C.) ☐ ppm 8.55 (dd, J = 4.73, 1.68 Hz, 1 H) 8.46-8.51 (m, 1 H) 7.75 (d, J = 8.54 Hz, 2 H) 7.56-7.61 (m, 1 H) 7.21 (d, J = 8.54 Hz, 2 H) 7.16-7.18 (m, 1 H) 4.46 (t, J = 8.24 Hz, 2 H) 4.02-4.16 (m, 2 H) 3.64-3.75 (m, 1 H) 3.44 (d, J = 12.21 Hz, 2 H) 2.82-2.96 (m, 2 H) 2.53-2.69 (m, 3 H) 2.10-2.29 (m, 2 H) 1.81-1.97 (m, 2 H) 1.61-1.71 (m, 2 H) 0.89 (s, 9 H) | (ESI(+)) m/e 421 (M + H)⁺ |
| 234 | N-{4-[1-(2-methylpentyl)piperidin-4-yl]phenyl}-3-(pyridin-3-yl)azetidine-1-carboxamide | $^1$H NMR (500 MHz, pyridine-$d_5$/$D_2O$ Temp = 90° C.) ☐ ppm 8.55 (dd, J = 4.58, 1.53 Hz, 1 H) 8.42 (s, 1 H) 7.75 (d, J = 8.54 Hz, 2 H) 7.55-7.60 (m, 1 H) 7.20 (d, J = 8.54 Hz, 2 H) 7.16-7.18 (m, J = 5.19 Hz, 1 H) 4.46 (t, J = 8.24 Hz, 2 H) 4.07-4.12 (m, J = 7.93, 6.10 Hz, 2 H) 3.64-3.73 (m, 1 H) 2.99-3.08 (m, 2 H) 2.43-2.54 (m, 1 H) 2.05-2.33 (m, J = 12.51 Hz, 4 H) 1.67-1.97 (m, 5 H) 1.24-1.50 (m, 3 H) 1.05-1.18 (m, J = 9.46 Hz, 1 H) 0.95 (d, J = 6.71 Hz, 3 H) 0.89 (t, J = 7.17 Hz, 3 H) | (ESI(+)) m/e 421 (M + H)⁺ |
| 235 | N-{4-[1-(2-methylpropyl)piperidin-4-yl]phenyl}-3-(pyridin-3-yl)azetidine-1-carboxamide | $^1$H NMR (500 MHz, pyridine-$d_5$/$D_2O$ Temp = 90° C.) ☐ ppm 8.55 (dd, J = 4.73, 1.68 Hz, 1 H) 8.41-8.43 (m, 1 H) 7.75 (d, J = 8.54 Hz, 2 H) 7.56-7.61 (m, 1 H) 7.20 (d, J = 8.54 Hz, 2 H) 7.16-7.18 (m, J = 4.58 Hz, 1 H) 4.46 (t, J = 8.39 Hz, 2 H) 4.08-4.12 (m, 2 H) 3.65-3.73 (m, 1 H) 3.00 (d, J = 2 H) 2.43-2.54 (m, 1 H) 2.19 (d, J = 7.02 Hz, 2 H) 2.07-2.17 (m, 2 H) 1.73-1.94 (m, 5 H) 0.92 (d, J = 6.71 Hz, 6 H) | (ESI(+)) m/e 393 (M + H)⁺ |
| 236 | N-{4-[1-(3-methylbutyl)piperidin-4-yl]phenyl}-3- | $^1$H NMR (500 MHz, pyridine-$d_5$/$D_2O$ Temp = 90° C.) ☐ ppm 8.55 (dd, J = 4.88, 1.53 Hz, 1 H) 8.44-8.49 (m, 1 H) 7.75 (d, J = 8.54 Hz, 2 H) 7.56-7.60 (m, 1 H) 7.21 (d, J = 8.54 Hz, 2 H) 7.16-7.18 (m, J = 4.88 | (ESI(+)) m/e 407 (M + H)⁺ |

TABLE 4-continued

The following Examples were prepared essentially as described in Example 231, substituting the appropriate amine in Example 231A and the appropriate aldehyde in Example 231C. Some products were purified by flash chromatography while others were purified by reverse-phase HPLC. Accordingly, some Examples were isolated as trifluoroacetic acid salts.

| Ex | Name | ¹H NMR | MS |
|---|---|---|---|
|  | (pyridin-3-yl)azetidine-1-carboxamide | Hz, 1 H) 4.46-4.48 (m, 2 H) 4.10 (dd, J = 7.93, 5.80 Hz, 2 H) 3.64-3.73 (m, 1 H) 3.31 (d, J = 12.21 Hz, 2 H) 2.68-2.75 (m, 2 H) 2.53-2.64 (m, 1 H) 2.41-2.51 (m, 2 H) 2.01-2.17 (m, 2 H) 1.87 (d, 2 H) 1.51-1.63 (m, 3 H) 0.87 (d, J = 6.10 Hz, 6 H) |  |
| 237 | N-{4-[1-(2-ethylbutyl)piperidin-4-yl]phenyl}-3-(pyridin-3-yl)azetidine-1-carboxamide | ¹H NMR (500 MHz, pyridine-d$_5$/D$_2$O Temp = 90° C.) ☐ ppm 8.55 (dd, J = 4.58, 1.53 Hz, 1 H) 8.40-8.48 (m, 1 H) 7.75 (d, J = 8.54 Hz, 2 H) 7.56-7.61 (m, 1 H) 7.21 (d, J = 8.54 Hz, 2 H) 7.16-7.18 (m, 1 H) 4.46 (t, J = 8.39 Hz, 2 H) 4.10 (dd, J = 7.93, 6.10 Hz, 2 H) 3.64-3.74 (m, 1 H) 3.14 (d, 2 H) 2.47-2.62 (m, 1 H) 2.37-2.43 (m, 2 H) 2.22-2.32 (m, 2 H) 1.93-2.06 (m, 2 H) 1.77-1.85 (m, 2 H) 1.50-1.63 (m, 1 H) 1.30-1.50 (m, 4 H) 0.88 (t, J = 7.32 Hz, 6 H) | (ESI(+)) m/e 421 (M + H)⁺ |
| 238 | N-{4-[1-(2,2-dimethylpropyl)piperidin-4-yl]phenyl}-3-(pyridin-3-yl)azetidine-1-carboxamide |  | (ESI(+)) m/e 407 (M + H)⁺ |
| 239 | N-{4-[1-(2-methylbutyl)piperidin-4-yl]phenyl}-3-(pyridin-3-yl)azetidine-1-carboxamide | ¹H NMR (500 MHz, pyridine-d$_5$/D$_2$O Temp = 90° C.) ☐ ppm 8.55 (d, J = 4.58 Hz, 1 H) 8.42 (s, 1 H) 7.75 (d, J = 8.54 Hz, 2 H) 7.56-7.61 (m, 1 H) 7.31-7.36 (m, 1 H) 7.20 (d, J = 8.54 Hz, 2 H) 4.46 (t, J = 8.39 Hz, 2 H) 4.07-4.12 (m, J = 8.09, 5.95 Hz, 2 H) 3.63-3.76 (m, 1 H) 2.90-3.02 (m, 2 H) 2.42-2.52 (m, 1 H) 2.16-2.27 (m, 1 H) 1.95-2.13 (m, 3 H) 1.73-1.86 (m, J = 3.66 Hz, 4 H) 1.42-1.64 (m, J = 49.13 Hz, 2 H) 1.07-1.23 (m, 1 H) 0.85-0.96 (m, 6 H) | (ESI(+)) m/e 407 (M + H)⁺ |
| 240 | N-[4-(1-butylpiperidin-4-yl)phenyl]-3-(pyridin-3-yl)azetidine-1-carboxamide | ¹H NMR (500 MHz, pyridine-d$_5$/D$_2$O Temp = 90° C.) ☐ ppm 8.55 (dd, J = 4.58, 1.53 Hz, 1 H) 8.42-8.48 (m, 1 H) 7.75 (d, J = 8.24 Hz, 2 H) 7.56-7.61 (m, 1 H) 7.20 (d, J = 8.54 Hz, 2 H) 7.16-7.18 (m, 1 H) 4.46 (t, J = 8.24 Hz, 2 H) 4.10 (dd, J = 8.09, 5.95 Hz, 2 H) 3.63-3.75 (m, 1 H) 3.24 (d, 2 H) 2.49-2.69 (m, 3 H) 2.32-2.41 (m, 2 H) 1.98-2.16 (m, 2 H) 1.78-1.87 (m, 2 H) 1.53-1.66 (m, 2 H) 1.24-1.37 (m, 2 H) 0.86 (t, 3 H) | (ESI(+)) m/e 393 (M + H)⁺ |
| 241 | N-[4-(1-propylpiperidin-4-yl)phenyl]-3-(pyridin-3-yl)azetidine-1-carboxamide | ¹H NMR (500 MHz, pyridine-d$_5$/D$_2$O Temp = 90° C.) ☐ ppm 8.55 (dd, J = 4.58, 1.53 Hz, 1 H) 8.44-8.49 (m, 1 H) 7.76 (d, J = 8.70 Hz, 2 H) 7.56-7.62 (m, 1 H) 7.20 (d, J = 8.54 Hz, 2 H) 7.16-7.18 (m, J = 5.49 Hz, 1 H) 4.46 (t, J = 8.39 Hz, 2 H) 4.04-4.16 (m, 2 H) 3.64-3.73 (m, 1 H) 3.26-3.36 (m, 2 H) 2.43-2.72 (m, 5 H) 2.04-2.20 (m, 2 H) 1.85 (d, 2 H) 1.57-1.72 (m, 2 H) 0.84 (t, J = 7.32 Hz, 3 H) | (ESI(+)) m/e 379 (M + H)⁺ |
| 242 | N-{4-[1-(2-cyclopropylethyl)piperidin-4-yl]phenyl}-3-(pyridin-3-yl)azetidine-1-carboxamide | ¹H NMR (500 MHz, pyridine-d$_5$/D$_2$O Temp = 90° C.) ☐ ppm 8.55 (dd, J = 4.73, 1.37 Hz, 1 H) 8.43-8.48 (m, 1 H) 7.75 (d, J = 8.24 Hz, 2 H) 7.58 (d, J = 7.93 Hz, 1 H) 7.18 (d, 2 H) 7.16-7.17 (m, 1 H) 4.33-4.38 (m, 2 H) 4.05-4.14 (m, J = 8.09, 5.95 Hz, 2 H) 3.62-3.77 (m, 1 H) 3.23-3.35 (m, 2 H) 2.75-2.86 (m, 2 H) 2.42-2.64 (m, 3 H) 2.00-2.18 (m, 2 H) 1.80-1.90 (m, 2 H) 1.53-1.63 (m, 2 H) 0.58-0.72 (m, 1 H) 0.36-0.44 (m, 2 H) 0.07 (q, J = 4.88 Hz, 2 H) | (ESI(+)) m/e 405 (M + H)⁺ |
| 243 | 3-(pyridin-3-yl)-N-{4-[1-(tetrahydrofuran-3-ylmethyl)piperidin-4-yl]phenyl}azetidine-1-carboxamide | ¹H NMR (500 MHz, pyridine-d$_5$/D$_2$O Temp = 90° C.) ☐ ppm 8.55 (dd, J = 4.88, 1.53 Hz, 1 H) 8.43 (s, 1 H) 7.75 (d, J = 8.24 Hz, 2 H) 7.56-7.62 (m, 1 H) 7.20 (d, J = 8.54 Hz, 2 H) 7.16-7.17 (m, 1 H) 4.46 (t, J = 8.24 Hz, 2 H) 4.10 (dd, J = 7.93, 5.80 Hz, 2 H) 3.87-3.93 (m, J = 8.24, 6.71 Hz, 1 H) 3.76-3.85 (m, 1 H) 3.65-3.73 (m, 1 H) 3.57 (dd, J = 8.39, 5.65 Hz, 1 H) 2.96-3.11 (m, 2 H) 2.39-2.55 (m, 4 H) 2.09-2.21 (m, 2 H) 1.72-2.01 (m, 5 H) 1.50-1.63 (m, 1 H) | (ESI(+)) m/e 421 (M + H)⁺ |
| 244 | N-{4-[1-(2,2-dimethylbutyl)piperidin-4-yl]phenyl}-3-(pyridin-3-yl)azetidine-1- | ¹H NMR (500 MHz, pyridine-d$_5$/D$_2$O Temp = 90° C.) ☐ ppm 8.55 (dd, J = 4.88, 1.53 Hz, 1 H) 8.42 (s, 1 H) 7.76 (d, J = 8.54 Hz, 2 H) 7.56-7.62 (m, 1 H) 7.20 (d, J = 8.54 Hz, 2 H) 7.16-7.18 (m, J = 4.88 Hz, 1 H) 4.46 (t, J = 8.39 Hz, 2 H) 4.07-4.14 (m, 2 H) 3.65-3.75 (m, 1 H) 2.90 (d, J = 11.90 Hz, 2 H) 2.40-2.45 | (ESI(+)) m/e 421 (M + H)⁺ |

TABLE 4-continued

The following Examples were prepared essentially as described in Example 231, substituting the appropriate amine in Example 231A and the appropriate aldehyde in Example 231C. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
|  | 1-carboxamide | (m, 1 H) 2.25-2.37 (m, 2 H) 2.12 (s, 2 H) 1.67-1.91 (m, 4 H) 1.30 (q, J = 7.43 Hz, 2 H) 0.87 (s, 6 H) 0.83 (t, J = 7.63 Hz, 3 H) |  |
| 245 | N-{4-[1-(cyclopentylmethyl)azetidin-3-yl]phenyl}-3-(pyridin-3-yl)azetidine-1-carboxamide | $^1$H NMR (400 MHz, DMSO-d$_6$/D$_2$O Temp = 90° C.) □ ppm 8.60 (d, J = 2.14 Hz, 1 H) 8.52 (dd, J = 5.04, 1.37 Hz, 1 H) 7.94 (d, J = 7.63 Hz, 1 H) 7.48-7.54 (m, 3 H) 7.27 (d, J = 8.54 Hz, 2 H) 3.88-4.54 (m, 10 H) 3.18-3.23 (m, 2 H) 2.09 (d, J = 7.63 Hz, 1 H) 1.78 (s, 2 H) 1.47-1.69 (m, 4 H) 1.15-1.29 (m, 2 H) | (ESI(+)) m/e 391 (M + H)$^+$ |
| 246 | N-{4-[1-(cyclohexylmethyl)azetidin-3-yl]phenyl}-3-(pyridin-3-yl)azetidine-1-carboxamide | $^1$H NMR (400 MHz, DMSO-d$_6$/D$_2$O Temp = 90° C.) □ ppm 8.62 (d, J = 2.14 Hz, 1 H) 8.54 (dd, J = 4.88, 1.22 Hz, 1 H) 7.99 (d, J = 7.93 Hz, 1 H) 7.47-7.59 (m, 3 H) 7.26 (d, J = 8.54 Hz, 2 H) 3.73-4.68 (m, 10 H) 3.11 (s, 2 H) 1.54-1.78 (m, 6 H) 1.10-1.37 (m, 3 H) 0.92-1.07 (m, J = 9.77 Hz, 2 H) | (ESI(+)) m/e 405 (M + H)$^+$ |
| 247 | N-{4-[1-(3,3-dimethylbutyl)azetidin-3-yl]phenyl}-3-(pyridin-3-yl)azetidine-1-carboxamide | $^1$H NMR (400 MHz, DMSO-d$_6$/D$_2$O Temp = 90° C.) □ ppm 8.64 (d, J = 2.14 Hz, 1 H) 8.56 (d, J = 4.88 Hz, 1 H) 8.05 (d, J = 7.93 Hz, 1 H) 7.60 (dd, J = 7.78, 5.04 Hz, 1 H) 7.51 (d, J = 8.54 Hz, 2 H) 7.26 (t, J = 7.78 Hz, 2 H) 3.88-4.53 (m, 10 H) 3.12-3.24 (m, 2 H) 1.35-1.47 (m, 2H) 0.93 (s, 9 H) | (ESI(+)) m/e 393 (M + H)$^+$ |
| 248 | N-{4-[1-(cyclopropylmethyl)azetidin-3-yl]phenyl}-3-(pyridin-3-yl)azetidine-1-carboxamide | $^1$H NMR (400 MHz, DMSO-d$_6$/D$_2$O Temp = 90° C.) □ ppm 8.63 (d, J = 2.14 Hz, 1 H) 8.52-8.55 (m, 1 H) 7.95-8.04 (m, 1 H) 7.57 (dd, J = 7.93, 5.19 Hz, 1 H) 7.51 (d, J = 8.54 Hz, 2 H) 7.27 (d, J = 8.54 Hz, 2 H) 3.90-4.51 (m, 10 H) 3.13 (s, 2 H) 0.95-1.07 (m, 1 H) 0.58-0.67 (m, 2 H) 0.35-0.43 (m, J = 5.04, 5.04 Hz, 2 H) | (ESI(+)) m/e 363 (M + H)$^+$ |
| 249 | N-{4-[1-(2-methylpentyl)azetidin-3-yl]phenyl}-3-(pyridin-3-yl)azetidine-1-carboxamide | $^1$H NMR (400 MHz, DMSO-d$_6$/D$_2$O Temp = 90° C.) □ ppm 8.60 (d, J = 2.44 Hz, 1 H) 8.49-8.53 (m, 1 H) 7.95 (d, J = 7.93 Hz, 1 H) 7.45-7.56 (m, 3 H) 7.23-7.31 (m, 2 H) 4.23-4.59 (m, 5 H) 3.86-4.24 (m, 6 H) 2.98-3.24 (m, 1 H) 1.72-1.87 (m, 1 H) 1.10-1.46 (m, 4 H) 0.83-0.96 (m, 6 H) | (ESI(+)) m/e 393 (M + H)$^+$ |
| 250 | 3-(pyridin-3-yl)-N-{4-[1-(tetrahydrofuran-2-ylmethyl)azetidin-3-yl]phenyl}azetidine-1-carboxamide |  | (ESI(+)) m/e 393 (M + H)$^+$ |
| 251 | N-{4-[1-(2-methylpropyl)azetidin-3-yl]phenyl}-3-(pyridin-3-yl)azetidine-1-carboxamide | $^1$H NMR (400 MHz, DMSO-d$_6$/D$_2$O Temp = 90° C.) □ ppm 8.60 (d, J = 2.14 Hz, 1 H) 8.50-8.53 (m, 1 H) 7.92-7.97 (m, 1 H) 7.47-7.56 (m, 3 H) 7.27 (d, J = 8.54 Hz, 2 H) 4.25-4.54 (m, 5 H) 3.92-4.14 (m, 5 H) 3.06-3.17 (m, 2 H) 1.88-1.97 (m, J = 7.02 Hz, 1 H) 0.96 (d, J = 6.71 Hz, 6 H) | (ESI(+)) m/e 365 (M + H)$^+$ |
| 252 | N-{4-[1-(3-methylbutyl)azetidin-3-yl]phenyl}-3-(pyridin-3-yl)azetidine-1-carboxamide | $^1$H NMR (400 MHz, DMSO-d$_6$/D$_2$O Temp = 90° C.) □ ppm 8.61 (d, J = 2.14 Hz, 1 H) 8.53 (d, J = 4.58 Hz, 1 H) 7.98 (d, J = 7.93 Hz, 1 H) 7.47-7.57 (m, 3 H) 7.26 (d, J = 8.54 Hz, 2 H) 3.86-4.53 (m, 10 H) 3.16-3.22 (m, 2 H) 1.56-1.74 (m, 1 H) 1.37-1.48 (m, 2 H) 0.92 (d, J = 6.71 Hz, 6 H) | (ESI(+)) m/e 379 (M + H)$^+$ |
| 253 | N-{4-[1-(2-ethylbutyl)azetidin-3-yl]phenyl}-3-(pyridin-3-yl)azetidine-1-carboxamide | $^1$H NMR (400 MHz, DMSO-d$_6$/D$_2$O Temp = 90° C.) □ ppm 8.66 (d, J = 2.14 Hz, 1 H) 8.57 (dd, J = 5.04, 1.37 Hz, 1 H) 8.09 (d, J = 7.93 Hz, 1 H) 7.63 (dd, J = 8.09, 5.04 Hz, 1 H) 7.51 (d, J = 8.54 Hz, 2 H) 7.26 (t, J = 8.09 Hz, 2 H) 3.88-4.54 (m, 10 H) 3.09-3.24 (m, 2 H) 1.50-1.62 (m, 1 H) 1.27-1.45 (m, 4 H) 0.88 (t, J = 7.48 Hz, 6 H) | (ESI(+)) m/e 393 (M + H)$^+$ |
| 254 | N-{4-[1-(2,2-dimethylpropyl)azetidin-3-yl]phenyl}-3-(pyridin-3-yl)azetidine-1-carboxamide | $^1$H NMR (400 MHz, DMSO-d$_6$/D$_2$O Temp = 90° C.) □ □ppm 8.66 (d, J = 2.14 Hz, 1 H) 8.58 (dd, J = 5.04, 1.37 Hz, 1 H) 8.10 (d, J = 7.93 Hz, 1 H) 7.64 (dd, J = 7.93, 5.19 Hz, 1 H) 7.43-7.58 (m, 2 H) 7.20-7.33 (m, 2 H) 4.29-4.65 (m, 5 H) 3.85-4.19 (m, 5 H) 3.13-3.20 (m, 2 H) 1.00 (s, 9 H) | (ESI(+)) m/e 379 (M + H)$^+$ |
| 255 | N-{4-[1-(2-methylbutyl)azetidin-3-yl]phenyl}-3- | $^1$H NMR (400 MHz, DMSO-d$_6$/D$_2$O Temp = 90° C.) □ □ ppm 8.57 (d, J = 1.83 Hz, 1 H) 8.49 (d, J = 3.66 Hz, 1 H) 7.84-7.90 (m, 1 H) 7.42-7.53 (m, 3 H) 7.27 (d, J = 8.54 Hz, 2 H) 3.84-4.56 (m, 11 H) | (ESI(+)) m/e 379 (M + H)$^+$ |

TABLE 4-continued

The following Examples were prepared essentially as described in Example 231, substituting the appropriate amine in Example 231A and the appropriate aldehyde in Example 231C. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
|  | (pyridin-3-yl)azetidine-1-carboxamide | 3.00-3.19 (m, 1 H) 1.61-1.83 (m, 1 H) 1.11-1.49 (m, J = 64.70 Hz, 2 H) 0.85-0.97 (m, 6 H) |  |
| 256 | 3-(pyridin-3-yl)-N-{4-[1-(tetrahydrofuran-3-ylmethyl)azetidin-3-yl]phenyl}azetidine-1-carboxamide | $^1$H NMR (400 MHz, DMSO-d$_6$/D$_2$O Temp = 90° C.) □ □ ppm 8.66 (d, J = 2.14 Hz, 1 H) 8.58 (dd, J = 5.04, 1.37 Hz, 1 H) 8.10 (d, J = 8.24 Hz, 1 H) 7.64 (dd, J = 8.09, 5.04 Hz, 1 H) 7.51 (d, J = 8.24 Hz, 2 H) 7.27 (d, J = 8.54 Hz, 2 H) 3.94-4.60 (m, 10 H) 3.72-3.84 (m, 2 H) 3.62-3.70 (m, 1 H) 3.38-3.47 (m, 1 H) 3.31 (d, J = 7.02 Hz, 2 H) 2.39-2.50 (m, 1 H) 2.00-2.16 (m, 1 H) 1.54-1.72 (m, 1 H) | (ESI(+)) m/e 393 (M + H)$^+$ |
| 257 | N-{4-[1-(2,2-dimethylbutyl)azetidin-3-yl]phenyl}-3-(pyridin-3-yl)azetidine-1-carboxamide | $^1$H NMR (400 MHz, DMSO-d$_6$/D$_2$O Temp = 90° C.) □ ppm 8.70 (d, J = 1.83 Hz, 1 H) 8.61 (d, J = 5.19 Hz, 1 H) 8.19 (d, J = 7.94 Hz, 1 H) 7.72 (dd, J = 7.78, 5.34 Hz, 1 H) 7.50 (s, 2 H) 7.28 (d, J = 8.54 Hz, 2 H) 3.93-4.63 (m, 10 H) 3.18 (s, 2 H) 1.32 (q, J = 7.43 Hz, 2 H) 0.95 (s, 6 H) 0.84 (t, J = 7.48 Hz, 3 H) | (ESI(+)) m/e 393 (M + H)$^+$ |

Example 336

N-[4-(1-benzoylpiperidin-4-yl)phenyl]-3-(pyridazin-3-yl)azetidine-1-carboxamide

Example 336A tert-butyl 4-(4-(3-(pyridazin-3-yl)azetidine-1-carboxamido)phenyl)piperidine-1-carboxylate The title compound was prepared as described in Example 1C, substituting tert-butyl 4-(4-aminophenyl)piperidine-1-carboxylate for tert-butyl 3-(4-aminophenoxy)azetidine-1-carboxylate and 3-(azetidin-3-yl)pyridazine hydrochloride for 3-(azetidin-3-yl)pyridine bis hydrochloride.

Example 336B

N-(4-(piperidin-4-yl)phenyl)-3-(pyridazin-3-yl)azetidine-1-carboxamide

The title compound was prepared as described in Example 1D, substituting tert-butyl 4-(4-(3-(pyridazin-3-yl)azetidine-1-carboxamido)phenyl)piperidine-1-carboxylate for tert-butyl 3-(4-(3-(pyridin-3-yl)azetidine-1-carboxamido)phenoxy) azetidine-1-carboxylate.

Example 336C

N-[4-(1-benzoylpiperidin-4-yl)phenyl]-3-(pyridazin-3-yl)azetidine-1-carboxamide

The title compound was prepared as described in Example 1E, substituting N-(4-(piperidin-4-yl)phenyl)-3-(pyridazin-3-yl)azetidine-1-carboxamide for N-(4-(azetidin-3-yloxy)phenyl)-3-(pyridin-3-yl)azetidine-1-carboxamide and benzoic acid for (S)-2-methylbutanoic acid. $^1$H NMR (400 MHz, DMSO) δ 9.16 (dd, J=4.5, 2.0 Hz, 1H), 8.48 (s, 1H), 7.77-7.61 (m, 2H), 7.54-7.36 (m, 7H), 7.18-7.12 (m, 2H), 4.74-4.49 (m, 1H), 4.38 (t, J=8.1 Hz, 2H), 4.27-4.08 (m, 3H), 3.69-3.55 (m, 1H), 3.26-2.65 (m, 3H), 1.93-1.48 (m, 4H); MS (ESI(+)) m/e 442 (M+H)$^+$.

TABLE 5

The following Examples were essentially prepared as described in Example 336, substituting an appropriate carboxylic acid in Example 336C.

| Ex | Name | MS |
|---|---|---|
| 337 | N-{4-[1-(2-fluorobenzoyl)piperidin-4-yl]phenyl}-3-(pyridazin-3-yl)azetidine-1-carboxamide | (ESI(+)) m/e 460 (M + H)$^+$ |
| 338 | N-{4-[1-(2-methylbenzoyl)piperidin-4-yl]phenyl}-3-(pyridazin-3-yl)azetidine-1-carboxamide | (ESI(+)) m/e 456 (M + H)$^+$ |
| 339 | N-{4-[1-(2,2-dimethylpropanoyl)piperidin-4-yl]phenyl}-3-(pyridazin-3-yl)azetidine-1-carboxamide | (ESI(+)) m/e 422 (M + H)$^+$ |
| 340 | N-{4-[1-(cyclopropylcarbonyl)piperidin-4-yl]phenyl}-3-(pyridazin-3-yl)azetidine-1-carboxamide | (ESI(+)) m/e 406 (M + H)$^+$ |
| 341 | N-[4-(1-acetylpiperidin-4-yl)pheny]-3-(pyridazin-3-yl)azetidine-1-carboxamide | (ESI(+)) m/e 380 (M + H)$^+$ |

TABLE 5-continued

The following Examples were essentially prepared as described in Example 336, substituting an appropriate carboxylic acid in Example 336C.

| Ex | Name | MS |
|---|---|---|
| 342 | N-{4-[1-(3,3-dimethylbutanoyl)piperidin-4-yl]phenyl}-3-(pyridazin-3-yl)azetidine-1-carboxamide | (ESI(+)) m/e 436 $(M + H)^+$ |
| 343 | N-{4-[1-(cyclobutylcarbonyl)piperidin-4-yl]phenyl}-3-(pyridazin-3-yl)azetidine-1-carboxamide | (ESI(+)) m/e 420 $(M + H)^+$ |
| 344 | 3-(pyridazin-3-yl)-N-{4-[1-(4,4,4-trifluorobutanoyl)piperidin-4-yl]phenyl}azetidine-1-carboxamide | (ESI(+)) m/e 462 $(M + H)^+$ |
| 345 | 3-(pyridazin-3-yl)-N-{4-[1-(3,3,3-trifluoropropano yl)piperidin-4-yl]phenyl}azetidine-1-carboxamide | (ESI(+)) m/e 448 $(M + H)^+$ |
| 346 | N-(4-{1-[(1-methylcyclopropyl)carbonyl]piperidin-4-yl}phenyl)-3-(pyridazin-3-yl)azetidine-1-carboxamide | (ESI(+)) m/e 420 $(M + H)^+$ |
| 347 | N-{4-[1-(cyclopropylacetyl)piperidin-4-yl]phenyl}-3-(pyridazin-3-yl)azetidine-1-carboxamide | (ESI(+)) m/e 420 $(M + H)^+$ |

Example 348

N-{4-[(1-benzoylpiperidin-4-yl)methyl]phenyl}-3-(pyridazin-3-yl)azetidine-1-carboxamide Example 348A 4-(pyridin-4-ylmethyl)aniline The title compound was prepared as described in Example 1B, substituting 4-(4-nitrobenzyl)pyridine for tert-butyl 3-(4-nitrophenoxy)azetidine-1-carboxylate.

Example 348B 2,2,2-trifluoro-N-(4-(pyridin-4-ylmethyl)phenyl) acetamide

A solution of 4-(pyridin-4-ylmethyl)aniline (21.6 g, 117 mmol) and triethylamine (19.61 ml, 141 mmol) in dichloromethane (586 ml) was cooled to 0° C. Trifluoroacetic anhydride (19.87 ml, 141 mmol) was added dropwise via additional funnel over a period of 20 minutes. The mixture was stirred at 0° C. for 1 hour and then at room temperature for 2 hours. The reaction mixture was then concentrated in vacuo and the resulting residue was purified by regular phase column chromatography to give the title compound.

Example 348C 2,2,2-trifluoro-N-(4-(piperidin-4-ylmethyl)phenyl) acetamide 2,2,2-Trifluoro-N-(4-(pyridin-4-ylmethyl)phenyl)acetamide (28.5 g, 102 mmol) and acetic acid (205 ml) were added to platinum(IV) oxide (3.42 g, 15.06 mmol) in a 500 mL stainless steel pressure bottle and the mixture was stirred for 16 hours at 40 psi. The mixture was filtered through a nylon membrane and concentrated in vacuo; and the resulting residue was taken up in methanol (100 mL) and poured into diethyl ether (600 mL). The precipitate was filtered, washed with ether and dried to afford the title compound.

Example 348D tert-butyl 4-(4-aminobenzyl)piperidine-1-carboxylate

A solution of 2,2,2-trifluoro-N-(4-(piperidin-4-ylmethyl) phenyl)acetamide (26.4 g, 92 mmol) in dichloromethane (369 ml) was cooled to 0° C. and triethylamine (19.28 ml, 138 mmol) was added slowly. To the resulting solution was added di-tert-butyl dicarbonate (22.14 g, 101 mmol) in dichloromethane (75 ml) via addition funnel over 10 minutes. The 0° C. mixture was stirred for 2 hours and warmed slowly overnight. The reaction mixture was recooled to 0° C., treated with 1 N sodium hydroxide (100 ml), warmed to room temperature and stirred for 1 hour. The bilayer was separated and the organics were washed with water and brine, dried with magnesium sulfate, filtered and concentrated in vacuo. The residue was purified by normal phase chromatography to give the title compound.

Example 348E tert-butyl 4-(4-(3-(pyridazin-3-yl)azetidine-1-carboxamido)benzyl)piperidine-1-carboxylate The title compound was prepared as described in Example 1C, substituting tert-butyl 4-(4-aminobenzyl)piperidine-1-carboxylate for tert-butyl 3-(4-aminophenoxy)azetidine-1-carboxylate and 3-(azetidin-3-yl)pyridazine hydrochloride for 3-(azetidin-3-yl)pyridine bis hydrochloride.

Example 348F

N-(4-(piperidin-4-ylmethyl)phenyl)-3-(pyridazin-3-yl)azetidine-1-carboxamide

The title compound was prepared as described in Example 1D, substituting tert-butyl 4-(4-(3-(pyridazin-3-yl)azetidine-1-carboxamido)benzyl)piperidine-1-carboxylate for tert-butyl 3-(4-(3-(pyridin-3-yl)azetidine-1-carboxamido)phenoxy) azetidine-1-carboxylate.

Example 348G

N-{4-[(1-benzoylpiperidin-4-yl)methyl]phenyl}-3-(pyridazin-3-yl)azetidine-1-carboxamide The title compound was prepared as described in Example 1E, substituting N-(4-(piperidin-4-ylmethyl)phenyl)-3-(pyridazin-3-yl)azetidine-1-carboxamide for N-(4-(azetidin-3-yloxy)phenyl)-3-(pyridin-3-yl)azetidine-1-carboxamide and benzoic acid for (S)-2-methylbutanoic acid. $^1$H NMR (400 MHz, DMSO) δ 9.16 (dd, J=4.5, 2.0 Hz, 1H), 8.45 (s, 1H), 7.70 (qd, J=8.5, 3.3 Hz, 2H), 7.43 (dt, J=12.3, 6.2 Hz, 5H), 7.38-7.27 (m, 2H), 7.04 (d, J=8.5 Hz, 2H), 4.51-4.31 (m, 3H), 4.26-4.06 (m, 3H), 3.54 (s, 1H), 2.83 (d, J=96.4 Hz, 2H), 2.46 (d, J=6.7 Hz, 2H), 1.83-1.41 (m, 3H), 1.11 (s, 2H), MS (ESI(+)) m/e 456 (M+H)$^+$.

TABLE 6

The following Examples were essentially prepared as described in Example 1, substituting 1,3-dihydro-2H-pyrrolo[3,4-c]pyridine for isoindoline in Example 1A and using an appropriate amine as described in Example 1C.

| Ex | Name | MS |
|---|---|---|
| 349 | N-(4-{[1-(2-fluorobenzoyl)piperidin-4-yl]methyl}phenyl)-3-(pyridazin-3-yl)azetidine-1-carboxamide | (ESI(+)) m/e 474 (M + H)$^+$ |
| 350 | N-(4-{[1-(2,2-dimethylpropanoyl)piperidin-4-yl]methyl}phenyl)-3-(pyridazin-3-yl)azetidine-1-carboxamide | (ESI(+)) m/e 474 (M + H)$^+$ |
| 351 | N-(4-{[1-(3,3-dimethylbutanoyl)piperidin-4-yl]methyl}phenyl)-3-(pyridazin-3-yl)azetidine-1-carboxamide | (ESI(+)) m/e 450 (M + H)$^+$ |
| 352 | N-(4-{[1-(2-ethylbutanoyl)piperidin-4-yl]methyl}phenyl)-3-(pyridazin-3-yl)azetidine-1-carboxamide | (ESI(+)) m/e 450 (M + H)$^+$ |
| 353 | 3-(pyridazin-3-yl)-N-(4-{[1-(4,4,4-trifluorobutanoyl)piperidin-4-yl]methyl}phenyl)azetidine-1-carboxamide | (ESI(+)) m/e 476 (M + H)$^+$ |
| 354 | N-(4-{[1-(2-methylpropanoyl)piperidin-4-yl]methyl}phenyl)-3-(pyridazin-3-yl)azetidine-1-carboxamide | (ESI(+)) m/e 422 (M + H)$^+$ |
| 355 | N-{4-[(1-acetylpiperidin-4-yl)methyl]phenyl}-3-(pyridazin-3-yl)azetidine-1-carboxamide | (ESI(+)) m/e 394 (M + H)$^+$ |
| 356 | N-[4-({1-[(2S)-2-methylbutanoyl]piperidin-4-yl}methyl)phenyl]-3-(pyridazin-3-yl)azetidine-1-carboxamide | (ESI(+)) m/e 436 (M + H)$^+$ |
| 357 | N-[4-({1-[(1-methylcyclopropyl)carbonyl]piperidin-4-yl}methyl)phenyl]-3-(pyridazin-3-yl)azetidine-1-carboxamide | (ESI(+)) m/e 434 (M + H)$^+$ |

What is claimed is:

1. A compound of formula (IA), or a therapeutically acceptable salt thereof,

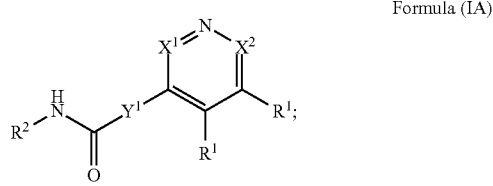

Formula (IA)

wherein $X^1$ is N and $X^2$ is $CR^1$; or
$X^1$ is $CR^1$ and $X^2$ is N; or
$X^1$ is $CR^1$ and $X^2$ is $CR^1$;

$Y^1$ is

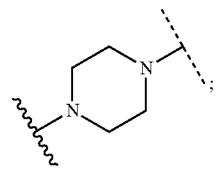

wherein ⌇ indicates the point of attachment to the carbonyl and ⌇ indicates the point of attachment to the nitrogen containing heteroaryl;

$R^1$, at each occurrence, is independently selected from the group consisting of hydrogen, alkyl, alkenyl, alkynyl, haloalkyl, hydoxyalkyl, alkoxy, OH, $NH_2$, CN, $NO_2$, F, Cl, Br and I;

$R^2$ is independently selected from the group consisting of $C_4$-$C_6$-alkyl, $C_4$-$C_6$-alkenyl, $C_4$-$C_6$-alkynyl, aryl, 3-12 membered heterocyclyl, cycloalkyl, and cycloalkenyl; wherein each $R^2$ $C_4$-$C_6$-alkyl, $C_4$-$C_6$-alkenyl, and $C_4$-$C_6$-alkynyl is substituted with one or more substituents independently selected from the group consisting of $R^3$, $OR^3$, $SR^3$, $S(O)R^3$, $SO_2R^3$, $C(O)R^3$, $CO(O)R^3$, $OC(O)R^3$, $OC(O)OR^3$, $NH_2$, $NHR^3$, $N(R^3)_2$, $NHC(O)R^3$, $NR^3C(O)R^3$, $NHS(O)_2R^3$, $NR^3S(O)_2R^3$, $NHC(O)OR^3$, $NR^3C(O)OR^3$, $NHC(O)NH_2$, $NHC(O)NHR^3$, $NHC(O)N(R^3)_2$, $NR^3C(O)NHR^3$, $NR^3C(O)N(R^3)_2$, $C(O)NH_2$, $C(O)NHR^3$, $C(O)N(R^3)_2$, $C(O)NHOH$, $C(O)NHOR^3$, $C(O)NHSO_2R^3$, $C(O)NR^3SO_2R^3$, $SO_2NH_2$, $SO_2NHR^3$, $SO_2N(R^3)_2$, $C(O)H$, $C(O)OH$, $C(N)NH_2$, $C(N)NHR^3$, $C(N)N(R^3)_2$, CNOH, $CNOCH_3$, OH, (O), CN, $N_3$, $NO_2$, F, Cl, Br and I; wherein each $R^2$ aryl, 3-12 membered heterocyclyl, cycloalkyl, and cycloalkenyl is substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, $CNOH$, $CNOCH_3$, $OH$, $CN$, $N_3$, $NO_2$, $F$, $Cl$, $Br$ and $I$;

$R^3$, at each occurrence, is independently selected from the group consisting of alkyl, alkenyl, alkynyl, aryl, cycloalkyl, cycloalkenyl, and heterocyclyl; wherein each $R^3$ alkyl, alkenyl, and alkynyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, $CNOH$, $CNOCH_3$, $OH$, $(O)$, $CN$, $N_3$, $NO_2$, $F$, $Cl$, $Br$ and $I$; wherein each $R^3$ aryl, cycloalkyl, cycloalkenyl, and heterocyclyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, $CNOH$, $CNOCH_3$, $OH$, $CN$, $N_3$, $NO_2$, $F$, $Cl$, $Br$ and $I$;

$R^4$, at each occurrence, is independently selected from the group consisting of heterocyclyl;

$R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one or more substituents independently selected from the group consisting of $R^8$, $OR^8$, $SR^8$, $S(O)R^8$, $SO_2R^8$, $NHR^8$, $N(R^8)_2$, $C(O)R^8$, $C(O)NH_2$, $C(O)NHR^8$, $C(O)N(R^8)_2$, $NHC(O)R^8$, $NR^8C(O)R^8$, $NHSO_2R^8$, $NHC(O)OR^8$, $SO_2NH_2$, $SO_2NHR^8$, $SO_2N(R^8)_2$, $NHC(O)NH_2$, $NHC(O)NHR^8$, $OH$, $(O)$, $C(O)OH$, $N_3$, $CN$, $NH_2$, $F$, $Cl$, $Br$ and $I$;

$R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one or more substituents independently selected from the group consisting of $R^9$, $OR^9$, $SR^9$, $S(O)R^9$, $SO_2R^9$, $NHR^9$, $N(R^9)_2$, $C(O)R^9$, $C(O)NH_2$, $C(O)NHR^9$, $C(O)N(R^9)_2$, $NHC(O)R^9$, $NR^9C(O)R^9$, $NHSO_2R^9$, $NHC(O)OR^9$, $SO_2NH_2$, $SO_2NHR^9$, $SO_2N(R^9)_2$, $NHC(O)NH_2$, $NHC(O)NHR^9$, $OH$, $(O)$, $C(O)OH$, $N_3$, $CN$, $NH_2$, $CF_3$, $CF_2CF_3$, $F$, $Cl$, $Br$ and $I$;

$R^8$, at each occurrence, is independently selected from the group consisting of alkyl, alkenyl, alkynyl, aryl, heterocyclyl, cycloalkyl, and cycloalkenyl;

$R^9$, at each occurrence, is independently selected from the group consisting of alkyl, alkenyl, alkynyl, aryl, heterocyclyl, cycloalkyl, and cycloalkenyl;

wherein the cyclic moieties represented by $R^4$, $R^5$, $R^6$, $R^8$, and $R^9$ are independently optionally substituted with one or more substituents independently selected from the group consisting of $R^{10}$, $OR^{10}$, $SR^{10}$, $S(O)R^{10}$, $C(O)C(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, $CNOH$, $CNOCH_3$, $OH$, $CN$, $N_3$, $NO_2$, $F$, $Cl$, $Br$ and $I$;

$R^{10}$, at each occurrence, is independently selected from the group consisting of alkyl, alkenyl, alkynyl, aryl, heterocyclyl, cycloalkyl, and cycloalkenyl; wherein each $R^{10}$ alkyl, alkenyl, and alkynyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $C(N)NH_2$, $C(N)NHR^{11}$, $C(N)N(R^{11})_2$, $CNOH$, $CNOCH_3$, $OH$, $(O)$, $CN$, $N_3$, $NO_2$, $F$, $Cl$, $Br$ and $I$; wherein each $R^{10}$ aryl, heterocyclyl, cycloalkyl, and cycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, $CNOH$, $CNOCH_3$, $OH$, $CN$, $N_3$, $NO_2$, $F$, $Cl$, $Br$ and $I$;

$R^{11}$, at each occurrence, is independently selected from the group consisting of alkyl, alkenyl, alkynyl, aryl, heterocyclyl, cycloalkyl, and cycloalkenyl; wherein each $R^{11}$ alkyl, alkenyl, and alkynyl is optionally substituted with alkyl or alkoxy; wherein each $R^{11}$ aryl, heterocyclyl, cycloalkyl, and cycloalkenyl is optionally substituted with alkyl or alkoxy; and $R^{12}$, at each occurrence, is independently selected alkyl.

2. The compound of claim 1, or a therapeutically acceptable salt thereof, wherein $X^1$ is $CR^1$ and $X^2$ is $CR^1$.

3. The compound of claim 1 or claim 2, or a therapeutically acceptable salt thereof, wherein $R^1$, at each occurrence, is hydrogen.

4. The compound of claim 1, or a therapeutically acceptable salt thereof, wherein $R^2$ is phenyl; wherein each $R^2$ phenyl is substituted with $OR^4$.

5. The compound of claim 1, or a therapeutically acceptable salt thereof, wherein $R^2$ is phenyl; wherein each $R^2$ phenyl is substituted with $R^4$.

6. The compound of claim 1, which is
4-(pyridin-3-yl)-N-(4-{[1-(tetrahydro-2H-pyran-4-ylacetyl)piperidin-4-yl]oxy}phenyl)piperazine-1-carboxamide;
and pharmaceutically acceptable salts thereof.

7. A composition comprising an excipient and a therapeutically effective amount of a compound of claim 1, or pharmaceutically acceptable salts thereof.

* * * * *